(12) United States Patent
Van Schalkwyk et al.

(10) Patent No.: US 11,278,700 B2
(45) Date of Patent: Mar. 22, 2022

(54) BREATHING ASSISTANCE APPARATUS

(71) Applicant: Fisher & Paykel Healthcare Limited, Auckland (NZ)

(72) Inventors: Andre Van Schalkwyk, Auckland (NZ); Andrew Paul Maxwell Salmon, Auckland (NZ); Joel Michael Lawson, Auckland (NZ); Russel William Burgess, Auckland (NZ); Cameron Alexander Lawrence, Auckland (NZ); Rachel Adeline Miller, Auckland (NZ); Dean Antony Barker, Auckland (NZ); Peter Geoffrey Hawkins, Auckland (NZ); Ella Marie Meisel, Auckland (NZ); Eamonn Bernard McKnight, Auckland (NZ); Kevin Peter O'Donnell, Auckland (NZ); Jae Chui Han, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 372 days.

(21) Appl. No.: 15/739,096

(22) PCT Filed: Jun. 24, 2016

(86) PCT No.: PCT/IB2016/053761
§ 371 (c)(1),
(2) Date: Dec. 21, 2017

(87) PCT Pub. No.: WO2016/207838
PCT Pub. Date: Dec. 29, 2016

(65) Prior Publication Data
US 2018/0185606 A1 Jul. 5, 2018

Related U.S. Application Data

(60) Provisional application No. 62/340,910, filed on May 24, 2016, provisional application No. 62/264,220, (Continued)

(51) Int. Cl.
*A61M 16/16* (2006.01)
*A61M 16/06* (2006.01)
(Continued)

(52) U.S. Cl.
CPC ........ *A61M 16/16* (2013.01); *A61M 16/0003* (2014.02); *A61M 16/0066* (2013.01);
(Continued)

(58) Field of Classification Search
None
See application file for complete search history.

(56) References Cited

U.S. PATENT DOCUMENTS 3,745,991 A 7/1973 Gauthier et al.
4,028,444 A 6/1977 Brown et al.
(Continued)

FOREIGN PATENT DOCUMENTS

AU 2003204474 B2 9/2008
CA 1289037 9/1991
(Continued)

OTHER PUBLICATIONS

International Search Report; PCT/IB2016/053761; dated Oct. 5, 2016.
(Continued)

*Primary Examiner* — Bradley H Philips
*Assistant Examiner* — Savannah L Gabriel
(74) *Attorney, Agent, or Firm* — Knobbe, Martens, Olson & Bear, LLP

(57) ABSTRACT

An apparatus for delivering a flow of gas, has a housing 3202' with a recess, and an outlet port 3210' for a flow of gas.
(Continued)

The recess is defined by at least one wall 3256, 3262 that is substantially continuous, gas impermeable, and unbroken, other than a gasflow passage from the recess to the outlet port of the housing.

21 Claims, 123 Drawing Sheets

Related U.S. Application Data filed on Dec. 7, 2015, provisional application No. 62/183,889, filed on Jun. 24, 2015.

(51) Int. Cl.
*A61M 16/10* (2006.01)
*A61M 16/00* (2006.01)

(52) U.S. Cl.
CPC ...... *A61M 16/0069* (2014.02); *A61M 16/024* (2017.08); *A61M 16/0672* (2014.02); *A61M 16/109* (2014.02); *A61M 16/1095* (2014.02); *A61M 16/161* (2014.02); *A61M 2016/0027* (2013.01); *A61M 2016/0039* (2013.01); *A61M 2205/3368* (2013.01); *A61M 2205/3569* (2013.01); *A61M 2205/3592* (2013.01); *A61M 2205/3653* (2013.01); *A61M 2205/42* (2013.01)

(56) References Cited

U.S. PATENT DOCUMENTS

| | | |
|---|---|---|
| 4,299,784 A | 11/1981 | Hense |
| 4,602,653 A | 7/1986 | Ruiz-Vela et al. |
| 4,889,116 A | 12/1989 | Taube |
| 5,080,093 A | 1/1992 | Raabe et al. |
| 5,165,397 A | 11/1992 | Arp |
| 5,343,551 A | 8/1994 | Glucksman |
| 5,551,419 A | 9/1996 | Froehlich et al. |
| 5,673,687 A | 10/1997 | Dobson et al. |
| 5,701,883 A | 12/1997 | Hete et al. |
| 5,878,743 A | 3/1999 | Zdrojkowski et al. |
| 6,216,691 B1 | 4/2001 | Kenyon et al. |
| 6,401,713 B1 | 6/2002 | Hill et al. |
| 6,435,180 B1 | 8/2002 | Hewson et al. |
| 6,543,449 B1 | 4/2003 | Woodring et al. |
| 6,546,930 B1 | 4/2003 | Emerson et al. |
| 6,581,595 B1 | 6/2003 | Murdock et al. |
| 6,672,300 B1 | 1/2004 | Grant |
| 6,848,444 B2 | 2/2005 | Smith et al. |
| 6,910,481 B2 | 6/2005 | Kimmel et al. |
| 7,111,624 B2 | 9/2006 | Thudor et al. |
| 7,314,046 B2 | 1/2008 | Schroeder et al. |
| 7,413,173 B2 | 8/2008 | DiMatteo et al. |
| 7,571,725 B2 | 8/2009 | Wickham et al. |
| 7,677,246 B2 | 3/2010 | Kepler et al. |
| 7,793,660 B2 | 9/2010 | Kimmel et al. |
| 7,874,290 B2 | 1/2011 | Chalvignac |
| 7,942,380 B2 | 5/2011 | Bertinetti et al. |
| 7,975,688 B1 | 7/2011 | Truitt |
| 8,006,691 B2 | 8/2011 | Kenyon et al. |
| 8,137,082 B2 | 3/2012 | Campbell |
| 8,186,345 B2 | 5/2012 | Payton et al. |
| 8,302,598 B2 | 11/2012 | Haase et al. |
| 8,453,640 B2 | 6/2013 | Martin et al. |
| 8,496,001 B2 | 7/2013 | Schermeier et al. |
| 8,517,012 B2 | 8/2013 | Daly et al. |
| 8,555,879 B2 | 10/2013 | Potharaju et al. |
| 8,627,819 B2 | 1/2014 | DeVries et al. |
| 8,701,662 B2 | 4/2014 | Pujol et al. |
| 8,739,780 B2 | 6/2014 | Tang et al. |
| 8,915,247 B2 | 12/2014 | Chalvignac et al. |
| 8,931,481 B2 | 1/2015 | Jones et al. |
| 9,072,860 B2 | 7/2015 | Lithgow et al. |
| 9,272,116 B2 | 3/2016 | Mayer et al. |
| 9,302,066 B2 | 4/2016 | Bertinetti et al. |
| 9,545,494 B2 | 1/2017 | Mayer et al. |
| 9,555,211 B2 | 1/2017 | Mayer et al. |
| 9,649,459 B2 | 5/2017 | Taylor et al. |
| 9,707,369 B2 | 7/2017 | DeSilva et al. |
| 9,750,907 B2 | 9/2017 | Librett et al. |
| 9,962,514 B2 | 5/2018 | Williams |
| 10,052,450 B2 | 8/2018 | Mayer et al. |
| 10,092,716 B2 | 10/2018 | Velzy et al. |
| 10,201,676 B2 | 2/2019 | Lithgow et al. |
| 2002/0022973 A1 | 2/2002 | Sun et al. |
| 2003/0066526 A1 | 4/2003 | Thudor et al. |
| 2003/0236450 A1 | 12/2003 | Kocinski |
| 2004/0211244 A1 | 10/2004 | Cardelius et al. |
| 2005/0103339 A1 | 5/2005 | Daly et al. |
| 2006/0150973 A1 | 7/2006 | Chalvignac |
| 2006/0213518 A1 | 9/2006 | DeVries et al. |
| 2006/0231097 A1 | 10/2006 | Dougherty et al. |
| 2007/0169776 A1* | 7/2007 | Kepler ............... A61M 16/109 128/200.23 |
| 2007/0193579 A1 | 8/2007 | Duquette et al. |
| 2007/0247009 A1* | 10/2007 | Hoffman ............ F04D 25/0606 310/51 |
| 2008/0000474 A1* | 1/2008 | Jochle ................ A61M 16/022 128/204.18 |
| 2008/0060647 A1 | 3/2008 | Messenger et al. |
| 2008/0105257 A1 | 5/2008 | Klasek et al. |
| 2009/0162226 A1 | 6/2009 | Campbell et al. |
| 2009/0241953 A1 | 10/2009 | Vandine et al. |
| 2010/0065051 A1 | 3/2010 | Potharaju et al. |
| 2010/0186744 A1 | 7/2010 | Andrieux |
| 2011/0180068 A1 | 7/2011 | Kenton et al. |
| 2011/0197884 A1 | 8/2011 | Duff et al. |
| 2012/0298099 A1* | 11/2012 | Lalonde ............. A61M 16/109 128/200.16 |
| 2013/0263854 A1 | 10/2013 | Taylor et al. |
| 2013/0280055 A1 | 10/2013 | Daly et al. |
| 2013/0306072 A1* | 11/2013 | Moir ................ A61M 16/0683 128/204.18 |
| 2014/0020684 A1 | 1/2014 | Klasek et al. |
| 2014/0202460 A1 | 7/2014 | Bath et al. |
| 2014/0261422 A1 | 9/2014 | Lang et al. |
| 2014/0299132 A1 | 10/2014 | Librett et al. |
| 2015/0000669 A1 | 1/2015 | Miller |
| 2015/0007815 A1 | 1/2015 | Duquette et al. |
| 2015/0023782 A1 | 1/2015 | Velzy et al. |
| 2015/0122685 A1 | 5/2015 | Wakeham et al. |
| 2015/0157818 A1 | 6/2015 | Darby et al. |
| 2015/0190605 A1 | 7/2015 | Martin et al. |
| 2015/0230750 A1 | 8/2015 | McDarby et al. |
| 2015/0250963 A1 | 9/2015 | Ramanan et al. |
| 2015/0290415 A1 | 10/2015 | Dunn |
| 2015/0335846 A1 | 11/2015 | Romagnoli et al. |
| 2016/0114121 A1 | 4/2016 | Holley et al. |
| 2017/0082116 A1 | 3/2017 | Nibu et al. |
| 2017/0157347 A1 | 6/2017 | Jones et al. |
| 2017/0182270 A1 | 6/2017 | Kenyon et al. |
| 2018/0236191 A1 | 8/2018 | Martin et al. |
| 2018/0344965 A1 | 12/2018 | Mayer et al. |
| 2018/0369521 A1 | 12/2018 | Velzy et al. |
| 2019/0038857 A1 | 2/2019 | Kenyon et al. |

FOREIGN PATENT DOCUMENTS

| | | |
|---|---|---|
| CN | 101325979 | 12/2008 |
| CN | 101583395 | 11/2009 |
| CN | 203169777 | 9/2013 |
| DE | 4020522 | 1/1992 |
| DE | 102005000819 | 7/2006 |
| EP | 0788805 | 6/1997 |
| EP | 1457223 A1 | 9/2004 |
| EP | 2 000 675 | 12/2008 |
| EP | 1648544 | 7/2011 |
| EP | 2112938 | 8/2016 |
| EP | 2822626 | 9/2017 |
| EP | 2992921 B1 | 9/2017 |
| EP | 3320940 | 5/2018 |

(56) References Cited

FOREIGN PATENT DOCUMENTS

| | | |
|---|---|---|
| EP | 3351281 | 7/2018 |
| EP | 2345449 | 5/2019 |
| EP | 3195892 | 9/2019 |
| EP | 2317150 | 12/2019 |
| EP | 3311869 | 3/2020 |
| EP | 2494213 | 9/2020 |
| EP | 3305355 | 9/2020 |
| EP | 3300756 | 10/2020 |
| FR | 2677437 | 9/1993 |
| JP | 3060967 U | 7/2000 |
| JP | 2008518640 | 6/2008 |
| JP | 2009513192 | 4/2009 |
| NZ | 544765 | 1/2009 |
| WO | WO 1999/047197 | 9/1999 |
| WO | WO 2000/045883 | 8/2000 |
| WO | WO 2000/072921 | 12/2000 |
| WO | WO 2001/032069 | 5/2001 |
| WO | WO 2004/112873 | 12/2004 |
| WO | WO 2005/028009 | 3/2005 |
| WO | WO 2007/004898 | 1/2007 |
| WO | WO 2007/038152 | 4/2007 |
| WO | WO 2007/048205 | 5/2007 |
| WO | WO 2007/149446 | 12/2007 |
| WO | WO 2008/056993 | 5/2008 |
| WO | WO-2008056993 A2 * | 5/2008 ........ A61M 16/0816 |
| WO | WO 2011/051462 | 5/2011 |
| WO | WO 2013/020167 | 2/2013 |
| WO | WO 2013/133889 | 9/2013 |
| WO | WO 2013/135318 | 9/2013 |
| WO | WO 2013/137753 | 9/2013 |
| WO | WO 2013/151447 | 10/2013 |
| WO | WO 2013/152403 | 10/2013 |
| WO | WO-2013151447 A1 * | 10/2013 ............ A61M 16/20 |
| WO | WO 2013/163685 | 11/2013 |
| WO | WO 2013/163687 | 11/2013 |
| WO | WO 2013/173219 | 11/2013 |
| WO | WO 2014/005191 | 1/2014 |
| WO | WO 2014/051436 | 1/2014 |
| WO | WO 2014/051436 | 4/2014 |
| WO | WO 2014/201513 | 12/2014 |
| WO | WO 2014/210380 | 12/2014 |
| WO | WO 2014/210382 | 12/2014 |
| WO | WO 2015/000025 | 1/2015 |
| WO | WO 2015/038013 | 3/2015 |
| WO | WO 2015/048857 | 4/2015 |
| WO | WO 2015/058255 | 4/2015 |
| WO | WO 2015/061848 | 5/2015 |
| WO | WO 2015/089582 | 6/2015 |
| WO | WO 2015/120521 | 8/2015 |
| WO | WO 2015/120522 | 8/2015 |
| WO | WO 2015/131219 | 9/2015 |
| WO | WO 2015/188227 | 12/2015 |
| WO | WO 2015/192186 | 12/2015 |
| WO | WO 2015/196255 | 12/2015 |
| WO | WO 2015/200877 | 12/2015 |
| WO | WO 2015/200879 | 12/2015 |
| WO | WO 2016/000040 | 1/2016 |
| WO | WO 2016/019292 | 2/2016 |
| WO | WO 2016/029265 | 3/2016 |
| WO | WO 2017/006189 | 1/2017 |
| WO | WO 2017/027906 | 2/2017 |

OTHER PUBLICATIONS

Dec. 7, 2018, European Search Report and Search Opinion for Application No. 16 813 828.7.

Search Report of TW Patent Application No. 105119993, dated Dec. 31, 2019.

Japanese Examination Report for Japanese patent application 2017-565970 dated Jun. 29, 2020, 3 pages.

* cited by examiner

FIGURE 74
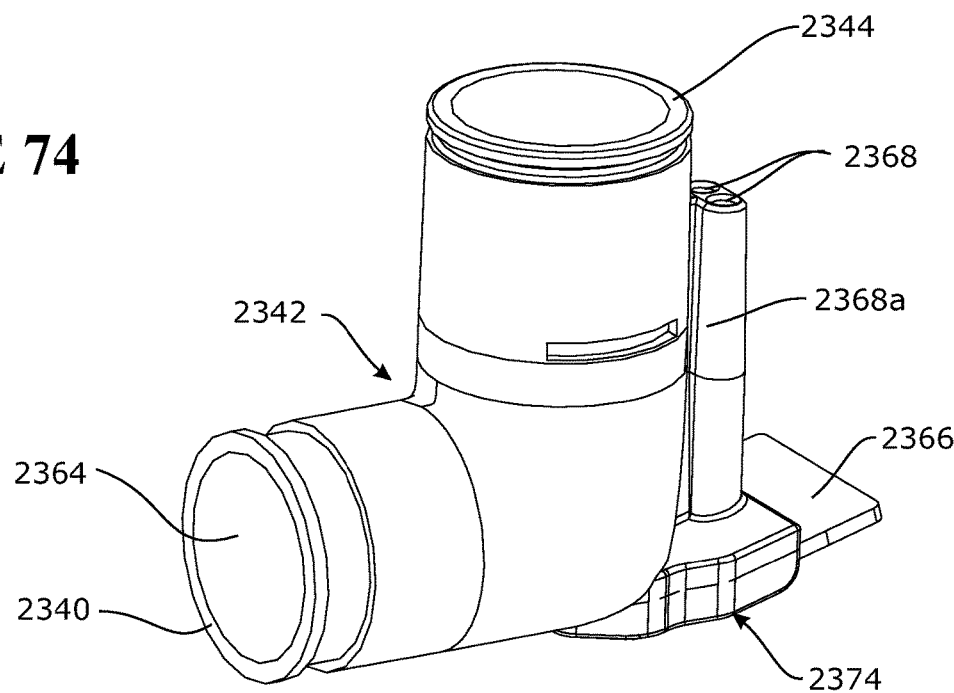
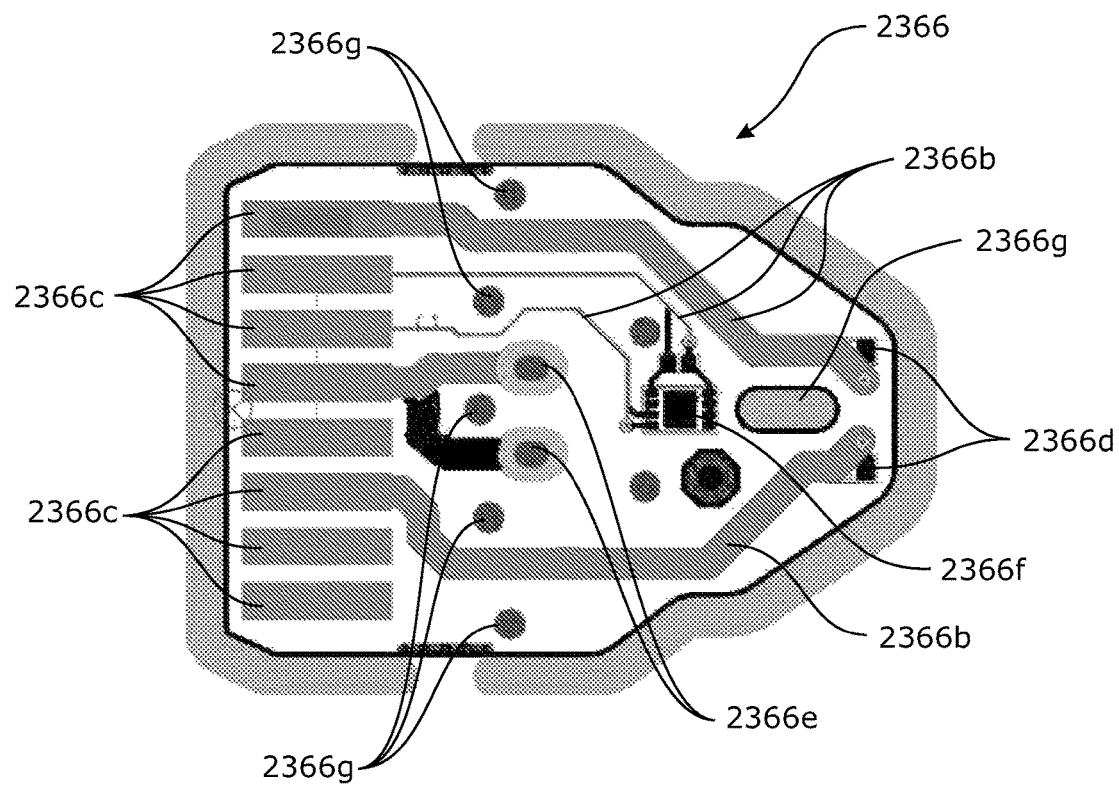
FIGURE 75

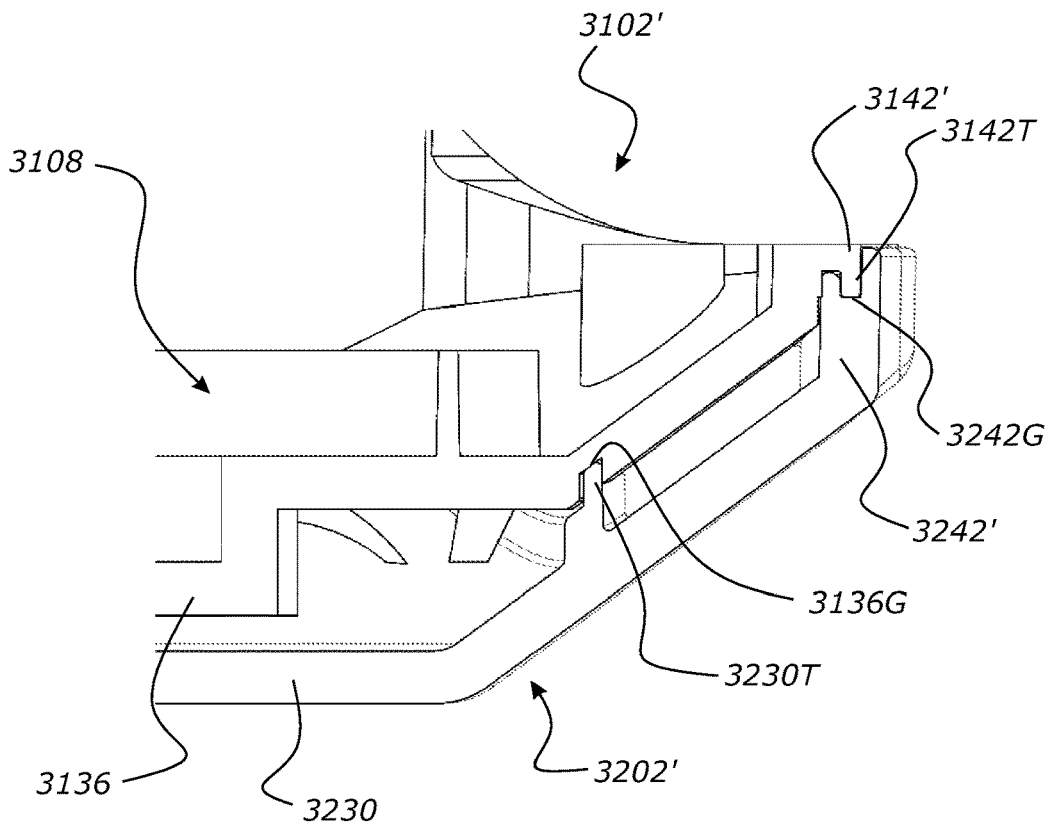
FIGURE 159
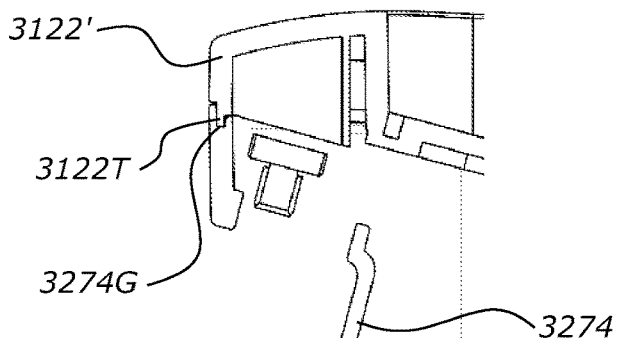
FIGURE 160
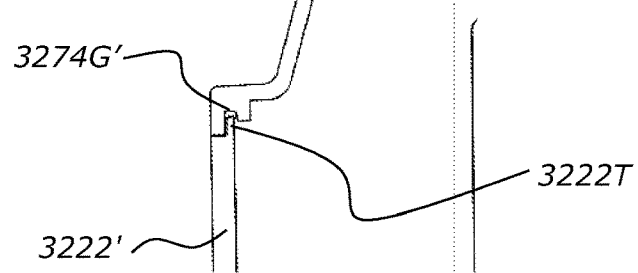

BREATHING ASSISTANCE APPARATUS

TECHNICAL FIELD

The present disclosure relates to a flow therapy apparatus for delivering gas to patients.

BACKGROUND ART

Breathing assistance apparatuses are used in various environments such as hospital, medical facility, residential care, or home environments to deliver a flow of gas to users or patients.

SUMMARY

The applicant has identified potential fire or explosion risk if some gases, such as high concentration oxygen for example, come into contact with electrical and/or electronics components in breathing assistance apparatuses.

The applicant has also identified potential difficulties in inserting and/or retaining and/or removing a liquid chamber in and/or from a chamber bay of a breathing assistance apparatus, particularly for users with limited mobility. Full or correct insertion and/or retention may be required to ensure that a satisfactory seal is obtained and maintained between the liquid chamber and other component(s) that form part of the gasflow path.

The applicant has also identified potential difficulties in keeping components clean and/or sterile when those components are fixed in the housing of a breathing assistance apparatus.

Accordingly, it would be desirable to provide an apparatus for delivering a flow of gas that isolates gas flow from electrical and/or electronic components.

Additionally or alternatively, it would be desirable to provide an apparatus for delivering a flow of gas that has one or more features that assist with inserting and/or retaining and/or removing a liquid chamber in and/or from a chamber bay.

Additionally or alternatively, it would be desirable to provide an apparatus for delivering a flow of gas that has one or more removable components to assist with the use, functioning, or configuration of the apparatus.

It is an object of one or more of the disclosed embodiments to provide an apparatus for delivering a flow of gas that has one or more features that assist with the use, functioning, or configuration of the apparatus or improves the safety of the apparatus, or that will at least provide the public or a medical professional with a useful choice.

Thus, in accordance with certain features, aspects and advantages of at least one of the embodiments disclosed herein, an apparatus for delivering a flow of gas is disclosed, the apparatus comprising:
a housing with:
  a recess for a motor and/or sensor module,
  an outlet port for a flow of gas, and
  a removable elbow for a flow of gas; and
a humidifier with:
  a heater,
  a chamber bay for receipt of a liquid chamber, and
  a lever and/or detent(s) for assisting with insertion and/or retention and/or removal of the liquid chamber in and/or from the chamber bay.

In some configurations, the apparatus comprises a liquid chamber for receipt in the chamber bay, the liquid chamber comprising an inlet port connectable to the outlet port, and an outlet port connectable to the removable elbow. In some configurations, at least one of the ports comprises one or more flexible fingers configured to provide positive engagement between that port and the port to which it is connectable.

In some configurations, the apparatus comprises a user interface.

In some configurations, the chamber bay is formed in the housing.

Additionally, in accordance with certain features, aspects and advantages of at least one of the embodiments disclosed herein, an apparatus for delivering a flow of gas is disclosed, the apparatus comprising:
a housing with a recess, and
an outlet port for a flow of gas,
wherein the recess is defined by at least one wall that is substantially continuous, gas impermeable, and unbroken, other than a gasflow passage from the recess to the outlet port of the housing.

In some configurations, the recess comprises a recess opening in an exterior wall of the housing, wherein the recess extends into the housing from the recess opening. In some configurations, the recess opening is in a bottom of the housing. Alternatively, the recess opening could be in a different part of the housing, such as a side, front, or top of the housing. In some configurations, the recess opening is in a top of the housing.

In some configurations, the recess is for receipt of a motor and/or sensor module.

In some configurations, the apparatus comprises a motor and/or sensor module positioned in the recess.

In some configurations, the apparatus is configured so that gases enter the housing via the recess and exit the housing via the outlet port. In some configurations, the gases are delivered by a gases passage from their entrance to the housing to the outlet port. In some configurations, the gases passage is provided by the motor and/or sensor module.

In some configurations, the motor and/or sensor module comprises a base, a sensing layer, and a cover layer assembled together to form a sub-assembly housing. In some configurations, the sub-assembly housing has a shape that is complementary to a shape of the recess.

In some configurations, the motor and/or sensor module comprises a motor with an impeller, the motor arranged to deliver gas to the outlet port of the housing. In some configurations, the motor is positioned on the base of the sub-assembly.

In some configurations, the base is configured to close the recess opening when the sub-assembly is positioned in the recess.

In some configurations, the sub-assembly is maintained in position in the recess by fasteners, clips, or a quick release arrangement.

In some configurations, the sensing layer comprises a gasflow path with one or more sensors. In some configurations, the gasflow path is arranged to deliver gas to the outlet port of the housing. In some configurations, the gas is or comprises oxygen. In some configurations, the gas comprises a blend of oxygen and ambient air.

In some configurations, the gasflow path comprises an elongate gasflow portion.

In some configurations, the gasflow path has a tangential entrance portion that is located at or adjacent an entrance end of the elongate gasflow portion.

In some configurations, the motor and/or sensor module comprises a gasflow path that comprises a sinuous arrangement.

In some configurations, the housing comprises electrical and/or electronic components, and wherein the recess is configured to isolate the electrical and/or electronic components from gasflow through or from the motor and/or sensor module. In some configurations, the gasflow passage is provided by a gasflow passage tube, wherein the gasflow passage tube extends through an outer tube that is integrally formed with a portion of the housing.

In some configurations, the apparatus is configured so that if a leak occurs in any of the seals of the motor and/or sensor module, oxygen will leak to the atmosphere rather than to the electrical and/or electronic components.

In some configurations, a seal is provided between part of the motor and/or sensor module and a wall of the recess, to seal the module to the housing. In some configurations, the seal comprises a soft seal such as an O-ring. In some configurations, the seal is provided between a base of the motor and/or sensor module and the wall of the recess. In some configurations, the base supports a motor with an impeller.

In some configurations, the motor and/or sensor module is removable from the recess. In some alternative configurations, the motor and/or sensor module may not be removable from the recess.

In some configurations, the motor and/or sensor module comprises a motor with an impeller and a gases outlet port, and the gases outlet port is coupled to an inlet port of an adjacent component by a flexible cuff. In some configurations, the motor and/or sensor module comprises a cuff support member that is configured to support the cuff. In some configurations, the cuff support member comprises an upstanding cuff support member that has an inwardly concave shape, and that is configured to receive and support the periphery of the cuff. In some configurations, a gases outlet port end of the cuff comprises an enlarged diameter that rests on an upper end of the cuff support member.

In some configurations, gas that is or comprises oxygen flows through the gasflow passage and/or the outlet port. In some configurations, the gas is isolated from electrical and/or electronics components in the housing. In some configurations, the gas comprises a blend of oxygen and ambient air.

Additionally, in accordance with certain features, aspects and advantages of at least one of the embodiments disclosed herein, a motor and/or sensor module for use in the apparatus is disclosed, the motor and/or sensor module having the feature(s) recited above.

Additionally, in accordance with certain features, aspects and advantages of at least one of the embodiments disclosed herein, an apparatus for delivering a flow of gas is disclosed, the apparatus comprising:
 a humidifier with:
 a heater,
 a chamber bay for receipt of a liquid chamber, and
 a lever for assisting insertion and/or retention and/or removal of the liquid chamber in and/or from the chamber bay.

In some configurations, the lever is configured for assisting with one of insertion, retention, removal of the liquid chamber. In some configurations, the lever is configured for assisting with two of insertion, retention, removal of the liquid chamber. In some configurations, the lever is configured for assisting with all three of insertion, retention, removal of the liquid chamber.

Different configurations may be configured for assisting with one, two, or all of insertion, retention, or removal of the liquid chamber in and/or from the chamber bay.

In some configurations, the chamber bay comprises opposed guide features to assist with guiding the liquid chamber into position in the chamber bay. In some configurations, the opposed guide features comprise opposed guide rails that are arranged to interact with an outwardly directed annular flange on a liquid chamber.

In some configurations, the lever is configured such that a liquid chamber can be inserted into or removed from the chamber bay when the lever is in a first position, and such that the lever inhibits or prevents removal of a liquid chamber from the chamber bay when the lever is in a second position.

In some configurations, the lever comprises at least one liquid chamber engaging feature to engage with part of the liquid chamber and drive the liquid chamber into engagement in the chamber bay when the lever is moved toward the second position. In some configurations, the apparatus comprises two liquid chamber engaging features, wherein the liquid chamber engaging features comprise inwardly directed protrusions.

In some configurations, the apparatus comprises a positive engagement feature to retain the handle in the second position.

In some configurations, the lever comprises a handle portion to enable the apparatus to be carried when the lever is in a raised position.

In some configurations, the lever is pivotally connected to a housing of the apparatus. In some configurations, only one side of the lever is pivotally connected to the housing.

In some configurations, the lever is pivotally and translationally connected to the housing of the apparatus. In some configurations, the apparatus comprises a lever retainer that is fixed to part of the housing, wherein the lever retainer and the part of the housing together provide pivoting and translational movement of the lever relative to the housing.

In some configurations, the lever is configured to move relative to the housing with a varying radius of movement.

In some configurations, the lever comprises a first pivot that is configured to move along a first pivot cavity, and the lever comprises a second pivot that is configured to move along a second pivot cavity.

In some configurations, the first pivot cavity is oriented in a substantially downward-upward orientation relative to the housing. In some configurations, the first pivot cavity is substantially straight.

In some configurations, the second pivot cavity is oriented in a substantially forward-rearward direction of the apparatus. In some configurations, the second pivot cavity is arcuate.

In some configurations, the apparatus comprises an engagement feature to retain the second pivot at or adjacent a rear end of the second pivot cavity, to retain the lever in a raised position.

In some configurations, the lever is configured for assisting with removal of the liquid chamber from the chamber bay.

Additionally, in accordance with certain features, aspects and advantages of at least one of the embodiments disclosed herein, an apparatus for delivering a flow of gas is disclosed, the apparatus comprising:
 a humidifier with:
 a heater, and
 a chamber bay for a liquid chamber;
wherein the apparatus comprises at least one detent for assisting with insertion and/or retention of the liquid chamber in the chamber bay.

In some configurations, the apparatus comprises only one detent. In some configurations, the apparatus comprises two or more detents.

In some configurations, the chamber bay comprises opposed guide features to assist with guiding the liquid chamber into position in the chamber bay.

In some configurations, a detent is provided adjacent one of the guide features. In some configurations, two detents are provided adjacent respective guide features.

In some configurations, a detent is provided on one of the guide features. In some configurations, two detents are provided on respective guide features.

In some configurations, the guide features comprise opposed guide rails that are arranged to interact with an outwardly directed annular flange on a liquid chamber, and wherein the detent(s) comprise(s) enlarged recess(es) in one or both of the guide rails. In some configurations, one or both of the guide rails comprise(s) inwardly directed ridge(s). In some configurations, the inwardly directed ridge(s) has/have sufficient resilience to deform as the liquid chamber is inserted between the guide rails and/or removed from the guide rails.

In some configurations, one or both of the guide features comprise(s) protrusion(s), wherein the liquid chamber comprises recess(es) to receive the protrusion(s).

Additionally, in accordance with certain features, aspects and advantages of at least one of the embodiments disclosed herein, an apparatus for delivering a flow of gas is disclosed, the apparatus comprising:

a housing and a removable gasflow tube that defines a gasflow passage for a flow of gas, and a removable retention cover, the removable retention cover configured such that with the removable retention cover removed from the housing, the removable gasflow tube can be removed from the housing, and with the removable retention cover connected to the housing, the removable gasflow tube cannot be removed from the housing.

In some configurations, the housing comprises a retainer for receipt of the removable gasflow tube, and wherein the removable retention cover is configured such that with the removable retention cover removed from the housing, the removable gasflow tube can be removed from the retainer, and with the removable retention cover connected to the housing, the removable gasflow tube cannot be removed from the retainer.

In some configurations, two discrete actions are required to remove the removable gasflow tube from the retainer. In some configurations, the removable retention cover is removable from the housing by moving the removable cover in a first direction, wherein the removable gasflow tube is removable from the retainer by moving the removable gasflow tube in a second direction that is substantially transverse to the first direction for at least part of the movement. In some configurations, the removable gasflow tube comprises a gas port for coupling with an outlet port on a liquid chamber that is arranged to be received in a chamber bay of the housing, and the second direction corresponds to a direction of removal of the liquid chamber from the chamber bay.

In some configurations, the removable gasflow tube comprises an electrical connector that is coupled to one or more sensors and/or power connectors in the removable gasflow tube. In some configurations, the electrical connector comprises a male connector portion that projects from a portion of the gasflow tube, wherein the housing comprises a complementary female connector for receipt of the male connector when the gasflow tube is connected to the housing. In some configurations, the housing comprises a male connector portion and the removable gasflow tube comprises a complementary female connector for receipt of the male connector when the gasflow tube is connected to the housing.

In some configurations, the removable gasflow tube comprises a port with an axis, and the electrical connector is oriented at an angle of between about −15 degrees and about +30 degrees relative to the axis, in some configurations between about 0 degrees and about +30 degrees relative to the axis, in some configurations between about 0 degrees and about +15 degrees relative to the axis, and in some configurations at an angle of about +15 degrees relative to the axis. In some configurations, the electrical connector is arranged to be oriented at a non-horizontal angle in use. In some configurations, the electrical connector is oriented at a non-parallel and non-coaxial angle relative to the axis. In some configurations, the electrical connector is oriented an angle of between about −5 degrees and about −15 degrees relative to the axis, or between about +5 degrees and about +30 degrees relative to the axis. In some configurations, the electrical connector is oriented at an angle of between about +5 degrees and about +30 degrees relative to the axis, in some configurations between about +5 degrees and about +15 degrees relative to the axis, and in some configurations at an angle of about +15 degrees relative to the axis.

In some configurations, the electrical connector of the removable gasflow tube is coupled to one or more temperature sensors to determine temperature of gas flowing through the gasflow tube.

In some configurations, the electrical connector of the removable gasflow tube is coupled to a power connector in the removable gasflow tube, the power connector for coupling to and powering heater wire(s) of a patient breathing conduit, the removable gasflow tube configured to provide a pneumatic and electrical connection to the patent conduit in a single action when a patient breathing conduit is connected to the removable gasflow tube.

In some configurations, the removable gasflow tube comprises a removable elbow.

Additionally, in accordance with certain features, aspects and advantages of at least one of the embodiments disclosed herein, an apparatus for delivering a flow of gas is disclosed, the apparatus comprising:

a housing comprising an upper chassis and a lower chassis, a gasflow passage defined in the housing between the upper and lower chassis, an electrical component in the housing, and a continuous, unbroken wall in the housing adapted to pneumatically isolate the electrical component from the gasflow passage.

In some configurations, gas that is or comprises oxygen flows through the gasflow passage. In some configurations, the gas is isolated from the electrical component. In some configurations, the gas comprises a blend of oxygen and ambient air.

In some configurations, the apparatus comprises a motor with an impeller to deliver gas through the gasflow passage, wherein the motor is pneumatically isolated from the electrical component. In some configurations, the wall, either alone, or in combination with one or more additional continuous unbroken walls, defines a recess which is pneumatically isolated from the electrical component, wherein the motor is positioned in the recess.

In some configurations, the motor is removable from the recess.

In some configurations, pressure is lower upstream of the motor impeller and pressure is higher downstream of the motor impeller, and the motor comprises an electrical connection that is positioned upstream of the motor impeller, in the lower pressure region.

In some configurations, the electrical component comprises a printed circuit board.

Additionally, in accordance with certain features, aspects and advantages of at least one of the embodiments disclosed herein, an apparatus for delivering a flow of gas is disclosed, the apparatus comprising:

a housing and a lever, wherein only one side of the lever is movably connected to the housing.

In some configurations, the apparatus comprises a heater and a chamber bay for receipt of a liquid chamber.

In some configurations, when the lever is in a raised position, liquid tube(s) can be fed through a space between the lever and the housing.

In some configurations, said one side of the lever is pivotally connected to the housing.

In some configurations, when the lever is in a closed position, the lever encloses a portion of the chamber bay.

In some configurations, said one side of the lever is pivotally and translationally connected to the housing.

In some configurations, when the lever is in a closed position, a portion of the lever projects sufficiently above a floor of the chamber bay that it prevents a liquid chamber from being removed from the chamber bay.

In some configurations, said one side of the lever is pivotally and translationally connected to the housing.

In some configurations, the apparatus comprises a lever retainer that is fixed to part of the housing, wherein the lever retainer and the part of the housing together provide pivoting and translational movement of the lever relative to the housing.

In some configurations, the lever is configured to move relative to the housing with a varying radius of movement.

In some configurations, the lever comprises a first pivot that is configured to move along a first pivot cavity, and wherein the lever comprises a second pivot that is configured to move along a second pivot cavity.

In some configurations, the first pivot cavity is oriented in a substantially downward-upward orientation relative to the housing. In some configurations, the first pivot cavity is substantially straight.

In some configurations, the second pivot cavity is oriented in a substantially forward-rearward direction of the apparatus. In some configurations, the second pivot cavity is arcuate.

In some configurations, the apparatus comprises an engagement feature to retain the second pivot at or adjacent a rear end of the second pivot cavity, to retain the lever in a raised position.

In some configurations, the lever comprises an arm on said one side of the lever, wherein the arm is pivotally, or pivotally and translationally, connected to the housing. In some configurations, the lever comprises a cross-member that is connected to the arm.

In some configurations, there is a space between the housing and the cross-member on a side of the lever opposite to the arm, when the lever is in a raised position.

In some configurations, a terminal end of the lever is arranged to be positioned generally above a centre of mass of the apparatus, when the lever is in a fully raised position.

In some configurations, the lever comprises one or more features for guiding liquid tube(s) to a liquid chamber.

In some configurations, the lever is configured for assisting insertion and/or retention and/or removal of the liquid chamber in and/or from the chamber bay.

In some configurations, the lever is gas injection moulded.

In some configurations, the lever comprises an external seal.

In some configurations, a face of the lever bears against a face of the housing throughout movement of the lever from a fully lowered position to a fully raised position.

In some configurations, the lever and/or housing comprise one or more magnets to retain the lever in a fully lowered and/or fully raised position.

Additionally, in accordance with certain features, aspects and advantages of at least one of the embodiments disclosed herein, an apparatus for delivering a flow of gas is disclosed, the apparatus comprising:

a housing with a recess in an external wall of the housing, and a connector arrangement positioned in the recess, wherein the connector arrangement comprises one or more ports, and wherein the port(s) is/are at a non-horizontal and non-vertical angle between 0 degrees and 90 degrees relative to a vertical axis.

That is, the port(s) face at least partly downwardly so that the insertion angle of plug(s) into the connector(s) is at least partly upward.

In some configurations, the port(s) is/are at an angle of between about 5 degrees and about 30 degrees relative to the vertical axis. In some configurations, the port(s) is/are at an angle of between about 10 degrees and about 20 degrees relative to the vertical axis. In some configurations, the port(s) is/are at an angle of about 15 degrees relative to the vertical axis.

In some configurations, a wall of the recesses is angled relative to the vertical direction at an insertion angle of the port(s).

In some configurations, one or more port(s) comprises communication port(s). In some configurations, one or more port(s) comprises USB port(s).

In some configurations, a lip is provided on the or each port to reduce the likelihood of water ingress into the port(s).

In some configurations, the apparatus comprises a sharp edge or a liquid deflector along an upper edge of the recess, to encourage liquid to drop off the sharp edge/liquid deflector rather than running into the recess.

Additionally, in accordance with certain features, aspects and advantages of at least one of the embodiments disclosed herein, an apparatus for delivering a flow of gas is disclosed, the apparatus comprising:

a housing;

and a removable gasflow tube for a flow of gas, wherein the removable gasflow tube comprises a port with an axis, and an electrical connector for coupling to a complementary connector when the gasflow tube is connected to the housing, wherein the electrical connector is oriented at an angle of between about −15 degrees and about +30 degrees relative to the axis.

In some configurations, the electrical connector is oriented at an angle of between about 0 degrees and about +30 degrees relative to the axis, in some configurations between about 0 degrees and about +15 degrees relative to the axis, and in some configurations at an angle of about +15 degrees relative to the axis.

In some configurations, the electrical connector is arranged to be oriented at a non-horizontal angle in use.

In some configurations, the electrical connector is oriented at a non-parallel and non-coaxial angle relative to the axis. In some configurations, the electrical connector is oriented an angle of between about −5 degrees and about −15 degrees relative to the axis, or between about +5 degrees and about +30 degrees relative to the axis. In some configurations, the electrical connector is oriented at an angle of between about +5 degrees and about +30 degrees relative to the axis, in some configurations between about +5 degrees and about +15 degrees relative to the axis, and in some configurations at an angle of about +15 degrees relative to the axis.

In some configurations, the removable gasflow tube comprises a removable elbow.

Additionally, in accordance with certain features, aspects and advantages of at least one of the embodiments disclosed herein, an apparatus for delivering a flow of gas is disclosed, the apparatus comprising:

a housing;

and a removable gasflow tube for a flow of gas, wherein the removable gasflow tube comprises an electrical connector for coupling to a complementary connector when the gasflow tube is connected to the housing, wherein a body of the removable gasflow tube is overmoulded onto the electrical connector.

In some configurations, the removable gasflow tube comprises power connector(s) that is/are embedded in part of the overmoulded gasflow tube body. In some configurations, the power connector comprises upwardly projecting pin connectors for coupling to and powering heater wire(s) in a patient breathing conduit. In some configurations, the pin connectors extend substantially parallel to a longitudinal axis of a gases outlet port of the elbow.

In some configurations, the electrical connector comprises a PCB electrical connector.

In some configurations, the removable gasflow tube comprises a removable elbow.

Additionally, in accordance with certain features, aspects and advantages of at least one of the embodiments disclosed herein, an apparatus for delivering a flow of gas is disclosed, the apparatus comprising:

a housing;

and a removable gasflow tube for a flow of gas, wherein the removable gasflow tube defines a gasflow passage and comprises an internal pool region in communication with the gasflow passage to allow pooling of liquid.

In some configurations, the pool region is provided by an enlarged region in the gasflow passage.

In some configurations, the enlarged region is a recess in a horizontal portion of the gasflow passage.

In some configurations, the gasflow tube comprises temperature sensor(s) located adjacent the pool region, the temperature sensor(s) arranged to determine a temperature that is representative of the gasflow passage and/or a gases characteristic.

In some configurations, the temperatures sensor(s) is/are used to estimate the humidity of the gases.

In some configurations, the removable gasflow tube comprises a removable elbow. In some configurations, the pool region is provided at an interface of a first and second port of the elbow.

Additionally, in accordance with certain features, aspects and advantages of at least one of the embodiments disclosed herein, an apparatus for delivering a flow of gas is disclosed, the apparatus comprising:

a housing;

and a removable gasflow tube that defines a gasflow passage for a flow of gas, wherein the removable gasflow tube comprises a PCB electrical connector for coupling to a complementary connector when the gasflow tube is connected to the housing.

In some configurations, a first end of the removable gasflow tube comprises a gas port for coupling with an outlet gas port on a liquid chamber. In some configurations, a second end of the removable gasflow tube is configured for connection to a patient breathing conduit.

In some configurations, the PCB electrical connector portion comprises a plurality of connector portions at one end for engagement with complementary conductors in a female connector. Alternatively, in some configurations the removable gasflow tube comprises a female connector for receipt of a complementary male connector.

In some configurations, the removable gasflow tube comprises one or more electrical connectors for coupling to and powering a heater wire in a patient breathing conduit. In some configurations, the electrical connectors are in electrical communication with connector portions of the PCB electrical connector.

In some configurations, the PCB electrical connector comprises surface mounted temperature sensor(s). The temperature sensor(s) may be thermocouple(s), digital temperature sensor(s), or thermistor(s) for example. In some configurations, the temperature sensor(s) are in electrical communication with connector portions of the PCB electrical connector. In some configurations, the temperature sensor(s) is/are embedded in a body of the gasflow tube.

In some configurations, the removable gasflow tube comprises a device that is configured to provide functionality including one or more of identification, calibration functionality, or information capture. In some configurations, the device is configured to provide information including one or more of: tracking data, how long the removable gasflow tube has been used, when the removable gasflow tube was first used, determining removable gasflow tube age (e.g. based on manufacturing date), how many times the removable gasflow tube has been used, determining and logging connection/disconnection of removable gasflow tube, determining whether disinfection has occurred, how many times the removable gasflow tube has been disinfected, time of use since last disinfection, when the removable gasflow tube should be disinfected, power levels, unique ID, calibration, when the removable gasflow tube should be replaced. In some configurations, the removable gasflow tube may have a specified usage life stored in the device, such as up to 5 years from manufacture for example. In some configurations, the removable gasflow tube may have a specified maximum number of disinfection cycles before the removable gasflow tube should be replaced stored in the device. For example, the maximum number of disinfection cycles may be a specified number of disinfection cycles per week, for a specified number of weeks. For example, for a removable gasflow tube having a maximum usage life of one year, the maximum number of disinfection cycles may be 52 cycles; one cycle per week for one year. As another example, for a removable gasflow tube having a maximum usage life of 5 years, the maximum number of disinfection cycles may be 260 cycles; one cycle per week for five years.

In some configurations, the device comprises one or more of a microprocessor, memory, or microprocessor with integrated memory. In some configurations, the device is an EEPROM. In some configurations, the device could be a flash memory or some other type of memory. In some configurations, the device may be configured to store functionality data or may be configured to communicate the functionality data to a controller of the apparatus via the connector portions or via a suitable wireless transmission protocol such as WI-FI, Bluetooth, or GSM for example.

In some configurations, a port of the removable gasflow tube comprises a T-seal or L-seal. In some configurations, a port of the removable gasflow tube comprises an O-ring.

In some configurations, electronics of the removable gasflow tube are sealed from liquid and/or gas ingress. In some configurations, the electronics are sealed by potting for example.

In some configurations, the removable gasflow tube comprises a removable elbow. In some configurations, the temperature sensor(s) is/are positioned adjacent an interface of a first and second port of the elbow.

Additionally, in accordance with certain features, aspects and advantages of at least one of the embodiments disclosed herein, an apparatus for delivering a flow of gas is disclosed, the apparatus comprising:

a motor and/or sensor module, the module comprising a motor with an impeller and a gases outlet port, and an outlet gasflow path and sensing layer, the sensing layer having a sensing and gasflow path, the sensing and gasflow path comprising a gasflow inlet port for receiving gases from the gases outlet port, and a gasflow outlet port;

wherein a pressure drop coefficient from the gases outlet port to the gasflow path and sensing layer gasflow outlet port is between about 5 mPa (L min$^{-1}$)$^{-2}$ and about 50 mPa (L min$^{-1}$)$^{-2}$.

In some configurations, the pressure drop coefficient is between about 10 mPa (L min$^{-1}$)$^{-2}$ and about 20 mPa (L min$^{-1}$)$^{-2}$. In some configurations, the pressure drop coefficient is about 15 mPa (L min$^{-1}$)$^{-2}$.

In some configurations, the gases outlet port is coupled to the gasflow inlet port by a flexible cuff. In some configurations, the motor and/or sensor module comprises a cuff support member that is configured to support the cuff. In some configurations, the cuff support member comprises an upstanding cuff support member that has an inwardly concave shape, and that is configured to receive and support the periphery of the cuff. In some configurations, a gases outlet port end of the cuff comprises an enlarged diameter that rests on the upper end of the cuff support member.

In some configurations, the motor and/or sensor module is removable from the recess. In some alternative configurations, the motor and/or sensor module may not be removable from the recess.

Additionally, in accordance with certain features, aspects and advantages of at least one of the embodiments disclosed herein, a motor and/or sensor module for use in the apparatus is disclosed, the motor and/or sensor module having the feature(s) recited above.

Additionally, in accordance with certain features, aspects and advantages of at least one of the embodiments disclosed herein, an apparatus for delivering a flow of gas is disclosed, the apparatus comprising:

a shroud for receipt of an electrical component, the shroud configured to at least partly surround and protect the electrical component, the shroud configured to support the electrical component but to enable movement of the electrical component in the shroud in at least one dimension.

In some configurations, the shroud is configured to enable movement of the electrical component in one dimension. In some configurations, the shroud is configured to enable movement of the electrical component in a first substantially horizontal dimension or in a second substantially horizontal dimension.

In some configurations, the shroud is configured to enable movement of the electrical component in two dimensions. In some configurations, the shroud is configured to enable movement of the electrical component in a first substantially horizontal dimension and in a second substantially horizontal dimension.

In some configurations, the shroud is configured to enable movement of the electrical component in three dimensions. In some configurations, the shroud is configured to enable movement of the electrical component in a first substantially horizontal dimension, in a second substantially horizontal dimension, and in a substantially vertical dimension.

In some configurations, the shroud is configured to allow limited movement of the electrical component in at least one dimension, the limited movement being sufficient to accommodate tolerance misalignment in components.

In some configurations, the electrical component is an electrical connector.

In some configurations, the shroud is provided in an apparatus for delivering a flow of gas. In some configurations, the shroud is provided in a motor and/or sensor module.

Additionally, in accordance with certain features, aspects and advantages of at least one of the embodiments disclosed herein, an apparatus for delivering a flow of gas is disclosed, the apparatus comprising:

a housing, a heater in the housing, a chamber bay in the housing for receipt of a liquid chamber, and a lever that is movably connected to the housing, wherein when the lever is in a closed position, the lever encloses a portion of the chamber bay.

In some configurations, when the lever in a closed position, a portion of the lever projects sufficiently above a floor of the chamber bay that it prevents a liquid chamber from being removed from the chamber bay.

In some configurations, only one side of the lever is movably connected to the housing.

In some configurations, the lever is pivotally connected to the housing.

Additionally, in accordance with certain features, aspects and advantages of at least one of the embodiments disclosed herein, an apparatus for delivering a flow of gas is disclosed, the apparatus comprising:

a gasflow tube for a flow of gas, the gasflow tube configured to couple to a gasflow outlet from a flow generator, wherein the coupling to the gasflow outlet is within an outer tube that allows venting of gas to atmosphere but that is pneumatically isolated from an electrical component by a continuous, unbroken wall.

In some configurations, the flow generator comprises a motor with an impeller, wherein the motor is pneumatically isolated from the electrical component by a continuous unbroken wall.

In some configurations, the wall, either alone, or in combination with one or more additional continuous unbroken walls, defines a recess which is pneumatically isolated from the electrical component, and wherein the motor is positioned in the recess.

In some configurations, pressure is lower upstream of the motor impeller and pressure is higher downstream of the motor impeller, and wherein the motor comprises an electrical connection that is positioned upstream of the motor impeller, in the lower pressure region.

In some configurations, coupling between the gasflow tube and gasflow outlet in the conduit comprises at least one seal between the gasflow tube, the gasflow outlet, and/or the outer tube. In some configurations, the at least one seal allows lateral movement of the gasflow outlet in the outer tube. The seal may comprise a face seal between the gasflow outlet and the gasflow tube for example. In some configurations, the at least one seal allows both lateral and axial movement of the gasflow outlet in the outer tube. The seal may comprise a bellows seal for example. Therefore, depending on the configuration, the seal(s) may comprise an O-ring, T-seal, L-seal, face seal, or foam, for example.

Additionally, in accordance with certain features, aspects and advantages of at least one of the embodiments disclosed herein, an apparatus for delivering a flow of gas is disclosed, the apparatus comprising:

a housing comprising an upper chassis and a lower chassis, and a substantially continuous tongue and groove arrangement between the upper chassis and lower chassis.

In some configurations, the upper chassis comprises a left side wall and a right side wall, and the lower chassis comprises a left side wall and a right side wall, and tongue and groove arrangements are provided between the left side walls and right side walls of the upper chassis and lower chassis.

In some configurations, the apparatus comprises a chamber bay for a receipt of a liquid chamber, and a tongue and groove arrangement is provided between the upper and lower chassis around substantially the entire perimeter of the chamber bay.

In some configurations, the apparatus comprises at least one tongue and groove with a chamfered edge. In some configurations, the apparatus comprises at least one tongue and groove arrangement with a space between part of the tongue and part of the groove.

Additionally, in accordance with certain features, aspects and advantages of at least one of the embodiments disclosed herein, an apparatus for delivering a flow of gas is disclosed, the apparatus comprising:

a housing, a mount for mounting the apparatus to a stand or pole, and a projection that is configured to cause the apparatus to lean towards the stand or pole when mounted thereto.

In some configurations, the mount comprises a tongue, and the projection is provided on the tongue.

In some configurations, the bump is configured to cause the apparatus to lean in towards the stand by a suitable angle, such as 1-15°, or 1-10°, or 1-7°, or 1-5°, or 1-2° for example.

Additionally, in accordance with certain features, aspects and advantages of at least one of the embodiments disclosed herein, an apparatus for delivering a flow of gas is disclosed, the apparatus comprising:

a housing, and a mount for mounting the apparatus to a stand or pole, wherein the mount is integrally formed with part of the housing.

Additionally, in accordance with certain features, aspects and advantages of at least one of the embodiments disclosed herein, an apparatus for delivering a flow of gas is disclosed, the apparatus comprising:

a housing, and a gasflow tube that defines a gasflow passage for a flow of gas, wherein the gasflow tube comprises a T-seal or an L-seal to assist with sealing a port of the gasflow tube to another component.

Additionally, in accordance with certain features, aspects and advantages of at least one of the embodiments disclosed herein, an apparatus for delivering a flow of gas is disclosed, the apparatus comprising:

a housing, a recess in the housing for receipt of a motor and/or sensor module, and a component for providing functionality to the apparatus and that is securable to the housing, wherein the component comprises a retention feature that is arranged to extend under a base of the motor and/or sensor module to maintain the motor and/or sensor module in position in the recess in the housing.

In some configurations, the component comprises a battery that is securable to the housing. In some configurations, the battery comprises a base flange or other projecting feature that is arranged to extend under a base of the motor and/or sensor module. In some configurations, the component comprises a different functional component.

Additionally, in accordance with certain features, aspects and advantages of at least one of the embodiments disclosed herein, an apparatus for delivering a flow of gas is disclosed, the apparatus comprising:

a housing, an electrical connector, the electrical connector comprising a receiving socket in the housing that is arranged to receive a plug of a power cord by movement of the plug in a first direction, the electrical connector comprising a retainer to maintain the plug in engagement with the socket by movement of the retainer in a second direction that is substantially transverse to the first direction.

In some configurations, the second direction is perpendicular to the first direction. In some configurations, the first direction is vertical and the second direction is horizontal.

Features from one or more embodiments may be combined with features of one or more other embodiments. Additionally, more than one embodiment may be used together during a process of respiratory support of a patient.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It should be understood that alternative embodiments may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

Specific embodiments and modifications thereof will become apparent to those skilled in the art from the detailed description herein having reference to the figures that follow, of which:

FIG. 74 is a front/side perspective view of the removable elbow of FIG. 72.

FIG. 75 is an overhead plan view of a PCB electrical connector of the removable elbow of FIG. 72.

FIG. 112 is a detail view of part of the handle/lever arrangement of FIG. 101, showing detail of a step feature in a pivot cavity for the front pivot of the handle/lever arrangement.

FIG. 113 is a plot showing the movement path of a terminal end of the handle/lever arrangement of the apparatus of FIG. 101.

FIG. 114 is a view showing an alternative configuration second pivot cavity to that of FIGS. 106 and 108 to 112.

FIG. 115 is a left side sectional view showing details of the handle/lever arrangement of the apparatus of FIG. 101, with the handle/lever in a partly raised position.

FIG. 116 is a view corresponding to FIG. 115, with the handle/lever in a fully raised position.

FIG. 117 is a left front overhead perspective view of the apparatus of FIG. 101, showing the handle/lever in a partly raised position.

FIG. 118 is a front overhead perspective view showing the housing, elbow arrangement, and removable retention cover of the apparatus of FIG. 101.

FIG. 119 is a front underside view showing details of the removable retention cover of FIG. 118.

FIG. 120 is a right front overhead perspective view showing the housing and an alternative removable retention cover of the apparatus of FIG. 101, with the retention cover removed from the housing.

FIG. 121 is a view similar to FIG. 120, but showing the retention cover engaged with the housing.

FIG. 122 is an overhead perspective view of an electrical connector arrangement of the apparatus of FIG. 101.

FIG. 123 is another overhead perspective view of the electrical connector arrangement of FIG. 122.

Figure 122:
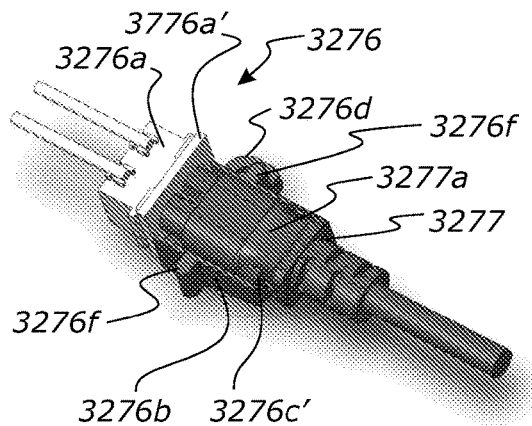
Figure 123:
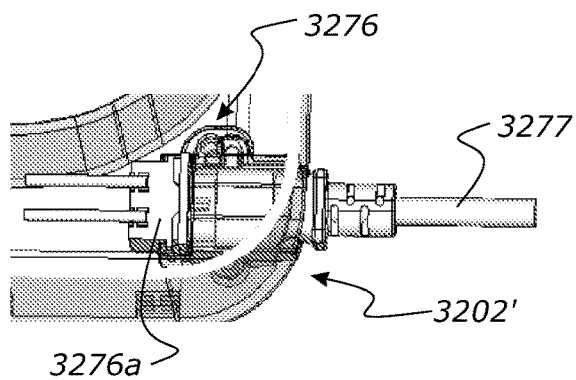
Figure 124:
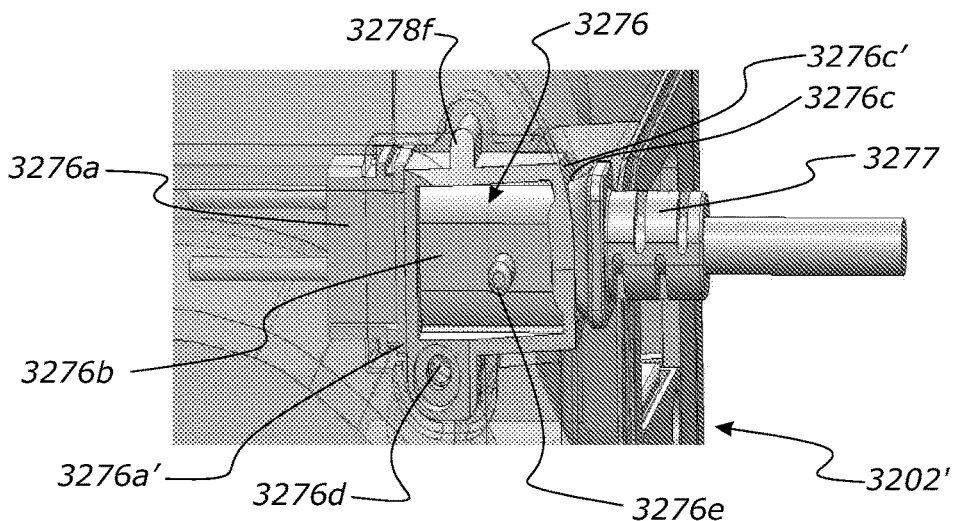

FIG. 124 is a bottom perspective view of the electrical connector arrangement of FIG. 122.

Figure 125:
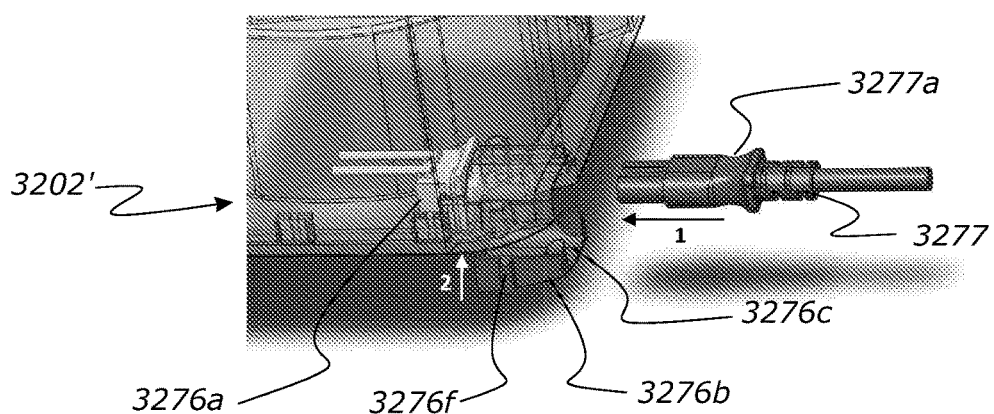

FIG. 125 is an overhead perspective view of the electrical connector arrangement of FIG. 122, showing the steps of coupling a power cord to the socket.

Figure 101:
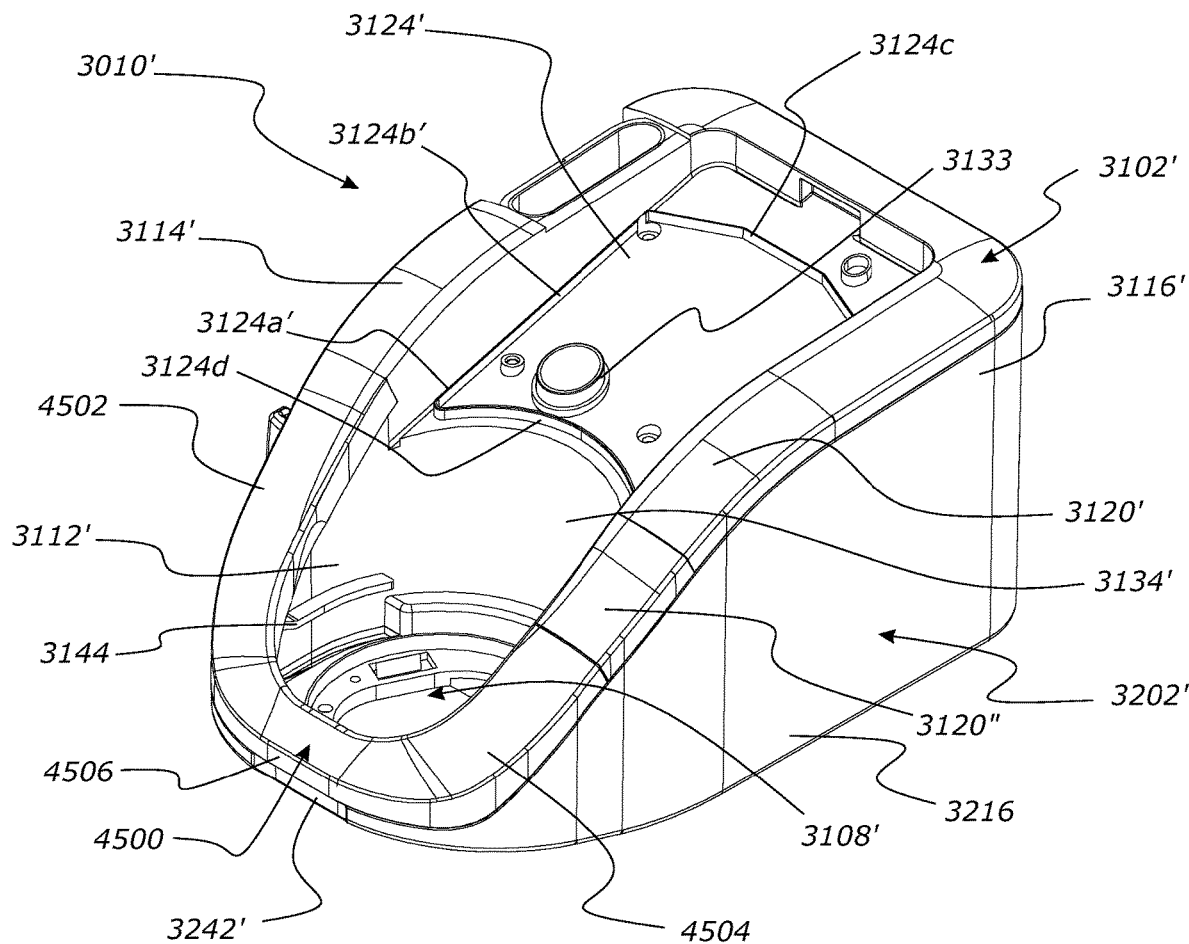
FIG. 101 is a front overhead perspective view of a flow therapy apparatus showing an alternative configuration handle/lever arrangement, with the handle/lever in a lowered or closed position.
Figure 126:
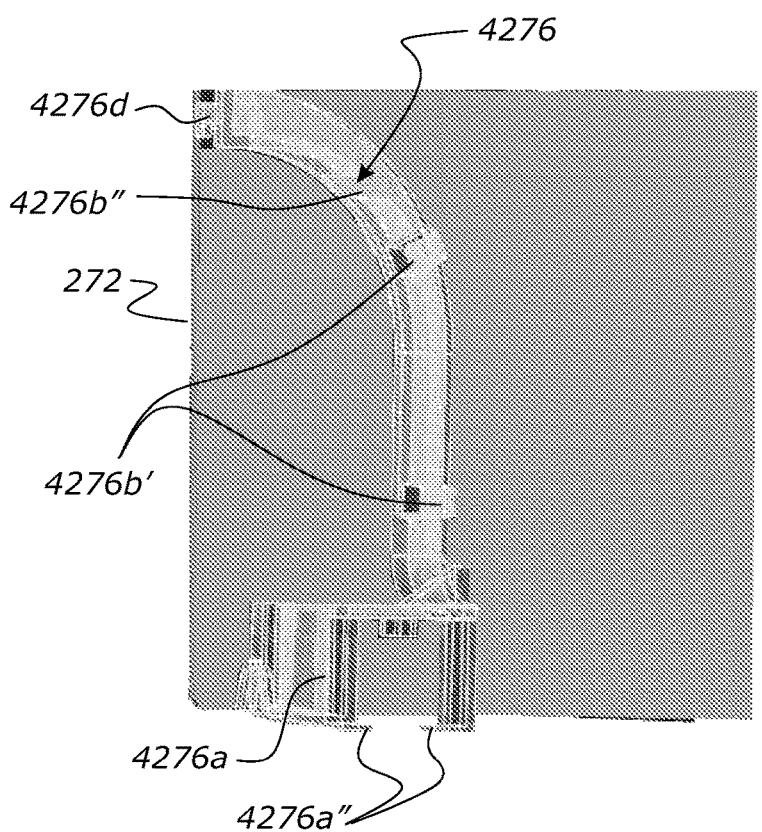

FIG. 126 is a perspective view of part of the interior of the apparatus of FIG. 101, showing a power harness guide.

Figure 127:
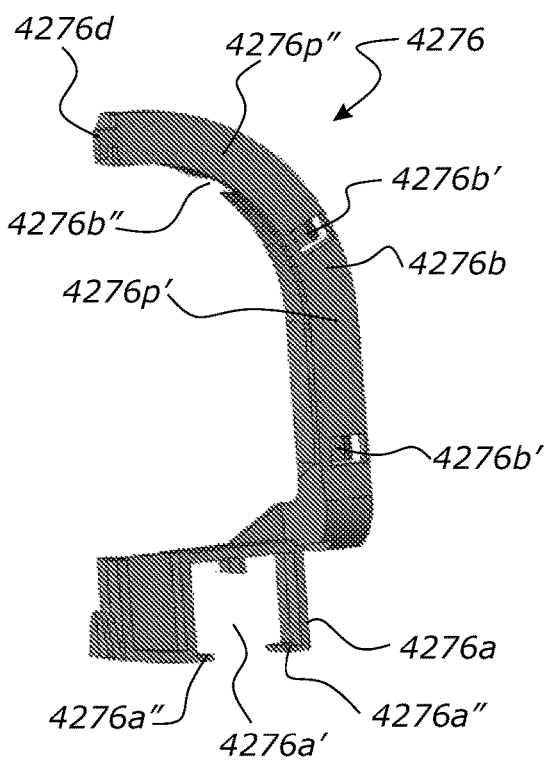

FIG. 127 is a perspective view of the power harness guide of FIG. 126.

Figure 128:
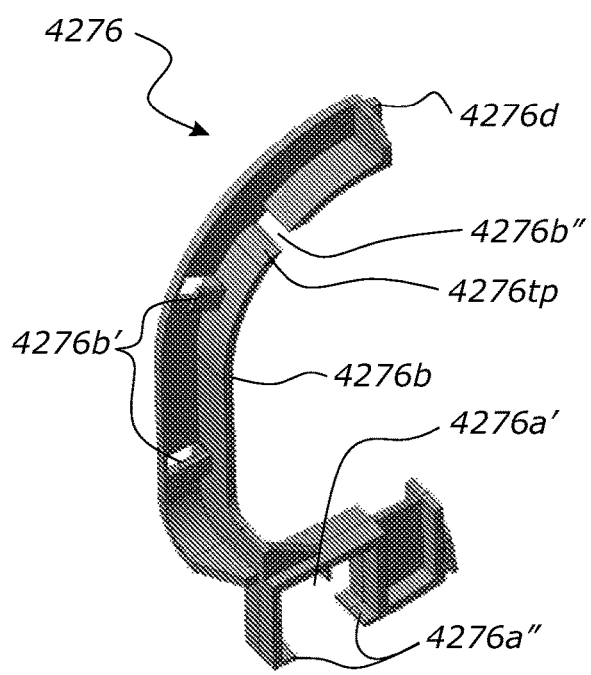

FIG. 128 is a perspective view of the power harness guide from the opposite side to FIG. 127.

Figure 129:
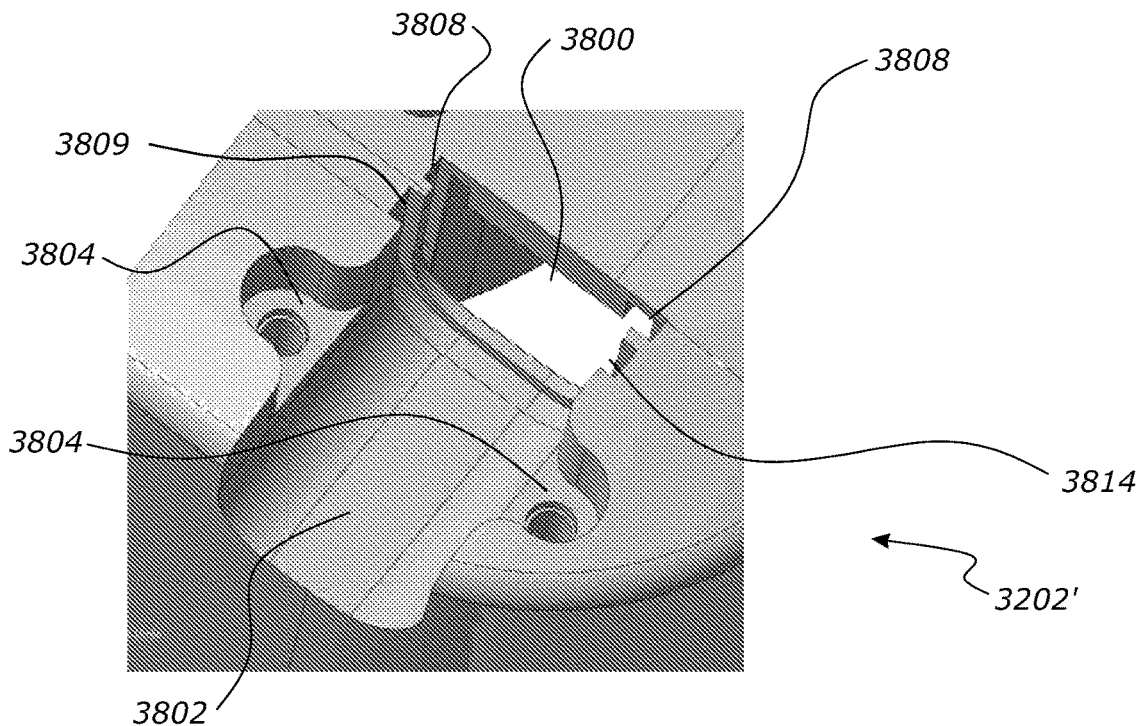

FIG. 129 is a bottom rear perspective view of a region of the housing of the apparatus of FIG. 101 that receives the power cord.

Figure 130:
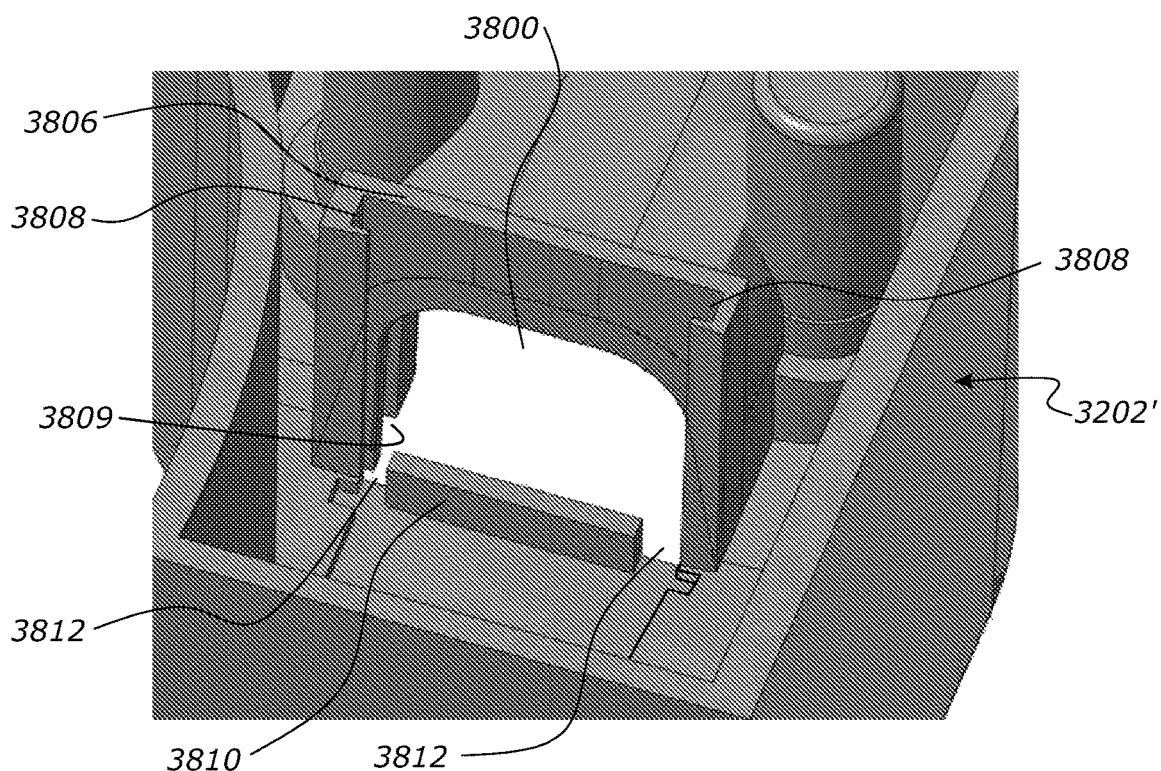

FIG. 130 is an overhead front perspective view from the interior of the housing, showing a region of the housing corresponding to that of FIG. 129.

Figure 131:
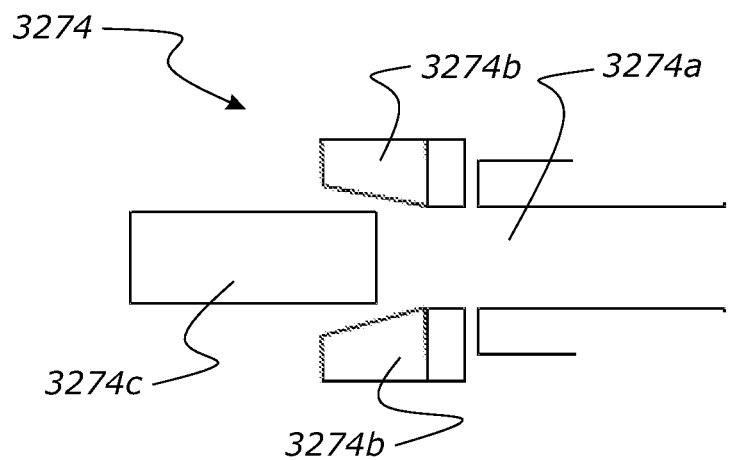

FIG. 131 is a side cross-sectional view through a USB connector arrangement of the apparatus of FIG. 101.

Figure 132:
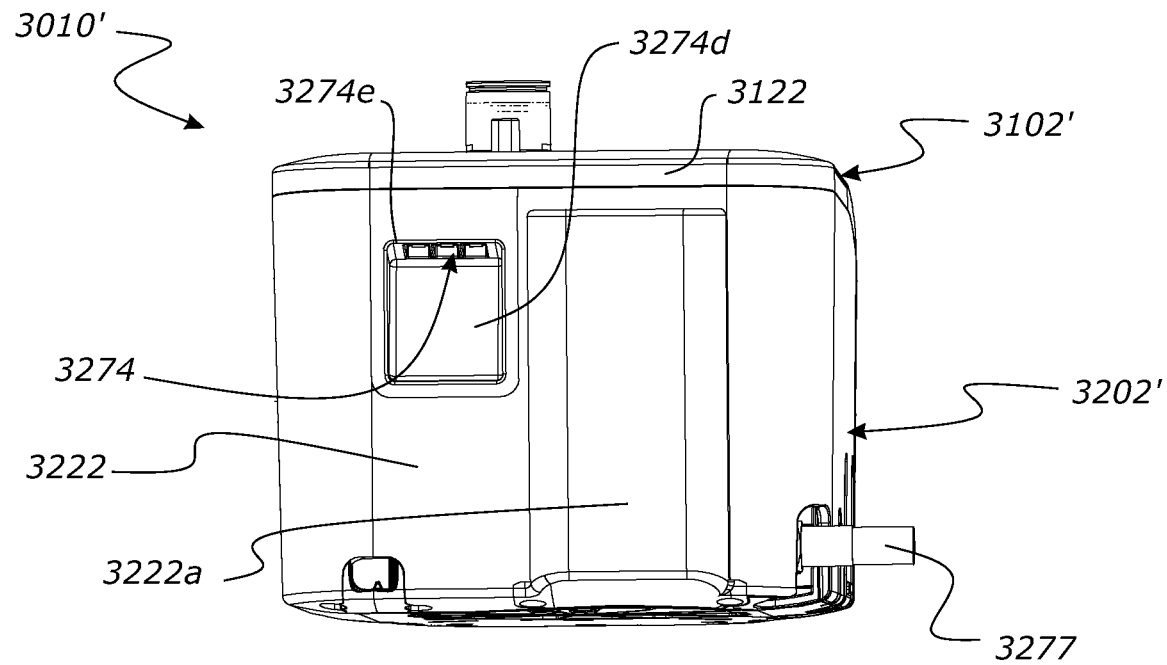

FIG. 132 is a rear perspective view of the apparatus of FIG. 101, showing a battery pack and the USB connector arrangement of FIG. 131.

Figure 133:
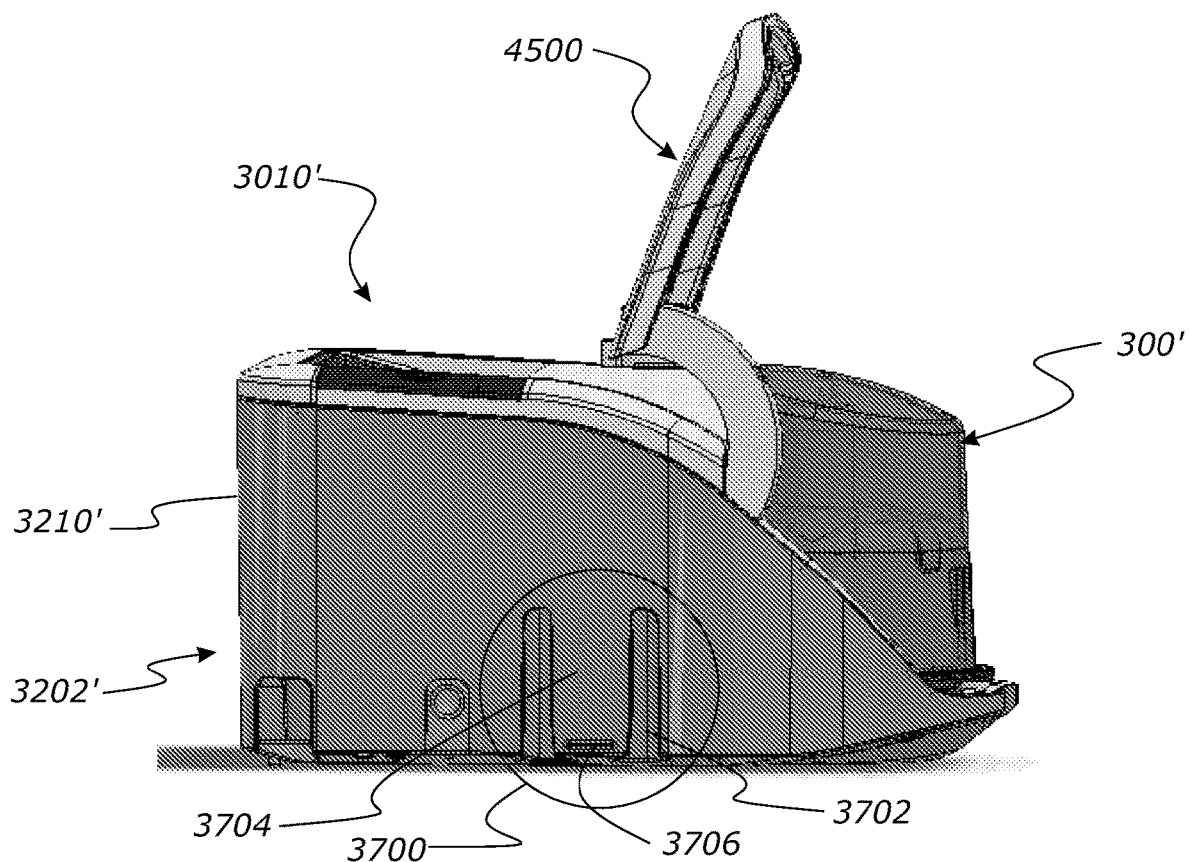

FIG. 133 is a side perspective view of the apparatus of FIG. 101, showing an integral mount to mount the apparatus to a pole or stand.

Figure 134:
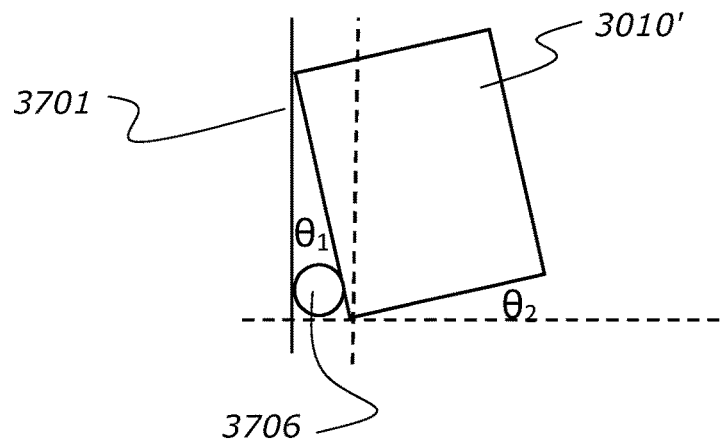

FIG. 134 is a schematic side perspective view of the apparatus of FIG. 101 mounted to a pole or stand.

Figure 135:
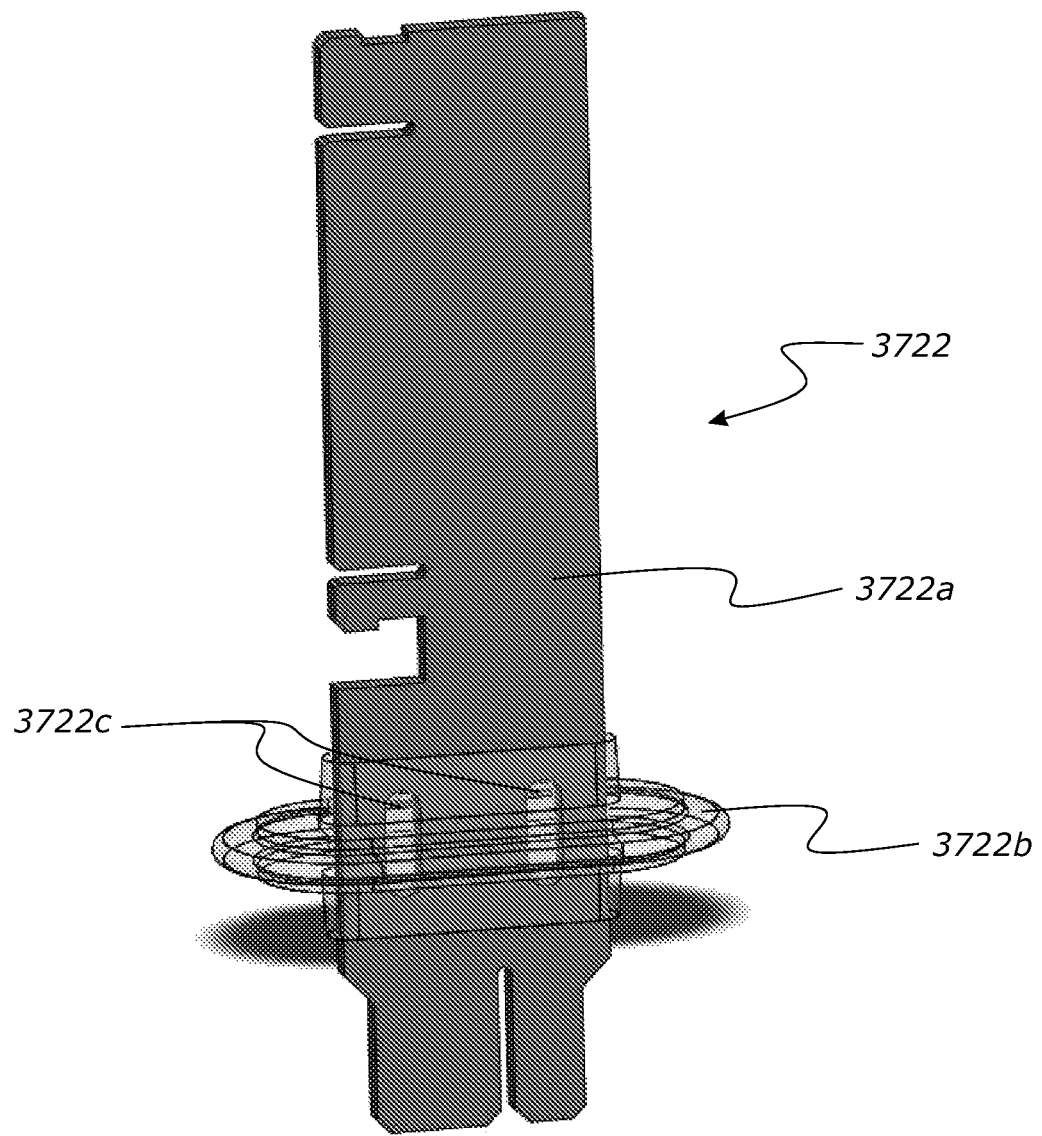

FIG. 135 is a perspective view of a PCB electrical connector of the apparatus of FIG. 101, the connector having an over-moulded collar.

Figure 136:
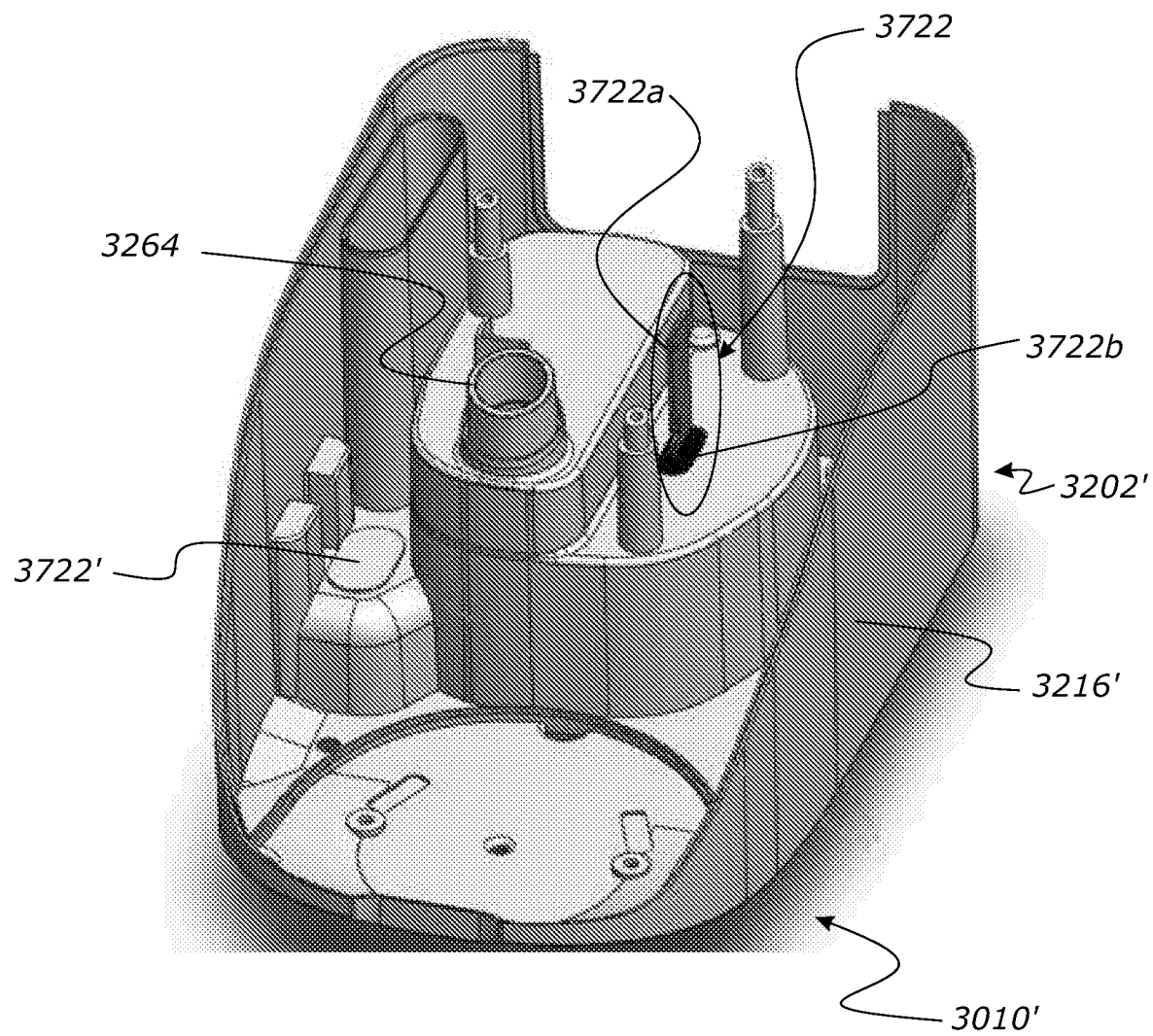

FIG. 136 is a front overhead perspective view of the lower chassis of the apparatus of FIG. 101, showing exemplary placements of the PCB electrical connector of FIG. 135.

Figure 72:
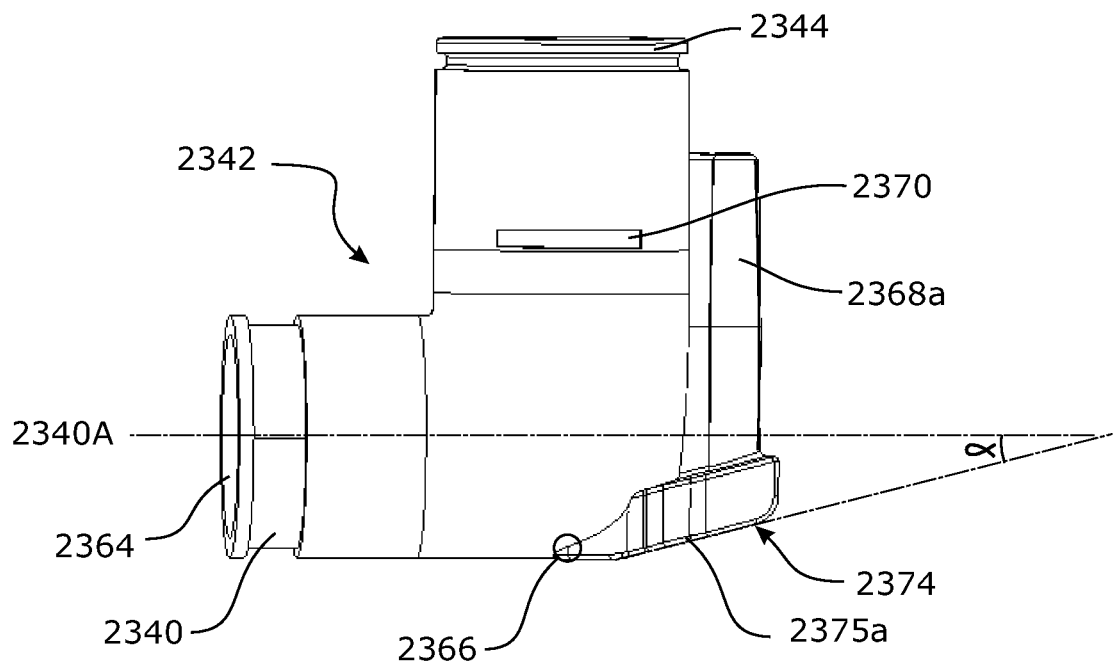
FIG. 72 is a side perspective view of another alternative removable elbow for use in the flow therapy apparatuses, the elbow shown removed from the main housing.
Figure 73:
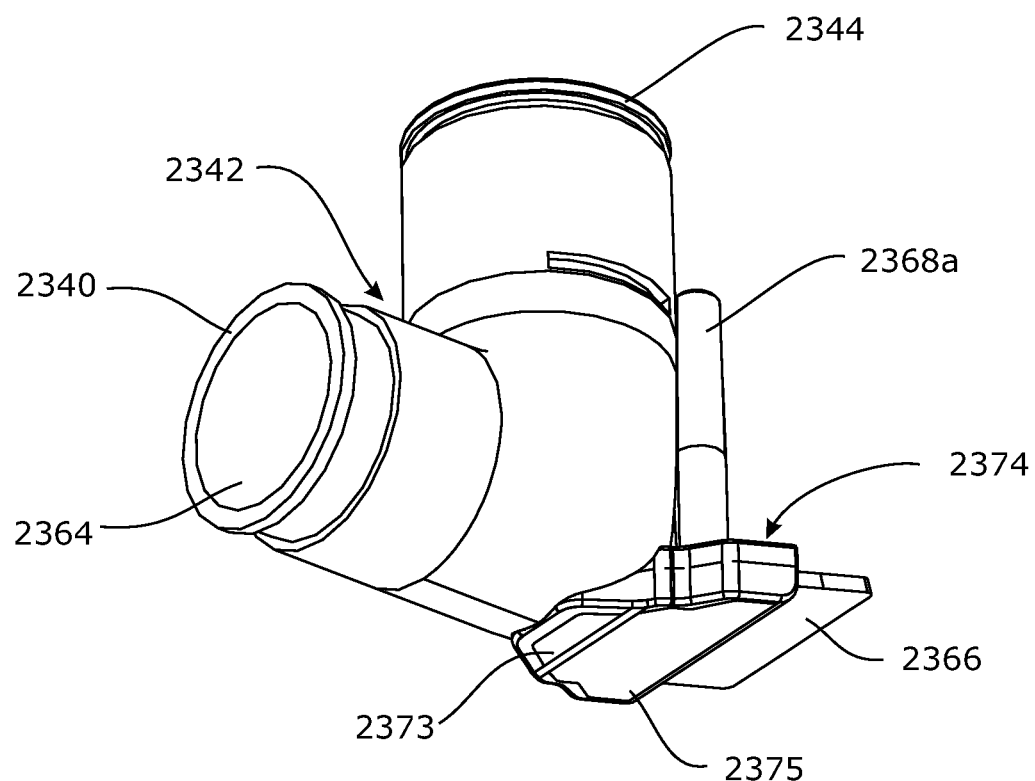
FIG. 73 is a rear underside perspective view of the removable elbow of FIG. 72.
Figure 137:
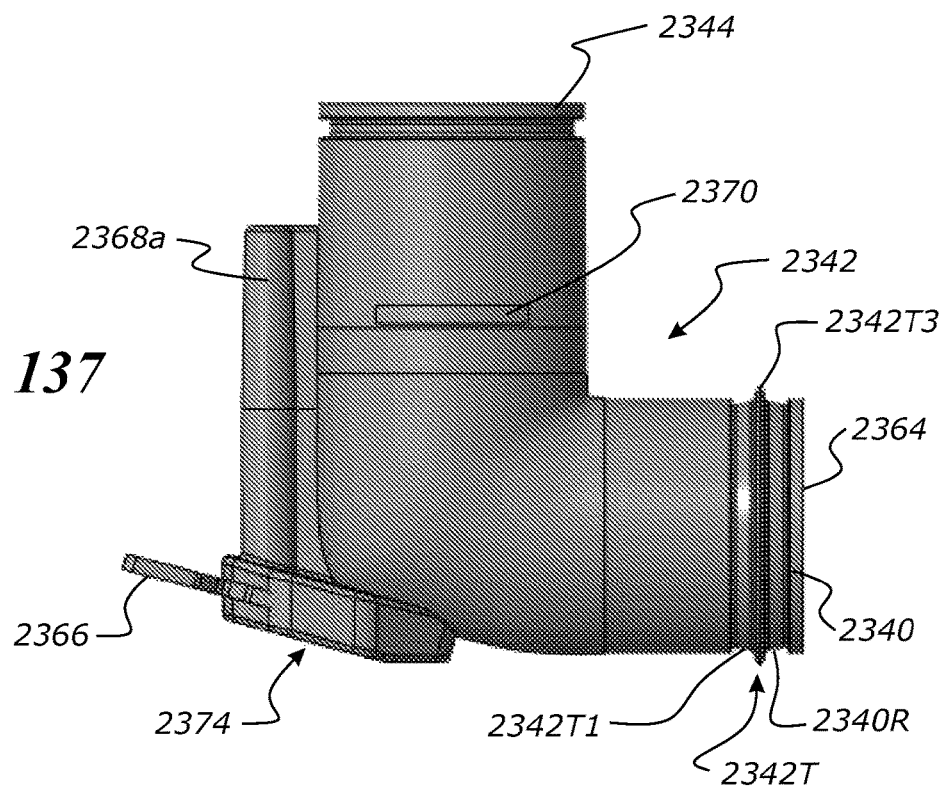

FIG. 137 is a side view of the removable elbow of FIG. 72, with a T-seal in place on the elbow.

Figure 138:
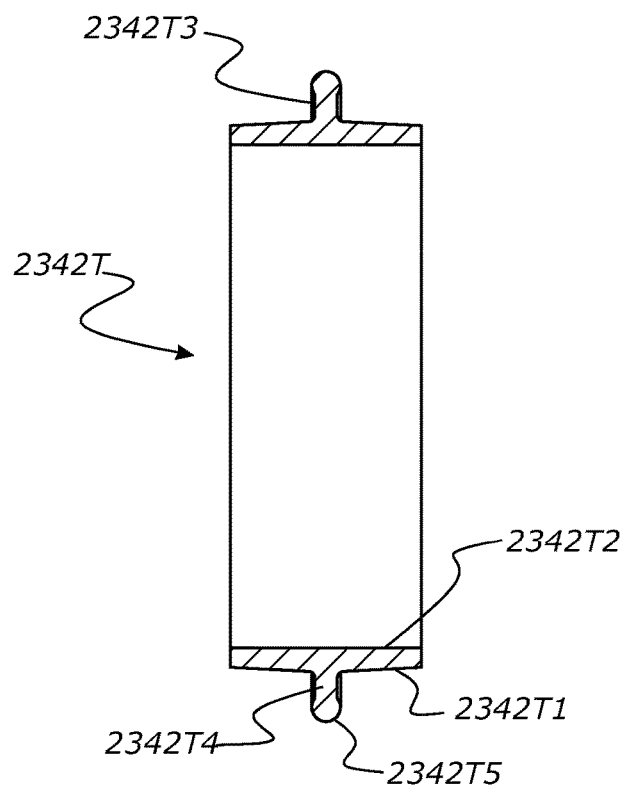

FIG. 138 is a cross-sectional view of the T-seal shown in FIG. 137, when not in place on the elbow.

Figure 139:
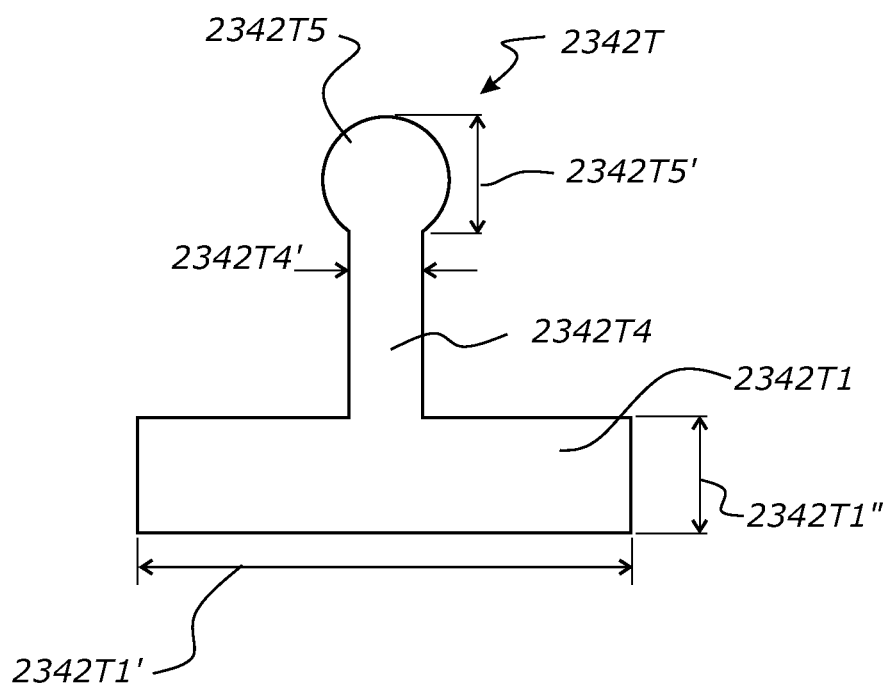

FIG. 139 is a schematic cross-sectional view of part of the T-seal of FIGS. 137 and 138, showing exemplary dimensions.

Figure 140:
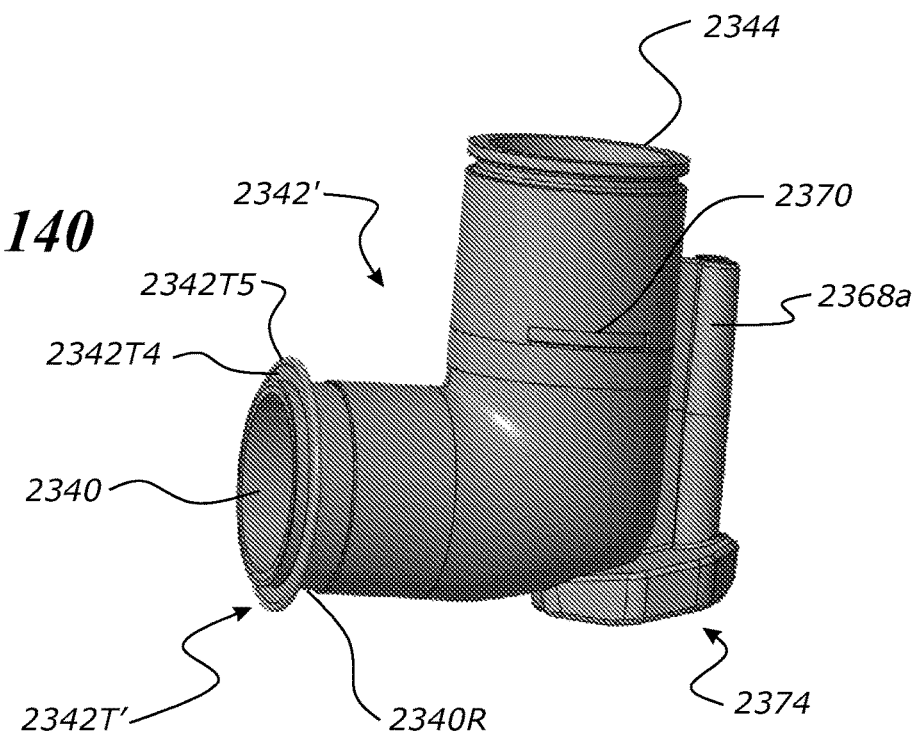

FIG. 140 is a perspective view of an alternative configuration removable elbow and alternative configuration T-seal for use in the flow therapy apparatuses.

Figure 141:
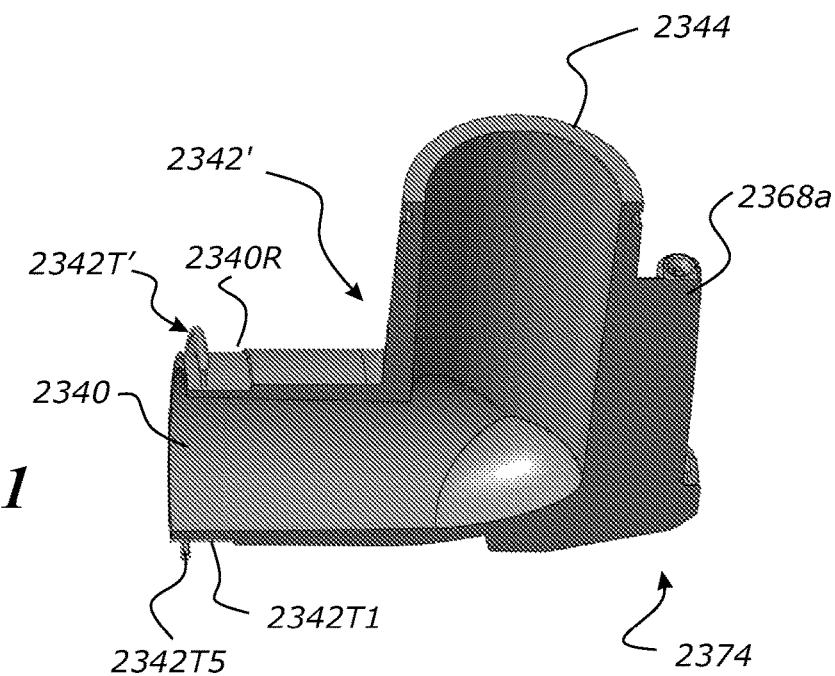

FIG. 141 is a cross-sectional perspective view of the removable elbow and T-seal of FIG. 140.

Figure 142:
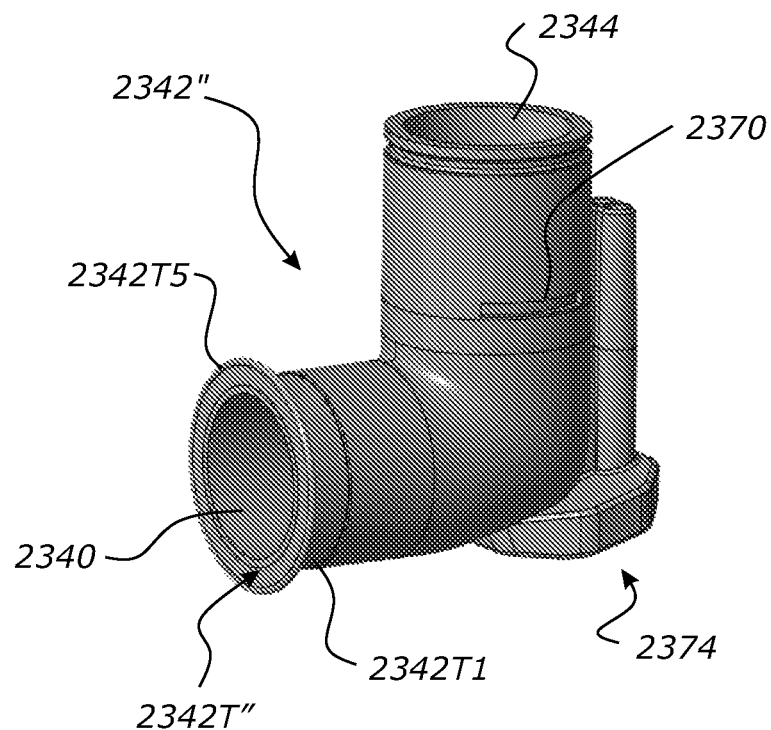

FIG. 142 is a perspective view of an alternative configuration removable elbow and adapted T-seal that resembles an L-seal for use in the flow therapy apparatuses.

Figure 143:
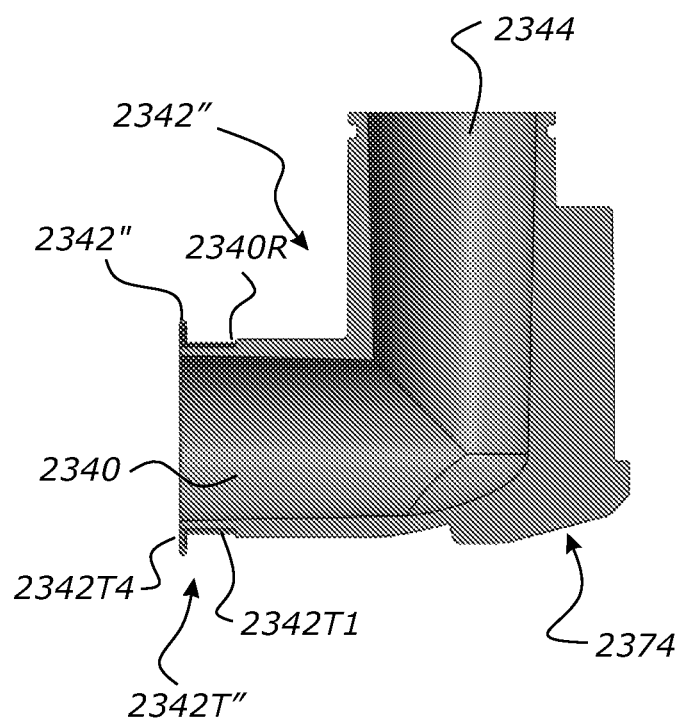

FIG. 143 is a cross-sectional perspective view of the removable elbow and seal of FIG. 142.

Figure 144:
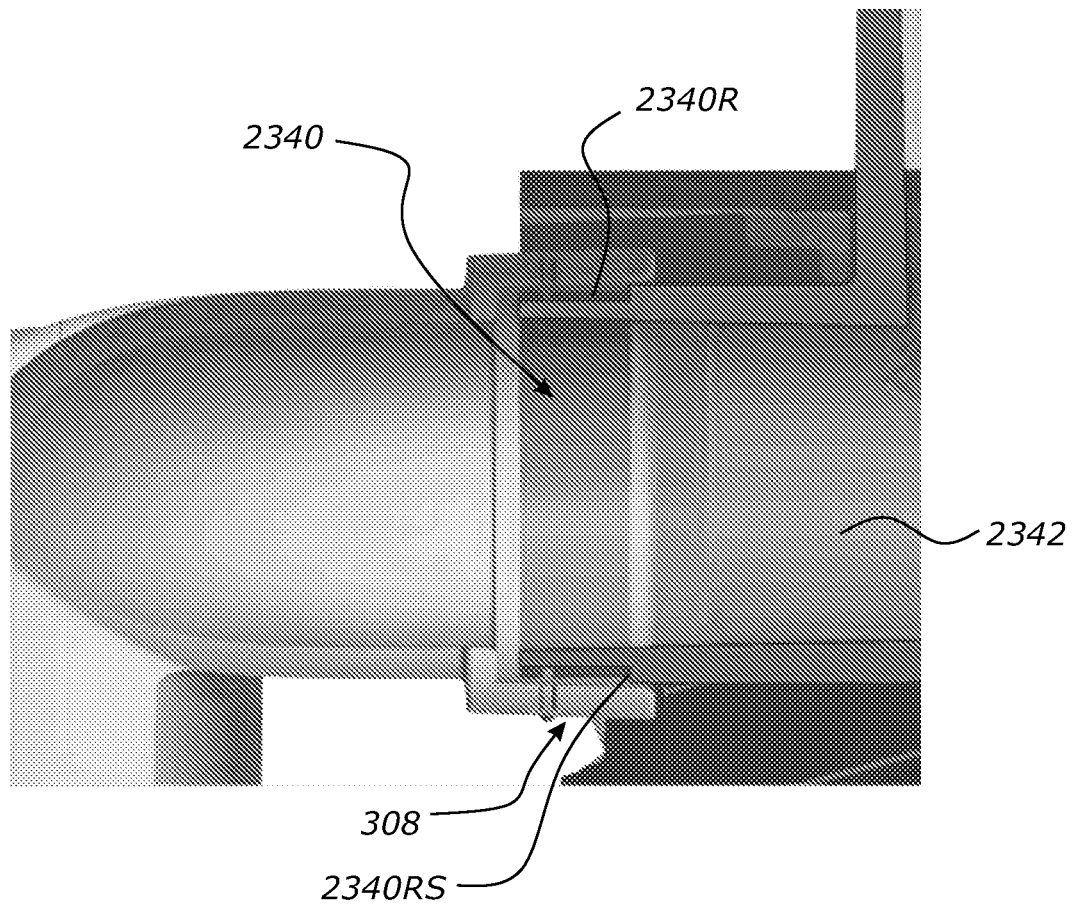

FIG. 144 shows an inlet port of the removable elbow coupled to the outlet port of a liquid chamber, showing a mechanical standoff feature.

Figure 145:
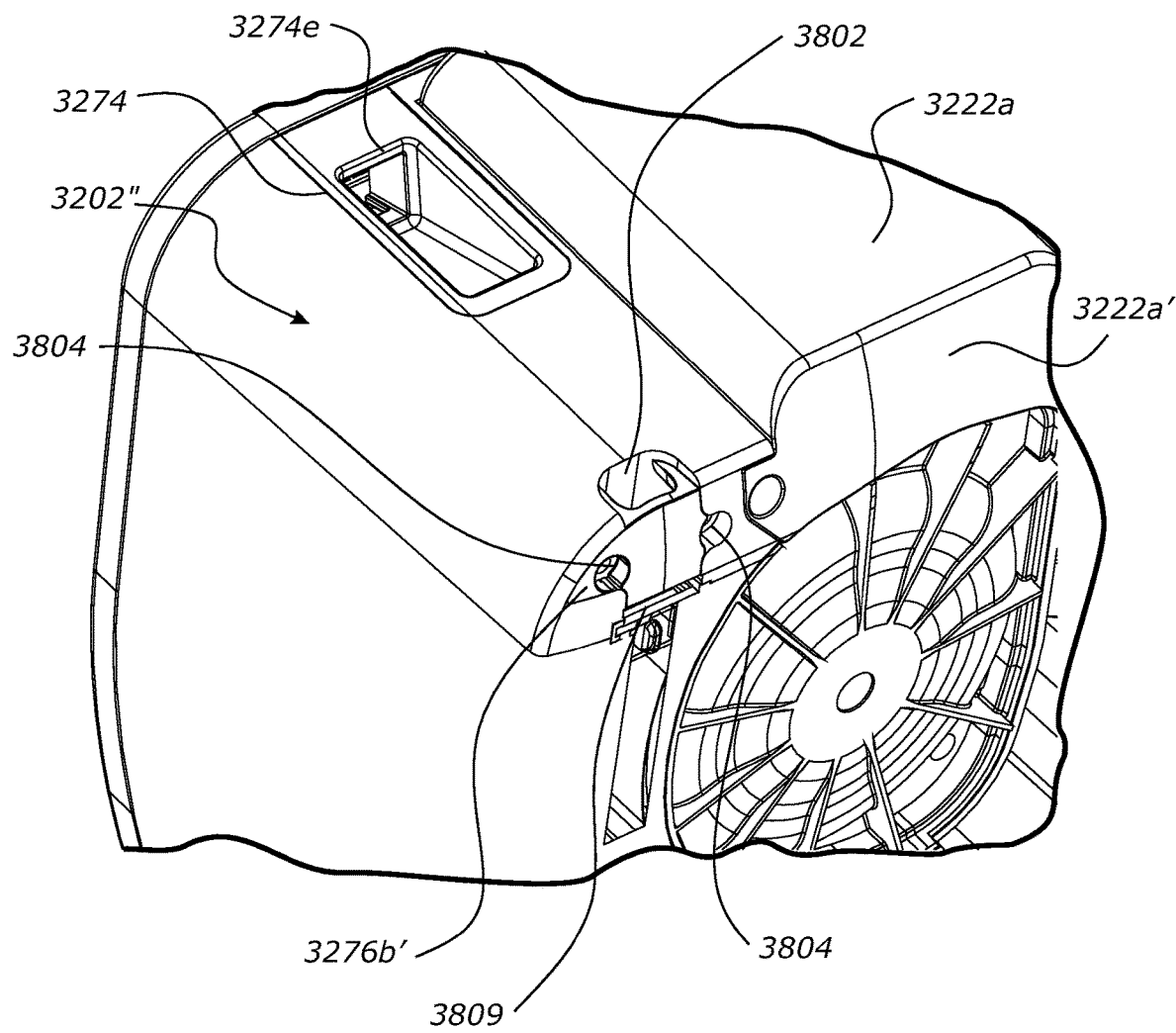

FIG. 145 is a rear underside perspective view of an alternative configuration of the lower chassis of the flow therapy apparatus of FIG. 101 in the region where the electrical connector is located.

Figure 146:
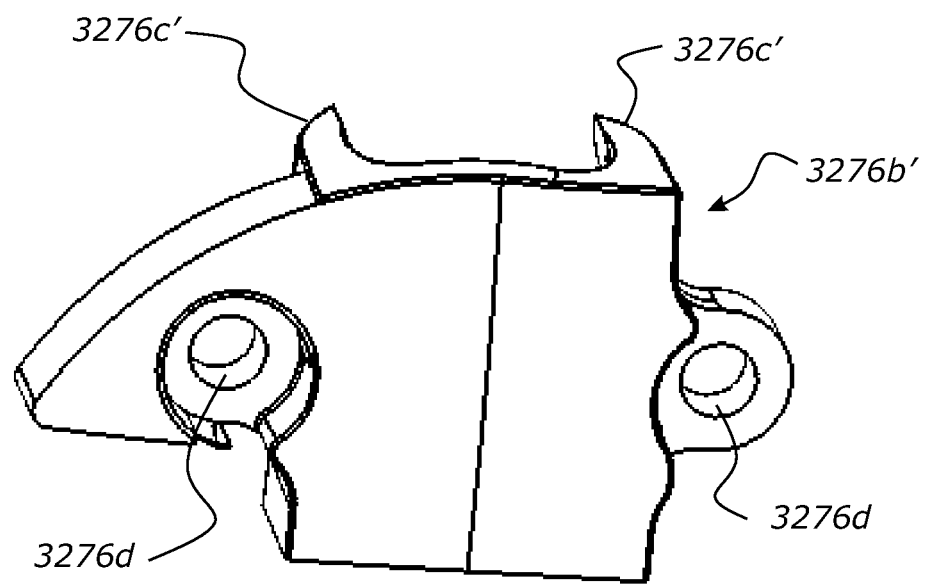

FIG. 146 is an underside perspective view of a retainer of the electrical connector of FIG. 145.

Figure 147:
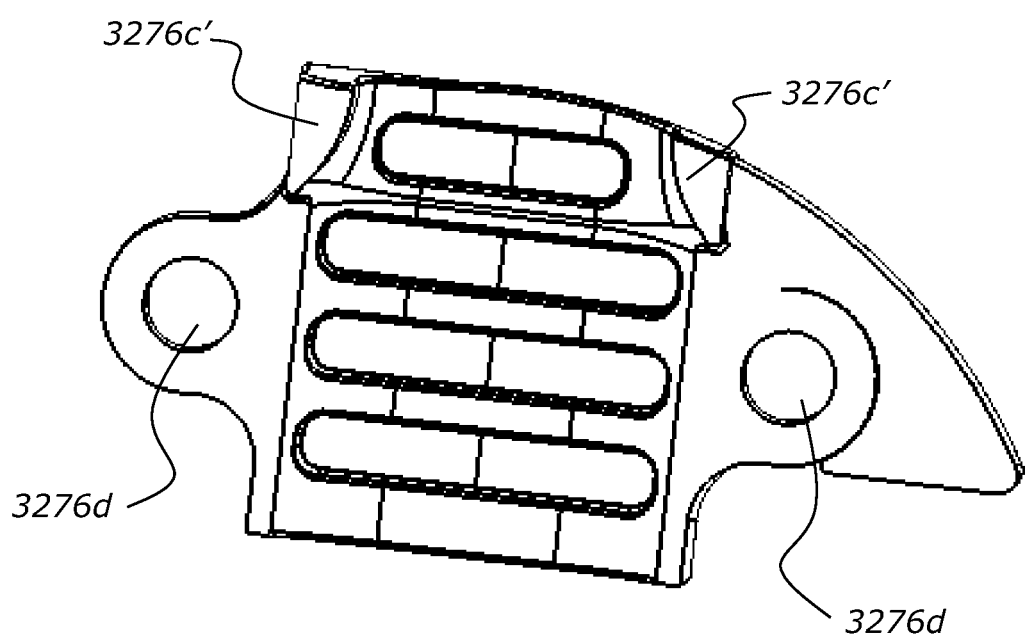

FIG. 147 is an overhead view of the retainer of FIG. 146.

Figure 148:
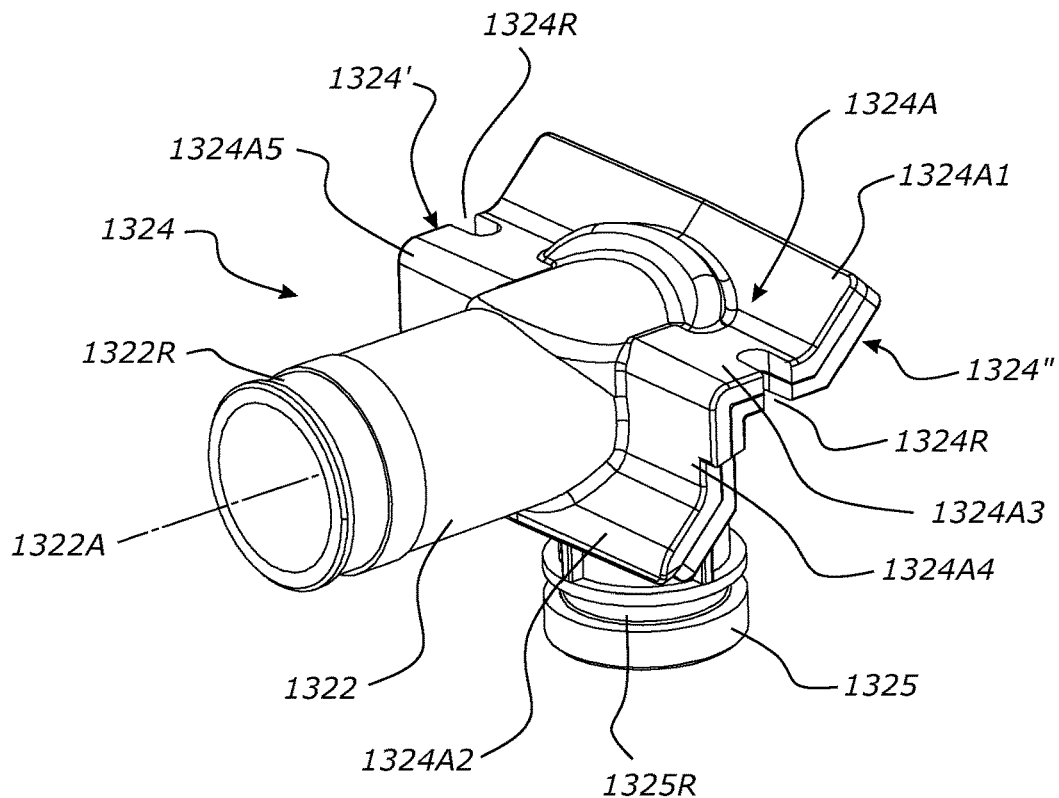

FIG. 148 is a front side overhead perspective view of an alternative configuration inlet elbow for use in the flow therapy apparatuses.

Figure 149:
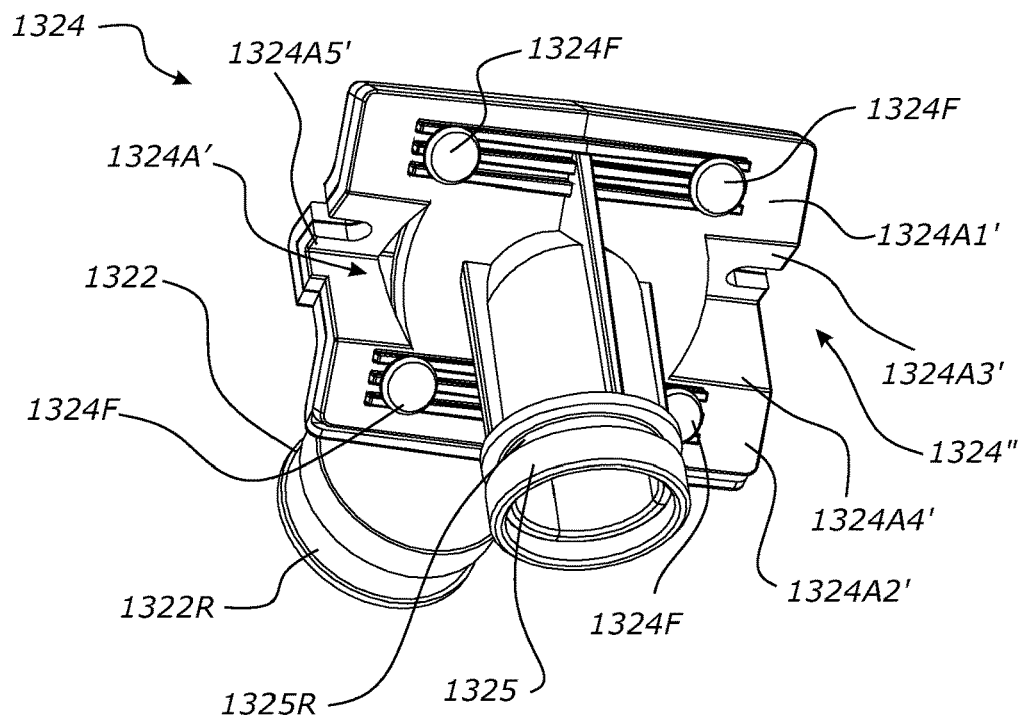

FIG. 149 is a rear underside perspective view of the inlet elbow of FIG. 148.

Figure 150:
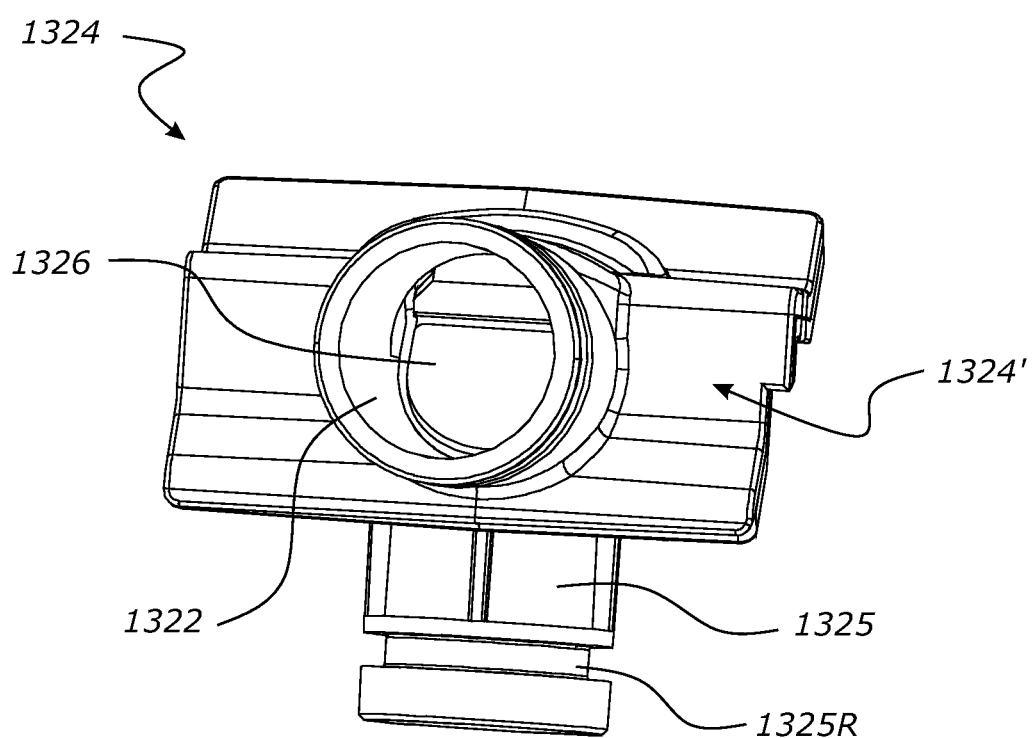

FIG. 150 is a front perspective view of the inlet elbow of FIGS. 148 and 149, showing a one-way valve.

Figure 151:
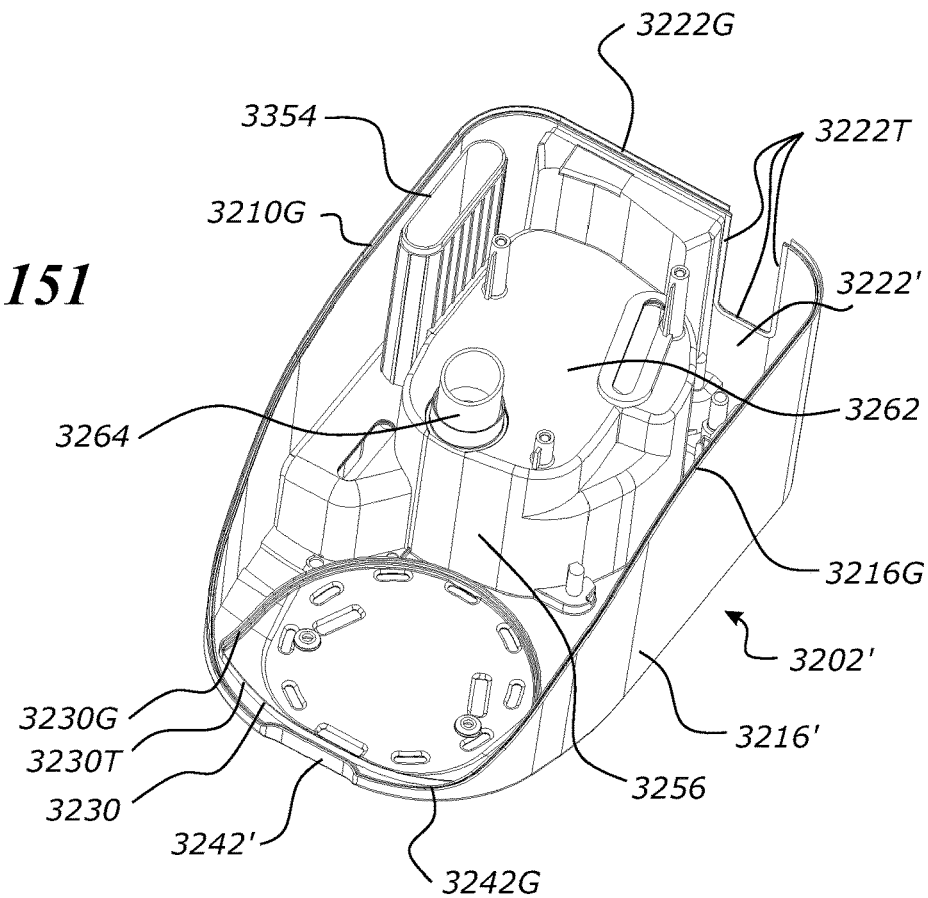

FIG. 151 is a front overhead perspective view of an alternative lower chassis of the flow therapy apparatus of FIG. 101, showing tongue and/or groove features.

Figure 152:
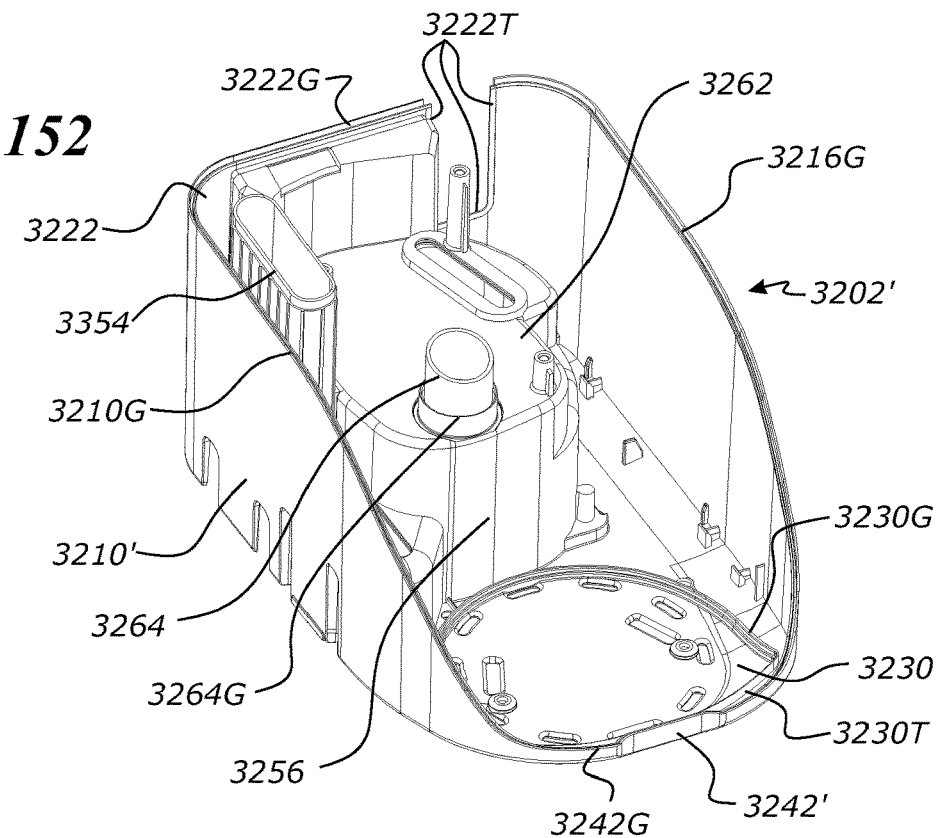

FIG. 152 is another front overhead perspective view of the lower chassis of FIG. 151, showing tongue and/or groove features.

Figure 153:
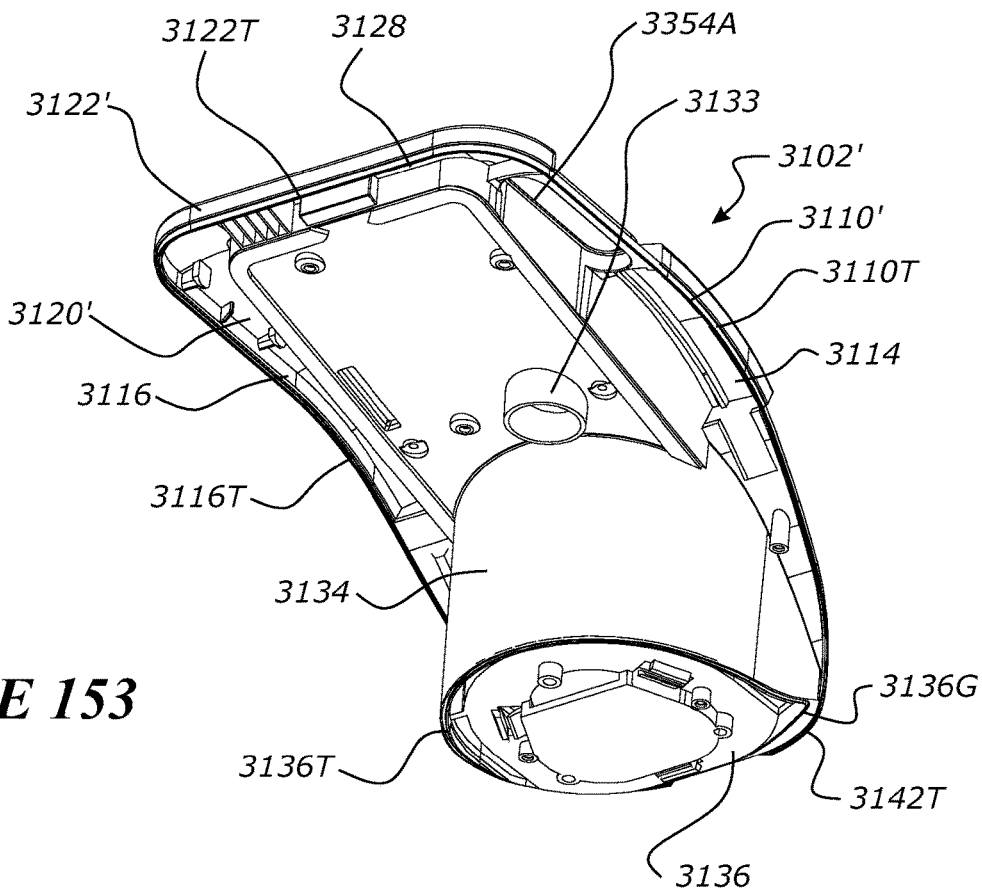

FIG. 153 is a rear underside perspective view of an alternative upper chassis of the flow therapy apparatus of FIG. 101, showing tongue and/or groove features.

Figure 154:
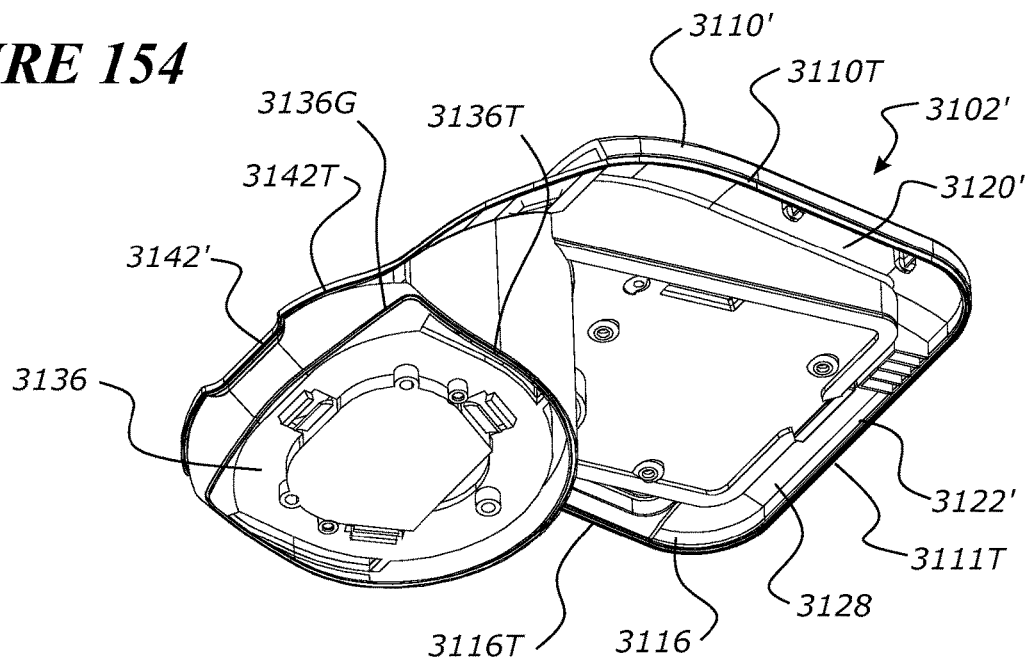

FIG. 154 is a front underside perspective view of the upper chassis of FIG. 153, showing tongue and/or groove features.

Figure 155:
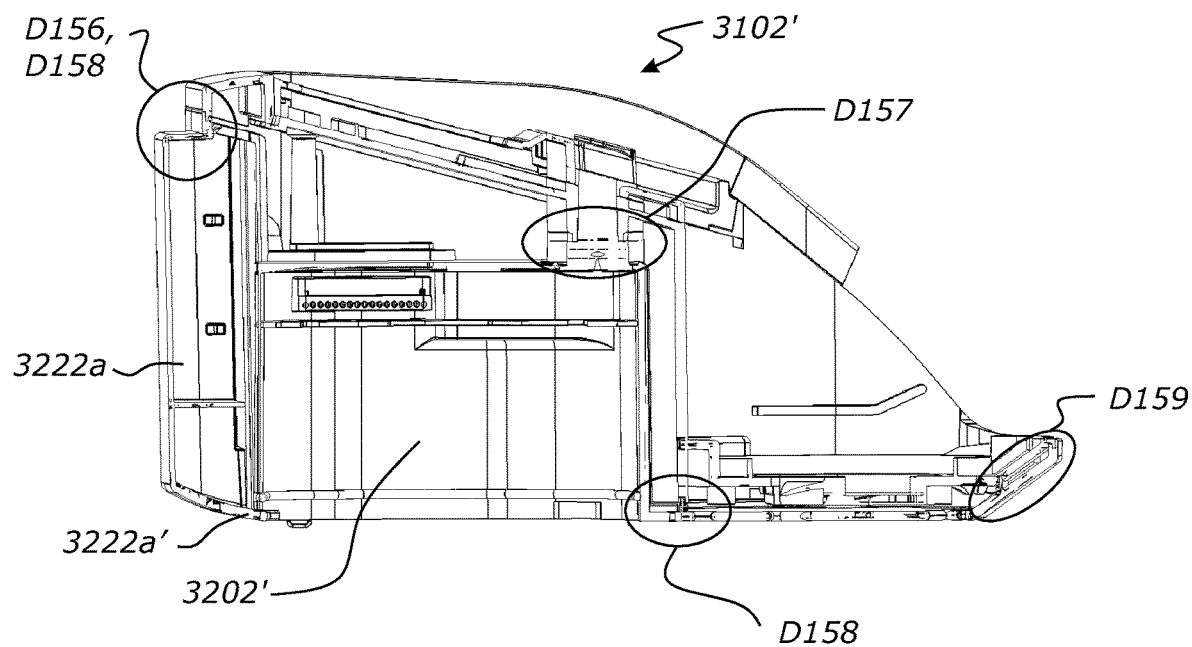

FIG. 155 is a side partial cross-sectional view of the flow therapy apparatus of FIG. 101 with the upper and lower chassis of FIGS. 151 to 154, showing locations of tongue and groove arrangements.

Figure 156:
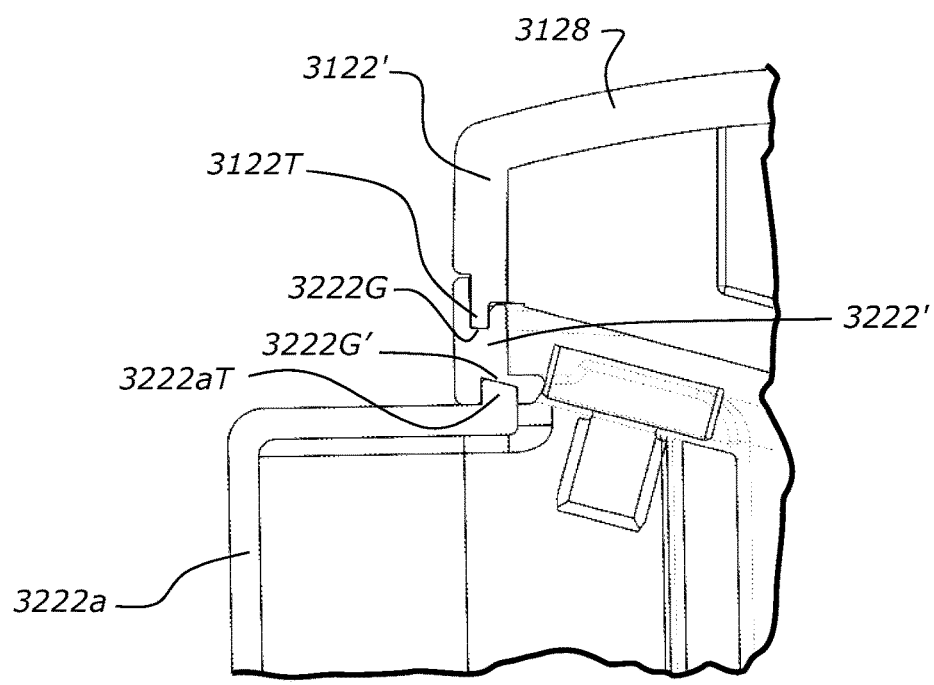

FIG. 156 is a view of detail D156 showing the tongue and groove arrangement in the region of the battery.

Figure 157:
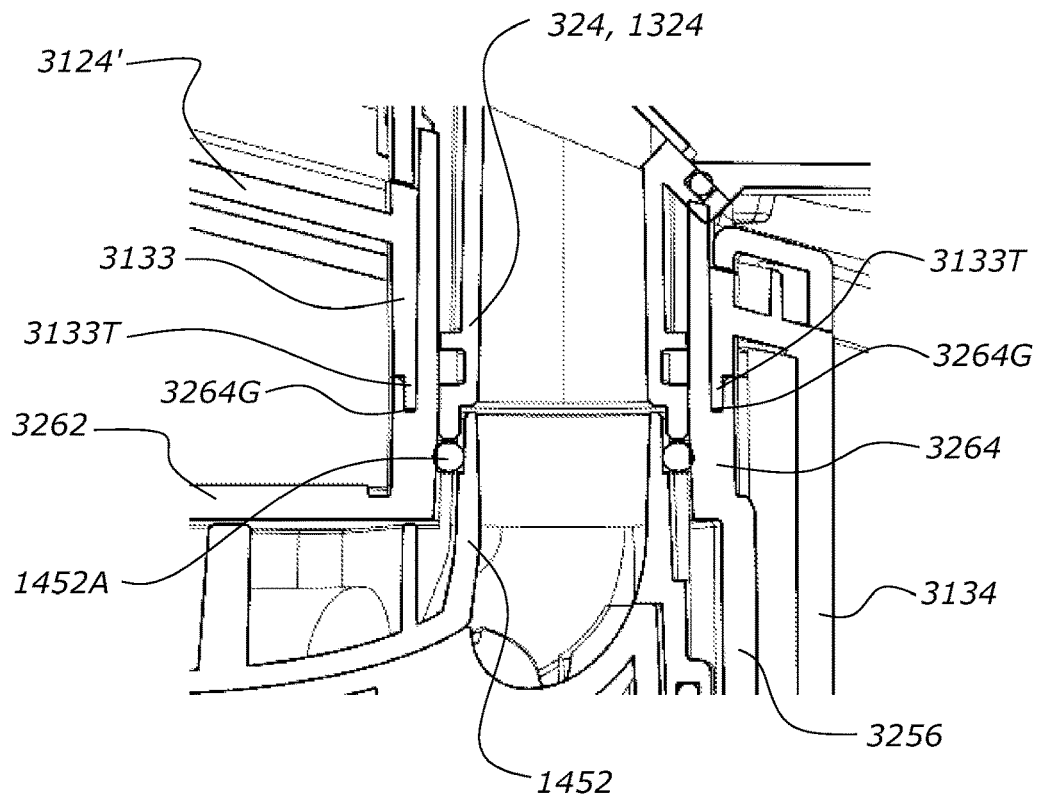

FIG. 157 is a view of detail D157 showing the tongue and groove arrangement.

Figure 158:
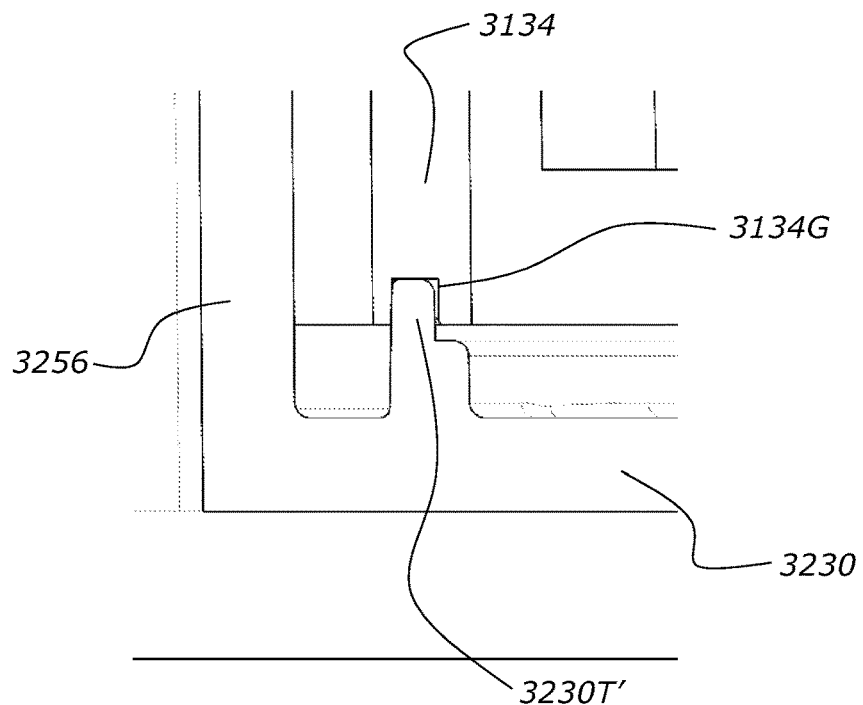

FIG. 158 is a view of detail D158 showing the tongue and groove arrangement.

FIG. 159 is a view of detail D159 showing the tongue and groove arrangement.

FIG. 160 is view of detail D160 of the tongue and groove arrangement in the region of the communication connector arrangement.

Figure 161:
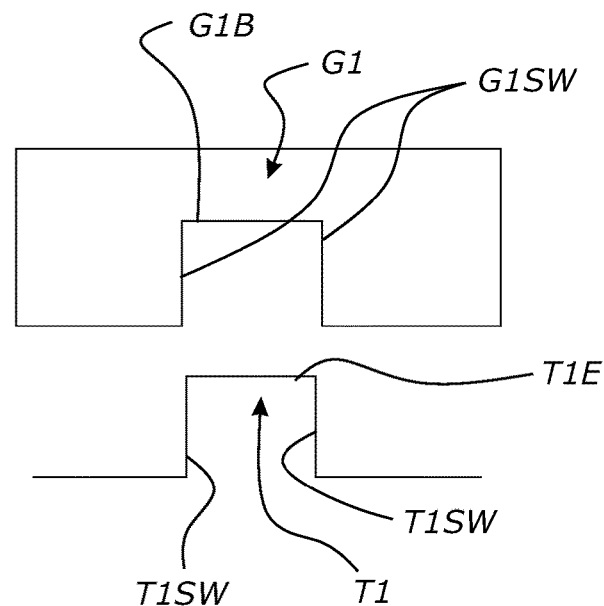

FIG. 161 is a schematic view of one configuration of tongue and groove arrangement for use in the flow therapy apparatuses.

Figure 162:
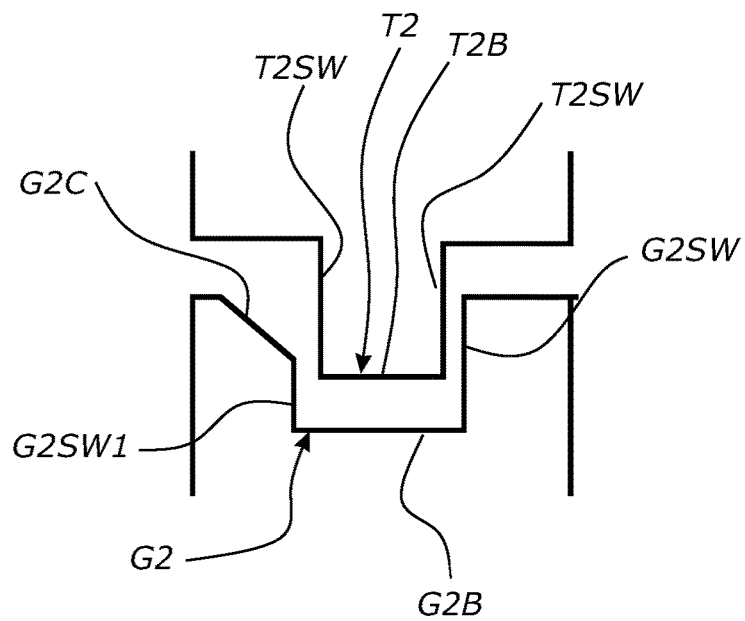

FIG. 162 is a schematic view of another configuration of tongue and groove arrangement for use in the flow therapy apparatuses.

Figure 163:
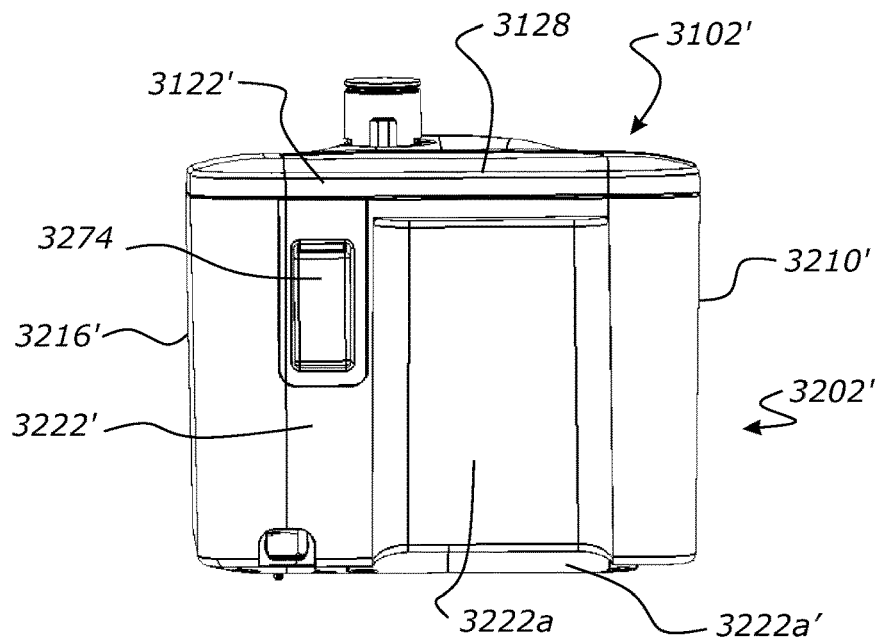

FIG. 163 is a rear view of the apparatus of FIG. 101, showing a larger battery in place on the rear of the apparatus.

Figure 164:
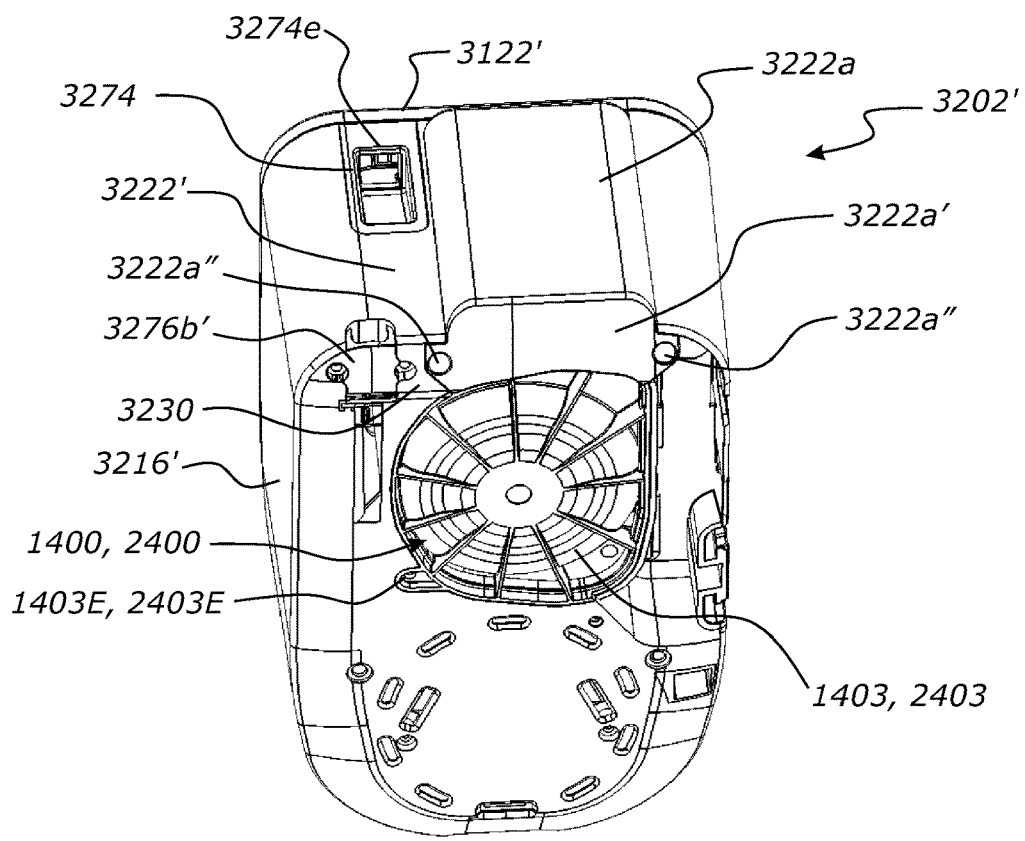

FIG. 164 is an underside rear perspective view the apparatus with the battery shown in FIG. 163, showing an overlap between a base flange of the battery and the motor and/or sensor module.

Figure 165:
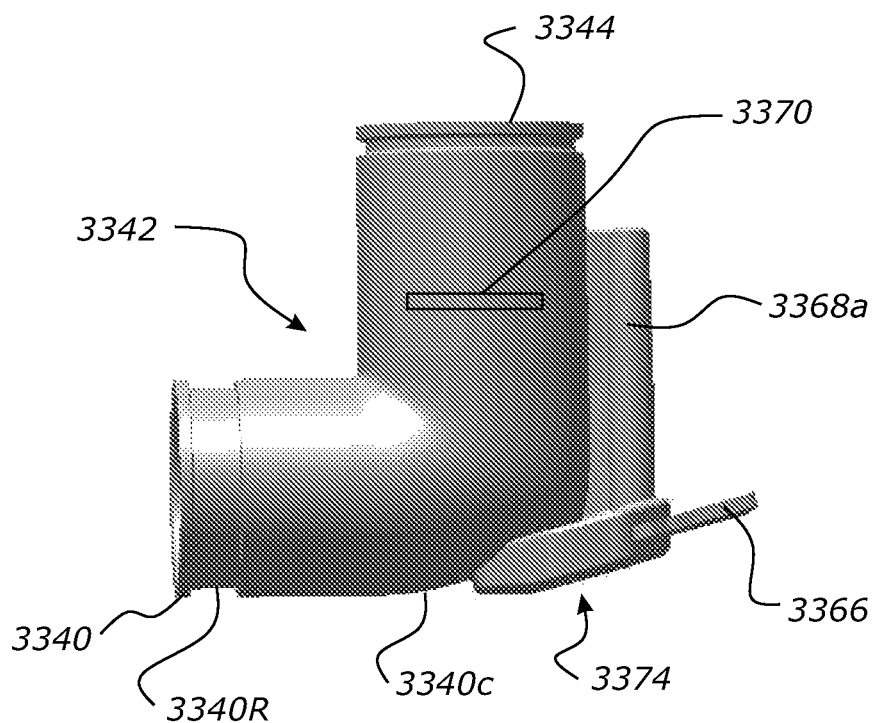

FIG. 165 is a side perspective view of an alternative removable elbow for use in the flow therapy apparatuses.

Figure 166:
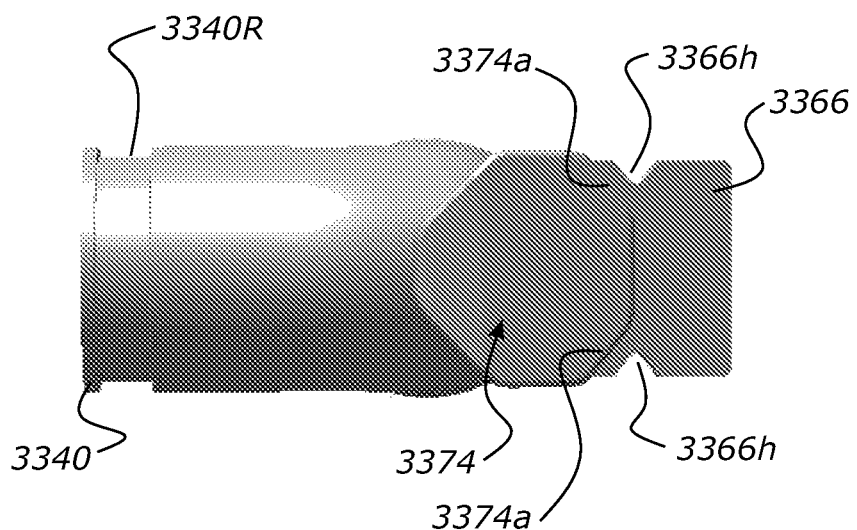

FIG. 166 is an underside view of the removable elbow of FIG. 165.

Figure 167:
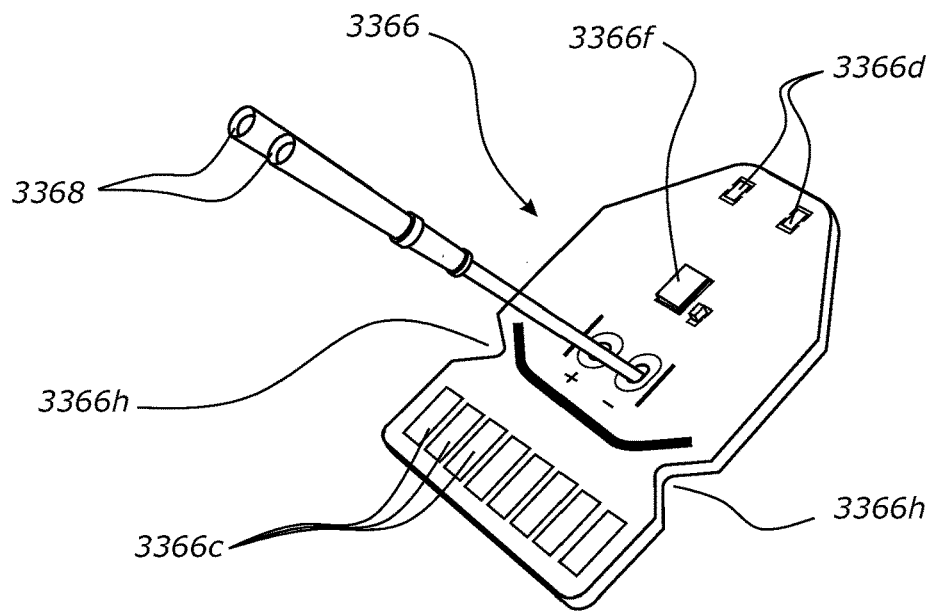

FIG. 167 is an overhead perspective view of a PCB electrical connector of the removable elbow of FIG. 166.

Figure 168:
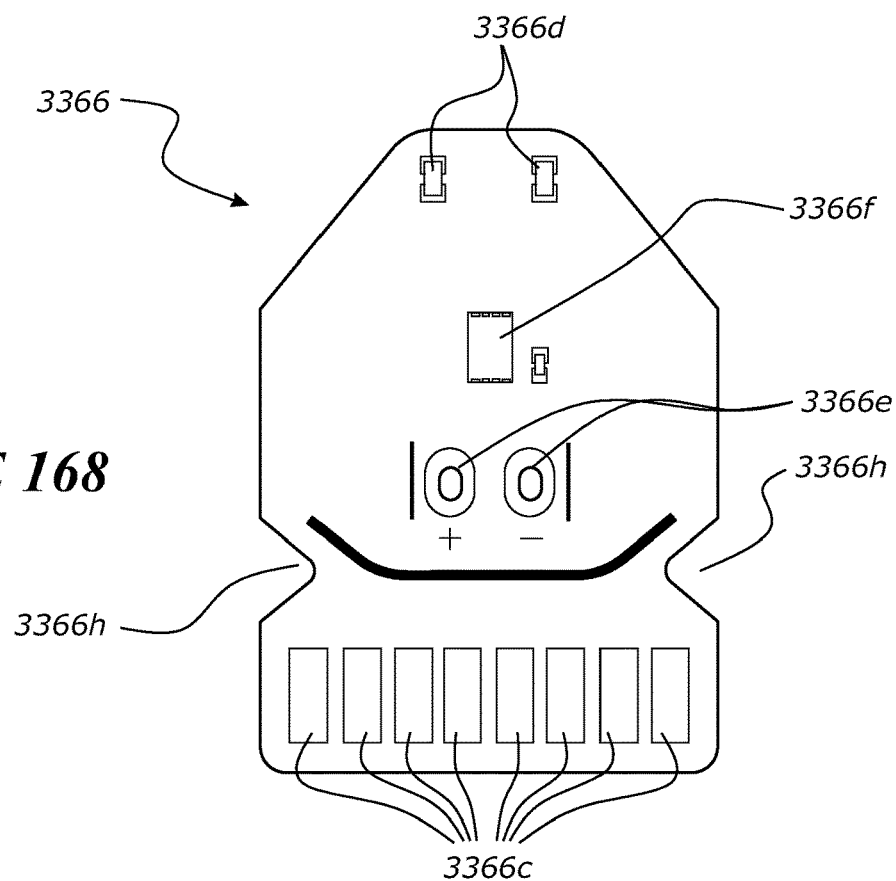

FIG. 168 is a plan view of the PCB electrical connector of FIG. 167.

Figure 169:
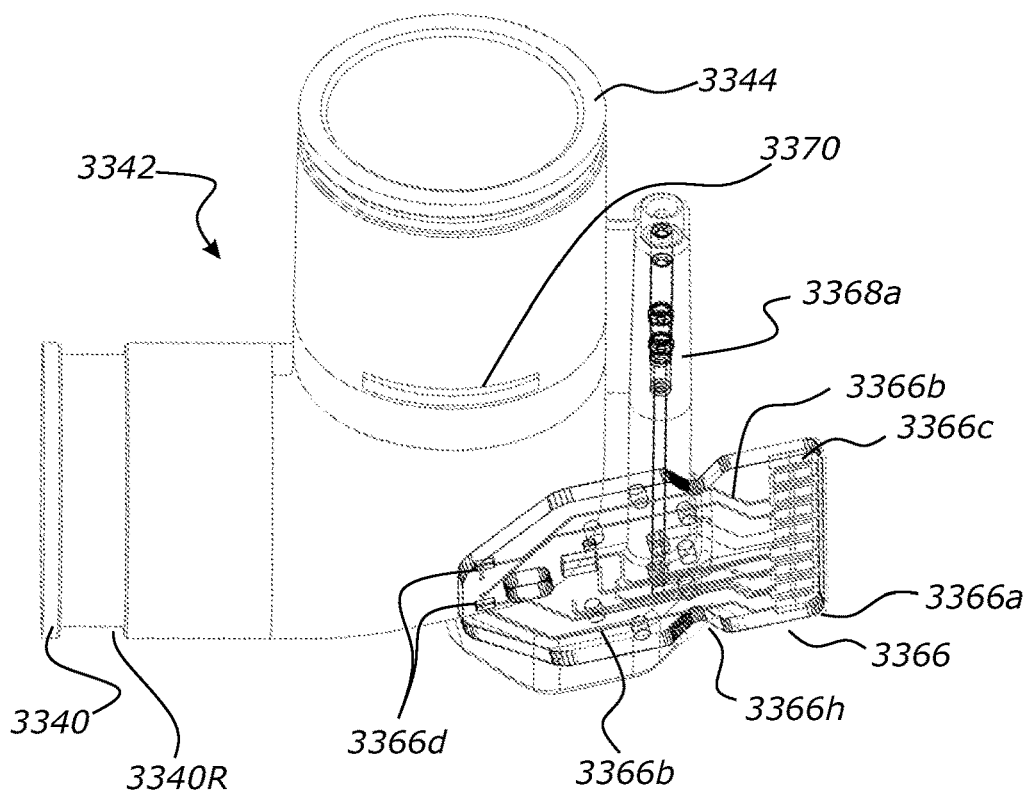

FIG. 169 is a partly transparent overhead perspective view of the removable elbow of FIG. 165, showing some details of the PCB electrical connector.

Figure 170:
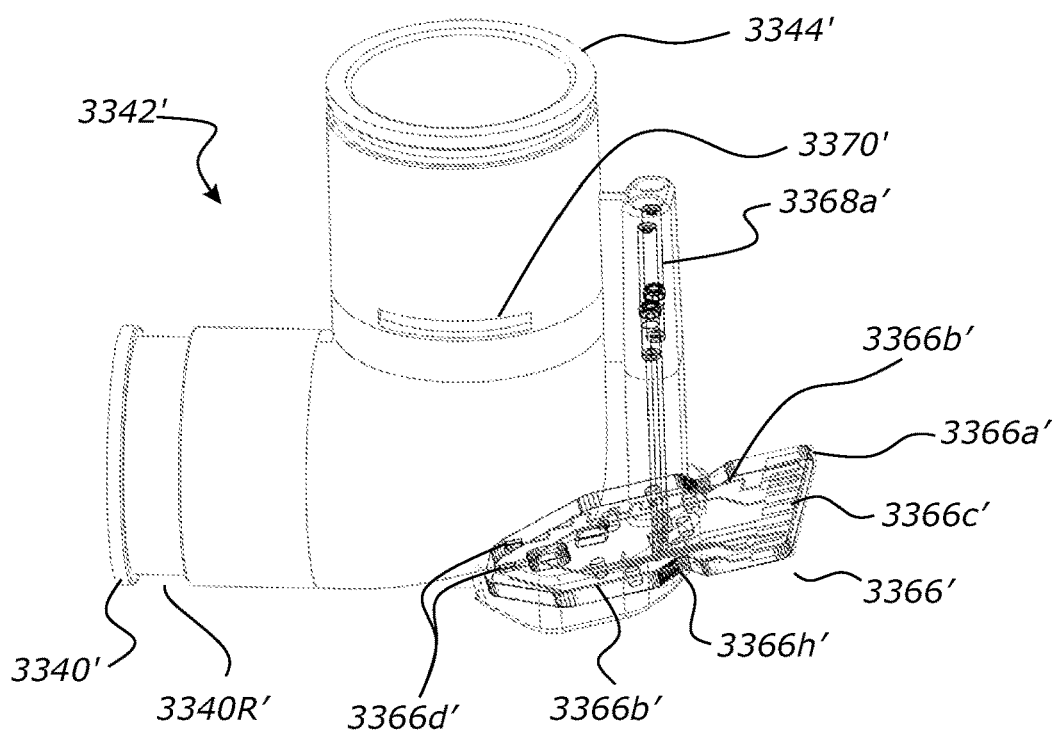

FIG. 170 is a partly transparent overhead perspective view of the removable elbow of FIG. 165 showing alternative details of the PCB electrical connector.

Figure 171:
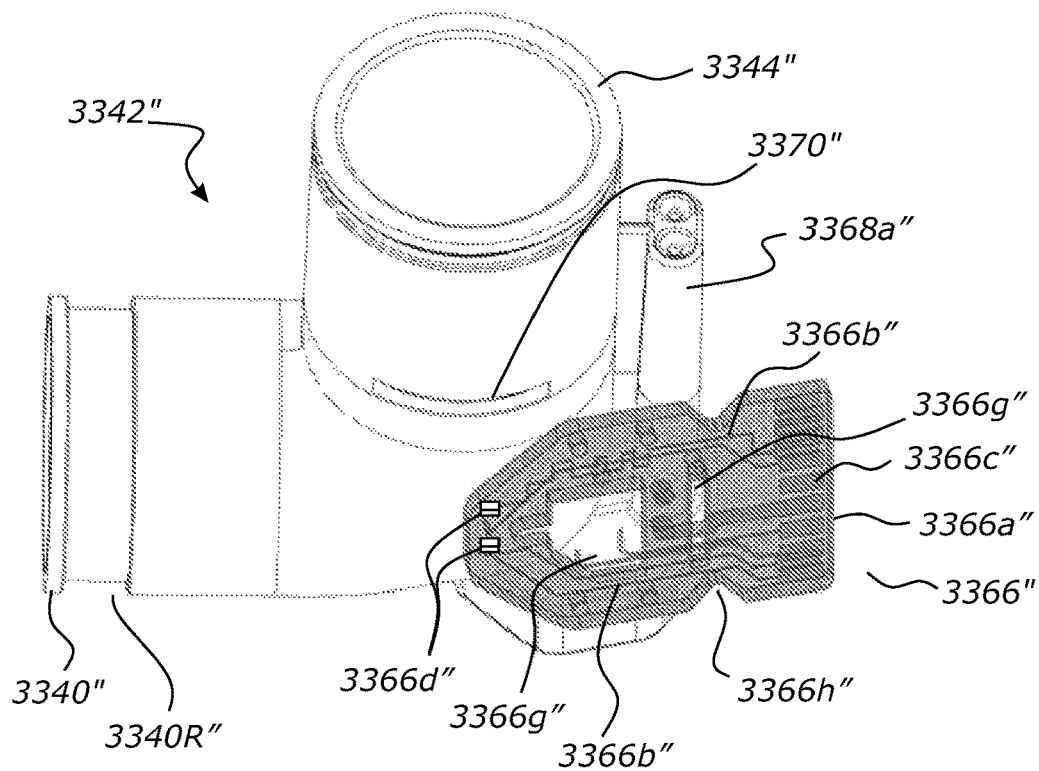

FIG. 171 is a partly transparent overhead perspective view of the removable elbow of FIG. 165 showing alternative details of the PCB electrical connector.

Figure 172:
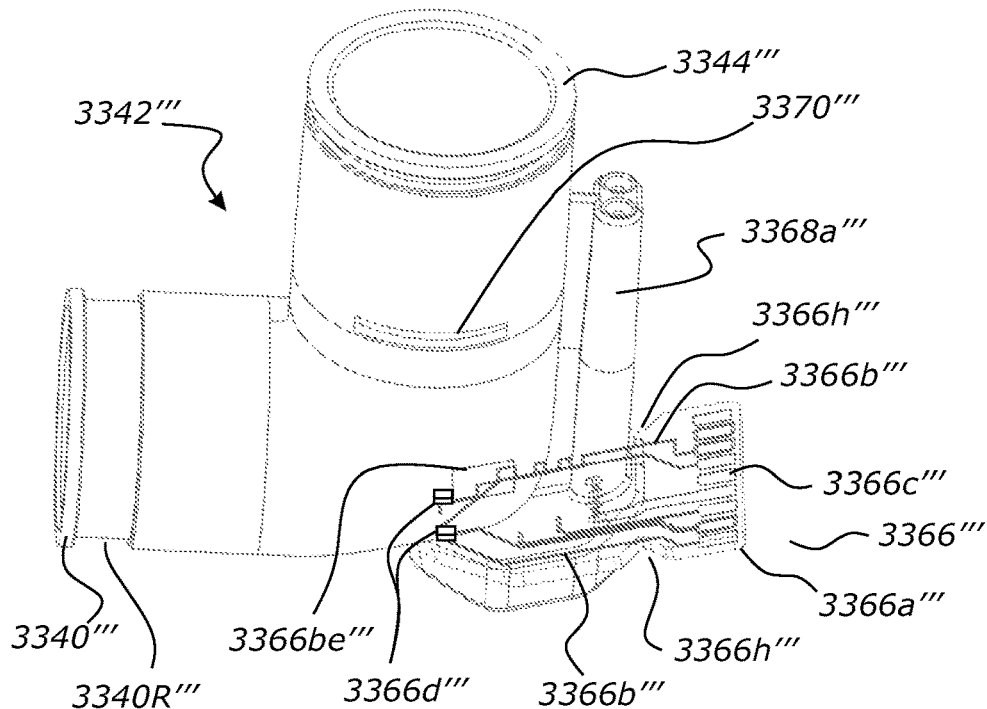

FIG. 172 is a partly transparent overhead perspective view of the removable elbow of FIG. 165 showing alternative details of the PCB electrical connector.

Figure 173:
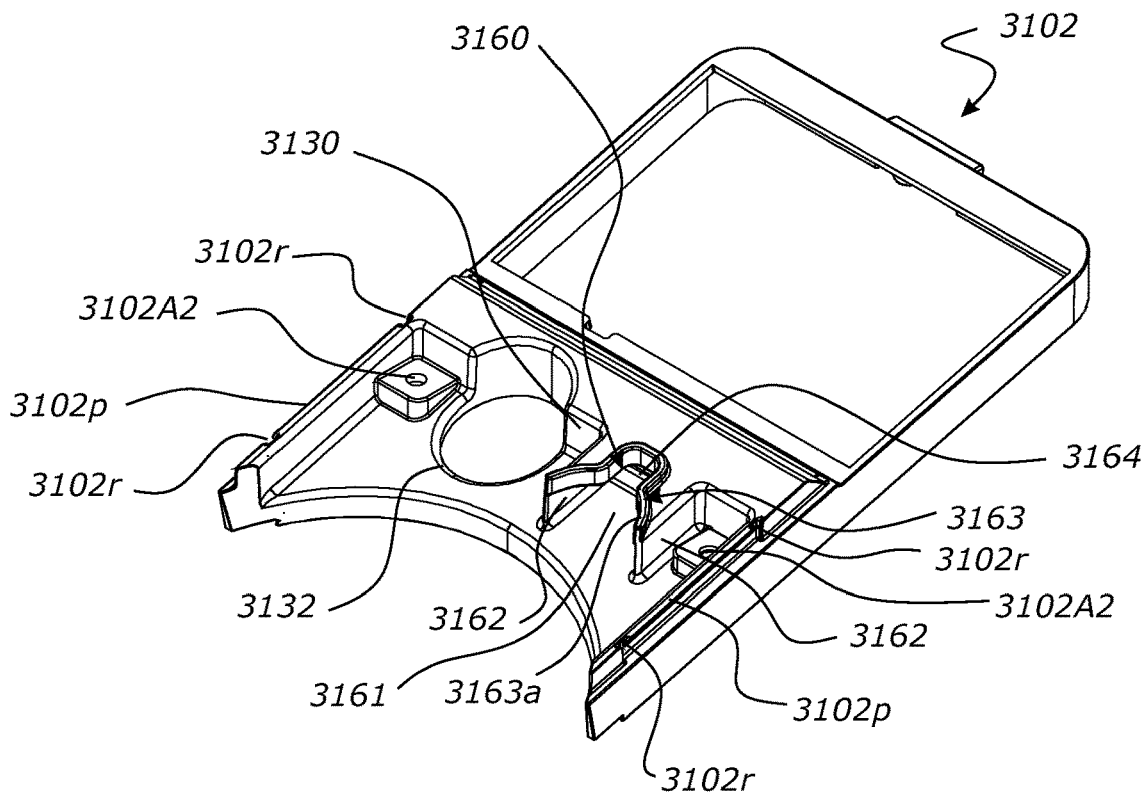

FIG. 173 is an overhead perspective view of a carrier for the display and user interface module, the carrier being part of the main housing of one of the flow therapy apparatuses.

Figure 174:
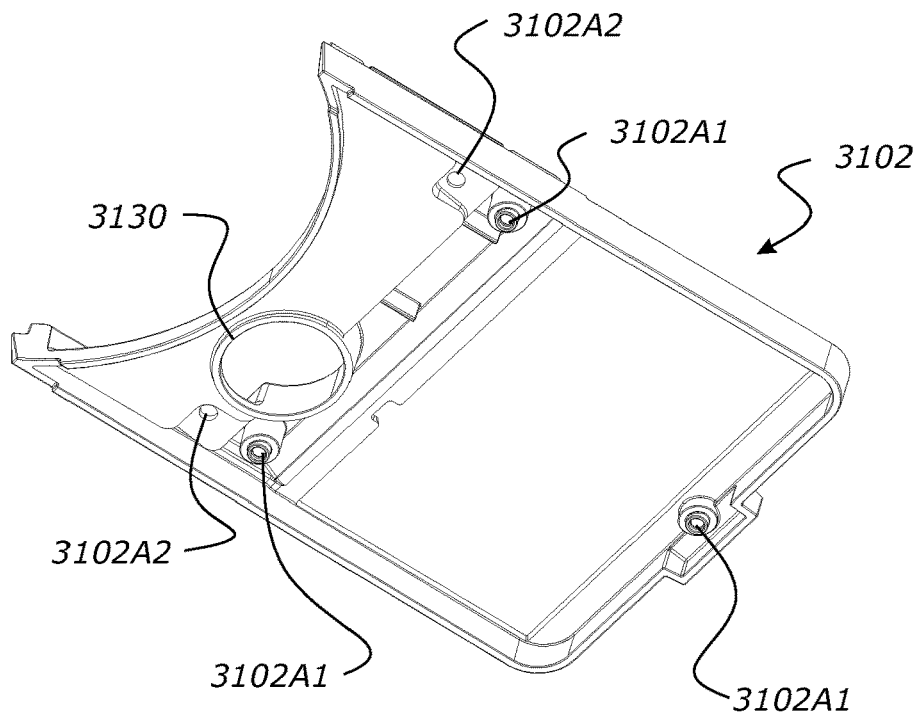

FIG. 174 is an underside perspective view of the carrier of FIG. 173.

Figure 175:
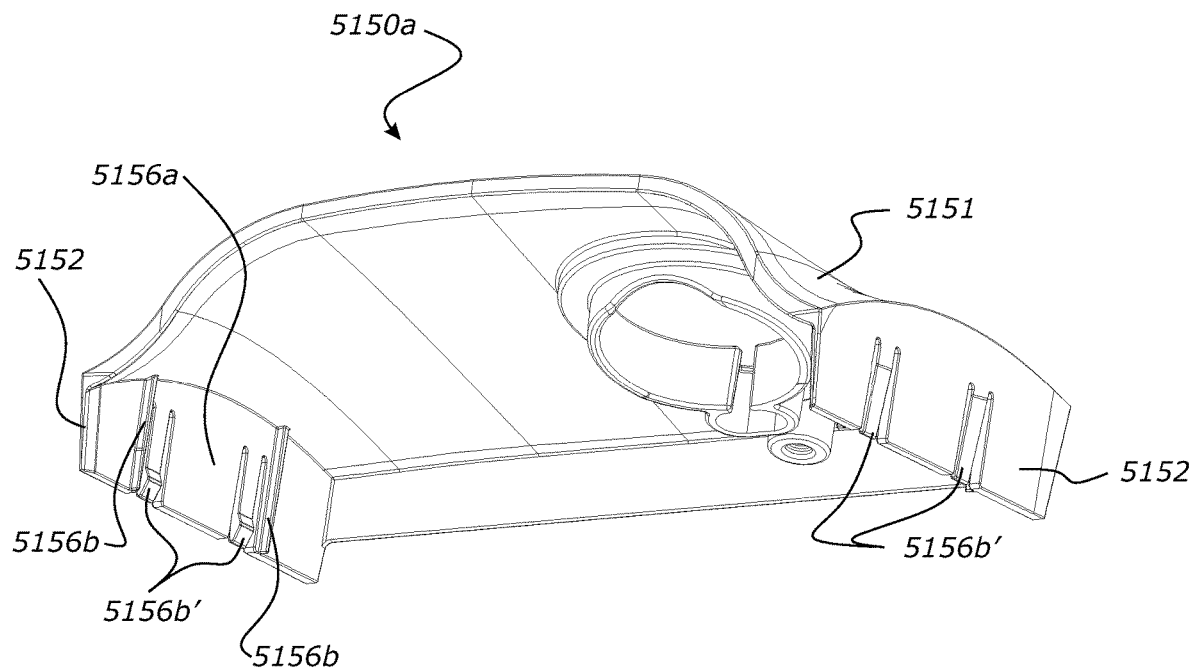

FIG. 175 is an underside perspective view of a removable retention cover for use with the carrier of FIGS. 173 and 174.

Figure 176:
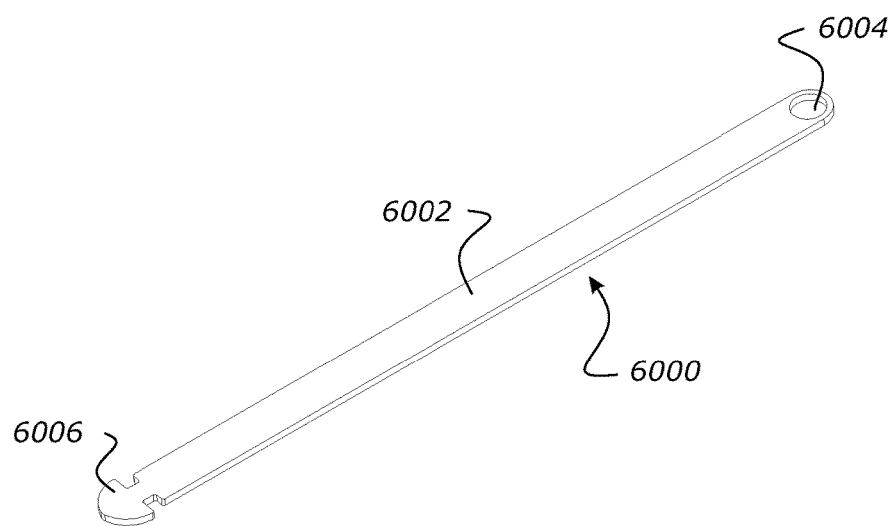

FIG. 176 is a perspective view of a flexible tether for coupling the removable retention cover of FIG. 175 to the carrier of FIGS. 173 and 174.

Figure 177:
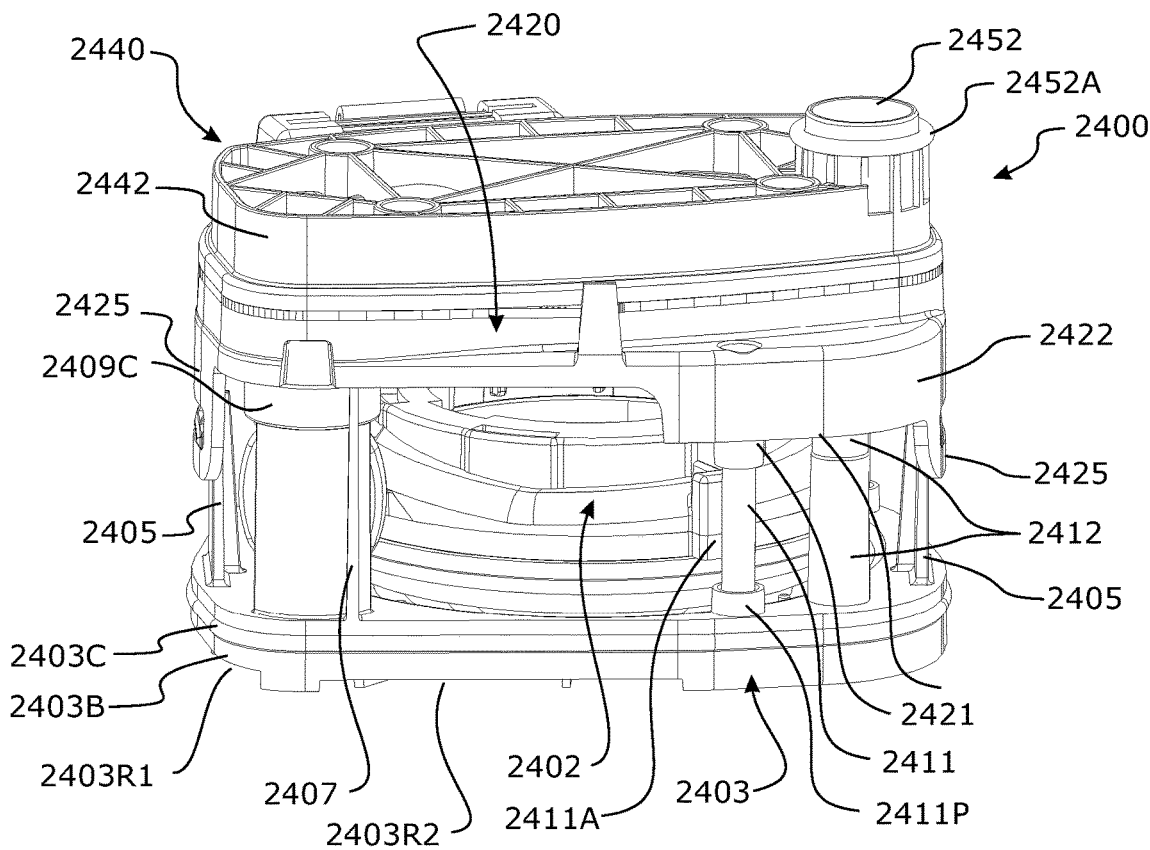

FIG. 177 is a perspective view of the motor and/or sensor sub-assembly for use in the flow therapy apparatuses.

Figure 178:
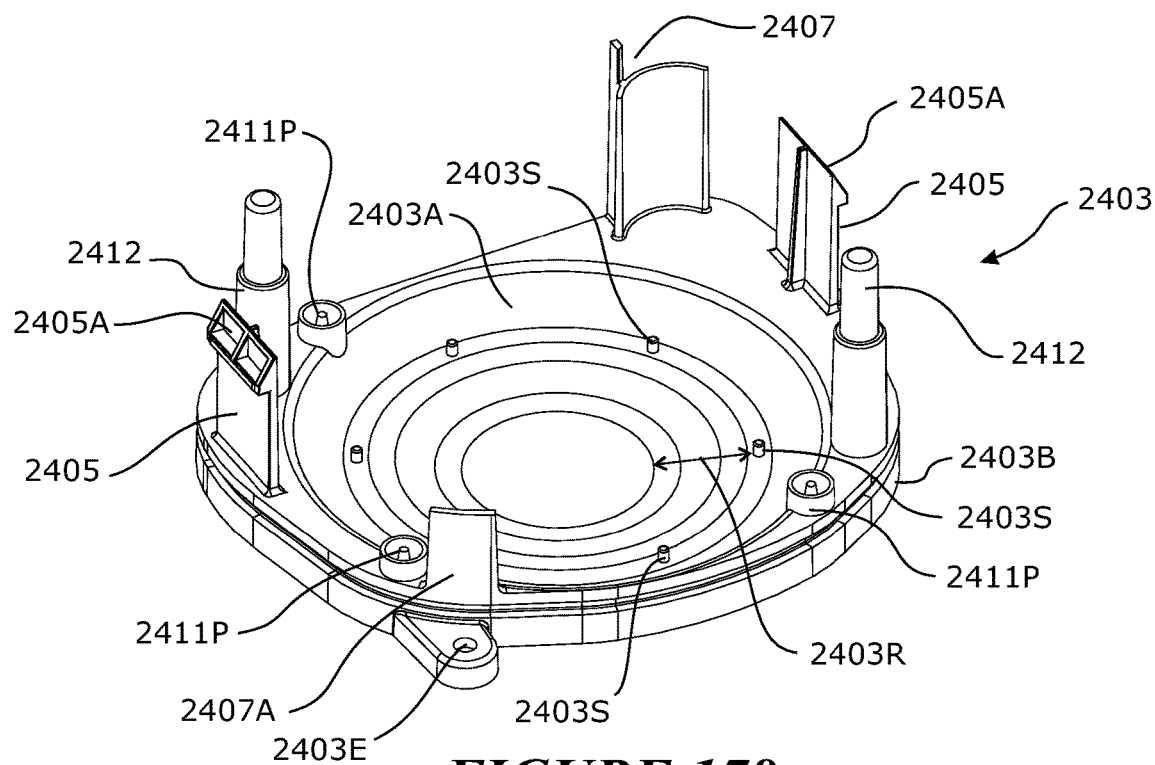

FIG. 178 is an overhead perspective view of the base of the motor and/or sensor sub-assembly.

Figure 179:
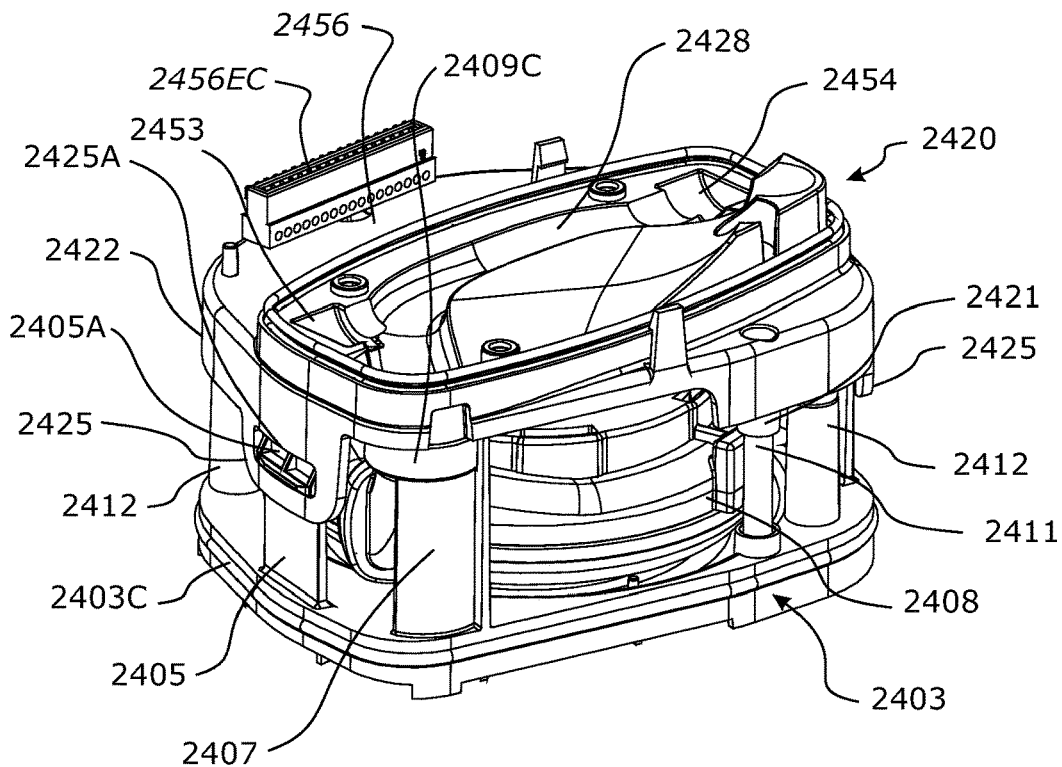

FIG. 179 is an overhead perspective view of the base and mid-section of the motor and/or sensor sub-assembly.

Figure 180:
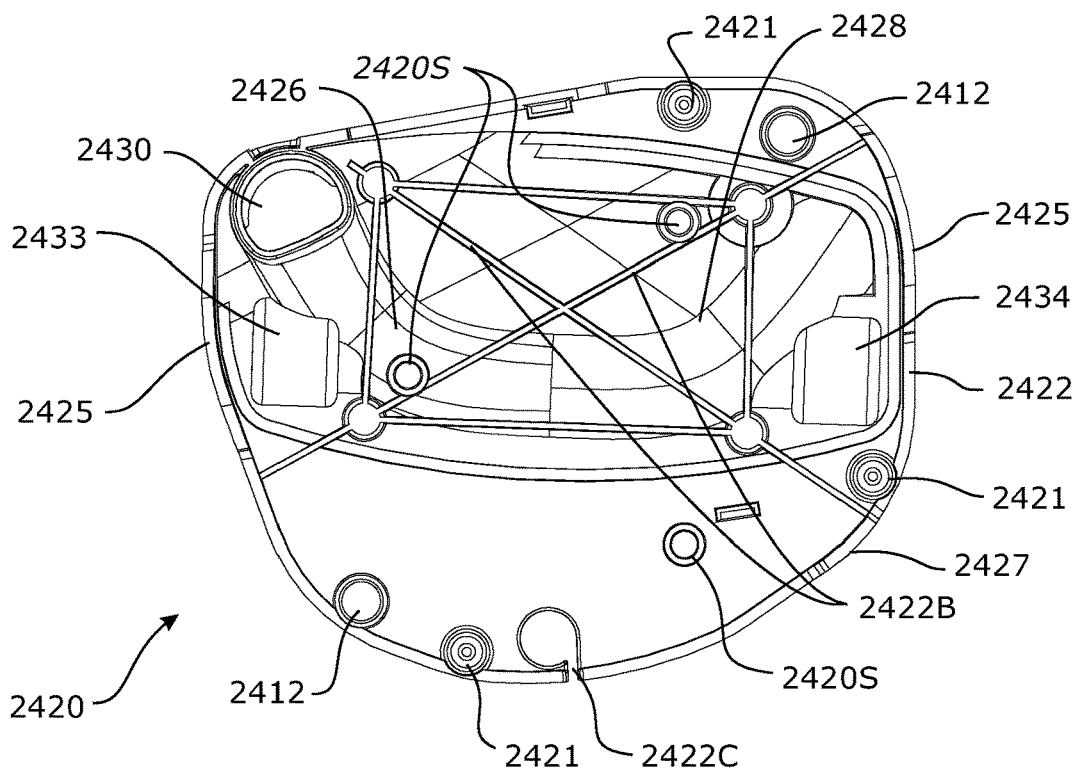

FIG. 180 is an underside view of the mid-section of the motor and/or sensor sub-assembly.

Figure 181:
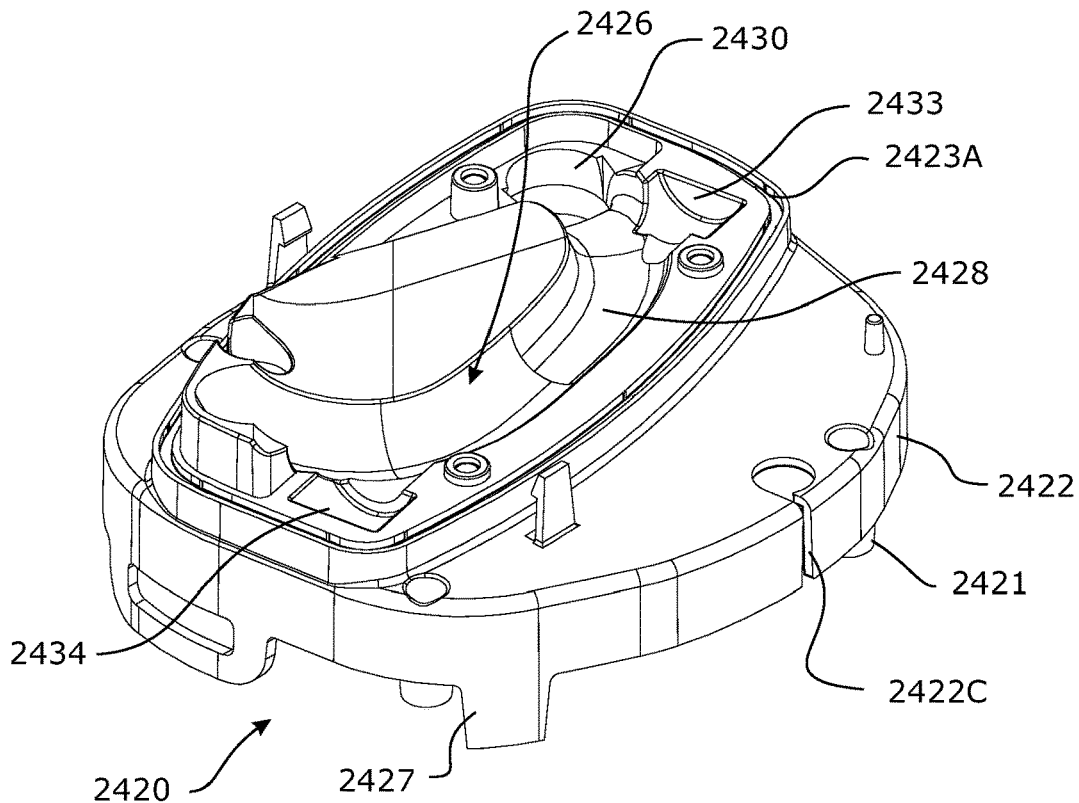

FIG. 181 is a perspective view of the mid-section of the motor and/or sensor sub-assembly.

Figure 182:
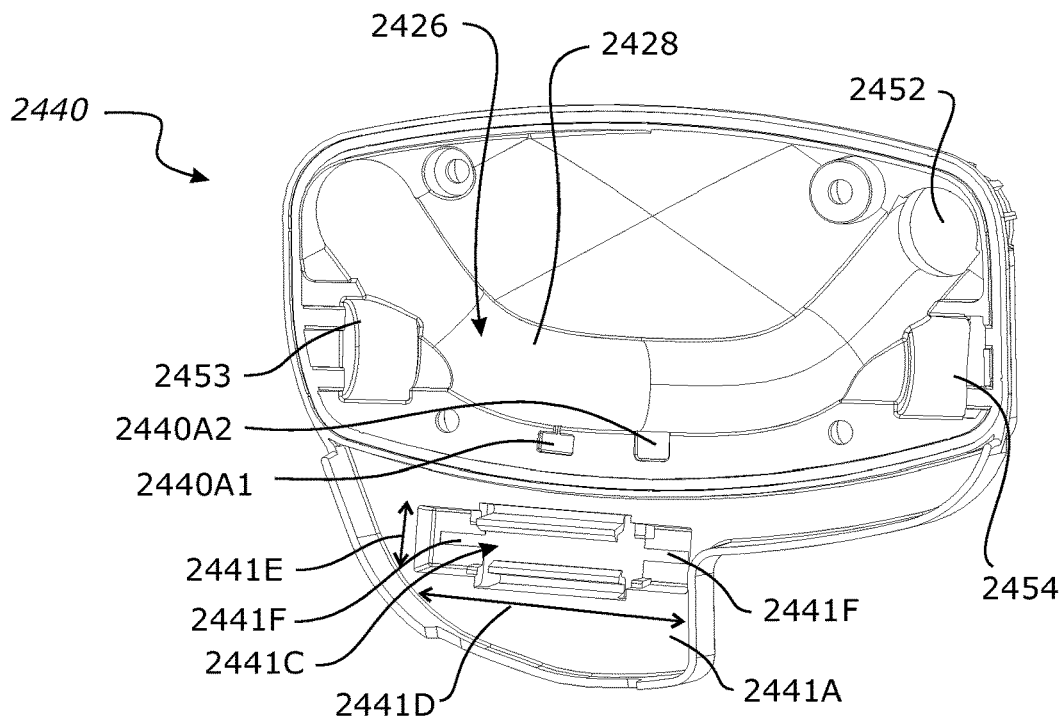

FIG. 182 is an overhead perspective view of the cover layer of the motor and/or sensor sub-assembly.

Figure 183:
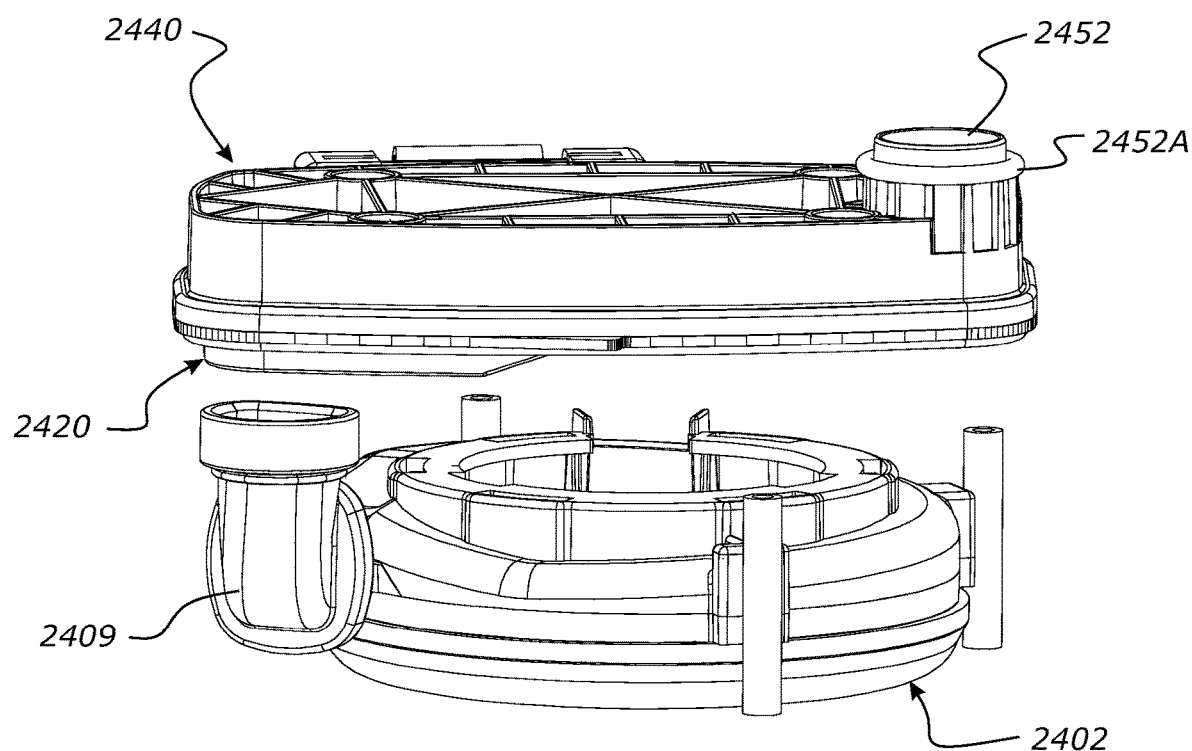

FIG. 183 is a partial exploded view of some of the components of the motor and/or sensor sub-assembly.

Figure 184:
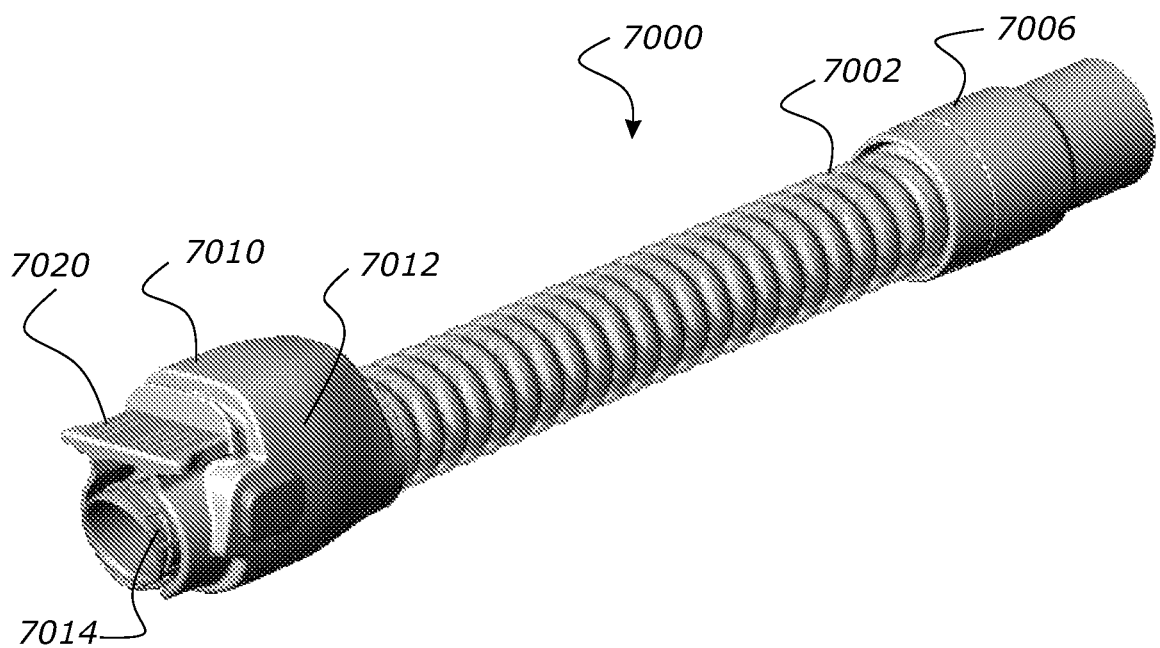

FIG. 184 is a perspective view of a patient breathing conduit arrangement that utilises a T-seal or L-seal.

Figure 185:
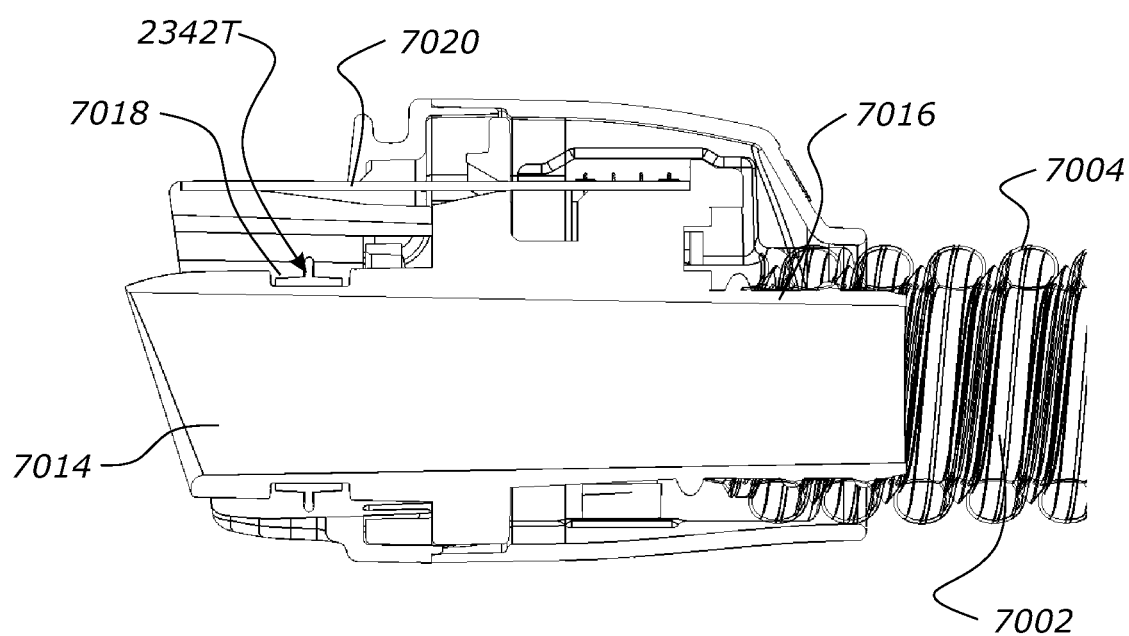

FIG. 185 shows an inner part of a connector of the patient breathing conduit arrangement of FIG. 184.

Figure 186:
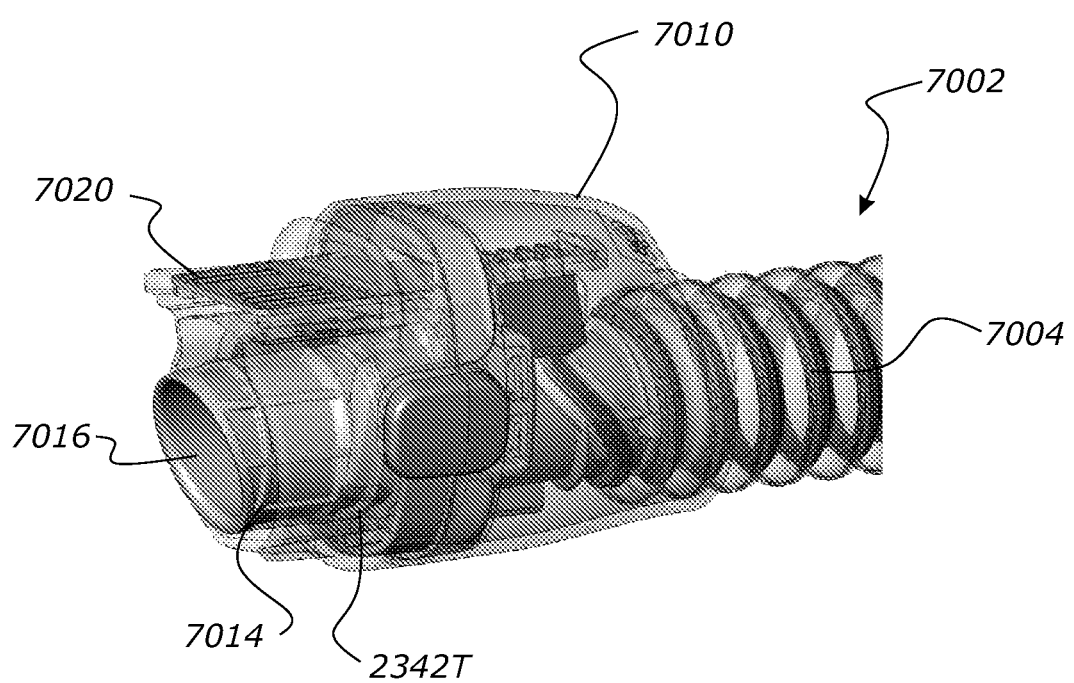

FIG. 186 is a partly transparent view of the connector of the patient breathing conduit arrangement of FIGS. 184 and 185.

DETAILED DESCRIPTION OF SPECIFIC EMBODIMENTS

1. Introduction

Figure 1:
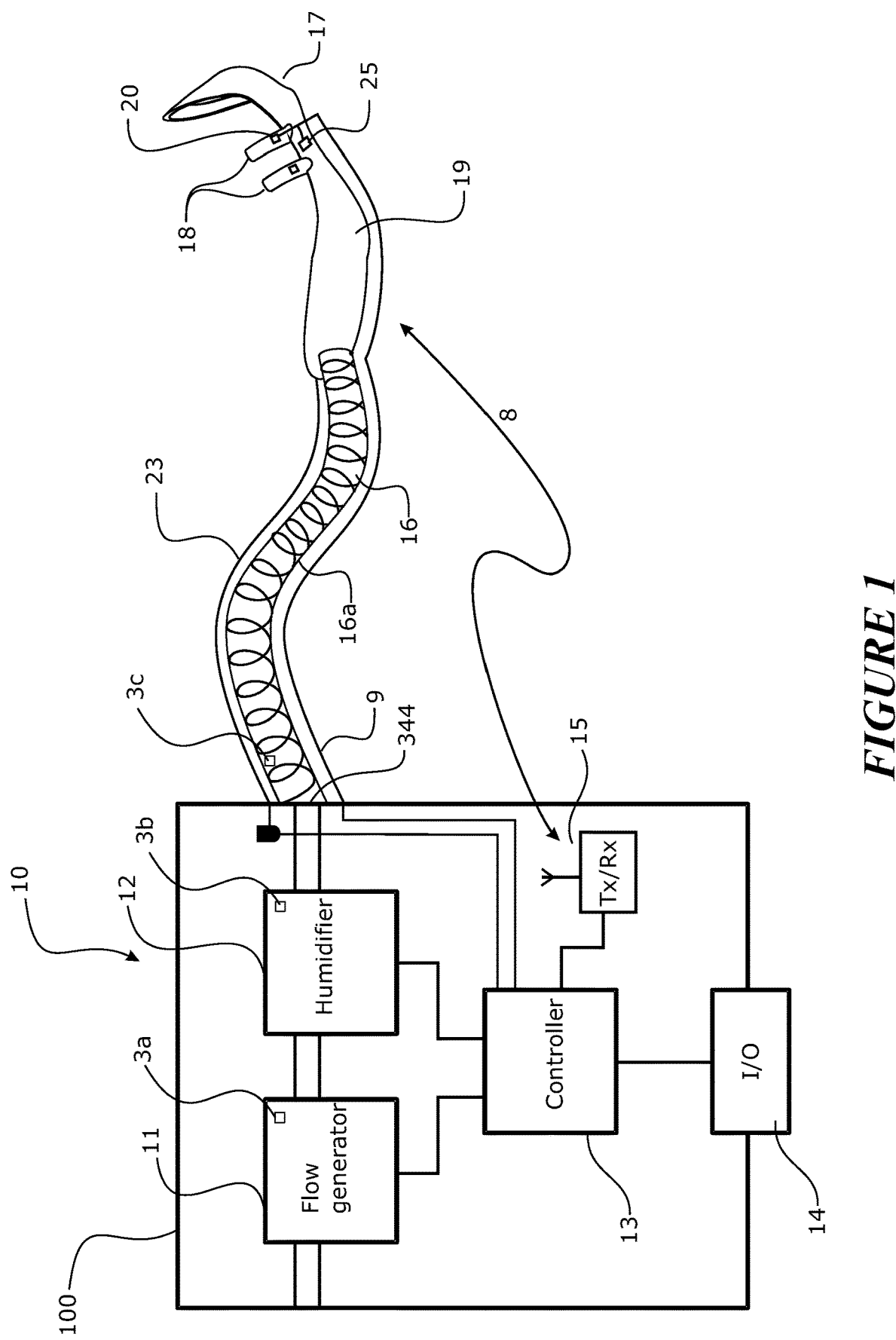
FIG. 1 shows in diagrammatic form a breathing assistance apparatus in the form of a flow therapy apparatus.

A flow therapy apparatus 10 is shown in FIG. 1. In general terms, the apparatus 10 comprises a main housing 100 that contains a flow generator 11 in the form of a motor/impeller arrangement, an optional humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gasflow) for delivery to a patient, operating the humidifier 12 (if present) to humidify and/or heat the generated gasflow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gasflow output 344 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gasflow, which may be humidified, that is generated by the flow therapy apparatus 10 is delivered to the patient via the patient breathing conduit 16 through the cannula 17. The patient breathing conduit 16 can have a heater wire 16a to heat gasflow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms the controller 13 controls the flow generator 11 to generate a gasflow of the desired flow rate, controls one or more valves to control the mix of air and oxygen or other alternative gas, and controls the humidifier 12 if present to humidify the gasflow and/or heat the gasflow to an appropriate level. The gasflow is directed out through the patient breathing conduit 16 and cannula 17 to the patient. The controller 13 can also control a heating element in the humidifier 12 and/or the heating element 16*a* in the patient breathing conduit 16 to heat the gas to a desired temperature that achieves a desired level of therapy and/or comfort for the patient. The controller 13 can be programmed with or can determine a suitable target temperature of the gasflow.

Operation sensors 3*a*, 3*b*, 3*c*, 20, 25 such as flow, temperature, humidity, and/or pressure sensors can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive 8 signals from the sensors and/or to control the various components of the flow therapy apparatus 10, including but not limited to the flow generator 11, humidifier 12, and heater wire 16*a*, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may be any suitable type of apparatus, but in some configurations may deliver a high gasflow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. 'High flow therapy' as used in this disclosure may refer to delivery of gases to a patient at a flow rate of greater than or equal to about 10 liters per minute (10 LPM). In some configurations, 'high flow therapy' may refer to the delivery of gases to a patient at a flow rate of between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

Figure 2:
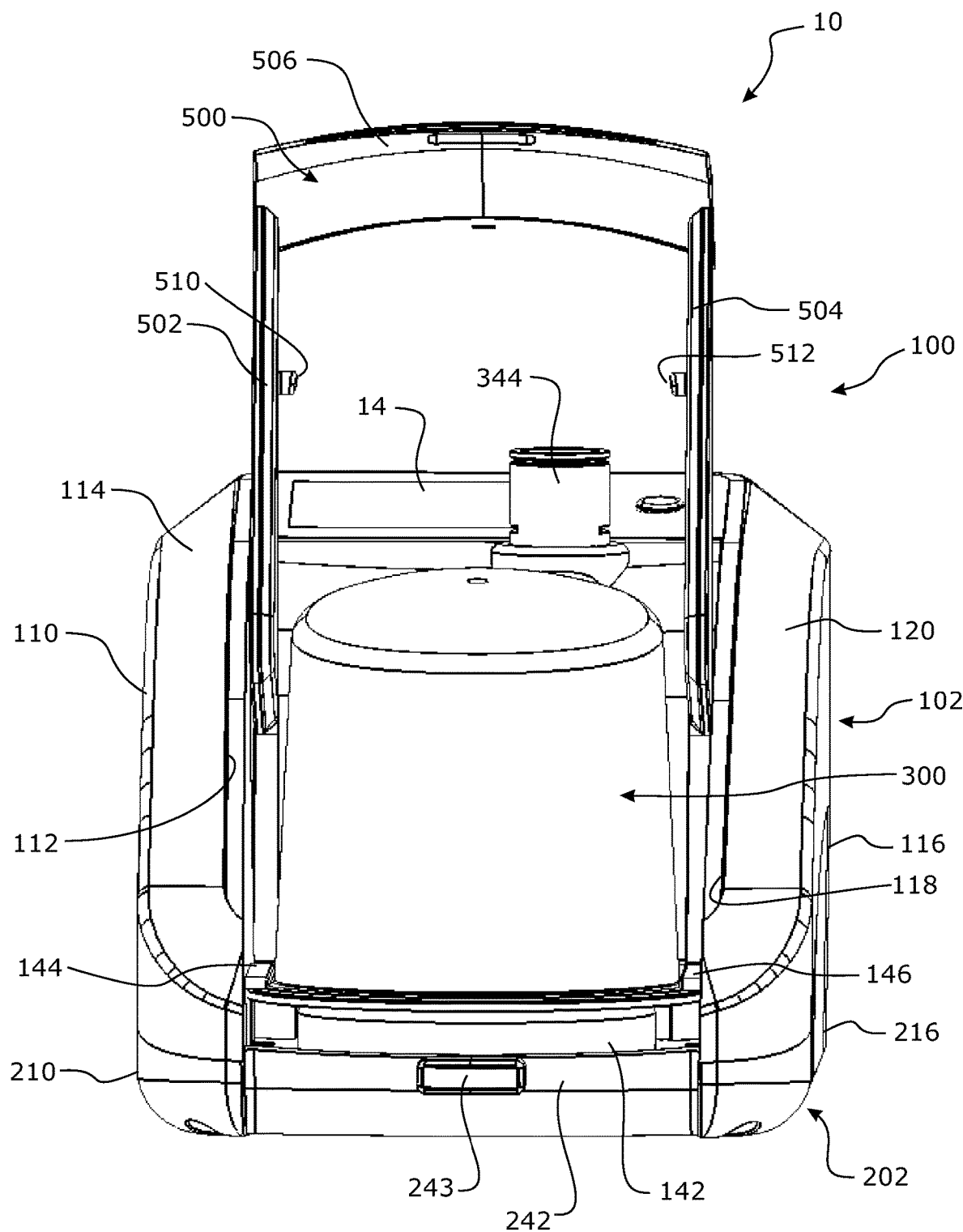
FIG. 2 is a front view of the flow therapy apparatus with a humidifier chamber in position and a raised handle/lever.
Figure 3:
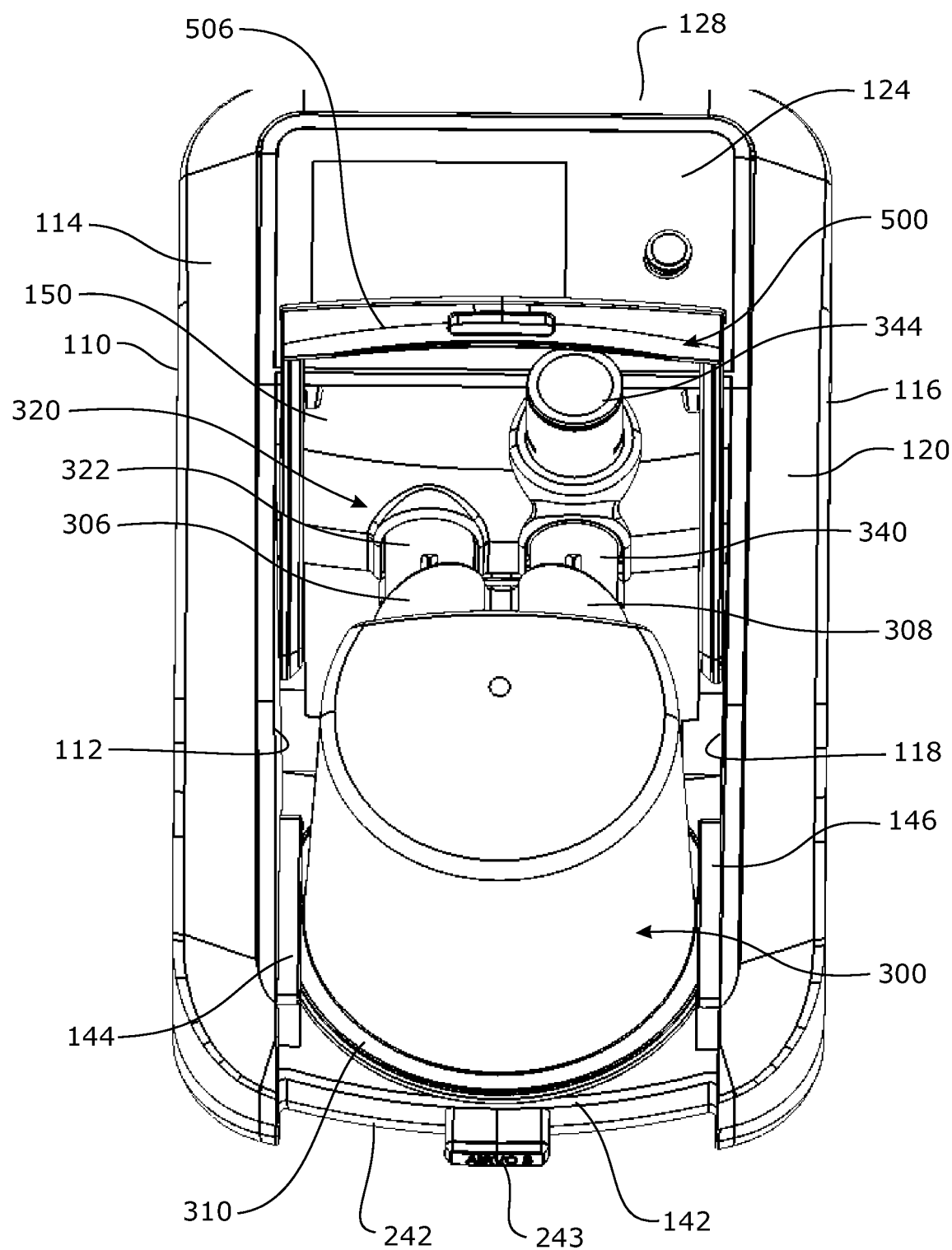
FIG. 3 is a top view corresponding to FIG. 2.
Figure 4:
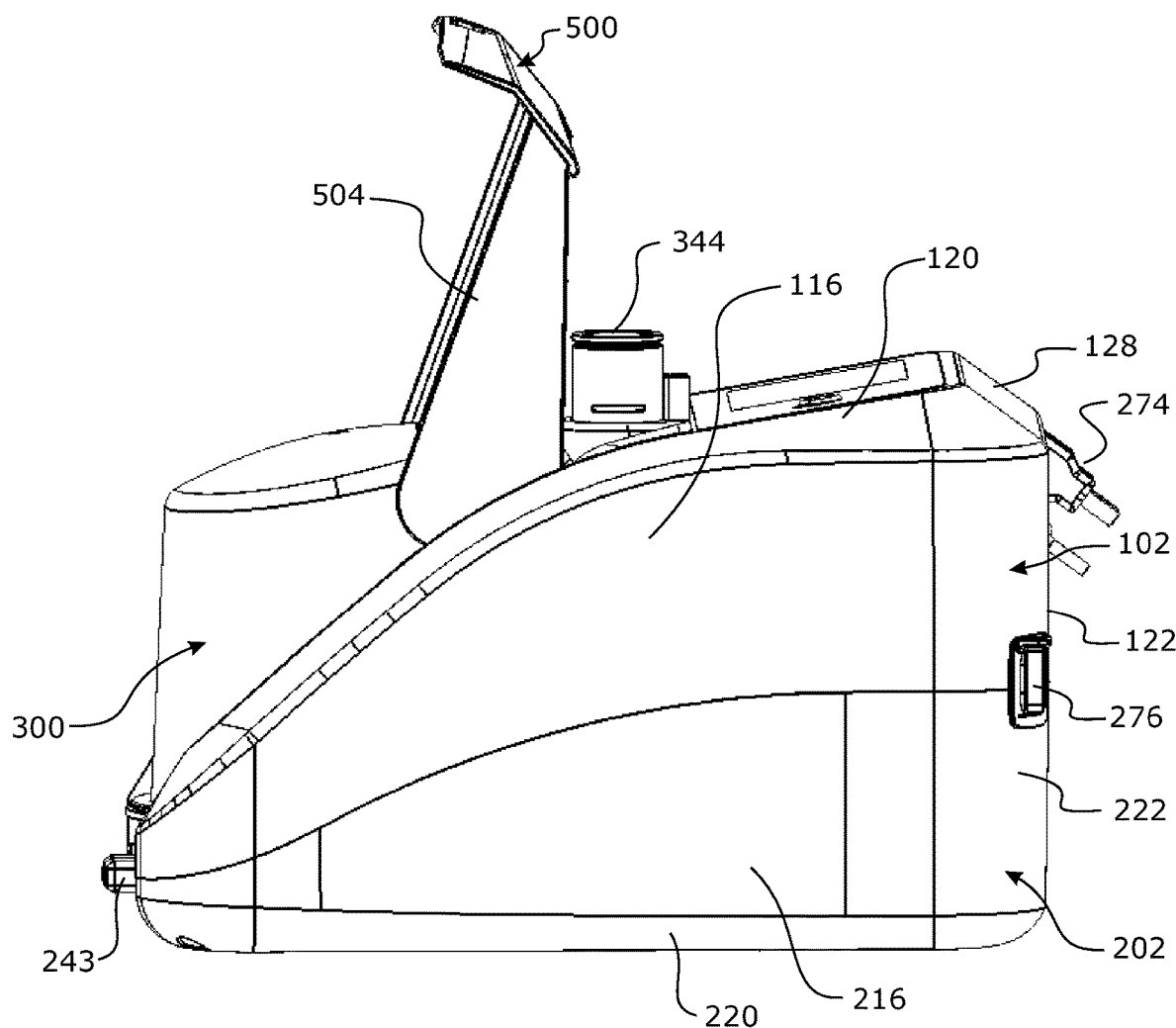
FIG. 4 is a right side view corresponding to FIG. 2.
Figure 5:
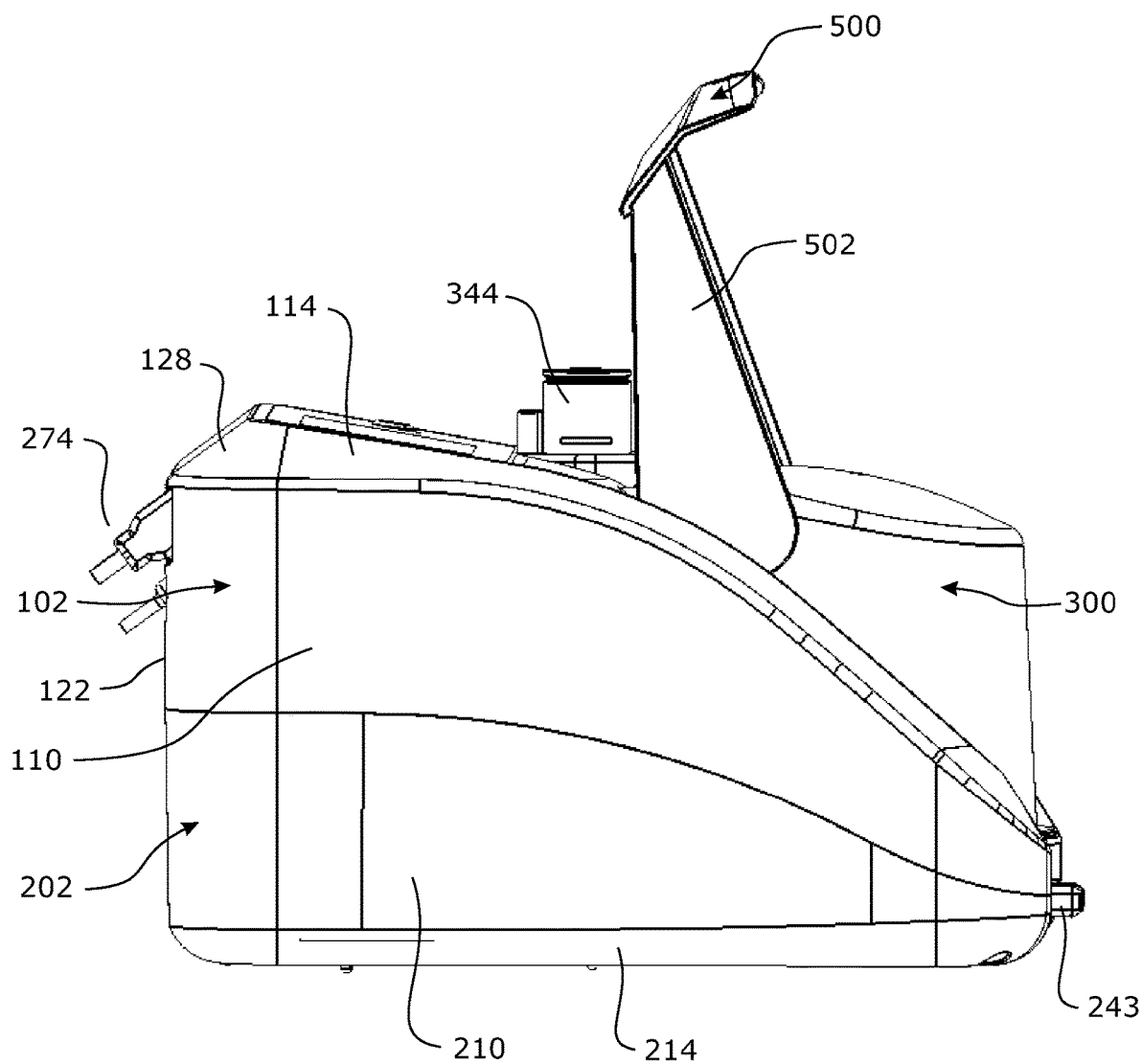
FIG. 5 is a left side view corresponding to FIG. 2.
Figure 6:
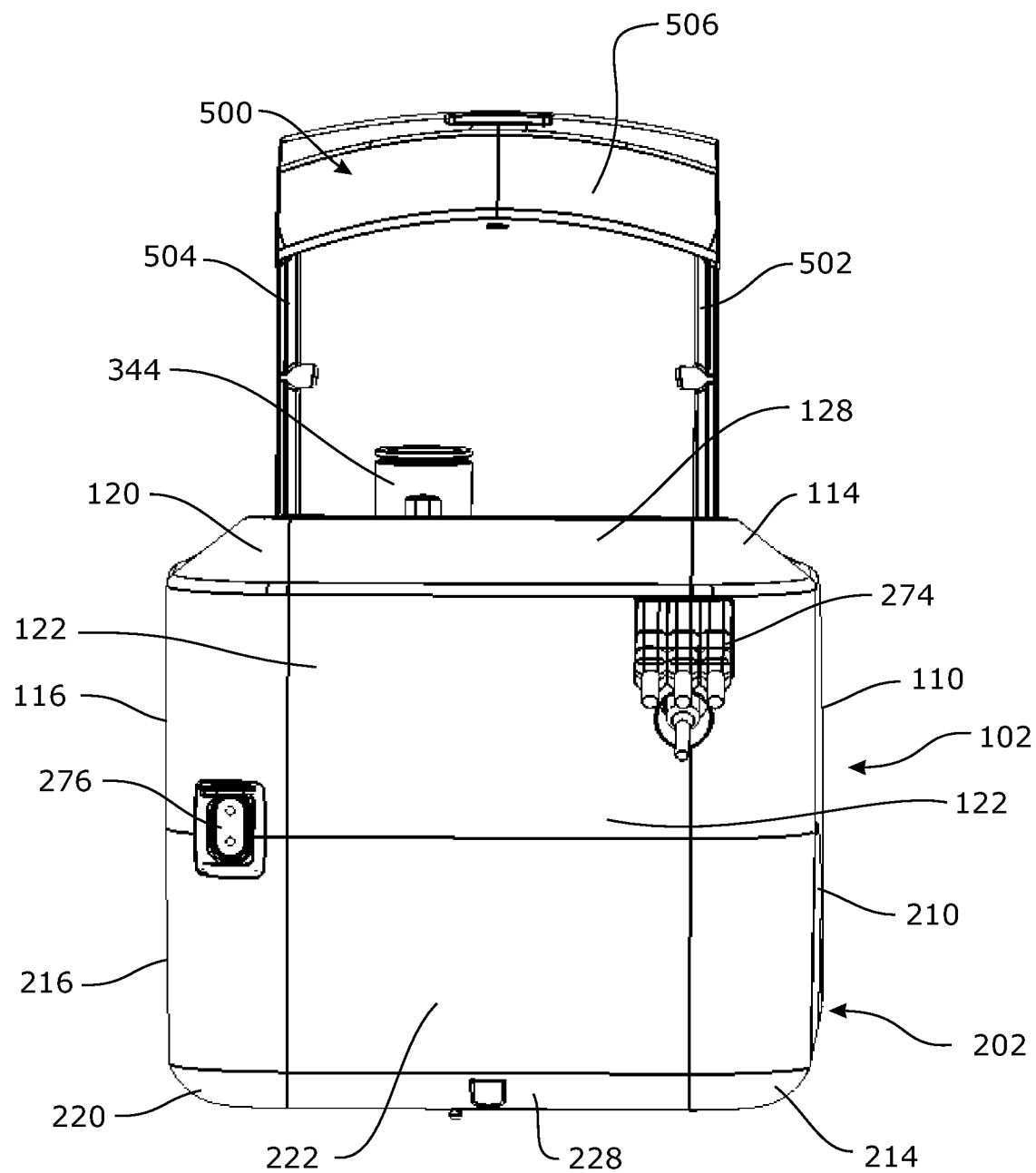
FIG. 6 is a rear view corresponding to FIG. 2.
Figure 7:
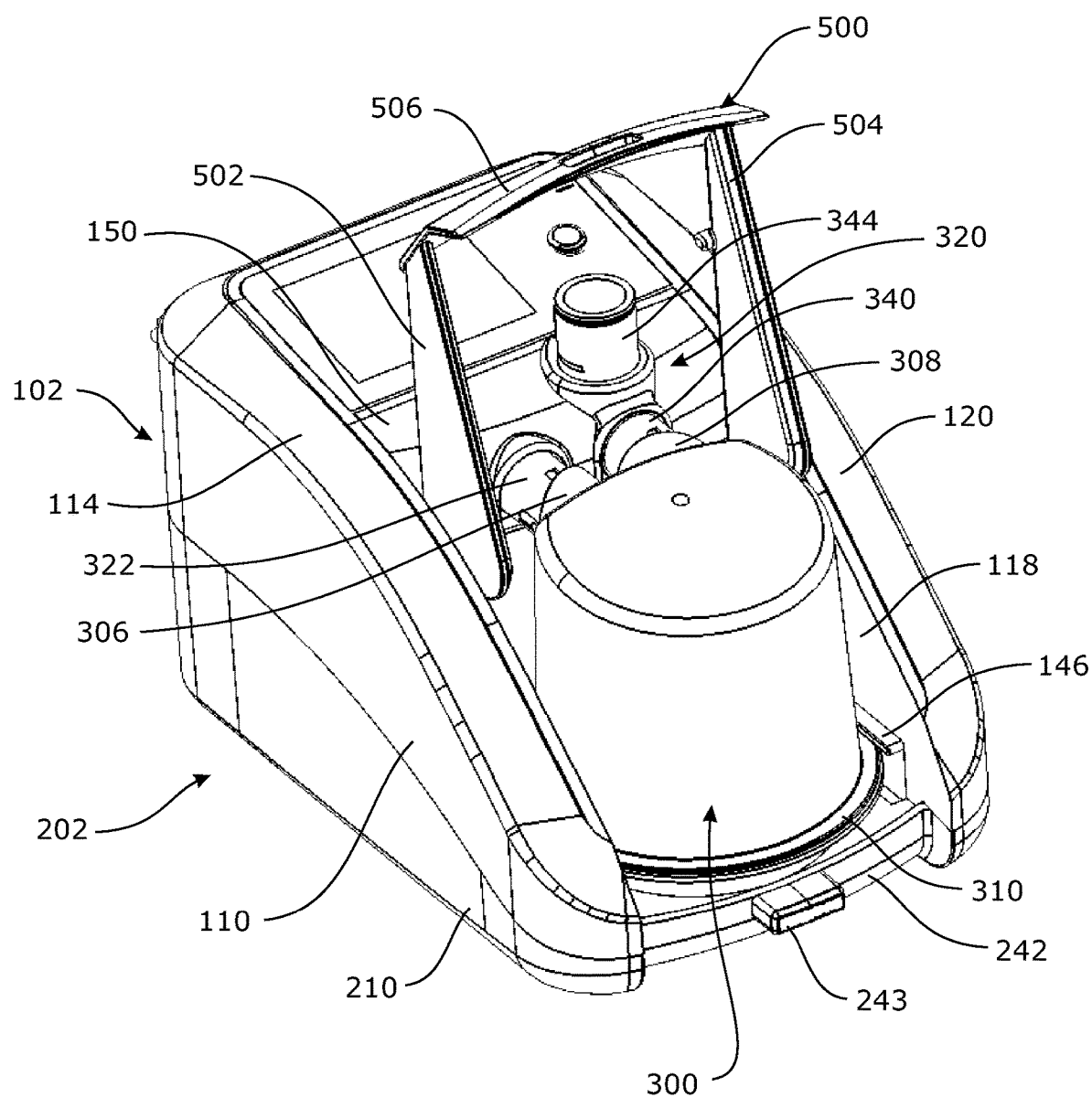
FIG. 7 is a front left perspective view corresponding to FIG. 2.
Figure 8:
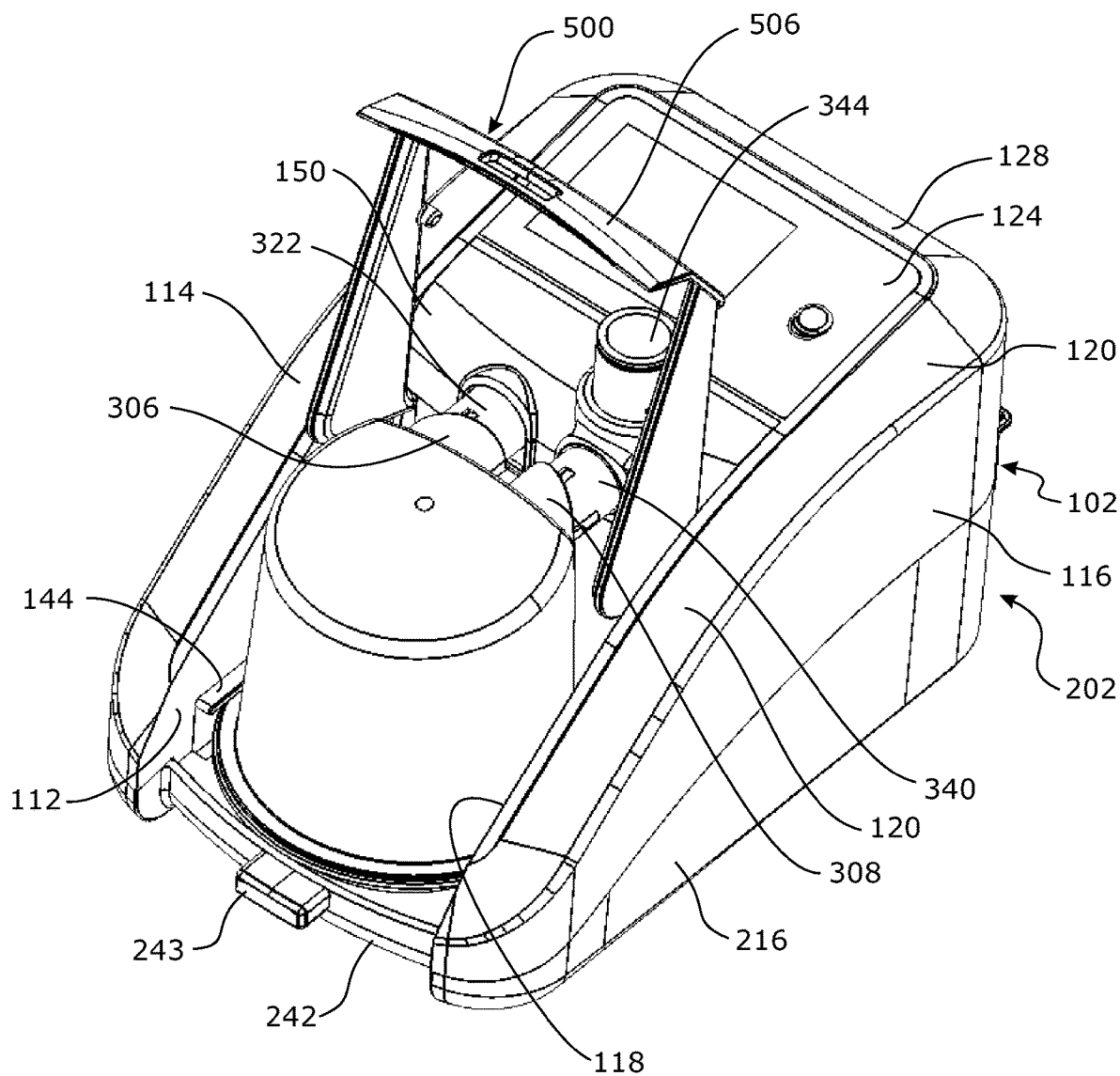
FIG. 8 is a front right perspective view corresponding to FIG. 2.
Figure 9:
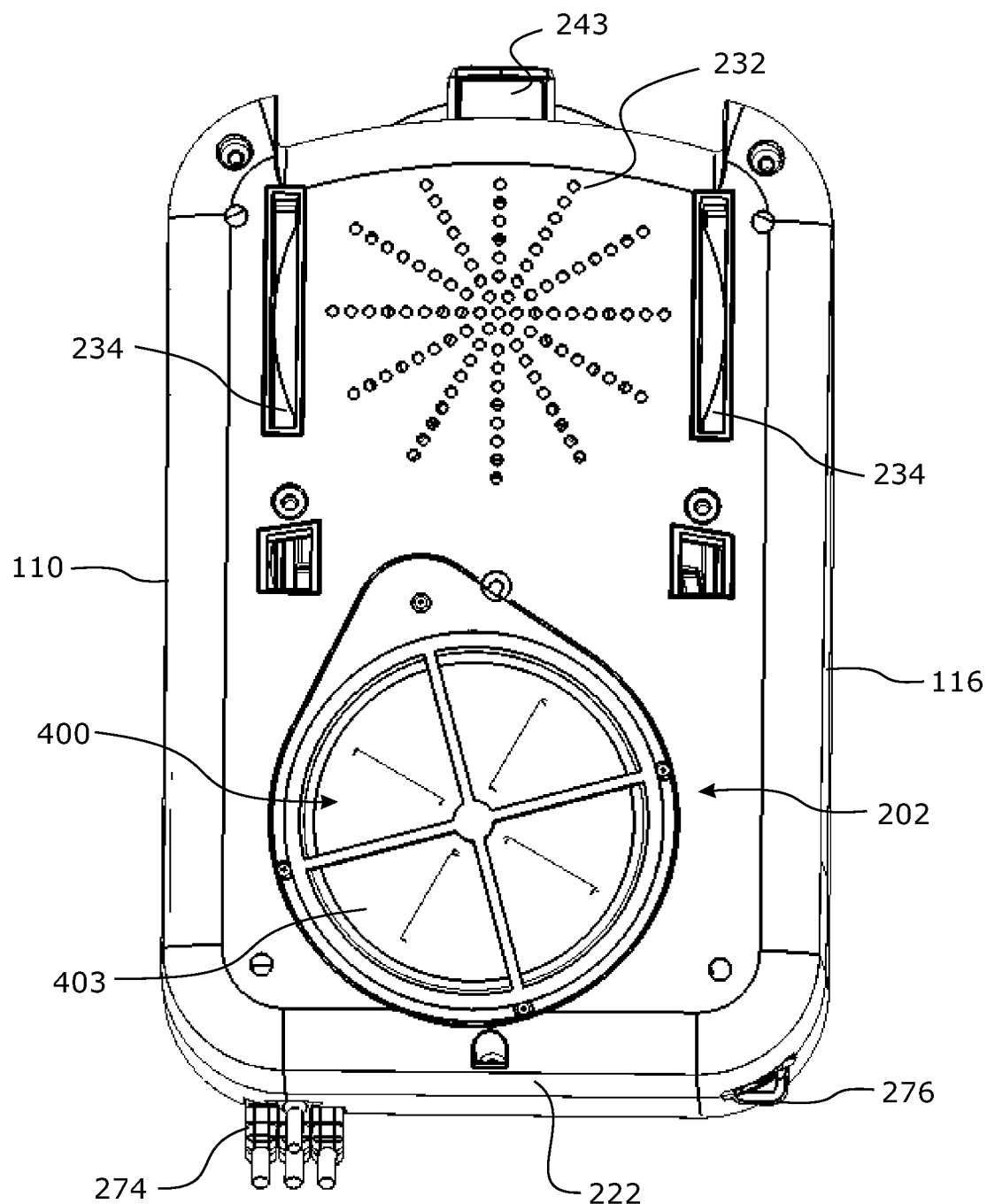
FIG. 9 is a bottom view corresponding to FIG. 2.
Figure 54:
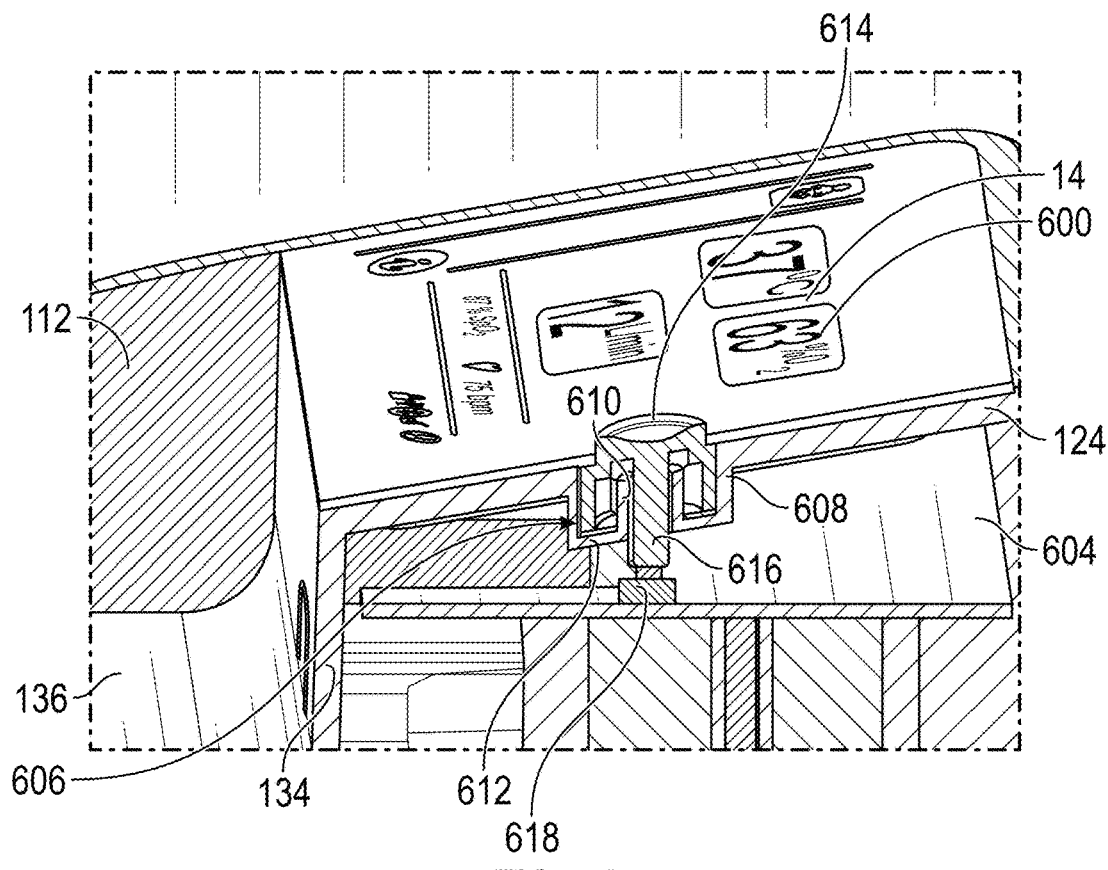
FIG. 54 is a longitudinal sectional view of the user interface display of FIG. 53 showing a button configuration.

As shown in FIGS. 2 to 54 and described below, the flow therapy apparatus 10 has various features to assist with the functioning, use, and/or configuration of the apparatus 10.

2. Overview Including Main Housing Description

As shown in FIGS. 2 to 18, the flow therapy apparatus 10 comprises a main housing 100. The main housing 100 has a main housing upper chassis 102 and a main housing lower chassis 202.

The main housing upper chassis 102 has a peripheral wall arrangement 106. The peripheral wall arrangement defines a humidifier or liquid chamber bay 108 for receipt of a removable liquid chamber 300. The removable liquid chamber 300 contains a suitable liquid such as water for humidifying gases that will be delivered to a patient.

In the form shown, the peripheral wall arrangement 106 of the main housing upper chassis 102 comprises a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 further comprises a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but could alternatively be substantially horizontal or inwardly angled.

The main housing upper chassis 102 further comprises a substantially vertical rear outer wall 122. An upper part of the main housing upper chassis 102 comprises a forwardly angled surface 124. The surface 124 has a recess 126 for receipt of a display and user interface module 14 shown in more detail in FIGS. 53 and 54. An interconnecting wall 128 extends between and interconnects the upper end of the rear outer wall 122 and the rear edge of the surface 124.

A substantially vertical wall portion 130 extends downwardly from a front end of the surface 124. A substantially horizontal wall portion 132 extends forwardly from a lower end of the wall portion 130 to form a ledge. A substantially vertical wall portion 134 extends downwardly from a front end of the wall portion 132 and terminates at a substantially horizontal floor portion 136 of the liquid chamber bay 108. The left side inner wall 112, right side inner wall 118, wall portion 134, and floor portion 136 together define the liquid chamber bay 108. The floor portion 136 of the liquid chamber bay 108 has a recess 138 to receive a heater arrangement such as a heater plate 140 or other suitable heating element(s) for heating liquid in the liquid chamber 300 for use during a humidification process.

The floor portion 136 of the liquid chamber bay 108 terminates short of the front edge of the left side inner wall 112 and the right side inner wall 118 to form a downwardly extending lip 142. The lip 142 forms part of a recess for receiving a handle portion 506 of a lever 500 for use in assisting with insertion of the liquid chamber 300, as will be described further below. The liquid chamber bay 108 further comprises opposed guide features in the form of left side and right side horizontally extending guide rails 144, 146 which extend toward a centre of the bay 108 from the respective left and right side inner walls 112, 118 to assist with guiding the liquid chamber 300 into position in the bay 108 as will be described in detail below.

The main housing lower chassis 202 is attachable to the upper chassis 102, either by suitable fasteners or integrated attachment features such as clips for example. The main housing lower chassis 202 comprises a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 further comprises a substantially vertical rear outer wall 222 that is contiguous with the rear outer wall 122 of the upper chassis 102.

The lower housing chassis 202 has a lip 242 that is contiguous with the lip 142 of the upper housing chassis 102, and also forms part of the recess for receiving the handle portion 506 of the lever 500. The lower lip 242 comprises a forwardly directed protrusion 243 that acts as a retainer for the handle portion 506 of the lever 500.

An underside of the lower housing chassis 202 comprises a bottom wall 230. Respective interconnecting walls 214, 220, 228 extend between and interconnect the substantially vertical walls 210, 216, 222 and the bottom wall 230. The bottom wall 230 comprises a grill 232 comprising a plurality of apertures to enable drainage of liquid in case of leakage from the liquid chamber 300 (e.g. from spills). The bottom wall 230 additionally comprises elongated forward-rearward oriented slots 234. The slots 234 additionally enable drainage of liquid in case of leakage from the liquid chamber 300, without the liquid entering the electronics housing. In the illustrated configuration, the heater plate 140 is not supported by outer portions of the bottom wall 230, and so the slots 234 can be wide and elongate relative to the apertures of the grill 232 to maximize the drainage of liquid.

Figure 19:
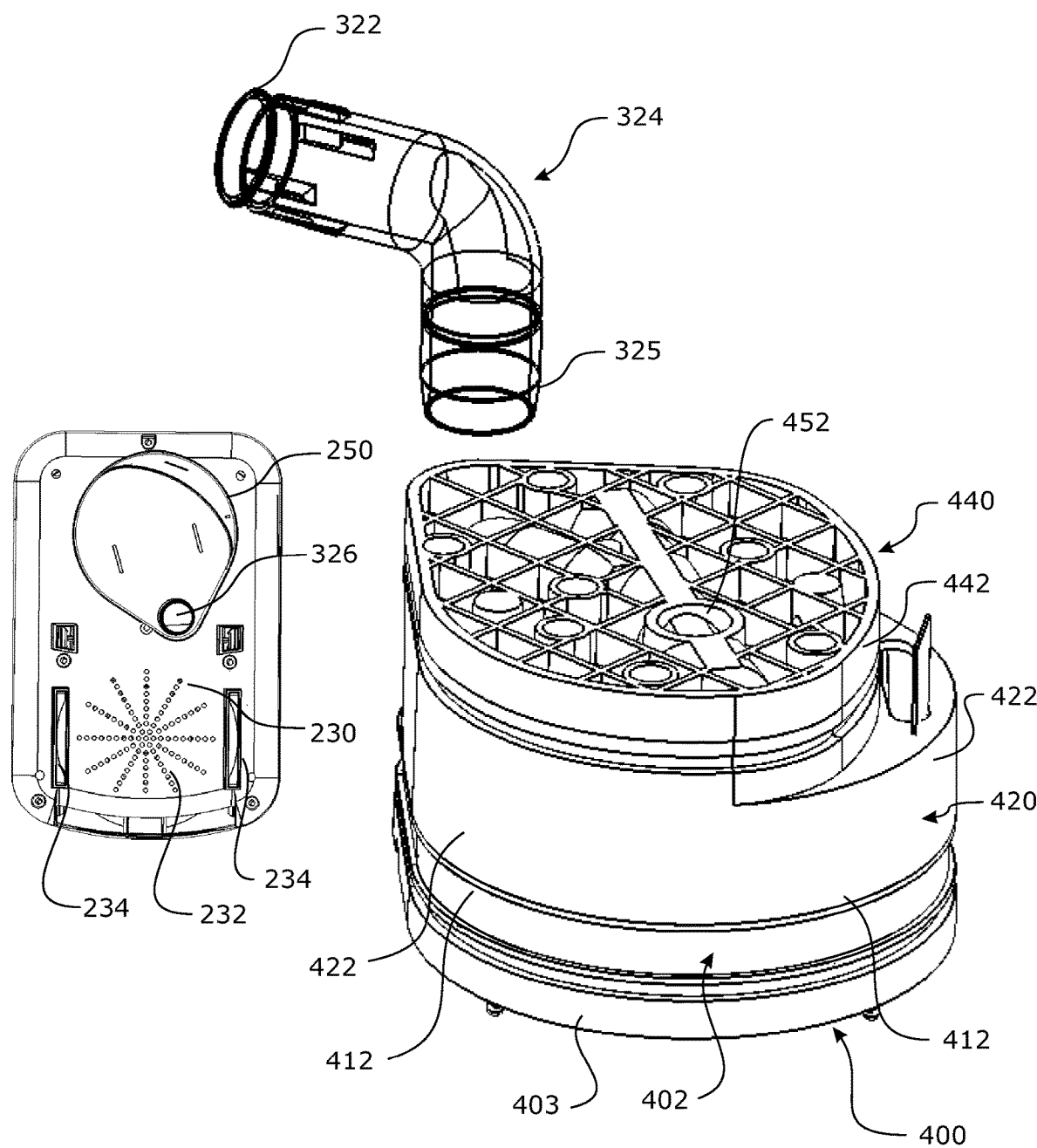
FIG. 19 is a perspective view of the motor and/or sensor sub-assembly, underside of the main housing, and fixed elbow of the flow therapy apparatus.
Figure 20:
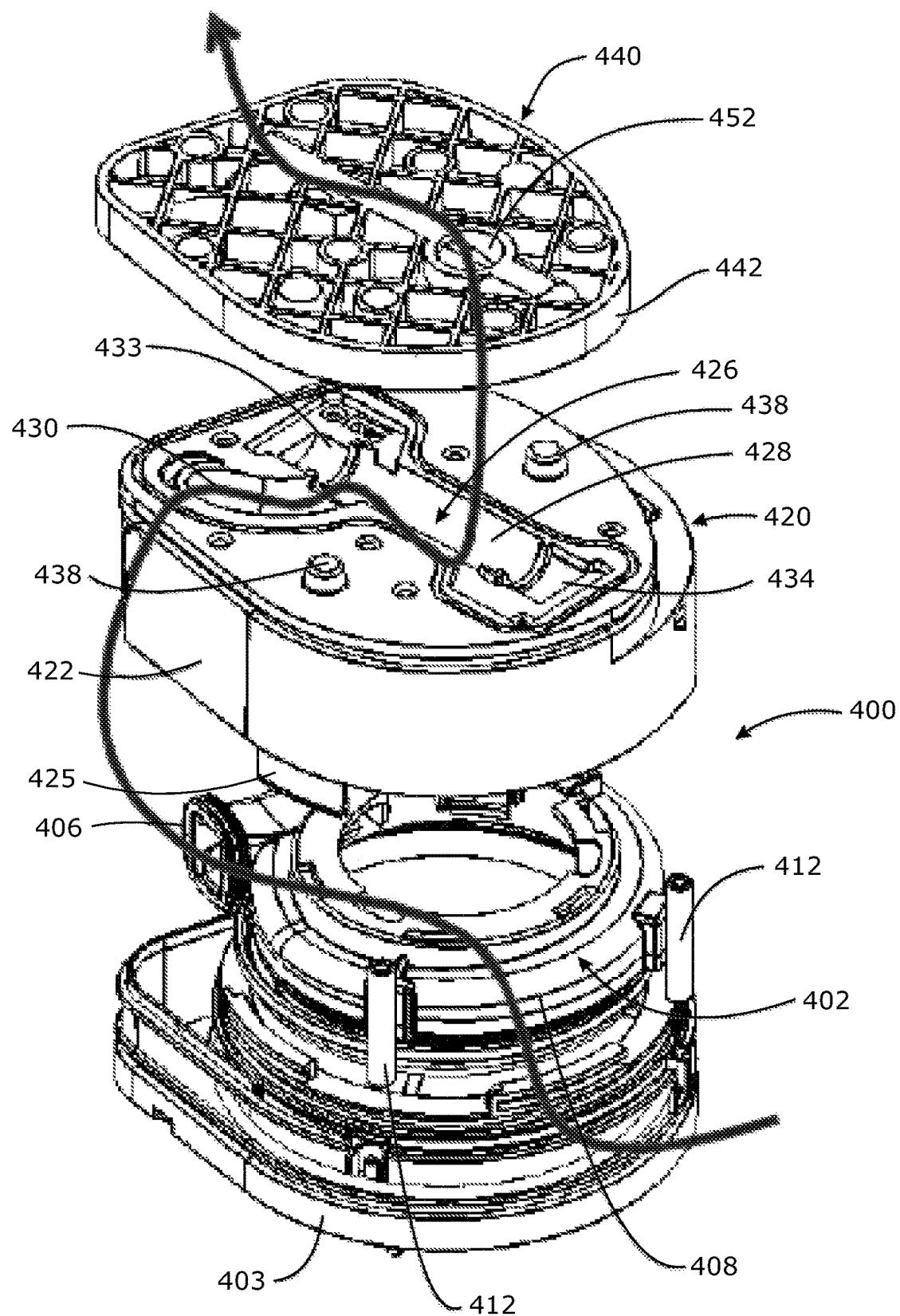
FIG. 20 is an exploded perspective view of components of the motor and/or sensor sub-assembly schematically showing by way of an arrow the gasflow path through the sub-assembly.
Figure 21:
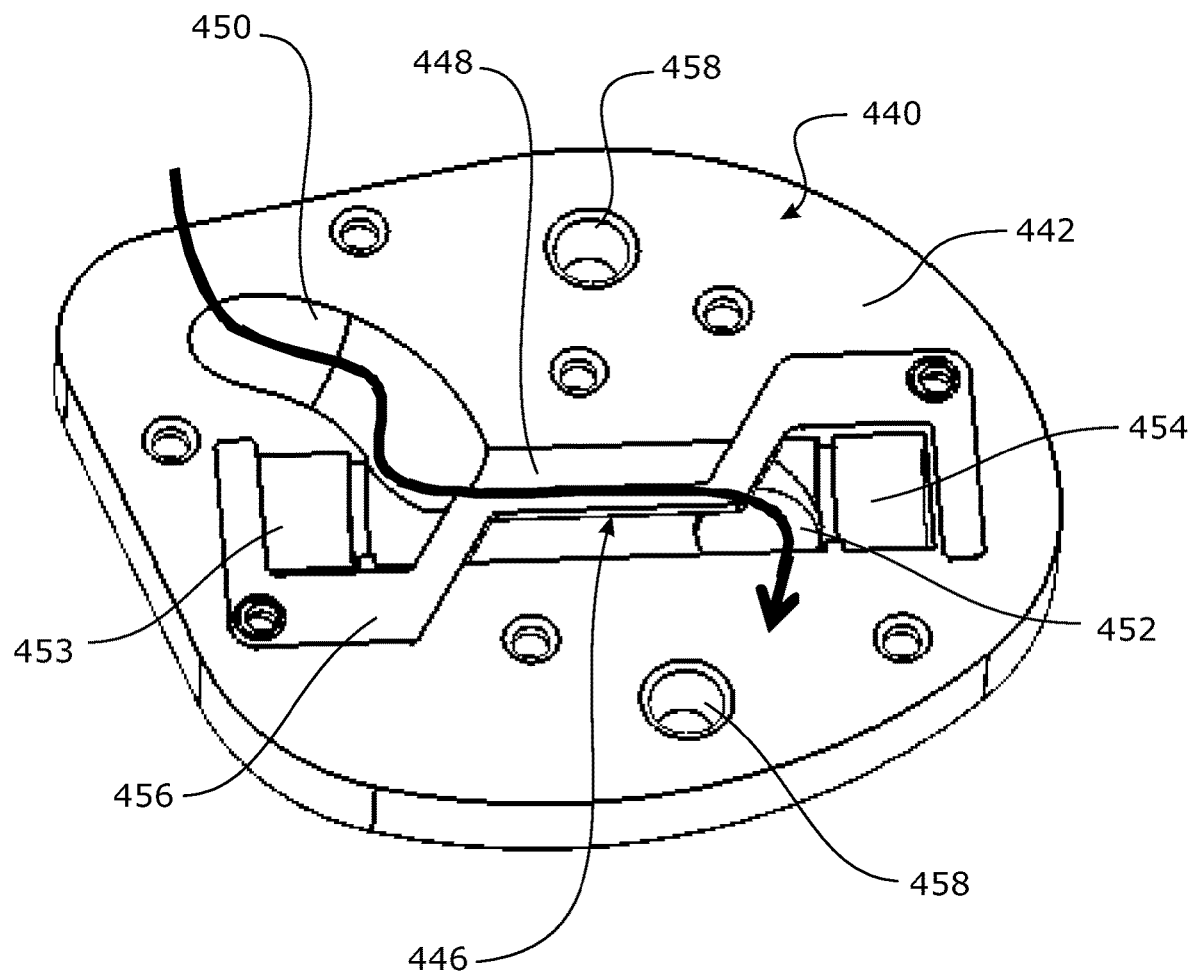
FIG. 21 is an underside view of a cover and sensing PCB of the motor and/or sensor sub-assembly showing the position of sensors.

As shown in FIGS. 17a to 22f, the lower chassis 202 has a motor recess 250 for receipt of a removable motor and/or sensor module 400 which is shown in FIGS. 19 to 21 and will be described in further detail below. A recess opening 251 is provided in the bottom wall 230 adjacent a rear edge thereof, for receipt of a removable motor/sensor module 400 which is shown in FIGS. 19 and 21 and FIGS. 22b to 22f and will be described in further detail below. A continuous, gas impermeable, unbroken peripheral wall 252 is integrally formed with the bottom wall 230 of the lower chassis 202 and extends upwardly from the periphery of the opening 251. A rearward portion 254 of the peripheral wall 252 has a first height, and a forward portion 256 of the peripheral wall 252 has a second height that is greater than the first height. The rearward portion 254 of the peripheral wall 252 terminates at a substantially horizontal step 258, which in turn terminates at an upper auxiliary rearward portion 260 of the peripheral wall 252. The forward portion 256 and upper auxiliary rearward portion 260 of the peripheral wall 252 terminate at a ceiling 262. All of the walls and the ceiling 262 are continuous, gas impermeable, and unbroken other than the gasflow passage. As can be seen most clearly in FIG. 22f, the tube 264 forming the gasflow passage is integrally formed with the ceiling 262, with the ceiling surrounding and extending outwardly from the tube 264. Therefore, the entire motor recess 250 is gas impermeable and unbroken, other than the gasflow passage.

Figure 22A:
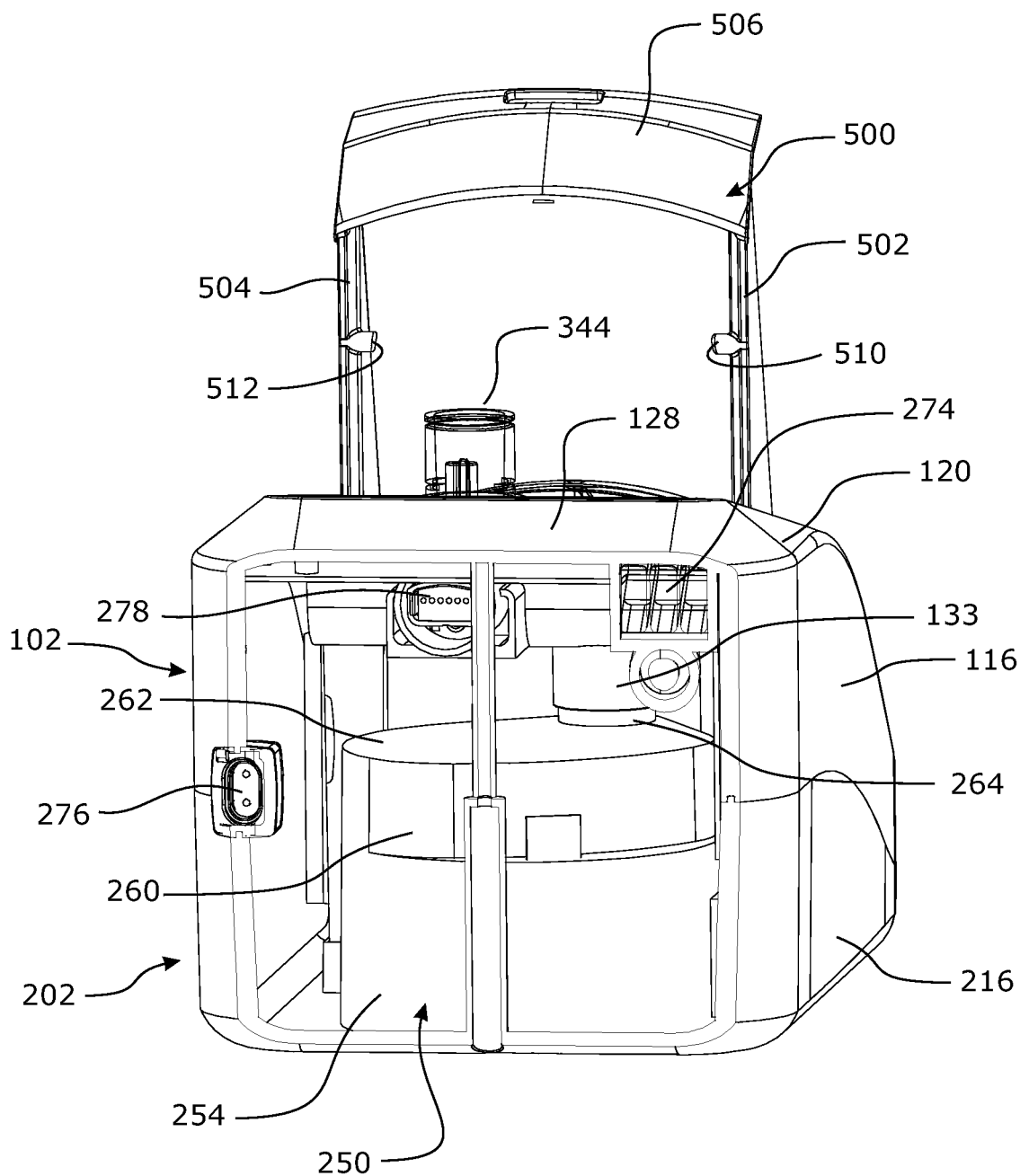
FIG. 22a is a rear perspective view of the flow therapy apparatus sectioned adjacent the rear edge of the apparatus, showing the arrangement of a portion of the main housing that provides the recess for receipt of the motor and/or sensor sub-assembly.
Figure 22B:
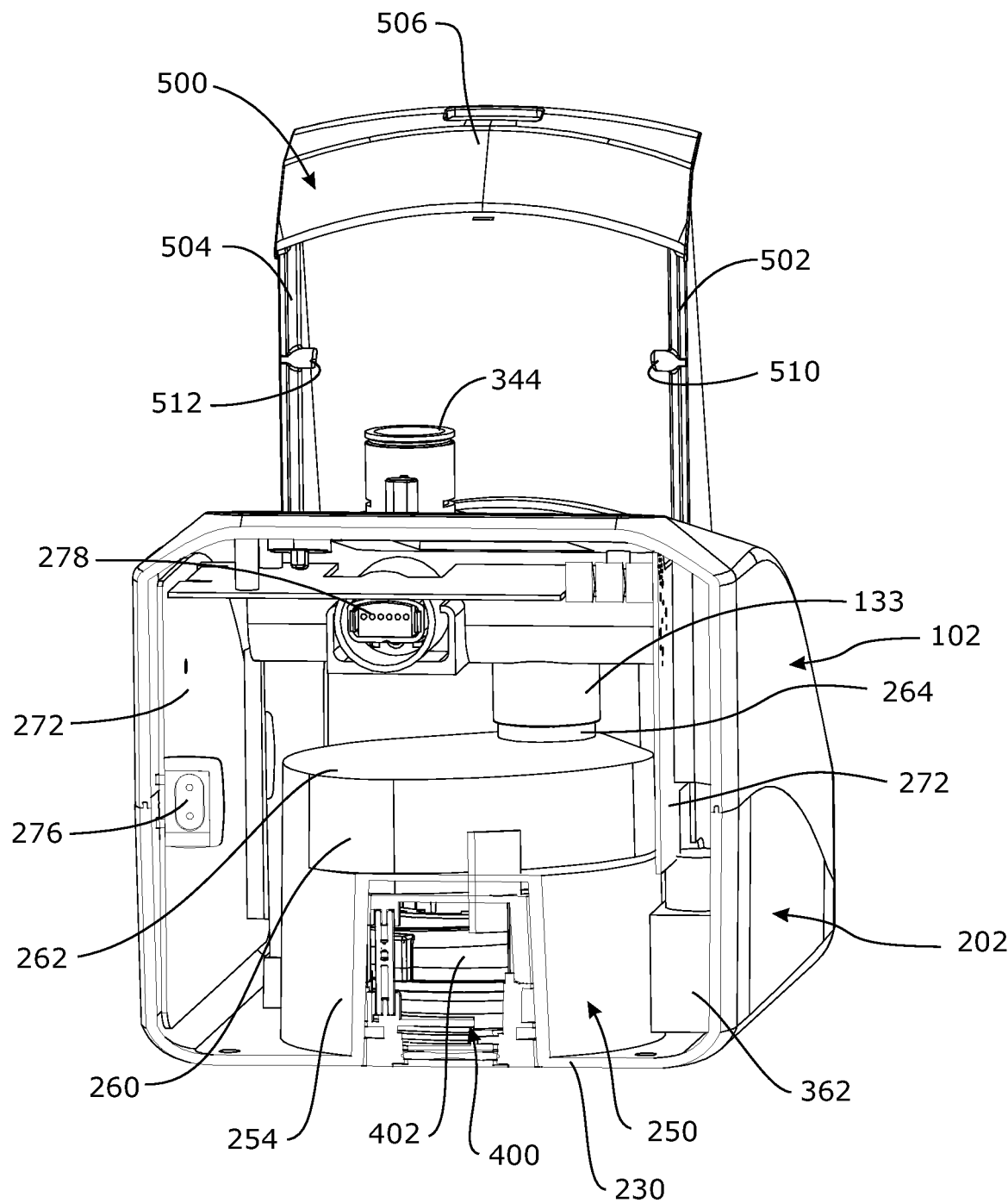
FIG. 22b is a view similar to FIG. 22a but sectioned closer to the front of the apparatus.
Figure 22C:
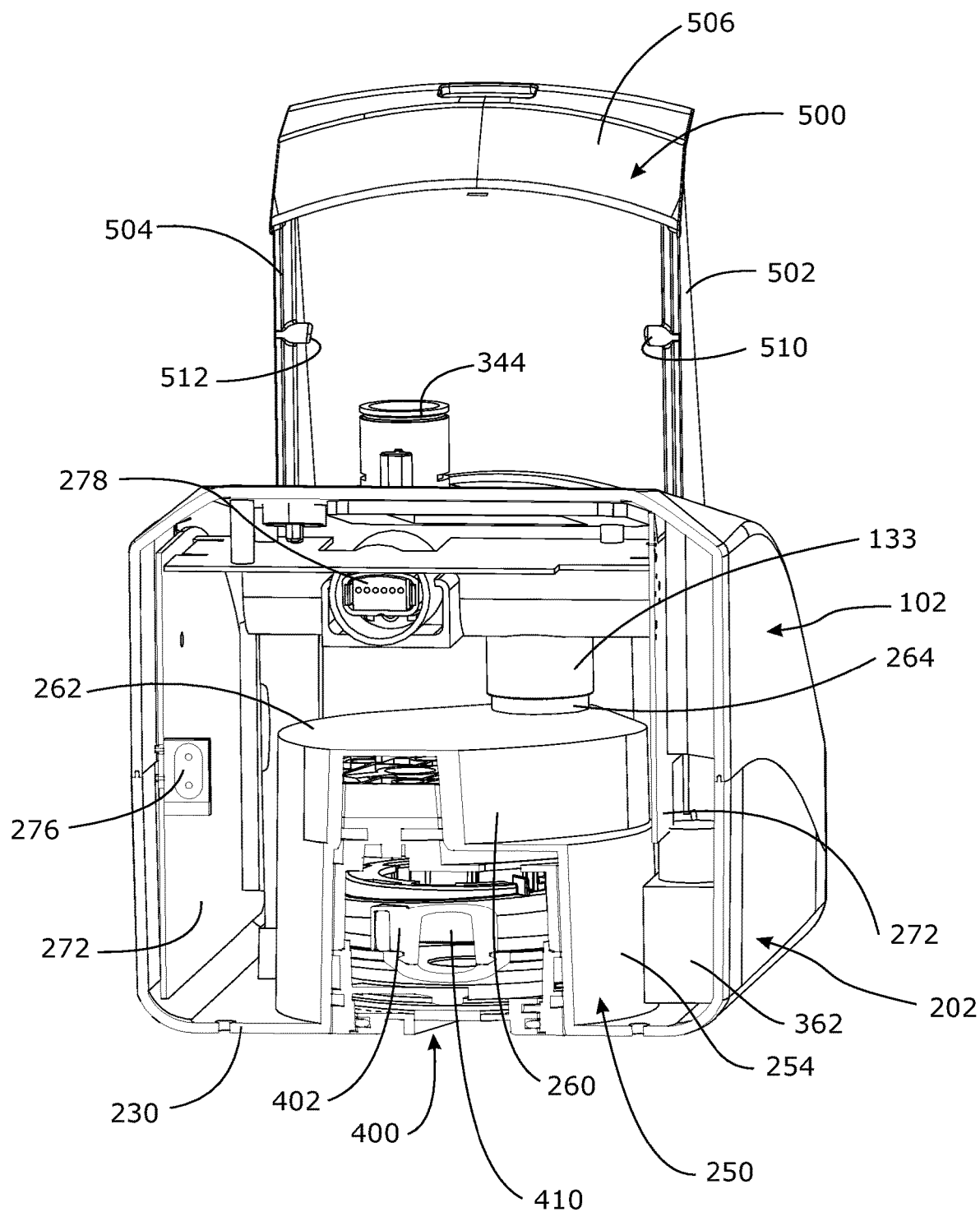
FIG. 22c is a view similar to FIG. 22b but sectioned closer to the front of the apparatus.
Figure 22D:
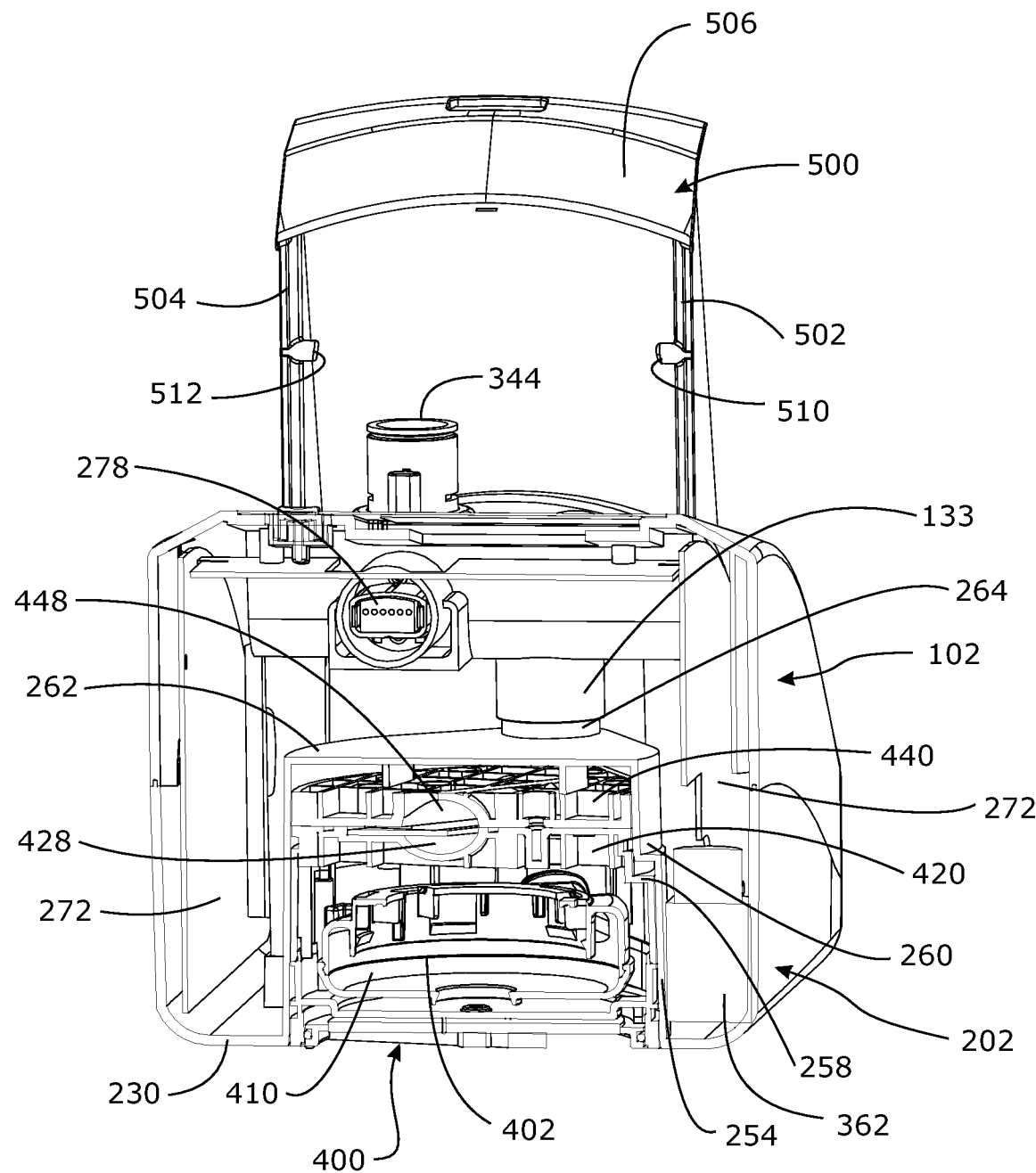
FIG. 22d is a view similar to FIG. 22c but sectioned closer to the front of the apparatus.
Figure 22E:
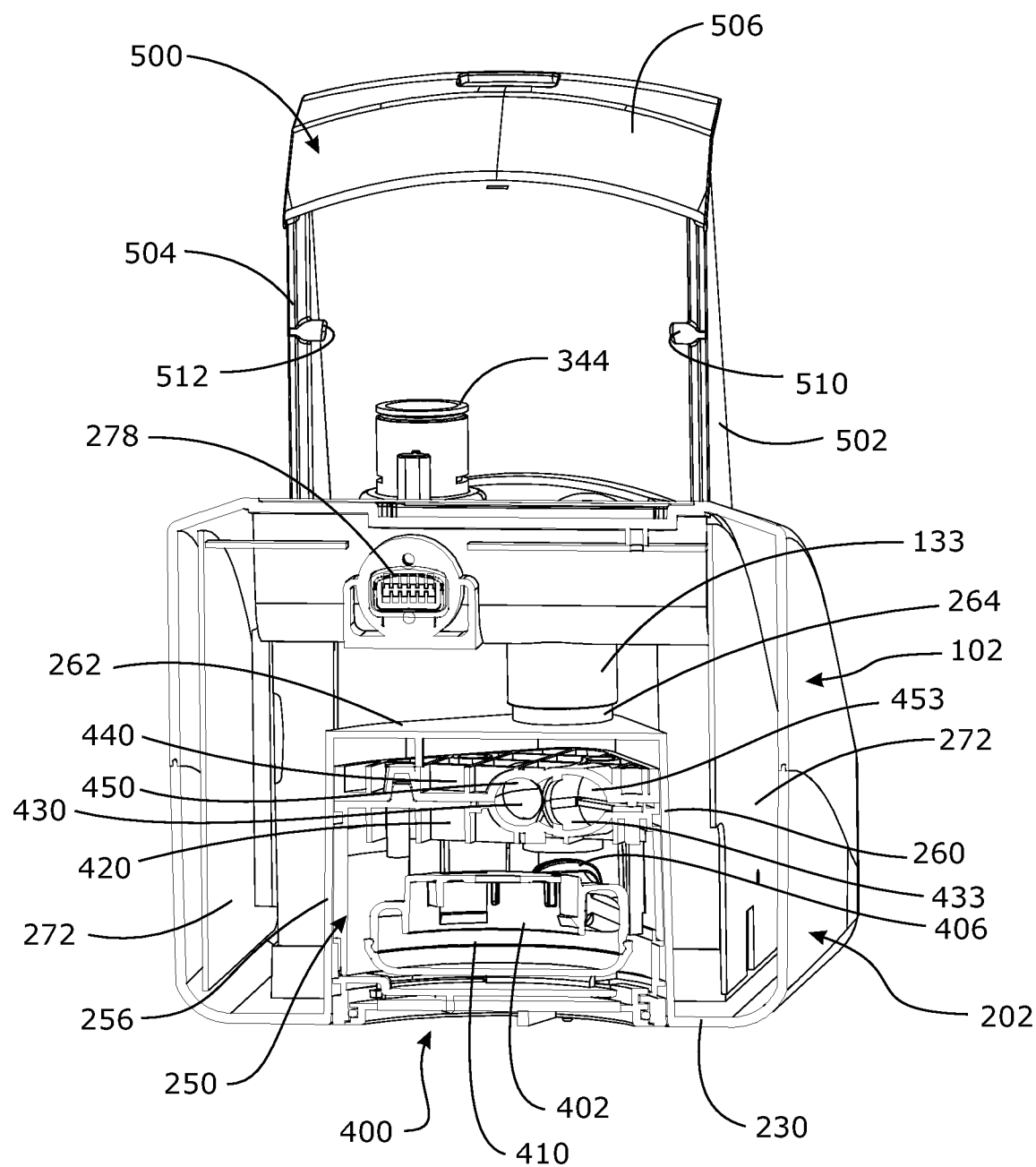
FIG. 22e is a view similar to FIG. 22d but sectioned closer to the front of the apparatus.
Figure 22F:
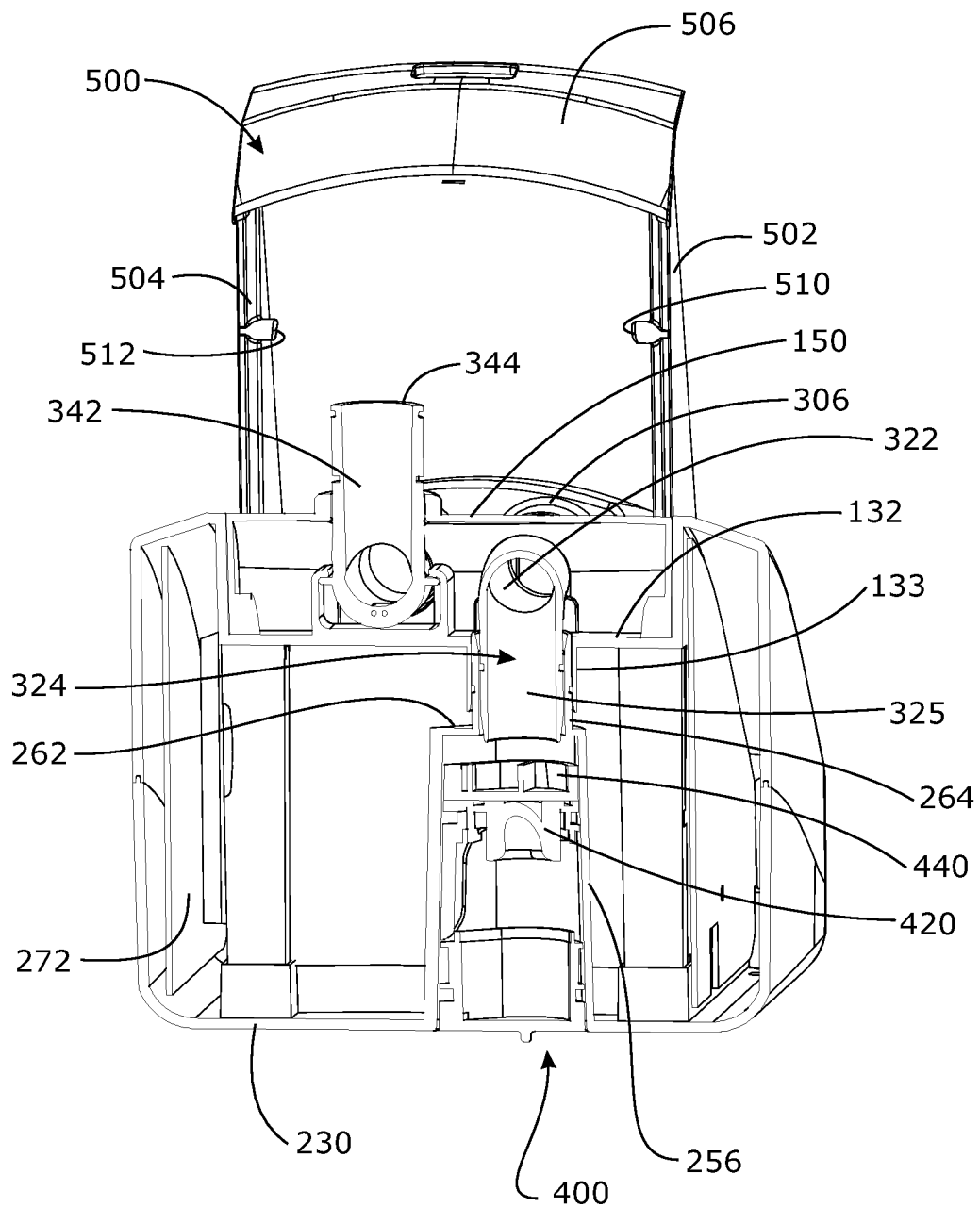
FIG. 22f is a view similar to FIG. 22e but sectioned closer to the front of the apparatus.

As shown in FIG. 22f, the tube 264 forming the gasflow passage extends upwardly through a downward outer extension tube or conduit 133 that is integrally formed with the ledge 132 in the upper housing chassis 102. The tube 264 extends at least as far as the ledge 132, and may extend to a point where it is vertically higher than the ledge 132. A soft seal such as an O-ring seal (not shown) is located between the exterior of the gasflow passage tube 264 and the interior of the downward outer extension tube 133, to provide a seal between the components when assembled. In other configurations, the gasflow passage tube 264 and the downward extension tube 133 could be configured to be fitted together via an interference or press fit arrangement while still providing for a seal between the components when assembled. Still other configurations including but not limited to latch/catch-style fittings and bayonet-style fittings between the gasflow passage tube 264 and the downward extension tube 133 are contemplated. The tube 264 terminates beneath the cover 150 which will be described in further detail below.

The configuration is such that if there is any leaking of gas from the motor or gasflow path following the motor via any seals, the gas will vent to atmosphere rather than ingressing into the interior of the main housing that contains the control boards and other electrical components as described below. The electrical components and electronics boards in the housing are pneumatically isolated from the gasflow path. The only way for gas to leak into the portion of the main housing 100 that contains the electronics boards and other electrical components will be if there is a physical crack in the housing 100 or another physical component. The pressure in the motor of the motor and/or sensor module 400 upstream of the impeller may be lower than the pressure in the portion of the main housing 100 that contains the electrical/electronic components, which also assists with any gas leaks venting to atmosphere.

There will be a pressure drop in the gasflow as it moves through the system due to the formation of gas turbulence and due to friction (e.g. as gas passes along walls defining the gas passages).

If there is a failure (e.g. crack) in the housing defining the motor and/or sensor module 400, the leak (to atmosphere) at the failure would more greatly decrease the pressure of gases downstream (e.g. in the portion of the main housing 100 that contains electrical/electronic components), which mitigates the probability or severity of leak to electrical/electronic components if additional failures are encountered downstream.

In the motor and/or sensor module 400, the pressure is lower before/upstream of the motor impeller, and the pressure is higher after/downstream of the motor impeller. An electrical connection will be provided for the motor upstream of the motor impeller, in the lower pressure region. If there is a failure in the housing in the portion near the electrical connection, air will be sucked into the low pressure side.

In an alternative configuration, the motor recess comprising items 252, 254, 256, 258, 260, 264 may be separately formed from the lower chassis 202. The motor assembly including the recess may be insertable into the recess opening 251 and attachable to the lower chassis 202. Upon insertion of the motor assembly and recess into the lower chassis 202, the gasflow passage tube 264 will extend through the downward extension tube 133 and be sealed by the soft seal.

In the form shown, the recess 250 comprises a recess opening in a bottom wall of the housing. Alternatively, the recess opening could be in a different part of the housing, such as a side, front, or top of the housing.

The described configuration provides a chamber shaped to receive a removable motor and/or sensor module 400 as described below with reference to FIGS. 19 and 20. The interior wall of the recess 250 (including but not limited to portions of the peripheral wall 252) may be provided with guides and/or mounting features to assist with locating and/or attaching the module 400 in the recess 250. The removable motor and/or sensor module 400 is a flow generator and comprises a motor 402 with an impeller that operates as a blower to deliver gases to the patient interface 17 via the liquid chamber 300. It will be appreciated that the shape of the chamber can vary depending on the shape of the motor/sensor module 400. However, the chamber will be provided with continuous, gas impermeable, and unbroken walls and a ceiling to isolate the gasflow from electrical and electronic components in the main housing 100.

Figures 23, 24:
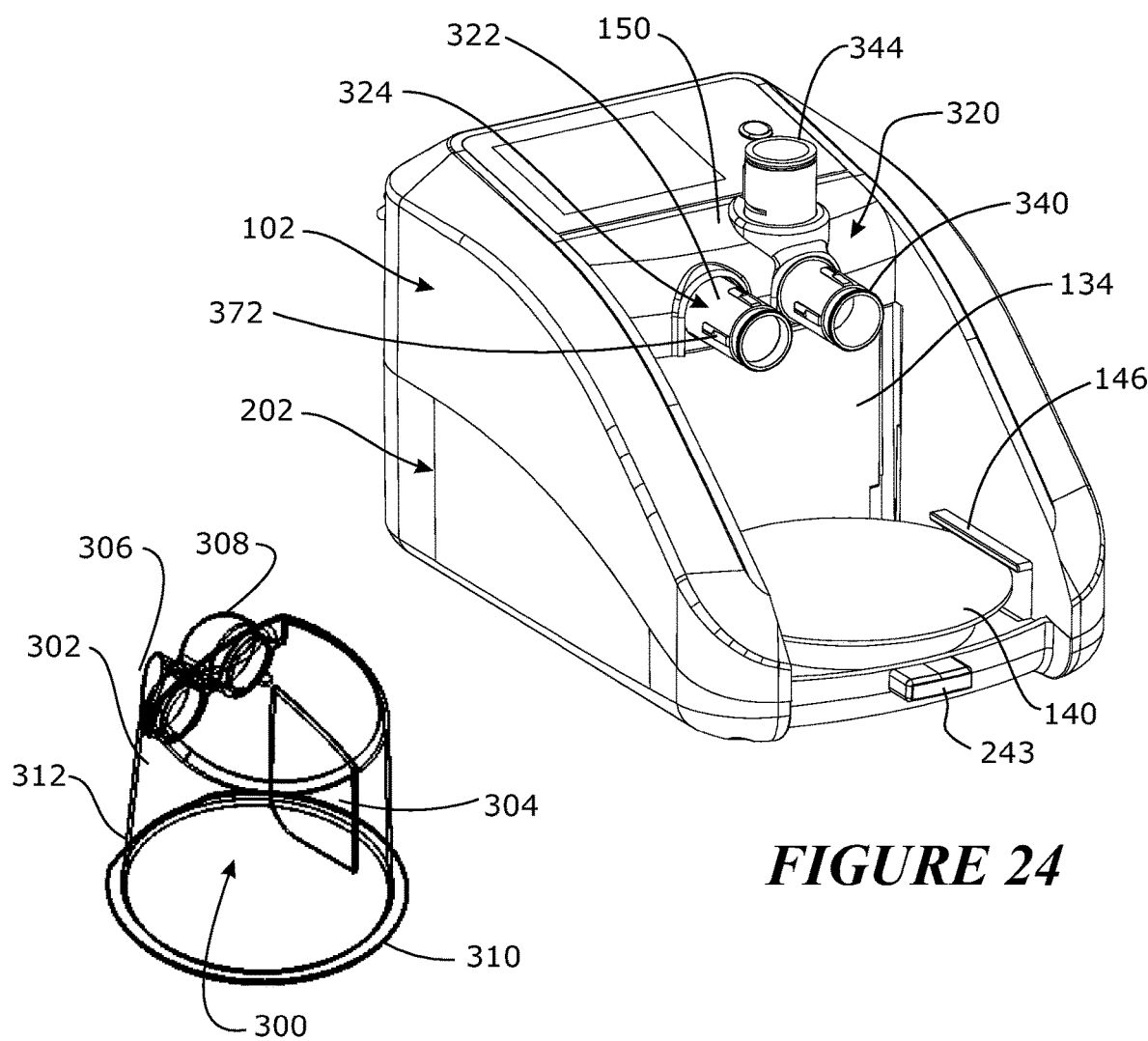
FIG. 23 is a front left side perspective view of a liquid chamber for use in the flow therapy apparatus.
FIG. 24 is a front left side perspective view of some of the components of the flow therapy apparatus.

With reference to FIG. 23, the removable liquid chamber 300 comprises an outer housing 302 defining a liquid reservoir, a liquid chamber gases inlet port 306 in fluid communication with the liquid reservoir, and a liquid chamber gases outlet port 308 in fluid communication with the liquid reservoir. A baffle 304 is provided internally in the liquid reservoir to define a flow path of gases through the liquid chamber 300. A lower edge of the liquid chamber 300 comprises an outwardly directed annular flange 310 which interacts with the guide rails 144, 146 in the chamber bay 108 for locating and retaining the liquid chamber 300 in the chamber bay 108. The flange 310 extends outwardly from the base of a peripheral wall 312 of the liquid chamber 300. A bottom wall of the liquid chamber 300 is heat conducting and is adapted for resting on the heater plate 140 for heating liquid in the liquid chamber 300.

The apparatus 10 comprises a connection manifold arrangement 320 for fluid coupling of the liquid chamber 300 to the apparatus 10. The liquid chamber 300 can be fluidly coupled to the apparatus 10 in a linear slide-on motion in a rearward direction of the liquid chamber 300 into the chamber bay 108, from a position at the front of the housing 100 in a direction toward the rear of the housing 100. The connection manifold arrangement 320 comprises a manifold gases outlet port 322 that is in fluid communication, via a fixed L shaped elbow 324, with the gasflow passage from the motor/impeller unit 402. As shown in FIG. 22*f*, the lower portion 325 of the elbow 324 that forms a gasflow inlet port of the elbow extends downwardly into the interior of the gasflow passage tube 264, preferably to a position below the lower end of the gasflow passage tube 264. A soft seal such as an O-ring seal is provided between the exterior of the lower portion 325 and the interior of the gasflow passage tube 264 to seal between those components.

The connection manifold arrangement 320 further comprises a manifold gases inlet port 340 (humidified gases return) that is embodied in a removable elbow 342. The removable elbow 342 is L-shaped, and further comprises a patient outlet port 344 for coupling to the patient breathing conduit 16 to deliver gases to the patient interface 17. The manifold gases outlet port 322, manifold gases inlet port 340, and patient outlet port 344 each comprise soft seals such as O-ring seals (not shown) to provide a sealed gases passageway between the apparatus 10, the liquid chamber 300, and the patient breathing conduit 16.

The liquid chamber gases inlet port 306 is complementary with the connection manifold gases outlet port 322, and the liquid chamber gases outlet port 308 is complementary with the connection manifold gases inlet port 340. The axes of those ports are preferably parallel to enable the liquid chamber 300 to be inserted into the chamber bay 108 in a linear movement.

Figure 10:
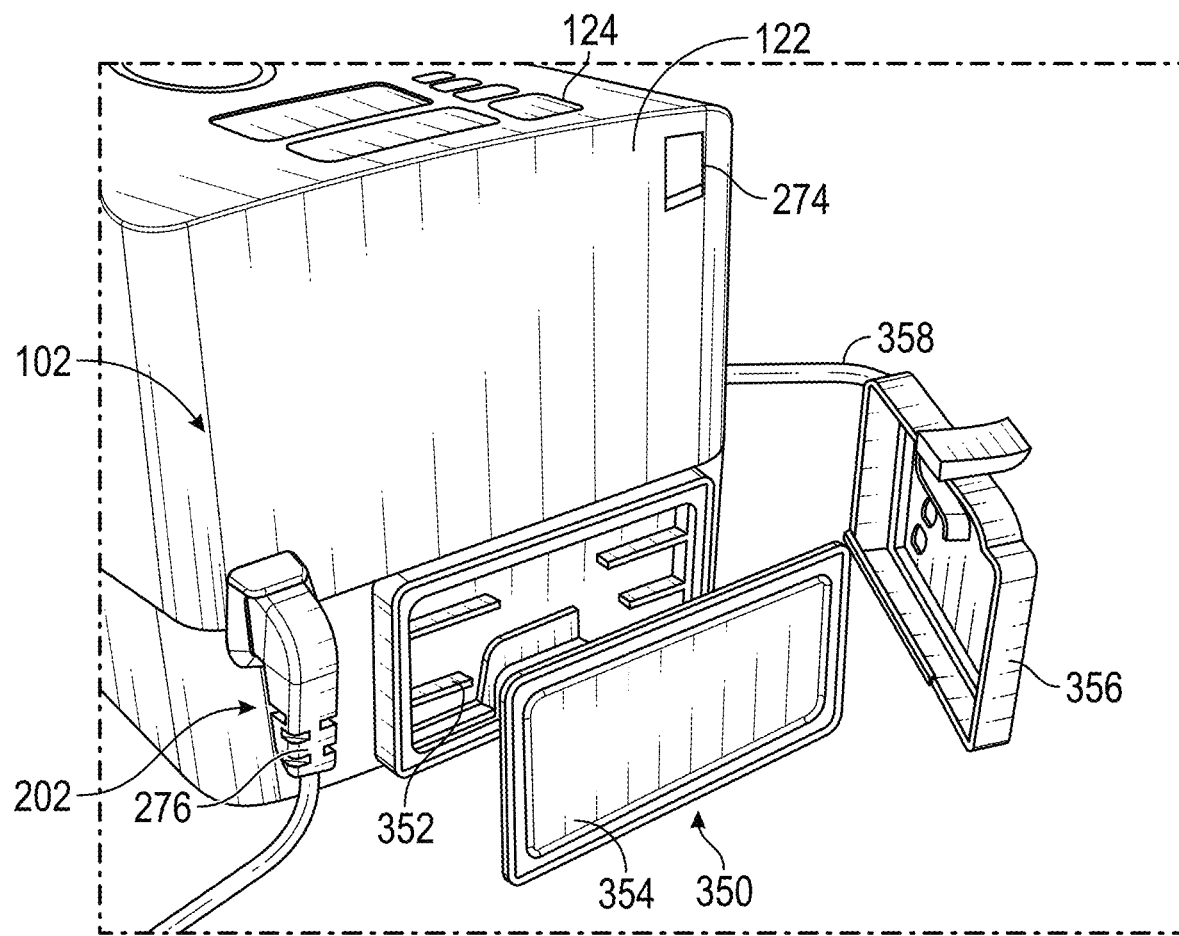
FIG. 10 shows a first configuration of an air and oxygen inlet arrangement of the flow therapy apparatus.
Figure 11:
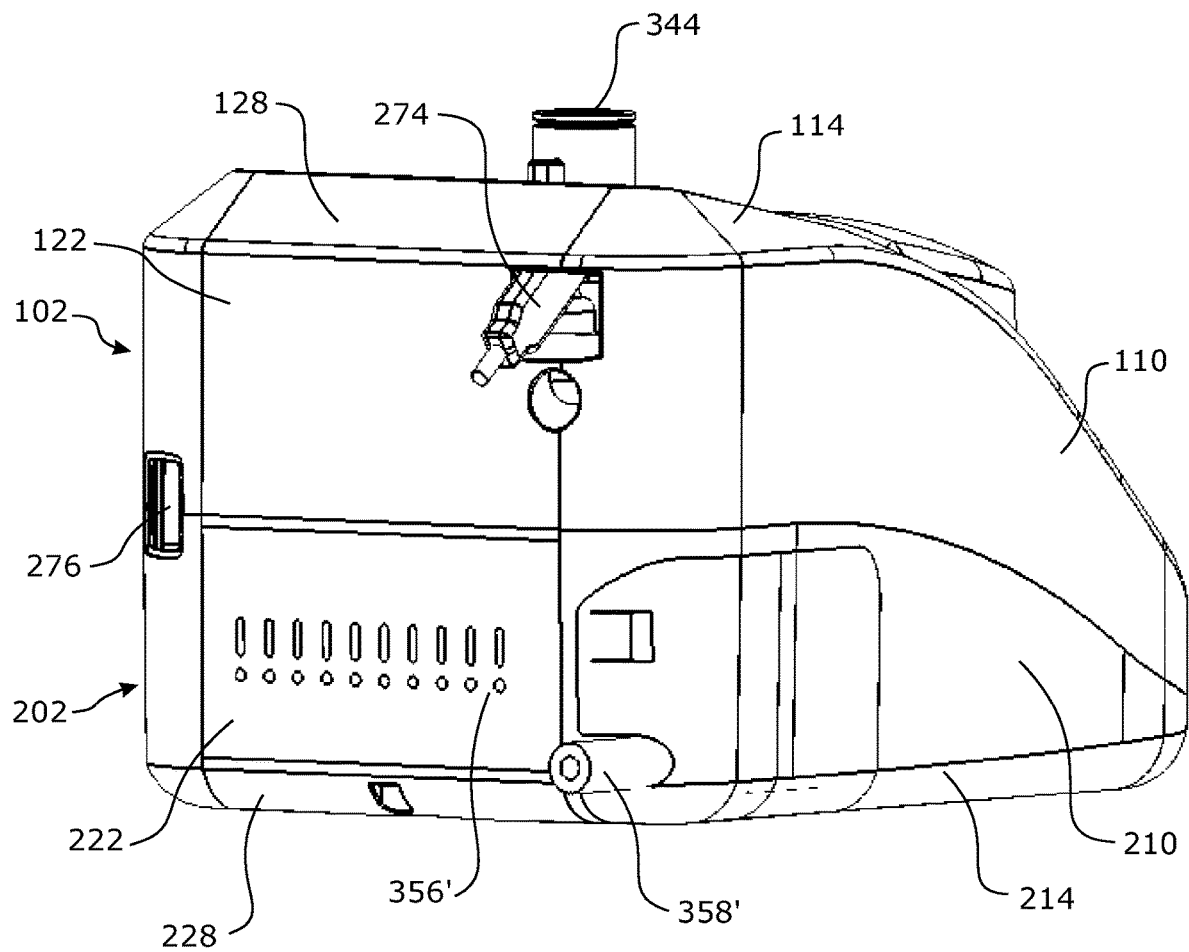
FIG. 11 shows a second configuration of an air and oxygen inlet arrangement of the flow therapy apparatus.
Figure 12:
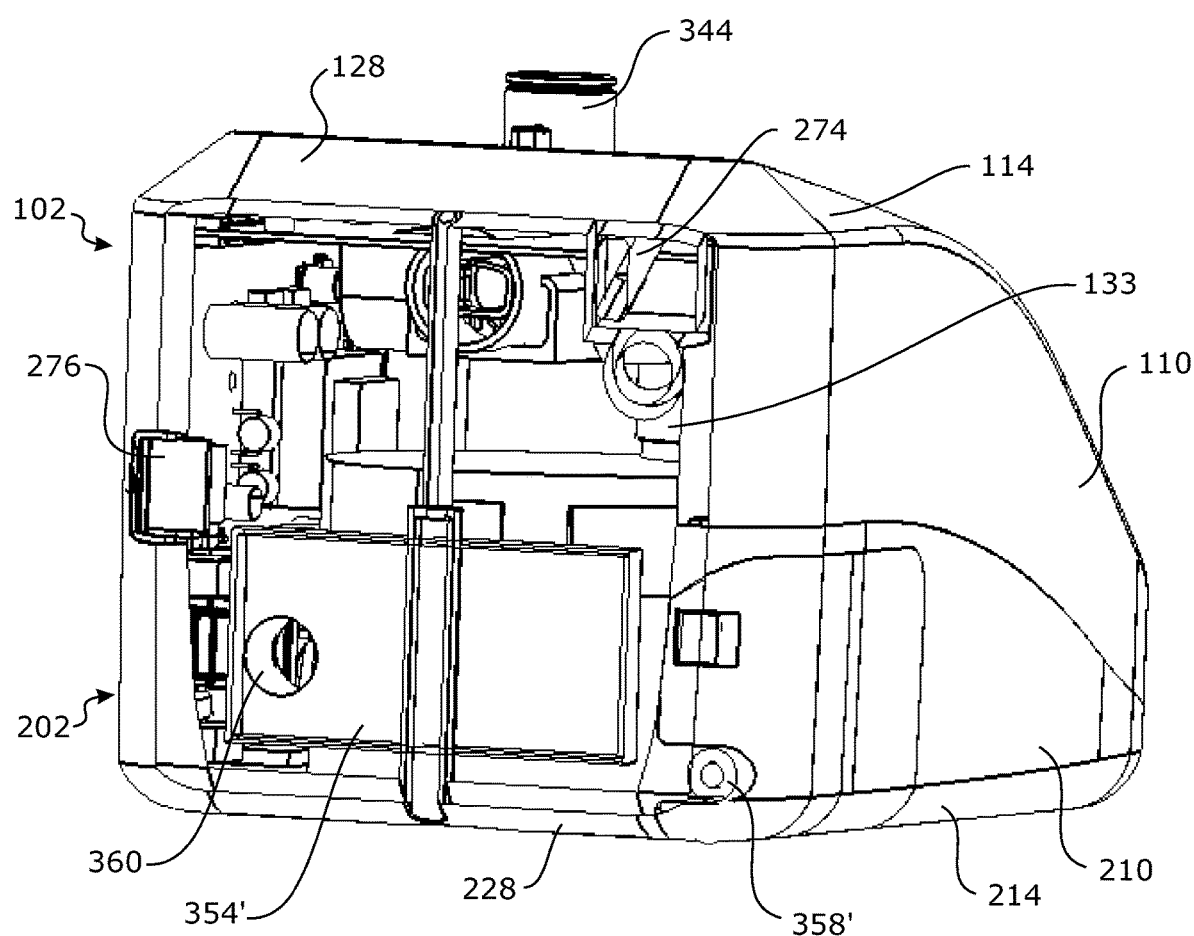
FIG. 12 is a transverse sectional view showing further detail of the air and oxygen inlet arrangement of FIG. 11.
Figure 13:
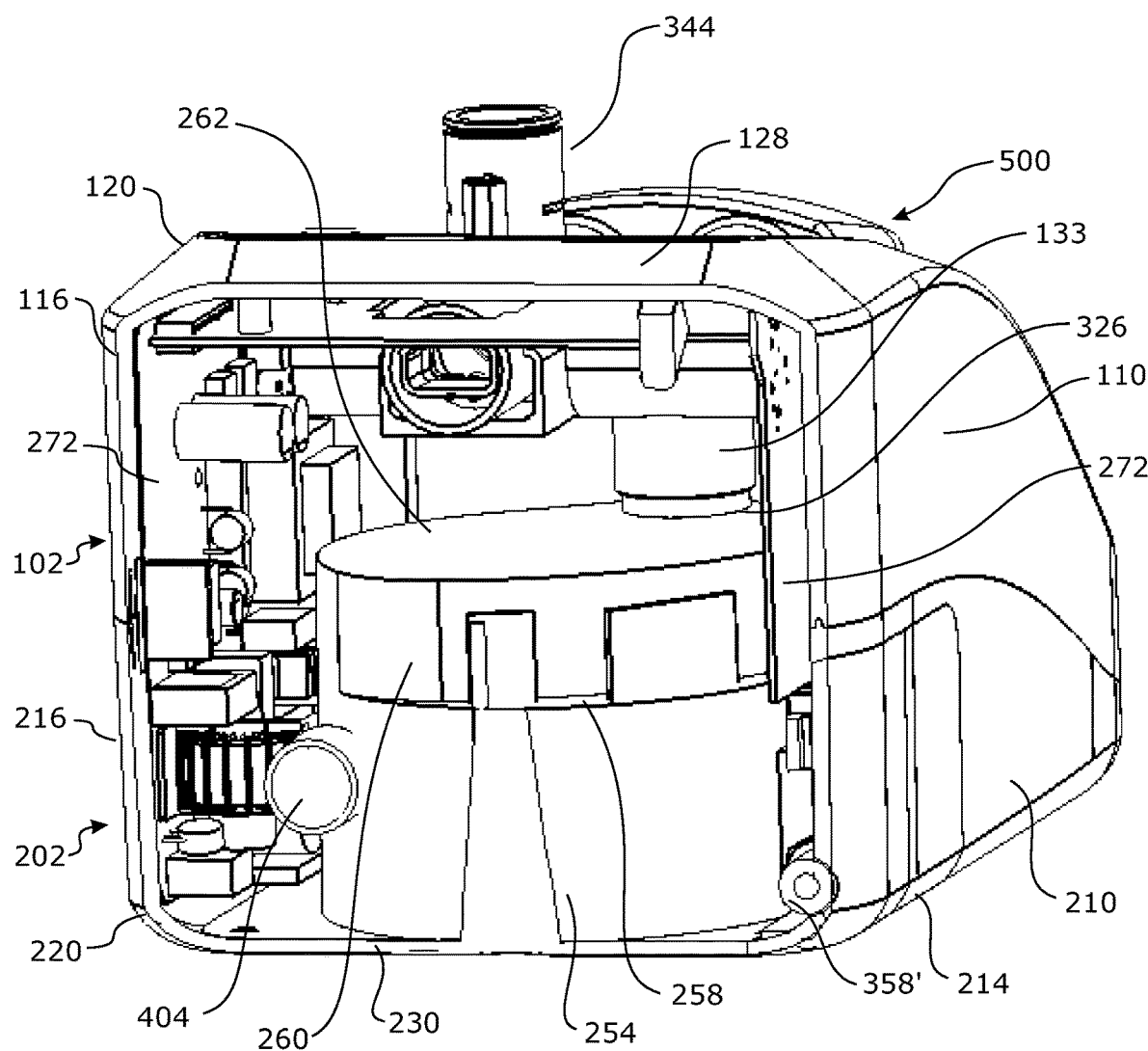
FIG. 13 is another transverse sectional view showing further detail of the air and oxygen inlet arrangement of FIG. 11.
Figure 14:
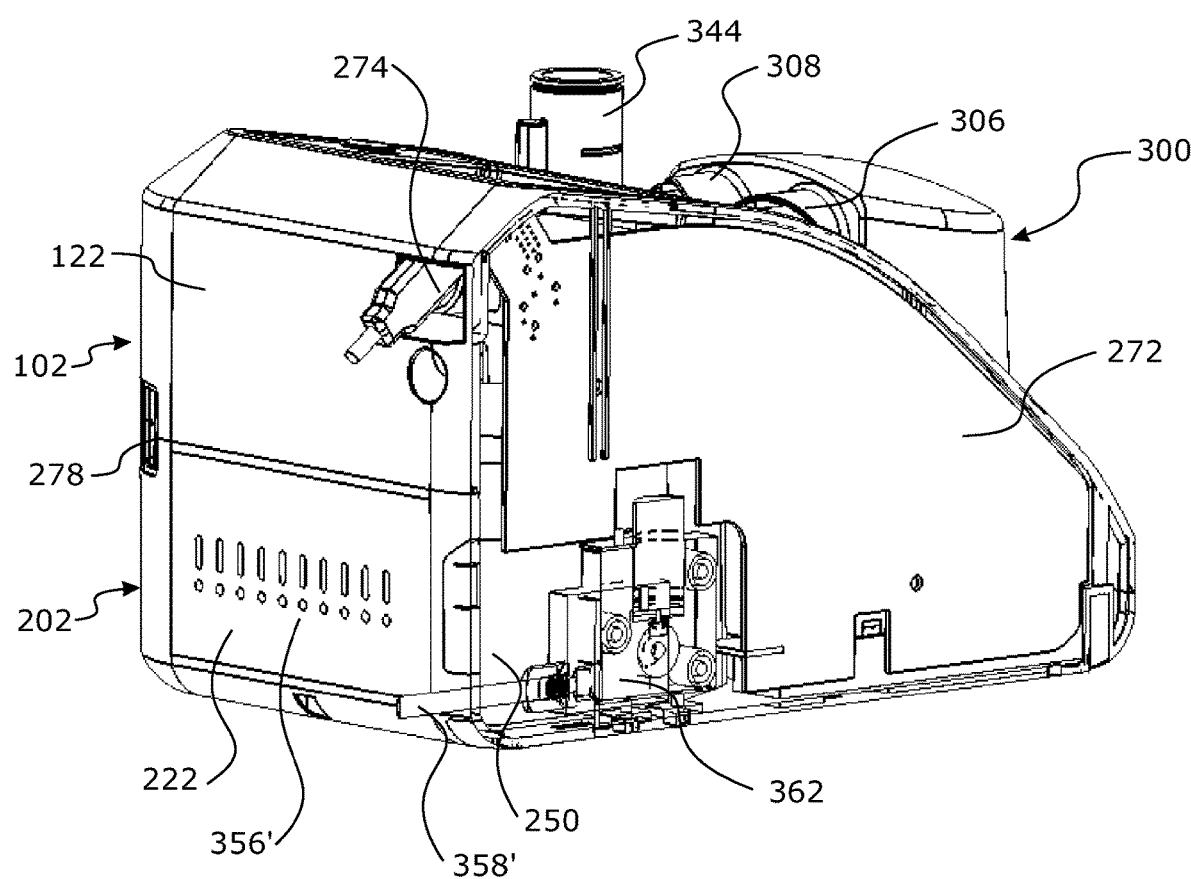
FIG. 14 is a longitudinal sectional view showing further detail of the air and oxygen inlet arrangement of FIG. 11.
Figure 15:
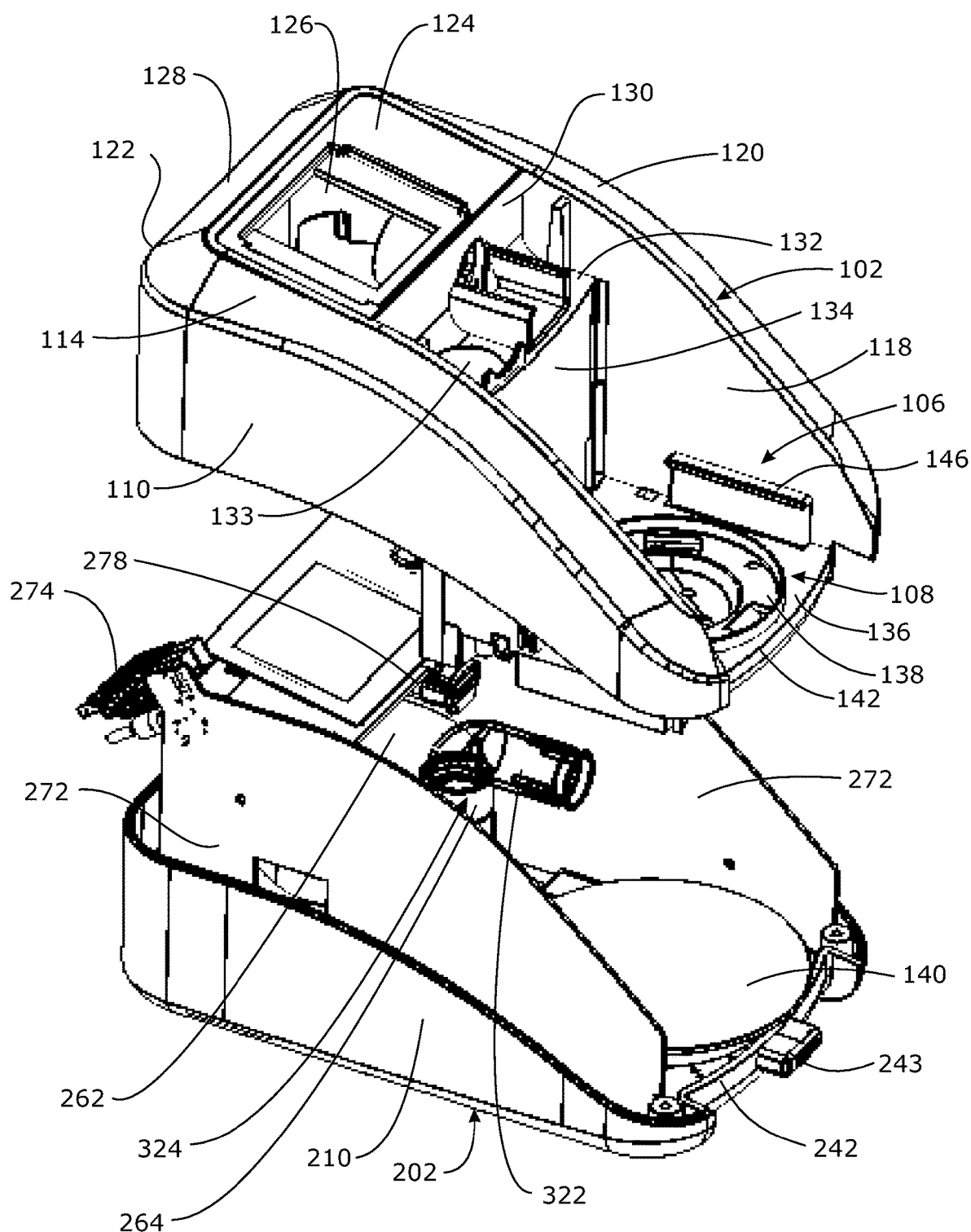
FIG. 15 is an exploded view of upper and lower chassis components of a main housing of the flow therapy apparatus.
Figure 16:
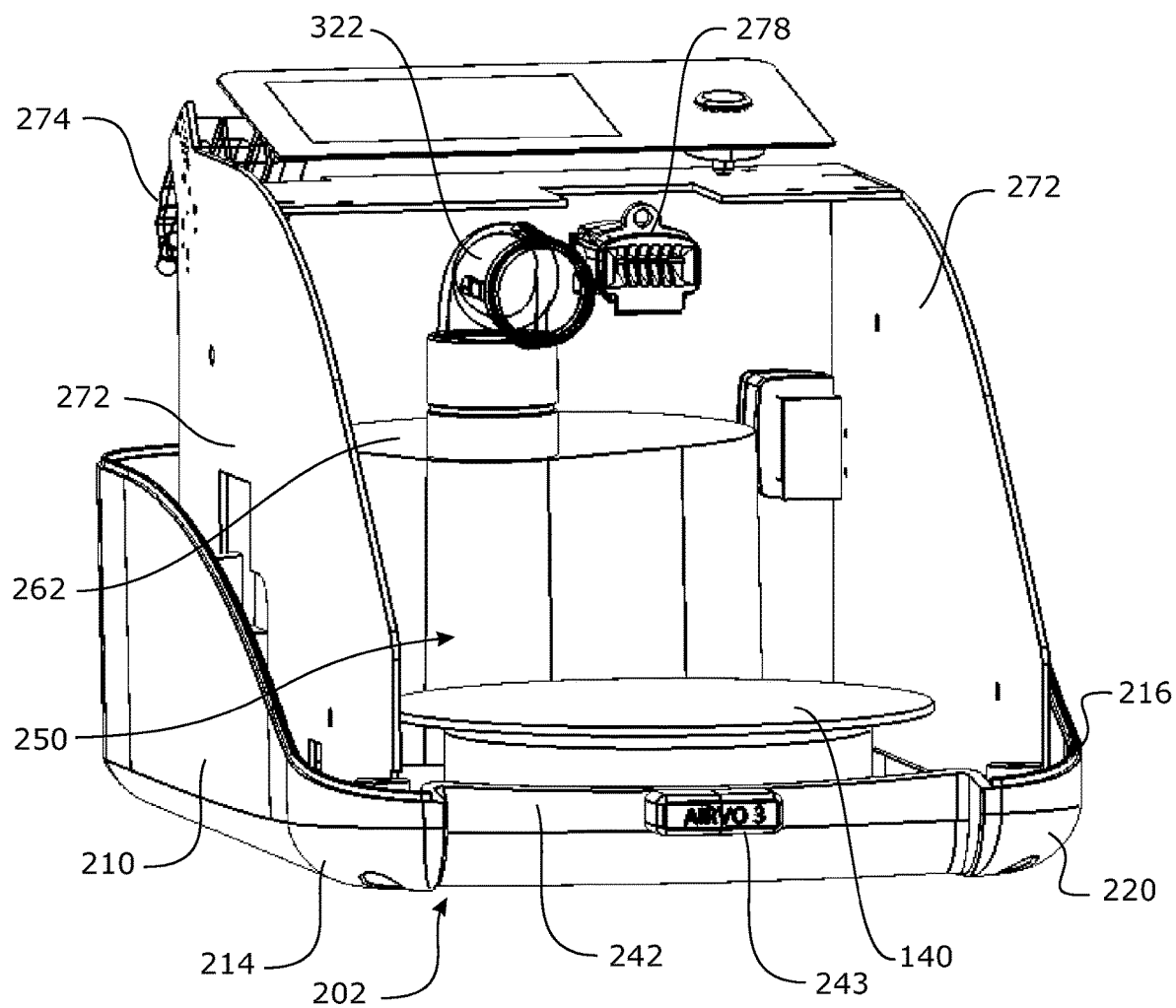
FIG. 16 is a front left side perspective view of the lower chassis of the main housing showing a housing for receipt of a motor and/or sensor module sub-assembly.

The apparatus 10 has air and oxygen (or alternative auxiliary gas) inlets in fluid communication with the motor 402 to enable the motor 402 to deliver air, oxygen, or a suitable mixture thereof to the liquid chamber 300 and thereby to the patient. In some configurations, the gas comprises a blend of oxygen and ambient air. As shown in FIG. 10 the apparatus 10 may have a combined air/oxygen (or alternative auxiliary gas) inlet arrangement 350. This arrangement comprises a combined air/oxygen port 352 into the housing 100, a filter 354, and a cover 356 with a laterally extending oxygen tube 358 that is in fluid communication with an oxygen source. The port 352 is fluidly coupled with the motor 402. For example, the port 352 may be coupled with the motor and/or sensor module 400 via a gasflow passage between the port 352 and an inlet aperture or port in the motor and/or sensor module 400, which in turn would lead to the motor. This arrangement may be of the type described in patent application US 2014/0345615, and the contents of that specification are incorporated herein in their entirety by way of reference.

Alternatively, the apparatus 10 may have the arrangement shown in FIGS. 11 to 14 to enable the motor 402 to deliver air, oxygen (or alternative auxiliary gas), or a suitable mixture thereof to the liquid chamber 300 and thereby to the patient. This arrangement comprises an air inlet 356' in the rear wall 222 of the lower chassis 202 of the housing 100. The air inlet 356' comprises a rigid plate with a suitable grill arrangement of apertures and/or slots. Sound dampening foam may be provided adjacent the plate on the interior side of the plate. An air filter box 354' is positioned adjacent the air inlet 356' internally in the main housing 100, and comprises an air outlet port 360 to deliver filtered air to the motor 402 via an air inlet port 404 in the motor and/or sensor module 400. The air filter box 354' may comprise a filter configured to remove particulates (e.g. dust) and/or pathogens (e.g. viruses or bacteria) from the gasflow. A soft seal such as an O-ring seal will be provided between the air outlet port 360 and air inlet port 404 to seal between the components. The apparatus 10 comprises a separate oxygen inlet port 358' positioned adjacent one side of the housing 100 at a rear end thereof, the oxygen port 358' for receipt of oxygen from an oxygen source such as a tank or source of piped oxygen. The oxygen inlet port 358' is in fluid communication with a proportional oxygen valve 362. The oxygen valve 362 will suitably be a solenoid valve that enables the control of the amount of oxygen that is added to the gasflow that is delivered to the liquid chamber 300. It should be understood that in alternative configurations the oxygen port 358' and proportional oxygen valve 362 may be used with other auxiliary gases to control the addition of other auxiliary gases to the gasflow. The other auxiliary gases may comprise any one or more of a number of gases useful for gas therapy, including but not limited to heliox and nitric oxide.

As shown in FIGS. 13 to 16 and 22*b* to 22*f*, the lower housing chassis 202 carries suitable electronics boards 272 such as printed circuit boards. The electronics boards are positioned adjacent respective outer side walls 210, 216 of the lower housing chassis 202. The electronics boards 272 contain, or are in electrical communication with, suitable electrical or electronics components such as but not limited to microprocessors, capacitors, resistors, diodes, operational amplifiers, comparators, and switches. Sensors may be used.

Components of the electronics boards 272 (such as but not limited to one or more microprocessors) act as the controller 13 of the apparatus.

One or both of the electronics boards 272 are in electrical communication with the electrical components of the apparatus 10, including the display unit and user interface 14, motor 402, oxygen valve 362, and the heater plate 140 to operate the motor 402 to provide the desired flow rate of gas, operate the humidifier 12 to humidify and heat the gasflow to an appropriate level, and supply appropriate quantities of oxygen (or in alternative configurations quantities of an alternative auxiliary gas) to the gasflow.

The electronics boards 272 are in electrical communication with a connector arrangement 274 projecting from the rear wall 122 of the upper housing chassis 102. The connector arrangement 274 may be coupled to a nurse alarm, pulse oximetry port, and/or other suitable accessories. The electronics boards 272 are also in electrical communication with an electrical connector 276 that is also provided in the rear wall 122 of the upper housing chassis 102 to provide mains or battery power to the components of the apparatus 10. The electronics boards 272 are also in electrical communication with an electrical connector 278 for the removable elbow 342, the purpose of which will be described in more detail below.

As mentioned above, operation sensors, such as flow, temperature, humidity, and/or pressure sensors can be placed in various locations in the flow therapy apparatus 10 and/or the patient breathing conduit 16 and/or cannula 17. The electronics boards 272 will be in electrical communication with those sensors. Output from the sensors can be received by the controller 13, to assist the controller 13 to operate the flow therapy apparatus 10 in a manner that provides optimal therapy, including meeting inspiratory demand.

As outlined above, the electronics boards 272 and other electrical and electronic components are pneumatically isolated from the gasflow path, thereby reducing or avoiding any fire or explosion risk that could otherwise occur if there was not that isolation.

Various aspects of the device will now be described in more detail.

3. Motor and/or sensor module

FIGS. 19 to 22*f* show the removable motor and/or sensor module or sub-assembly 400 in greater detail. As discussed above, the lower chassis 202 comprises a recess 250 for receipt of the motor and/or sensor module 400.

In the form shown in FIGS. 19 to 21, the motor and/or sensor module 400 comprises a stacked arrangement of three main components; a base 403 of the sub-assembly 400 (on which is positioned the motor 402), an outlet gasflow path and sensing layer 420 positioned above the base 403, and a cover layer 440. The base 403, the sensing layer 420, and the cover layer 440 assemble together to form a sub-assembly housing that has a shape that is complementary to that of the recess 250 so that the sub-assembly 400 can be received in the recess 250. The base 403 is configured to close the recess opening 251 when the sub-assembly 400 is positioned in the recess 250. The sub-assembly 400 may be maintained in position in the recess in any suitable way such as with fasteners, clips, or a quick release arrangement for example.

The sensing layer comprises a gasflow path with one or more sensors, the gasflow path arranged to deliver gas to the outlet port of the housing.

Figure 65:
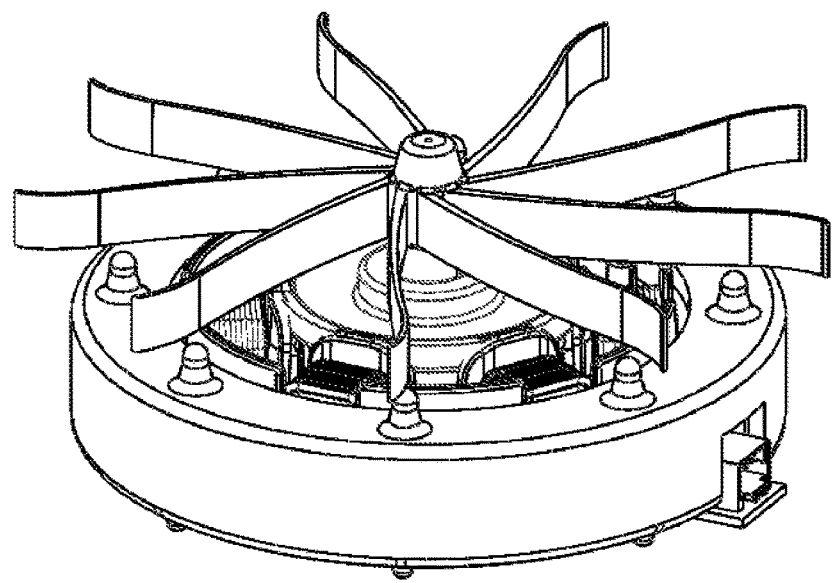
FIG. 65 is a view of the motor for use in the motor and/or sensor module sub-assembly of FIGS. 19-21 or FIGS. 78-101.
Figure 66:
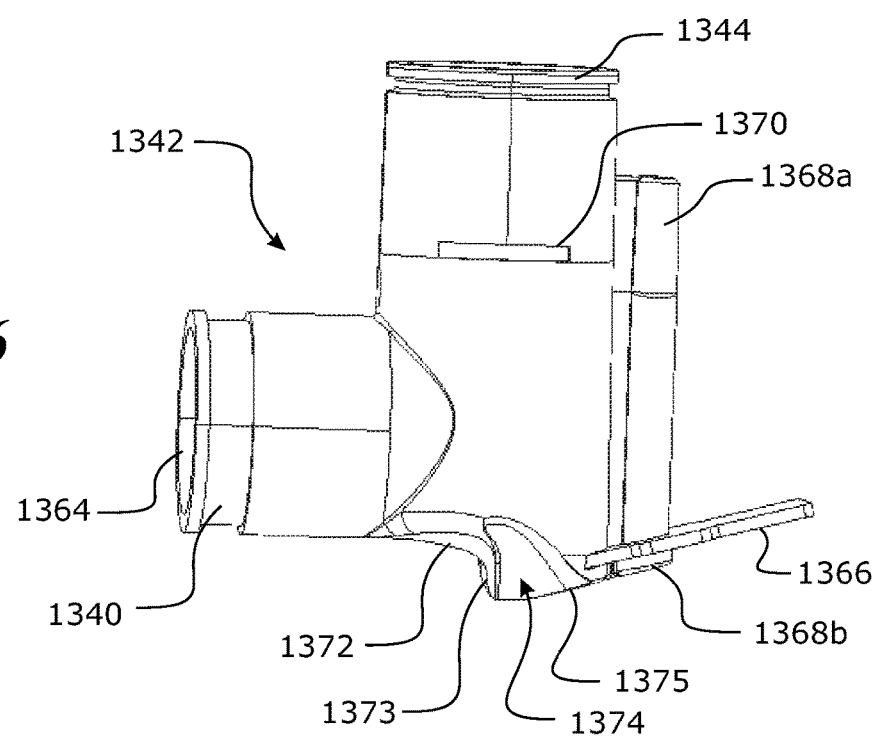
FIG. 66 is a side perspective view of an alternative removable elbow for use in the flow therapy apparatuses, the elbow shown removed from the main housing.
Figure 67:
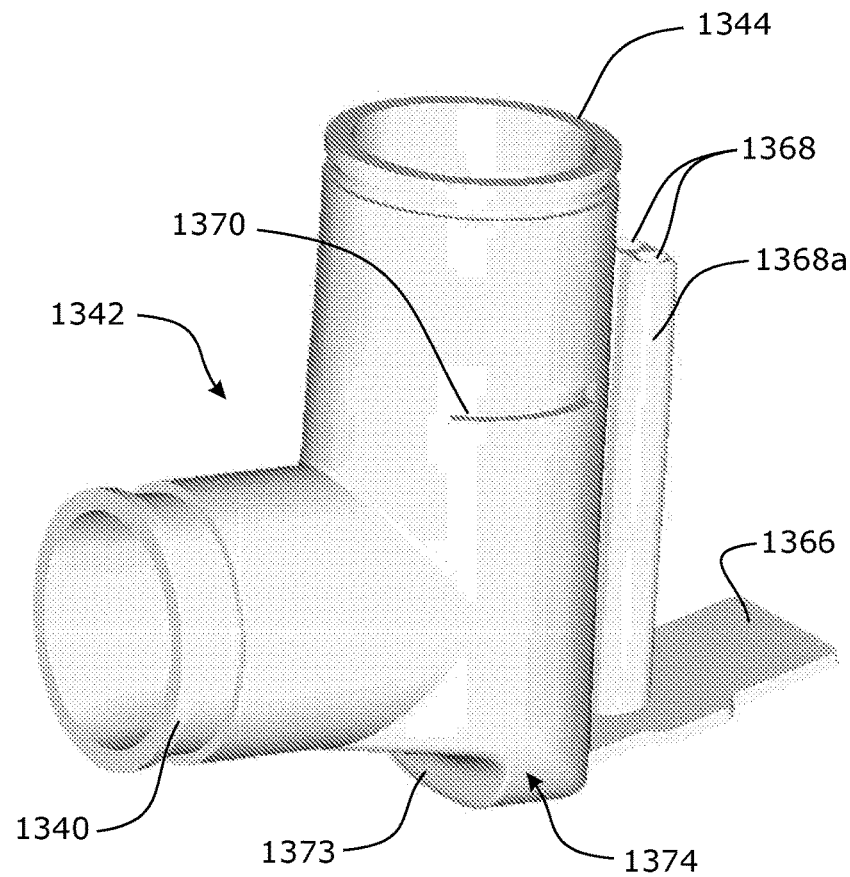
FIG. 67 is a front/side perspective view of the removable elbow of FIG. 66.
Figure 68:
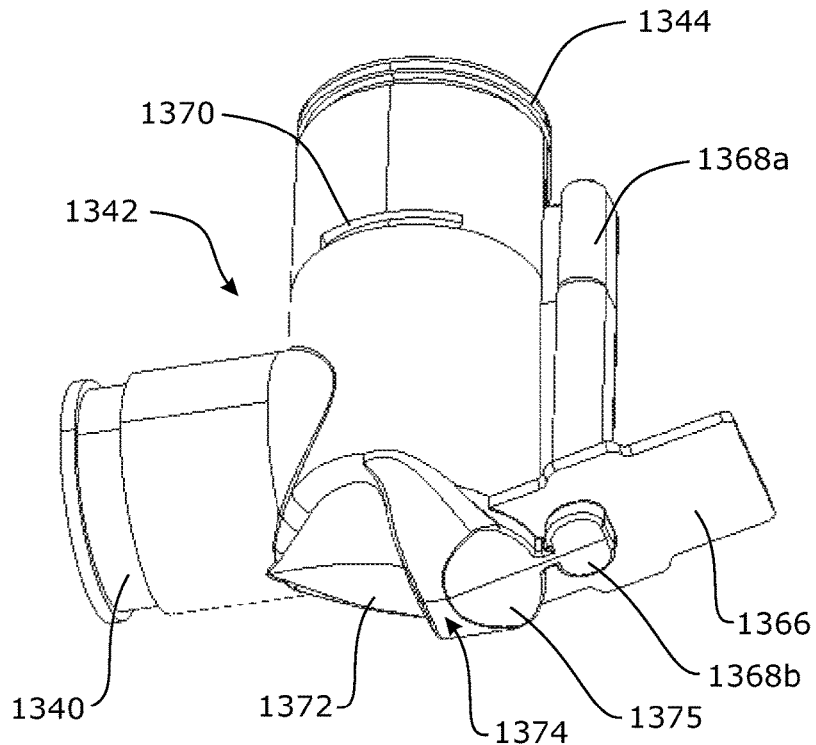
FIG. 68 is a rear underside perspective view of the removable elbow of FIG. 66.

The motor 402 has a body 408 that defines an impeller chamber that contains an impeller. The motor 402 could be any suitable gas blower motor, and may for example be a motor and impeller assembly of the type described in published PCT specification WO2013/009193 and shown in FIG. 65 for example. The contents of that specification are incorporated herein in their entirety by way of reference.

A plurality of vibration isolation structures 412 are located in spaced apart positions around the periphery of the body 408. The vibration isolation structures 412 are configured to absorb vibrations caused by movement of the impeller or of other components of the motor 402 during operation. The absorption of vibrations can mitigate rattling of the motor 402 inside of the sub-assembly housing, which in turn can reduce noise emitted by the motor 402. The absorption of vibrations can also mitigate material fatigue on various components of the sub-assembly 400. The vibration isolation structures 412 may be constructed from a silicone material. In other configurations, other resilient materials including but not limited to acrylic resins and polyurethane resins might be used. In the form shown, the vibration isolation structures 412 comprise upright plastic posts with resilient cylindrical sleeves positioned over the posts. The vibration isolation structures are mounted to the body 408 and are received in recesses in the base and the sensor layers. Alternatively, the arrangement could be reversed. In another alternative, a mounting post could be provided on each of the base and sensor layers, with the posts mating against or connecting to each other in the resilient sleeve. In other configurations, the vibration isolation structures 412 could be in a different form. For example, in alternative configurations, the vibration isolation structures 412 might comprise one or more overmoulded features on the body 408. In still other alternative configurations, the vibration isolation structures 412 might comprise one or more springs, resilient structures (e.g. nipples, protrusions, blocks, sheets, etc), or foam structures (e.g. encapsulations, 'ring'-like fittings around the periphery of the body 408, etc) affixed to one or more sides of the body 408. In still other configurations, inner walls of the base 403 and/or sensing layer 420 might comprise vibration isolation structures that vibrationally isolate the body 408.

A gases outlet 406 is in fluid communication with a gases inlet of the outlet gasflow path and sensing layer 420, which is stacked on top of the motor. This layer 420 comprises a body 422 which comprises a plurality of mounting legs 425 that can be inserted into a plurality of mounting slots (not shown) of the base 403 to secure the body 422 to the base 403. In other configurations, other structures or arrangements may be used to secure the body 422 to the base 403, including but not limited to fasteners, clips, or quick release arrangements. In one configuration, the body 422 defines a gasflow path that couples the gases outlet 406 with the gases inlet of the gasflow path and sensing layer 420. An alternative configuration such as but not limited to a coupling tube could be used to couple the gases outlet 406 with that gases inlet.

The body 422 defines a lower portion 426 of a sensing and gasflow path. The cover layer 440 has a body 442 that defines the upper portion 446 of the sensing and gasflow path, with the shape of the upper and lower portions 426, 446 corresponding substantially to each other.

As shown in FIGS. 20 and 21, the gasflow path comprises a linear elongate gasflow portion 428, 448. The inlet is in fluid communication with a tangential entrance portion 430, 450 of the gasflow path, which is located at or adjacent an entrance end of the linear elongate portion 428, 448 of the gasflow path. Recesses 433, 453 and 434, 454 may be provided at opposite ends of the linear elongate portion of the gasflow path.

Figure 17A:
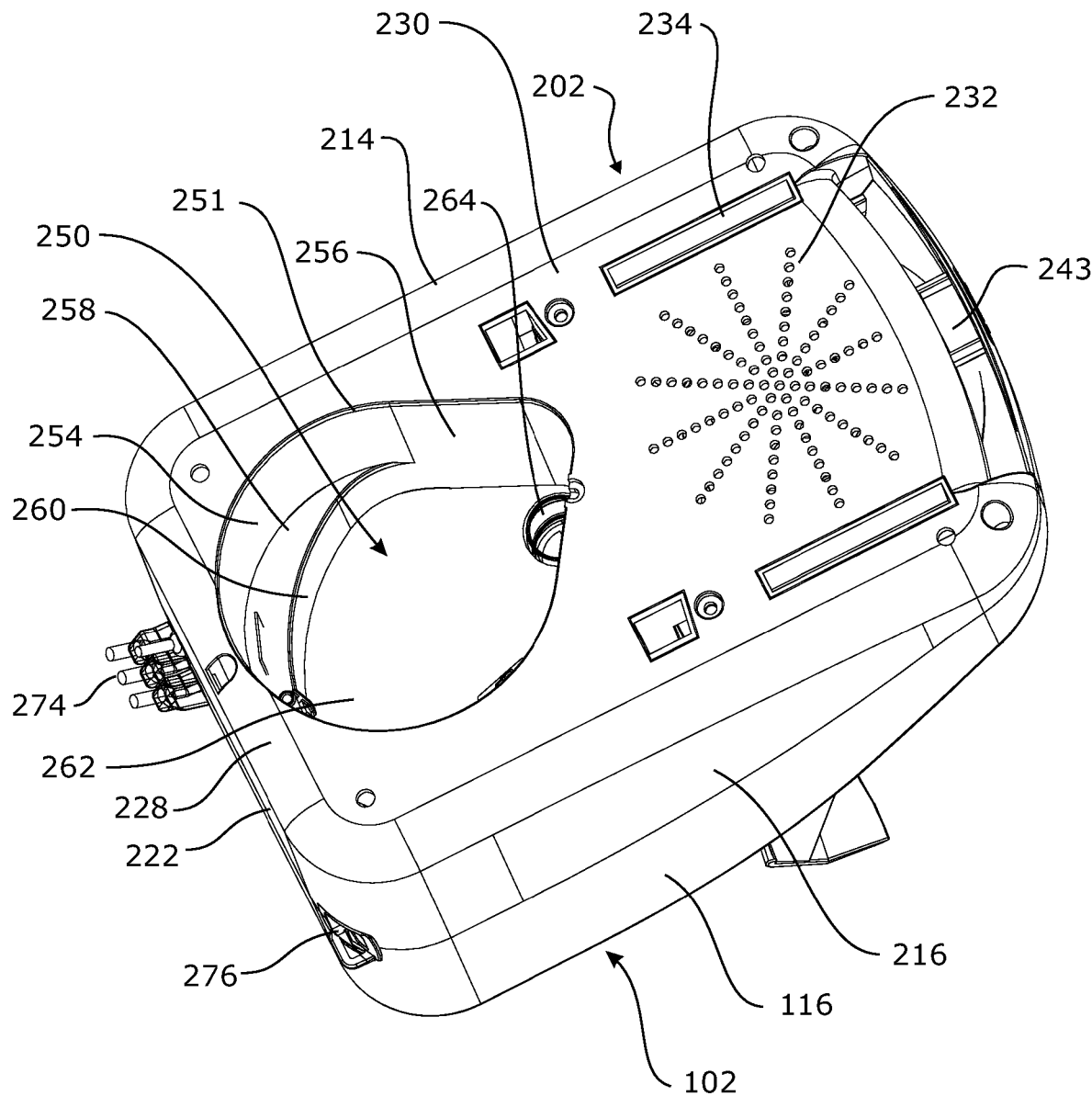
FIG. 17a is a first underside perspective view of the main housing of the flow therapy apparatus showing a recess inside the housing for the motor and/or sensor module sub-assembly.
Figure 17B:
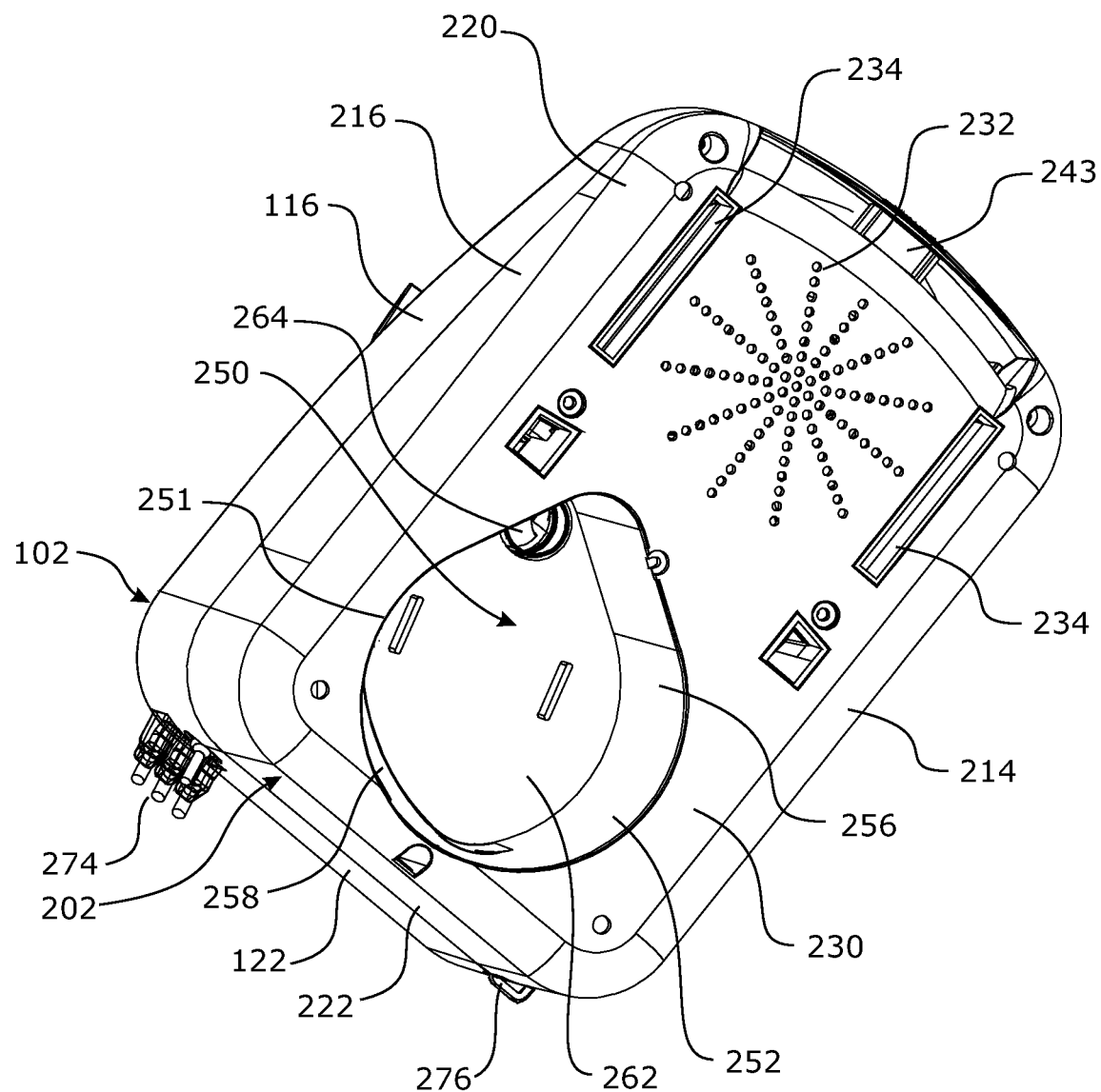
FIG. 17b is a second underside perspective view of the main housing of the flow therapy apparatus showing the recess for the motor and/or sensor module sub-assembly.
Figure 18:
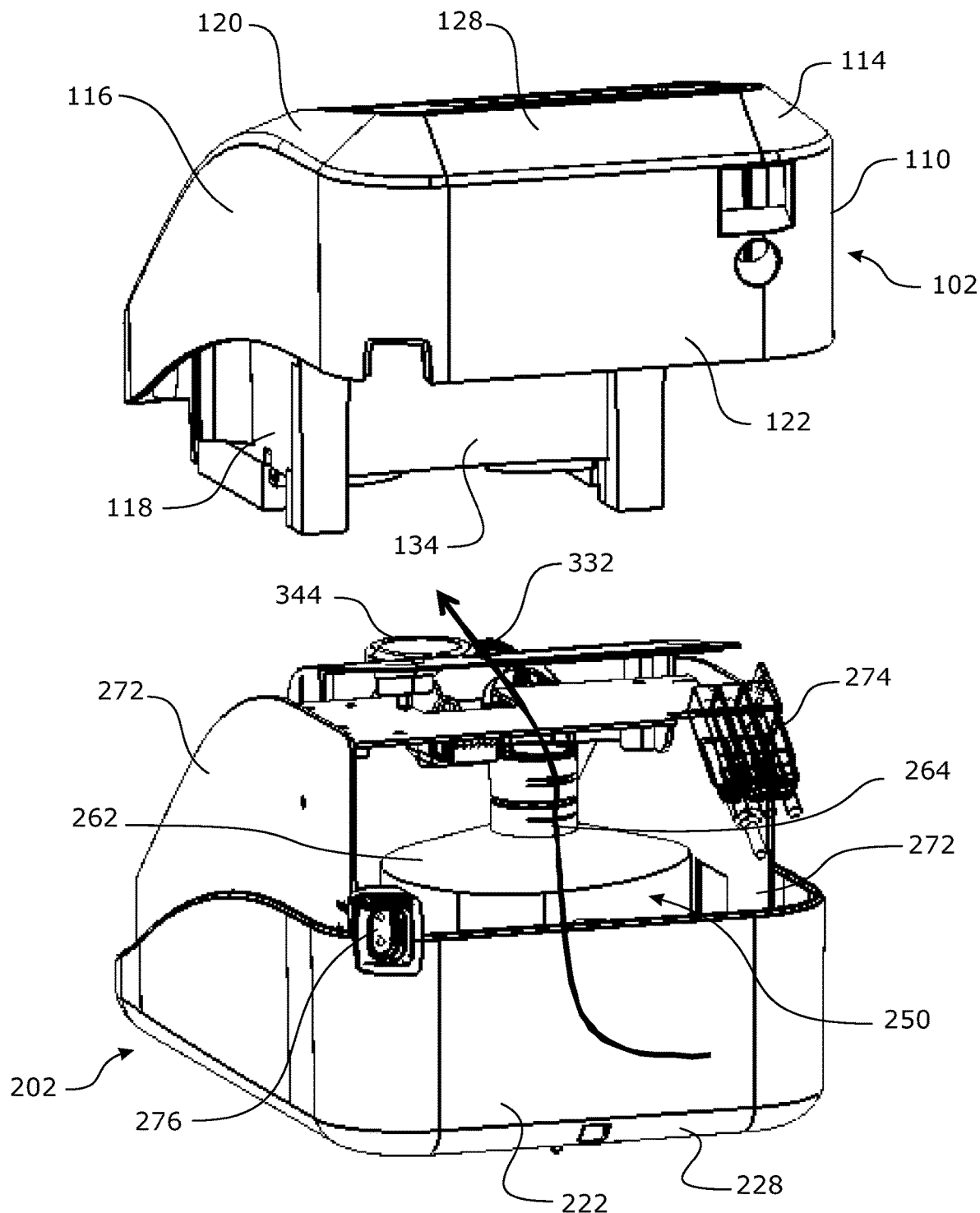
FIG. 18 is an exploded rear perspective view schematically showing by way of an arrow the gasflow path through the flow therapy apparatus.

A gasflow outlet port 452 extends vertically through the body 442 of the cover layer 440, and is located at or adjacent an opposite exit end of the linear elongate portion 428, 448 of the gasflow path. As shown in FIGS. 22*d* and 22*e* for example, the gas outlet port 452 is in fluid communication with an upper portion of the motor recess 250, which in turn is in fluid communication with the gasflow passage. Again, due to the wall 252 and ceiling 262 configuration of the recess 250, if there is gas leakage from the motor/sensor module 400, that will be vented to atmosphere rather than entering the portion of the main housing 100 that contains the bulk of the electronics and control equipment. The recess 250 may comprise spacer(s), such as lugs that protrude downwardly from ceiling 262 as shown in FIG. 17*b*, to maintain a suitable spacing for gasflow from the gas outlet port 452 and the ceiling of the recess 262.

It can be seen from FIG. 20 that that at least part of the gasflow path through and out of the motor and/or sensing module 400 has a tortuous or sinuous configuration. For example, the direction of gasflow travel through the elongate portions 428, 448 is generally opposite to the direction of gasflow travel from the gas outlet port 452 to the entrance of the gasflow passage through elbow 324.

As shown in FIG. 21, the cover layer 440 comprises a sensing printed circuit board (PCB) 456. The cover layer 440 may also comprise one or more temperature sensors such as thermistors that sit in the elongate portion 428, 448 of the gasflow path. One sensor will measure gas temperature and the other can act as a redundant temperature sensor. Alternatively, one of the thermistors could be used as a reference flow sensor (e.g. via use as a constant-temperature thermistor), and the measured temperatures could be used to determine the gasflow rate through the portion 428, 448 of the gasflow path. The one or more temperature sensors may be located on a portion of the sensing PCB 456 that faces the gasflow. The sensing PCB 456 may additionally comprise other sensors including but not limited to pressure sensors, humidity sensors and dew point sensors.

One or both of the electronics boards 272 will be in electrical communication or coupled with the sensors to process information received from the sensors and operate the apparatus 10 based on the information received from the sensors.

The sensing layer 420 and cover layer 440 comprise complementary locating features 438, 458 to correctly locate the layers relative to each other. In the form shown, the locating features comprise projections 438 and complementary recesses 458; however, other features could be provided. The base 403, sensing layer 420 and cover layer 440 (and optionally the motor 402) can be fastened together using fasteners (e.g. screws) that extend through apertures of components of the sub-assembly 400. Alternatively, a different fastening arrangement could be used. For example, the layers 403, 420, 440 could be adhered or fused together.

The cover layer 440 has a grid arrangement of vertical walls on its upper surface to minimise water ingress in the event of leakage of water from the fixed elbow 324. The grid arrangement may thus help to prevent water that would have entered the sub-assembly 400 (due to, for example, accidental tilting of a filled liquid chamber 300 in the chamber bay 108) from entering the gas outflow port 452 and disrupting electrical components of the sub-assembly 400. In alternative configurations, the upper surface of the cover layer 440 may define a basin having a bottom wall lower than the upper portion of the gas outflow port 452 to receive water.

In an alternative configuration, the motor/impeller unit may be provided remotely from the apparatus 10. In that configuration, the module received in the recess 250 may only comprise a gasflow path and various sensors, to deliver gases to the fixed elbow 324 and thereby to the liquid chamber 300. In an alternative configuration, the module received in the recess 250 may only comprise the motor and a gasflow path, but no sensors.

In another alternative configuration the motor and/or sensor module 400 may not be removable from the recess 250, but instead may be permanently mounted therein. The benefits of the gas isolation from the electrical/electronics components would still be provided in that configuration.

The removable motor and/or sensor module allows the module to be cleaned, and/or replaced if there are any faults. The removable module allows for a more compact flow path, and a reduced distance flow path. This reduces resistance to flow since the flow does not need to travel as far.

The flow path is compact, and has reduced turns/sharp turns which reduces flow separation and reduces resistance to flow.

The arrangement of the motor and flow path provides another layer of isolation because of the wall arrangement.

Having a modular motor and/or sensor module enables the various parts of the module to be taken apart if needed for cleaning and/or servicing.

There are advantageously no leak paths in the motor and/or sensor module. While the motor and/or sensor module may be a potential leak point, a leak in that region would result in the oxygen venting to atmosphere or into the liquid chamber.

4. Removable Gasflow Tube or Elbow

As discussed above, the apparatus 10 comprises a removable gasflow tube in the form of a removable elbow 342 for receiving humidified gases from the liquid chamber 300 and directing the humidified gases toward the patient interface 17 through the patient breathing conduit 16. The elbow 342 and related features will now be described with reference to FIGS. 24 to 32. A benefit of having a removable tube is that the parts in contact with potential condensation are removable for cleaning, disinfection, and/or sterilisation.

Figure 29:
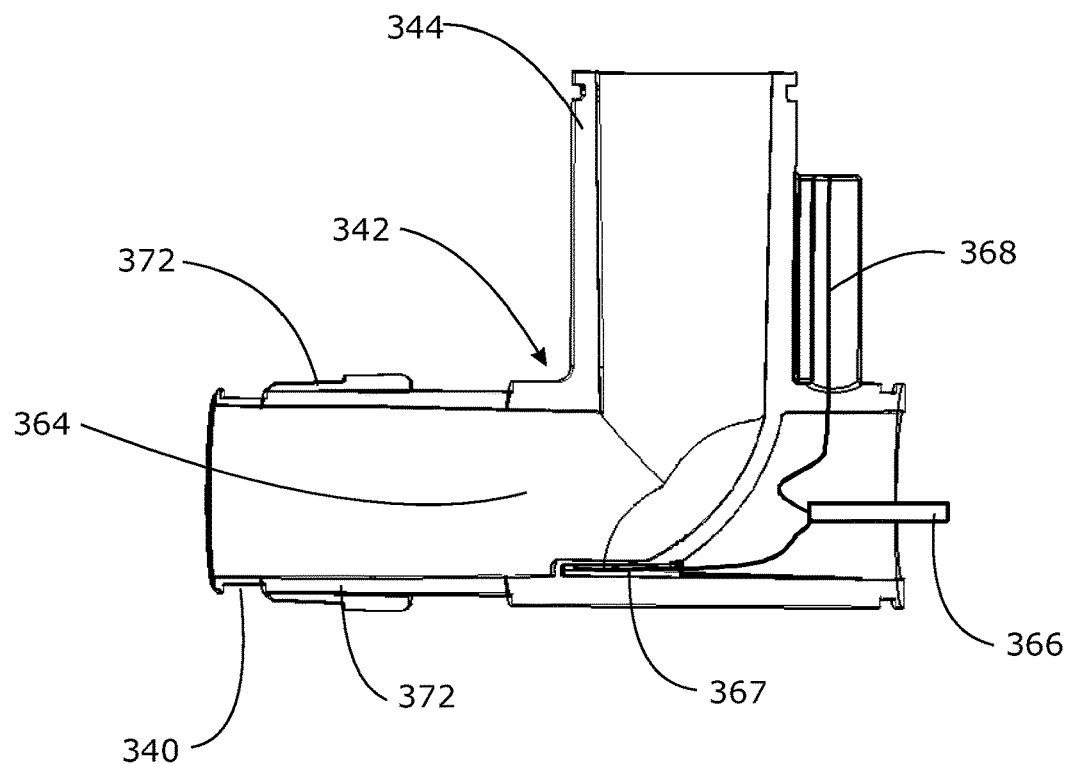
FIG. 29 is a sectional view of the removable elbow showing electrical components and a gasflow path.

The removable elbow 342 is substantially L-shaped and has the manifold gases inlet port 340 (humidified gases return) and the patient outlet port 344 for coupling to the patient breathing conduit 16 to deliver gases to the patient interface 17. As shown in FIG. 29, the elbow 342 comprises a gasflow passage 364 that extends through the elbow from the inlet port 340 to the outlet port 344.

Figure 28:
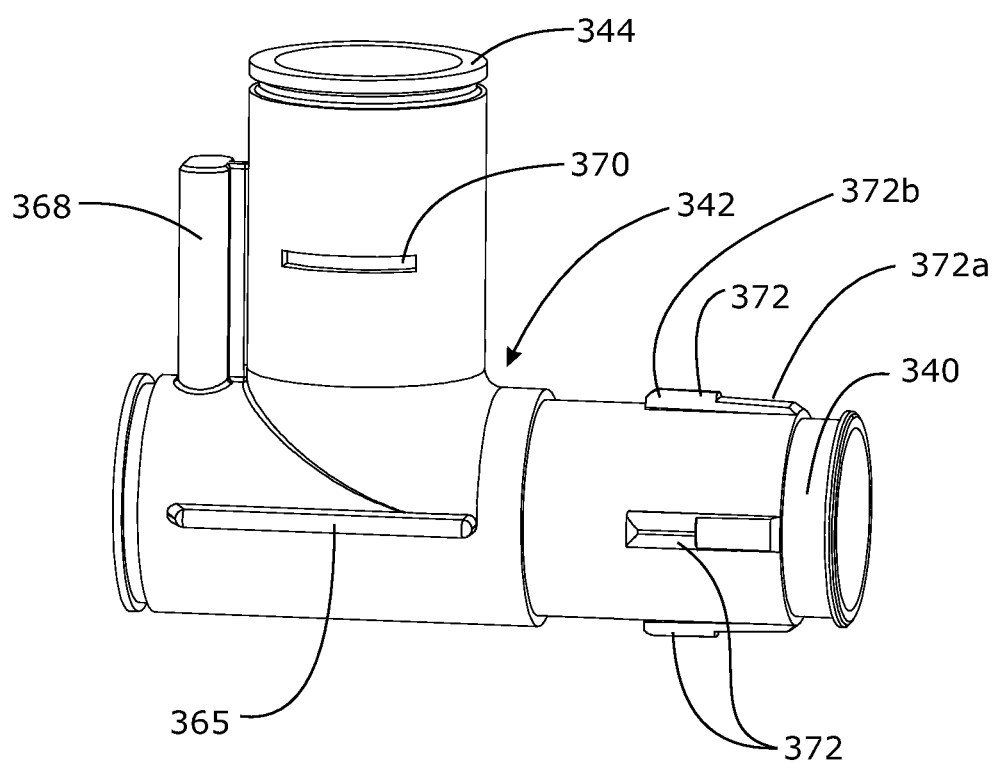
FIG. 28 is a perspective view of the removable elbow.
Figure 30:
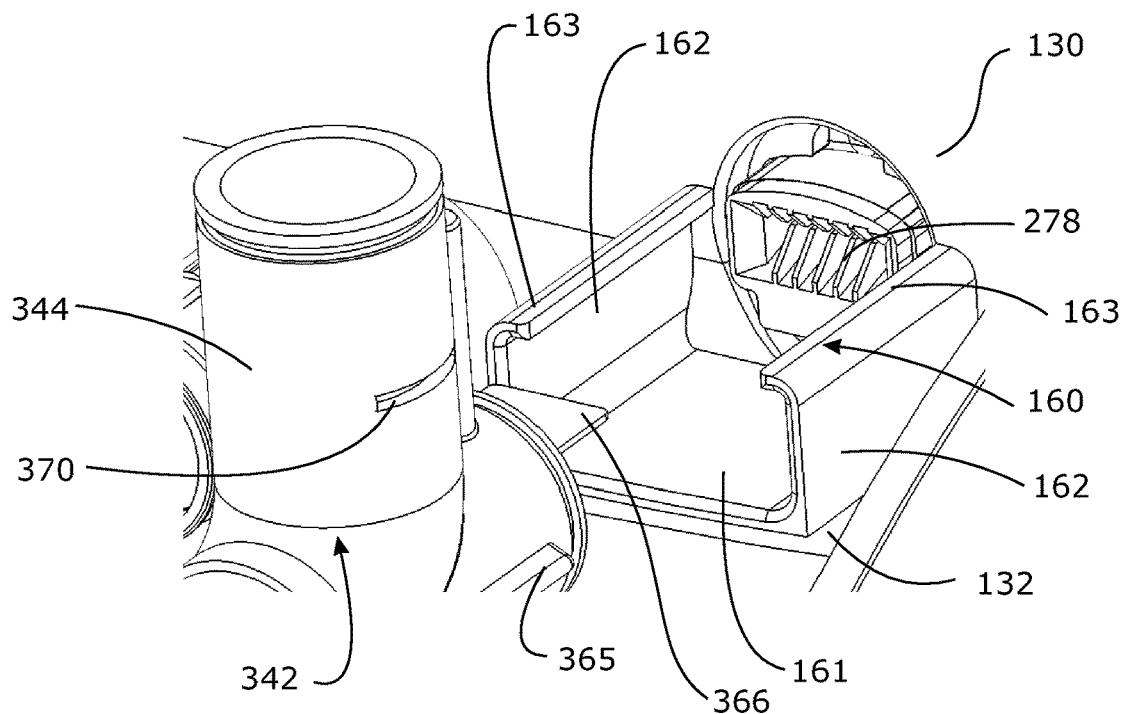
FIG. 30 is an exploded view showing the removable elbow disconnected from an electrical connector of the main housing.
Figure 31:
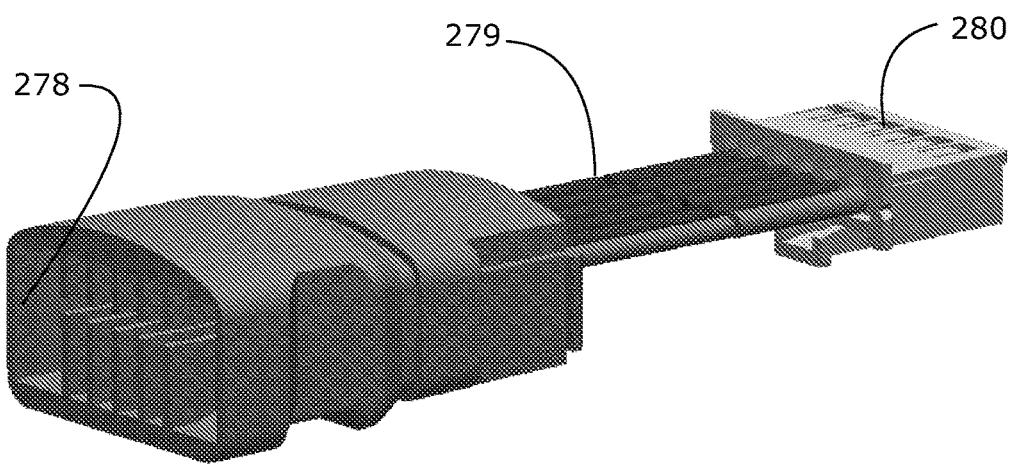
FIG. 31 shows an exemplary electrical connector for use in the main housing.
Figure 32:
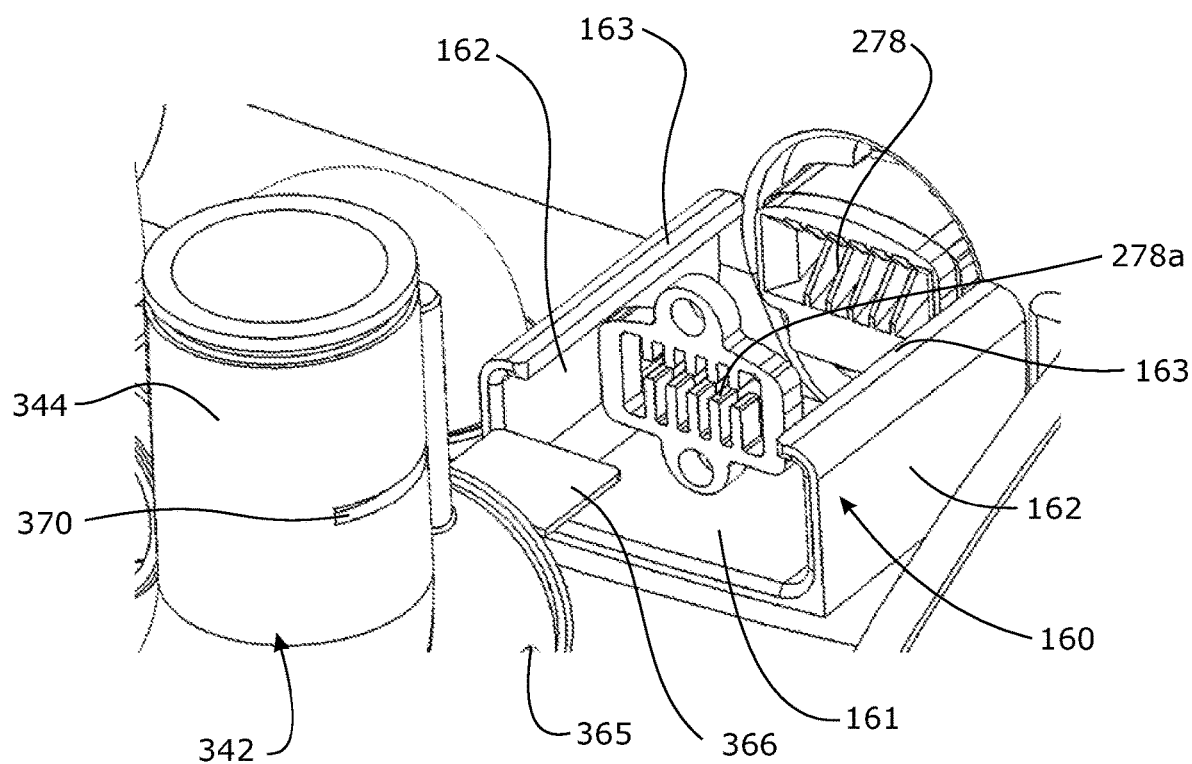
FIG. 32 is an exploded view showing a connector guard of the electrical connector of FIGS. 30 and 31.

The upper chassis 102 comprises an elbow retainer 160 extending forwardly from wall 130. The retainer 160 comprises a base wall 161 and two spaced apart upright side walls 162. Inwardly directed flanges 163 extend towards each other from the upper ends of the side walls 162, with a spacing between the flanges 163 being large enough to enable the patient outlet port 344 to extend upwardly therebetween. As shown in FIGS. 28, 30, and 32, the body of the elbow 342 comprises elongate ribs 365 extending transversely outwardly from opposite sides thereof. The ribs 365 and flanges 163 are advantageously both substantially horizontally orientated. The ribs 365 and flanges 163 are sized and configured such that the elbow 342 can be engaged with the elbow retainer 160 by moving the elbow 342 rearwardly in a horizontal direction. However, once the elbow 342 is engaged with the elbow retainer 160, it can only be removed by moving the elbow 342 forwardly in a horizontal direction. The elbow 342 cannot be lifted upwardly to disengage it from the elbow retainer 160, because the ribs 365 and flanges 163 will prevent that movement.

Figure 25:
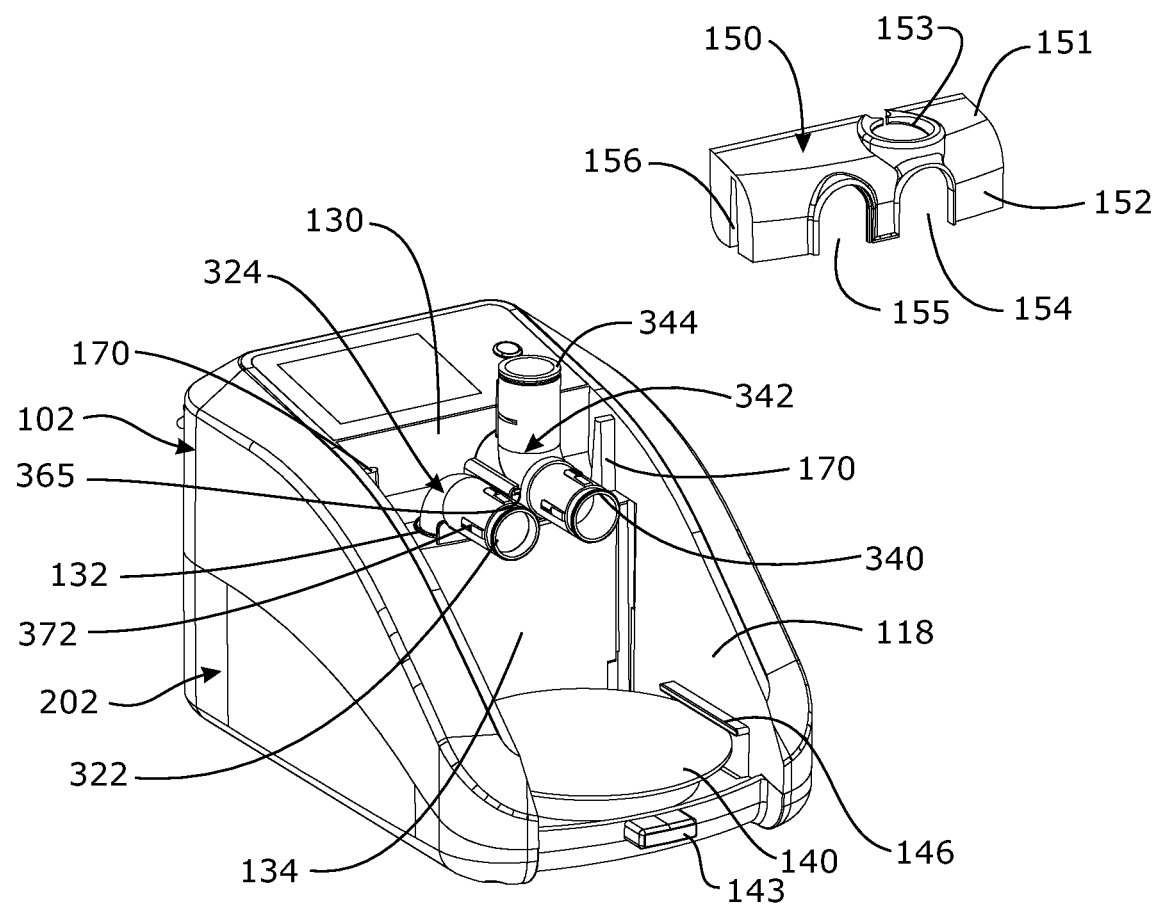
FIG. 25 is a view similar to FIG. 24, but with a removable elbow retention cover removed from the main housing.
Figure 26A:
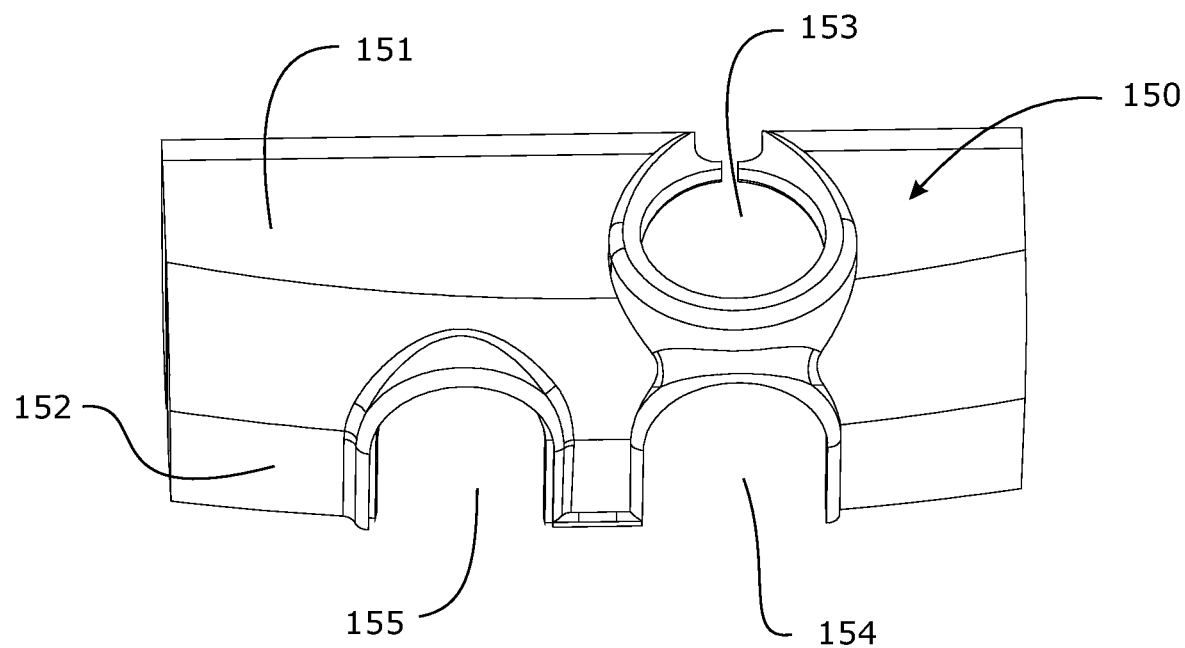
FIG. 26a is an overhead perspective view of the removable elbow retention cover of FIG. 25.
Figure 26B:
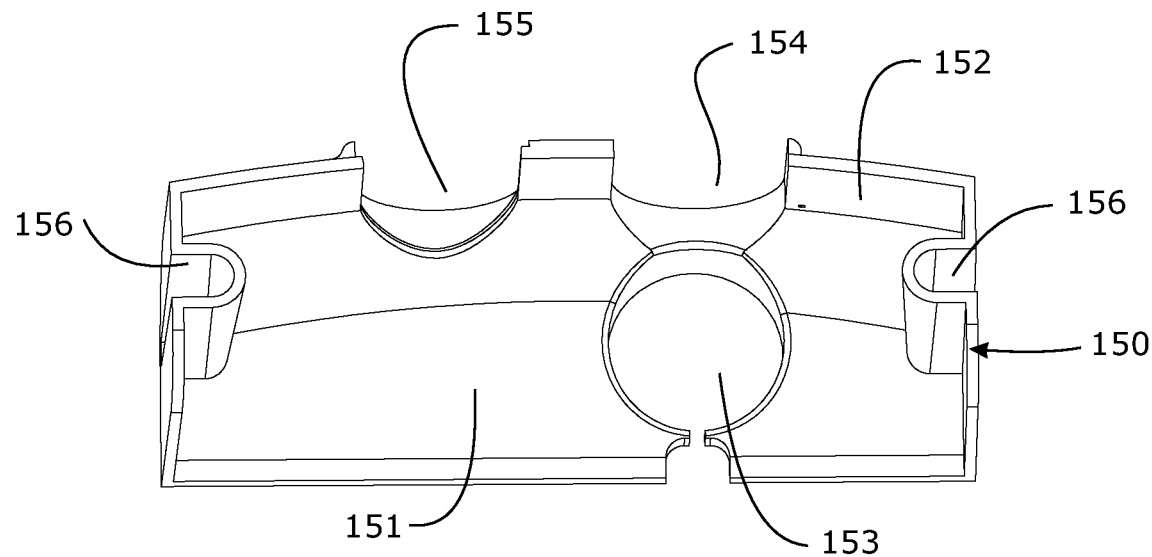
FIG. 26b is an underside perspective view of the removable elbow retention cover of FIG. 25.
Figure 27:
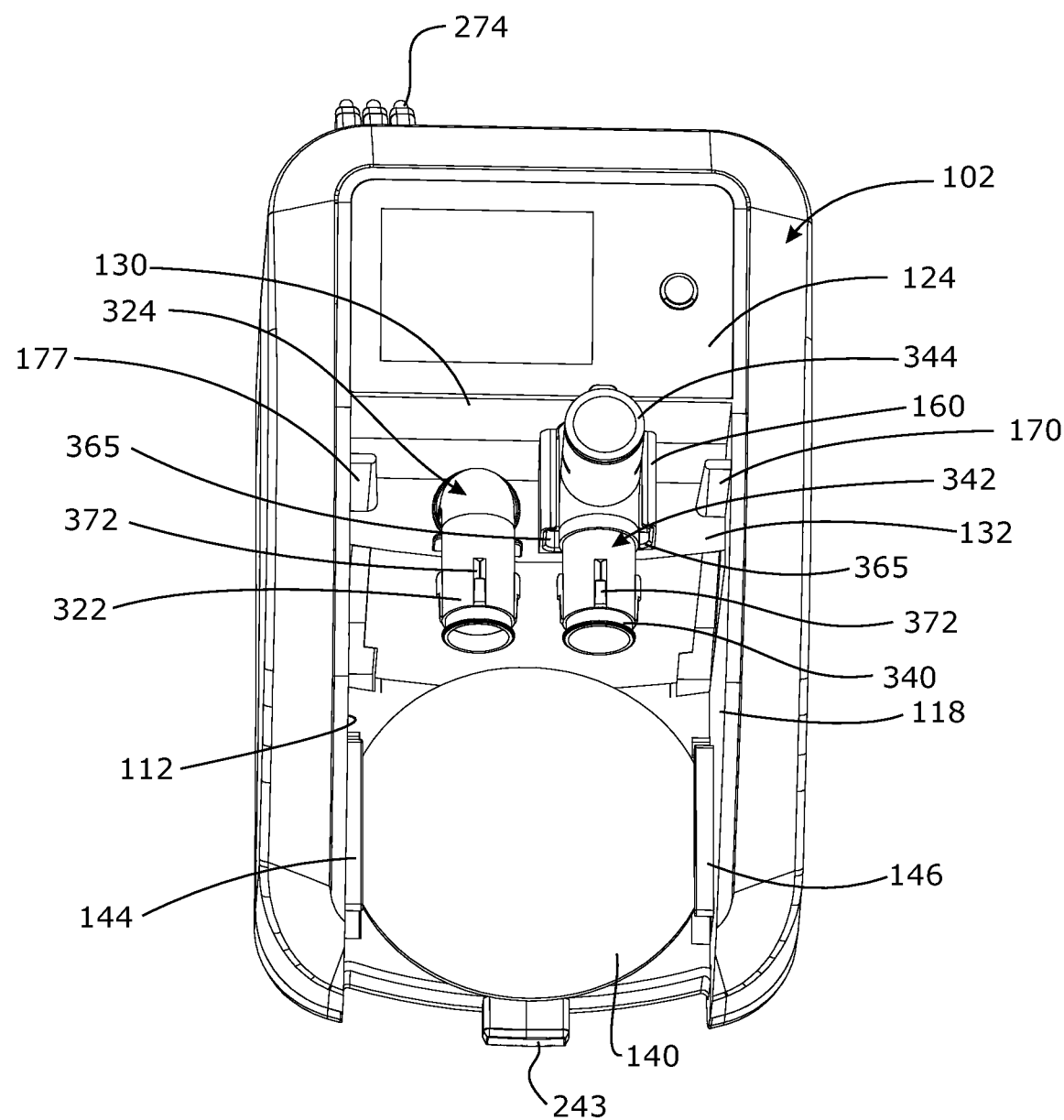
FIG. 27 is an overhead perspective view of the removable elbow when attached to the main housing.

The upper housing chassis 102 comprises a removable retention cover 150 as shown in FIGS. 25-26b. With the removable retention cover 150 removed from the upper chassis 102, the elbow 342 can be removed from the elbow retainer 160. With the removable retention cover 150 connected to the upper chassis 102, the elbow 342 cannot be removed from the elbow retainer 160.

The retention cover 150 is generally L-shaped in cross section, and has an upper ceiling portion 151 and a substantially vertical wall portion 152 extending downwardly from a front edge thereof. The ceiling portion 151 comprises a recess 153 for receipt of the patient outlet port 344 of the removable elbow 342. The wall portion 152 comprises two recesses 154, 155; one for receipt of the manifold gases outlet port 322 and one for receipt of the manifold gases inlet port 340 (humidified gases return).

The retention cover 150 is configured such that it can only be removed from the upper chassis 102 of the housing 100 by moving it in a direction that is at least in part substantially transverse to the removal and insertion direction of the elbow 342. To that end, opposite sides of the retention cover 150 comprise retainment features 156 that co-operate with complementary retainment features 170 extending inwardly from the inner walls 112, 118 of the upper chassis 102. In the form shown, the retainment features 156 in the cover 150 comprise elongate recesses that extend substantially vertically, and the retainment features 170 of the upper chassis 102 comprise elongate slats that extend substantially vertically. Alternatively, the configuration could be reversed such that the cover 150 comprises the slats and the upper chassis 102 comprises the recesses. Alternatively one of the components could have a plurality of projections rather than slats. Preferably, the slats and recesses are tapered so that upper ends of the recesses and slats are narrower than their lower ends, to provide positive engagement of the cover 150 and upper chassis 102.

If the cover 150 is in position in the housing 100 and the elbow 342 is in position in the elbow retainer 160, attempting to pull elbow 342 forward will be unsuccessful, because of engagement between the retainment features 156, 170 between the retainment cover 150 and the upper chassis 102. It is necessary to lift the cover 150 upwardly relative to the housing 100 so that the retainment features 156, 170 clear each other, at which time the cover 150 can be removed, and the elbow 342 can be disengaged from the elbow retainer 160. After cleaning the removable elbow 342, the elbow 342 can be reengaged with the elbow retainer 160, and the cover 150 can be moved downwardly relative to the housing 100 to reengage with the housing 100, and to retain the elbow 342 in position in the housing 100.

This configuration has the benefit that two discrete actions are required to remove the elbow 342 from the housing 100, the movement of the cover 150 in a first direction to release that from the housing 100 followed by the movement of the elbow 342 in a second direction that is transverse to the first direction, to remove the elbow 342 from the elbow retainer 160. The result is that a user is unlikely to accidentally disconnect the elbow 342, but the arrangement enables easy removal and reconnection of the elbow 342 without the use of fasteners or great force, which is particularly beneficial for users with limited mobility. This arrangement is also beneficial where the direction of connection and disconnection of the liquid chamber 300 with the main housing 100 (and the ports) corresponds to the direction of connection and disconnection of the elbow 342 and the housing 100.

The described arrangement will prevent accidental removal of the removable elbow 342 as the liquid chamber 300 is removed from the chamber bay 108.

It will be appreciated that while the movement direction of the retention cover 150 is shown as being normal or perpendicular to that of the elbow 342, the same result could be achieved with a smaller relative angle between the two movements, provided the movements are at least substantially transverse to one another for at least part of the movement. Additionally, it will be appreciated that the first direction of movement of the retention cover 150 does not necessarily need to be vertical. For example, the retention cover 150 could be removable from the main housing 100 and reconnectable thereto by moving it in a lateral or sideways direction.

An electrical connector 366 projects from a rear portion of the elbow 342 in a direction opposite to that of the gases inlet port 340. The electrical connector 366 is suitably a printed circuit board that forms a male connector portion that protrudes outward from the elbow and that is adapted for receipt in the female electrical connector 278 in the upper chassis 102. The electrical connector 366 is advantageously a male connector portion to avoid difficulties with space constraints in the elbow 342 and for electrical safety to prevent over-currents. Alternatively, the electrical connector 366 may be or may comprise a female connector to receive a complementary male connector. The electrical connector 366 is configured to be in electrical communication with the electrical connector 276 that is provided in the rear wall 122 of the upper housing chassis 102 to receive mains or battery power from the same source as the electrical connector 276. In alternative configurations, the electrical connector 366 can be connected to a separate mains or battery power source.

The connector 366 is coupled to one or more temperature sensors to determine the temperature of the gas flowing through the gases inlet port 340. In one configuration, the temperature sensor(s) may comprise thermistor(s) 367 that is/are coupled to the electrical connector 366. In an alternative configuration, at least part of the removable elbow 342 may be a material that is transparent to infrared wavelengths (such as transparent polycarbonate for example), and the temperature sensor 367 may comprise an infrared temperature sensor. This may provide a reduced number of wires and more accurate sensing. In some alternative configurations, if part of the removable elbow 342 is of a material that is transparent to infrared wavelengths, the infrared temperature sensor 367 may instead be located elsewhere within a wall of the elbow 342, or may be located within a portion of the housing 100 proximal to the elbow 342. In an alternative configuration, digital temperature sensor(s) may be used instead of thermistor(s).

In one configuration, the electrical connector 366 is also coupled to a power connector comprising a pin connector or inductive power connector 368 for coupling to and powering the heater wire(s) 3c in the patient breathing conduit. The connector 368 is in the form of a chimney portion. The connector 368 extends upwardly adjacent to the gasflow outlet 344 and is positioned above the top of the retention cover 150, and is configured such that when the patient breathing conduit 16 is pneumatically coupled to the gasflow outlet, the heater wire 3c electrically couples to the connector 368 in the same single action.

The elbow comprises depressions 370 on part of the gasflow outlet 344 for engagement with complementary protrusions on a sliding locking collar connected to the heated patient interface tube 16.

The electrical connector 366 is electrically coupled to one or both of the electronics boards 272 via the female electrical connector 278 and cable 279 which is connected to one of the electronics boards by a detachable connector 280. This enables the electronics board(s) 272 to power the sensors and electrical connector 366 in the removable elbow 342 and receive and process data from the sensors.

A connector guard 278a (FIG. 32) may be provided and fastened to the female connector 278 to minimise the likelihood of bending pins of the connector, to prevent a user's finger from touching a live portion of the connector 278, and to assist with maintaining the female connector in position.

The removable elbow 342 comprises retainment features 372 on or adjacent the gases inlet port 340 to positively engage with the liquid chamber gases outlet port 308. The gases outlet port may have feature(s) (not shown) that are adapted to accept or interface with the retainment features 372, such as a lip and/or O-ring seal for example. In the form shown, the retainment features 372 comprise a plurality of resilient fingers on a portion of the inlet port 340 adjacent a recess for receipt of an O-ring seal. The resilient fingers are positioned at discrete locations around the periphery of the inlet port 340. In the configuration shown, there are four resilient fingers around the periphery of the inlet port 340, with an even angular spacing between the fingers. Alternatively, there may be two or more resilient fingers located with any suitable angular spacing.

The resilient fingers each comprise a relatively narrow portion 372a positioned toward an outer end of the gases inlet port 340, and an enlarged head portion 372b positioned further from the outer end of the gases inlet port 340. It can be seen from FIG. 28 that at least the enlarged heads 372b project transversely outward beyond a portion of the gases inlet port 340 adjacent the fingers. The liquid chamber gases outlet port 308 has a cylindrical region with an internal diameter slightly larger than the outer diameter of the portion of the gases inlet port 340 adjacent the fingers. As the gases inlet port 340 is inserted into the liquid chamber gases outlet port 308, the O-ring seal will initially seal against the interior of the gases outlet port 308. Upon further insertion, the fingers 372 will deform inwardly against the interior of the gases outlet port 308 until they pass a lip in that interior, at which time the fingers 372 move outward to positively engage against the lip and minimise the likelihood of accidental removal of the liquid chamber 300. When the liquid chamber 300 is to be removed from the apparatus 10, the chamber 300 will need to be moved outwardly with sufficient force to force the fingers 372 inwardly to clear the lip.

The fingers 372 may provide significant resistance against movement of the liquid chamber 300 inwardly or outwardly. In some configurations, movement of the chamber 300 into or out of engagement with the housing 100 may be entirely manual by a user pushing directly on the liquid chamber 300. In alternative configurations, the apparatus 10 may be provided with a handle/lever arrangement as described below, to assist with engaging and/or disengaging the liquid chamber 300 with/from the housing 100.

In the form shown, the manifold gases outlet port 322 is also shown as having the resilient fingers 372. The engagement and operation of the resilient fingers 372 with the liquid chamber gases inlet port 306 will be the same as that described above. In some configurations, the manifold gases outlet port 322 and manifold gases inlet port 340 will both have the resilient fingers. In other configurations, only one of those ports may have the resilient fingers, as that may be sufficient to minimise the likelihood of accidental disengagement of the liquid chamber 300.

In an alternative configuration, the ports on the housing 322, 340 may be larger than the ports 306, 308 on the liquid chamber 300, so that ports 306, 308 are received within ports 322, 340. Soft seals, such as O-ring seals, will again be provided to seal between the ports. In that configuration, if resilient fingers are provided they will be provided on one or both of the ports 306, 308. Alternatively, the resilient fingers could be provided on one or both of the larger ports, and be inwardly directed to interact with an outer surface of the smaller port(s). The apparatus 10 may have any combination of these alternatives.

In an alternative configuration, snap-fit features, bayonet connections, or other features may be provided instead of the resilient fingers.

Rather than being in the form of an elbow, the gasflow tube could have any other suitable configuration depending on the configuration of the apparatus. For example, the gasflow tube could be substantially linear or a non-liner configuration, with the manifold gases inlet port 340 and the patient outlet port 344 at ends of the tube. The inlet and outlet ports will typically be offset from each other. The direction of insertion and removal of the gasflow tube into and from the retainer 160 (e.g. forward and rearward) will be at an angle to the movement direction of the retention cover 150 as described above. The retainer 160 may be modified as required, depending on the configuration of the gasflow tube.

5. Humidifier/Liquid Chamber Bay

The liquid chamber bay 108 and handle/lever arrangement will now be described in more detail with reference to FIGS. 33 to 52.

As discussed, the liquid chamber bay 108 comprises opposed left side and right side guide rails 144, 146 which extend toward a centre of the bay 108 from the respective left and right side inner walls 112, 118. The guide rails 144, 146 assist with guiding the liquid chamber 300 into position in the bay 108. The guide rails 144, 146 are parallel to the floor 136 of the liquid chamber 300 and/or with the upper surface of the heater plate 140, to enable the flange 310 of the liquid chamber 300 to slide therebetween. Insertion of the liquid chamber 300 into the bay 108 is shown in FIGS. 34 to 38.

The main housing 100 comprises a handle/lever 500 for assisting with insertion and/or retention and/or removal of the liquid chamber 300 in and/or from the chamber bay 108. Different configurations may be configured for assisting with one, two, or all of insertion, retention, removal of the liquid chamber 300 in and/or from the chamber bay 108. One example configuration is described below with reference to FIGS. 44 to 52.

Figure 33:
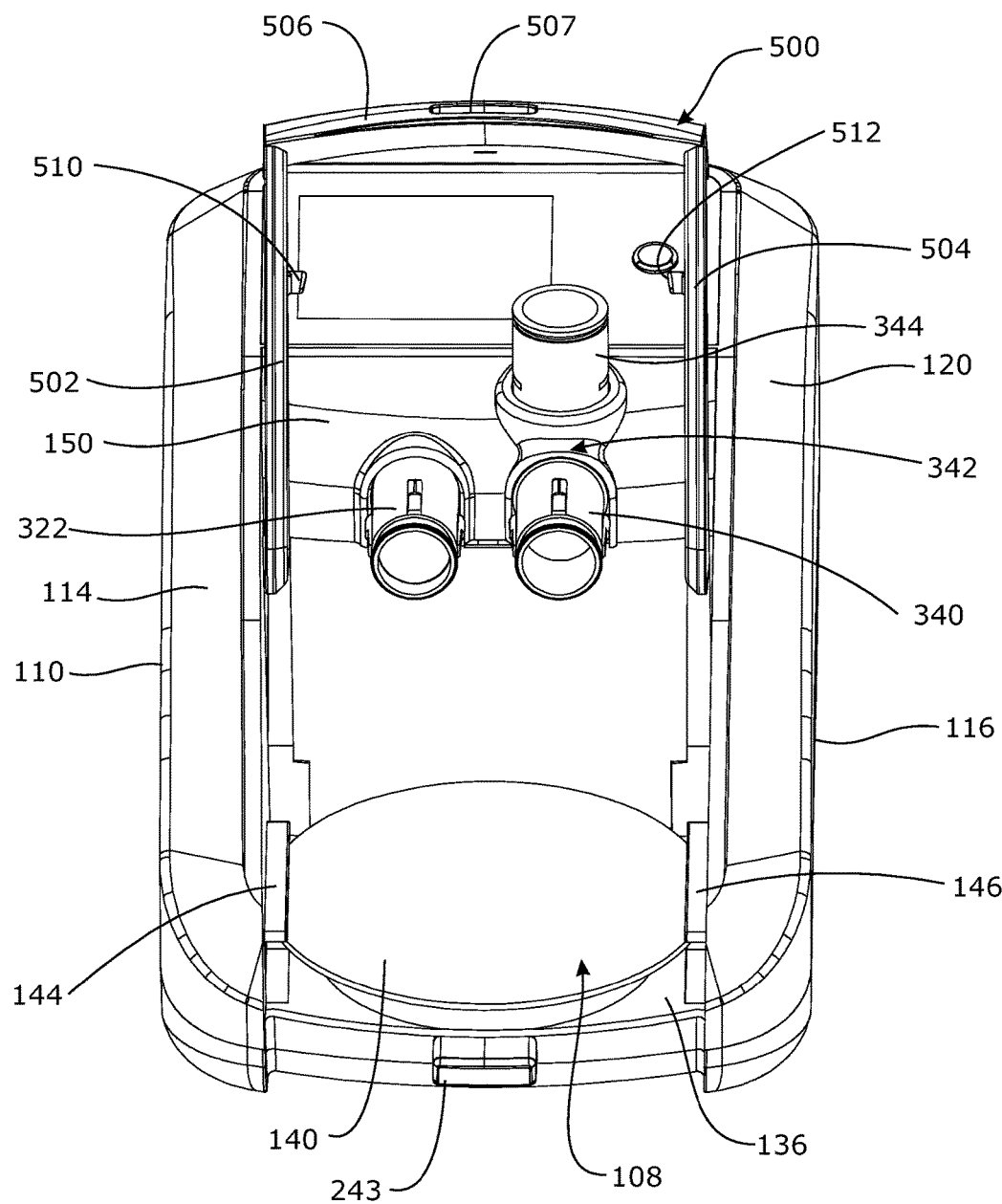
FIG. 33 is a front perspective view of the flow therapy apparatus showing a first configuration humidifier bay for receipt of a humidifier chamber, with a handle/lever in a raised position.
Figure 38:
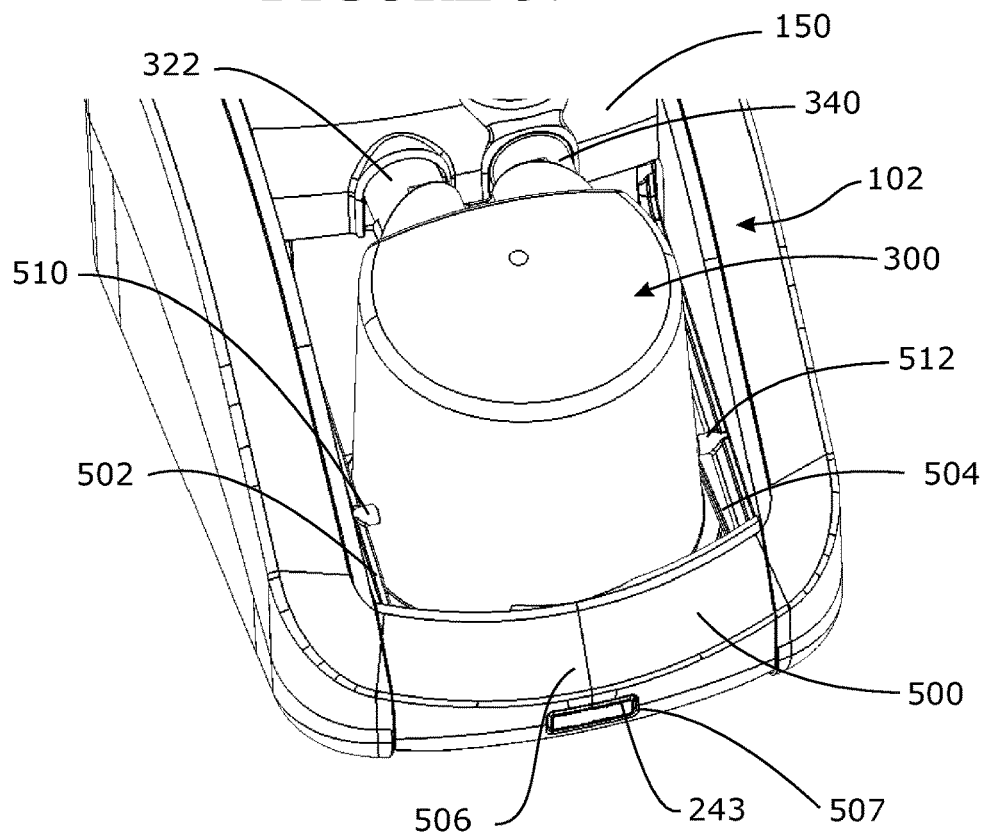
FIG. 38 is a view similar to FIG. 37 with the handle/lever fully lowered and engaged with a retaining feature.
Figure 39:
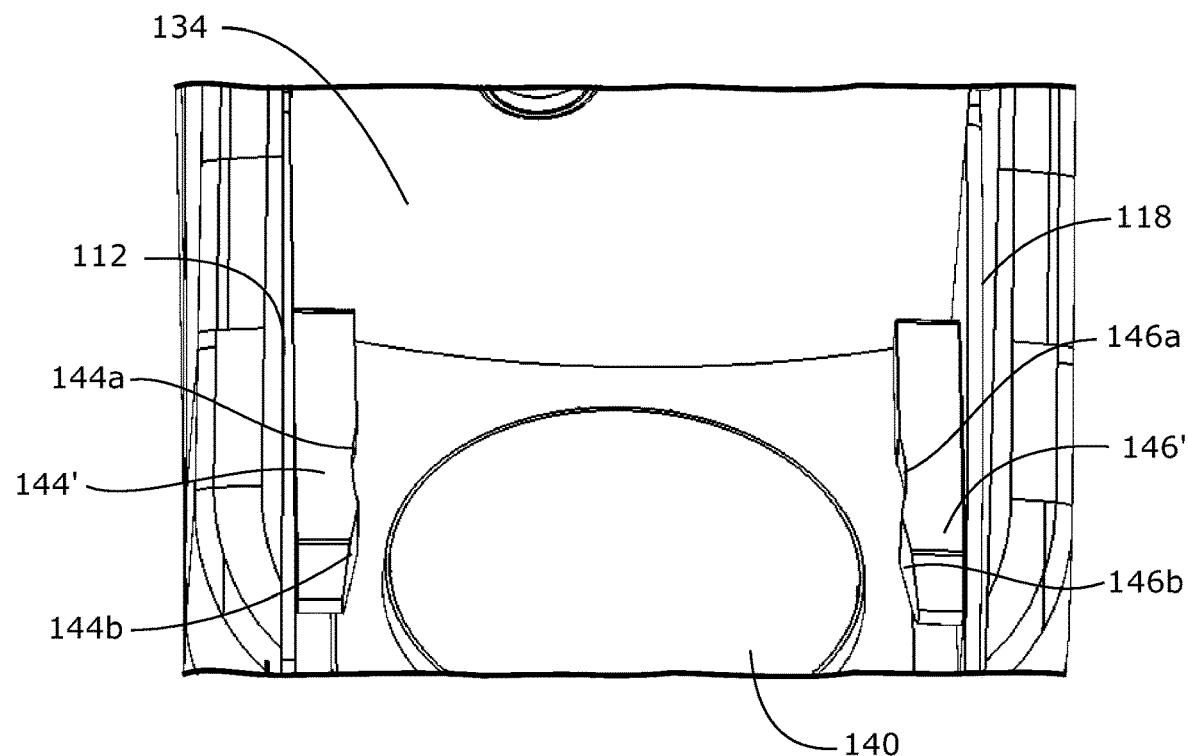
FIG. 39 is a front overhead perspective view of the flow therapy apparatus showing a second configuration humidifier bay for receipt of the humidifier chamber, having an alternative configuration of guide rails with detents for locating the chamber in the humidifier bay, and with the handle/lever being configured for assisting with removal of the liquid chamber from the chamber bay.
Figure 40:
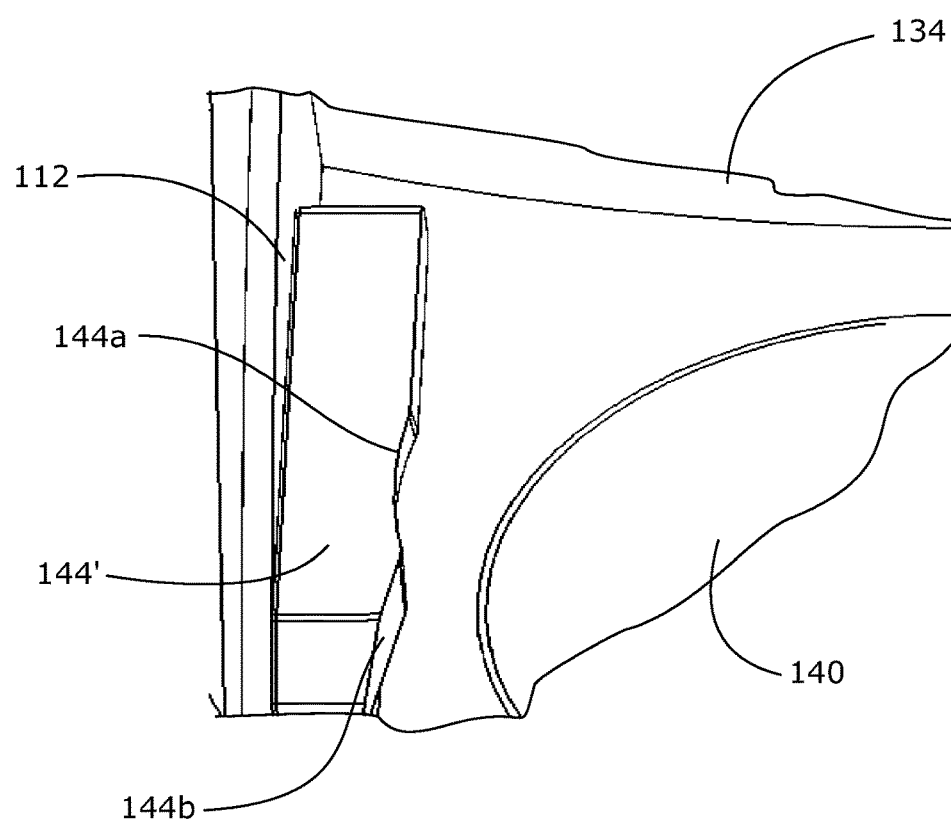
FIG. 40 is a front overhead perspective view of the left side guide rail and detent.
Figure 41:
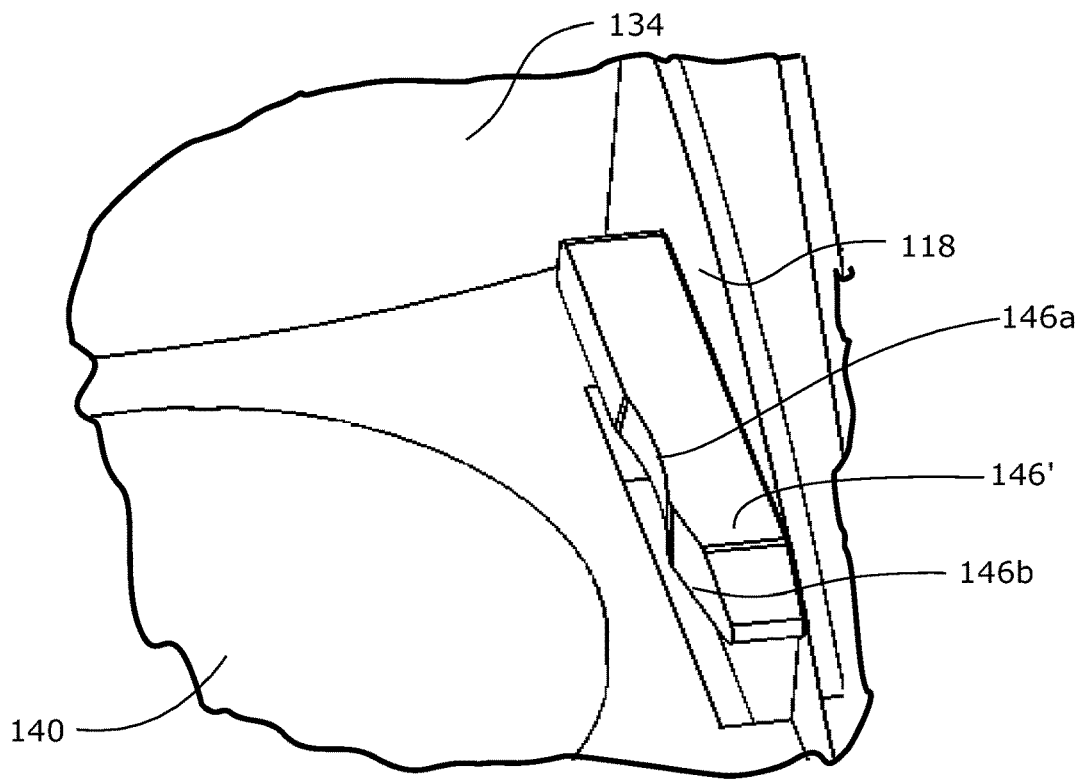
FIG. 41 is a front overhead perspective view of the right side guide rail and detent.
Figure 42:
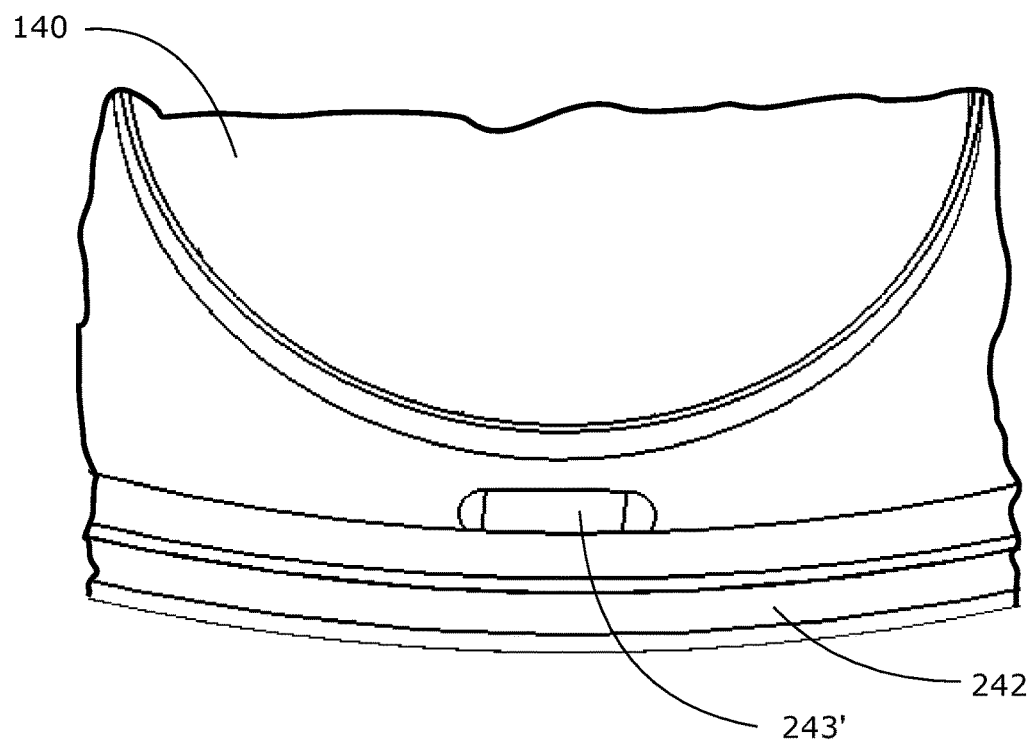
FIG. 42 is an overhead perspective view of a retaining feature for engaging the handle/lever in a lowered or closed position.
Figure 43:
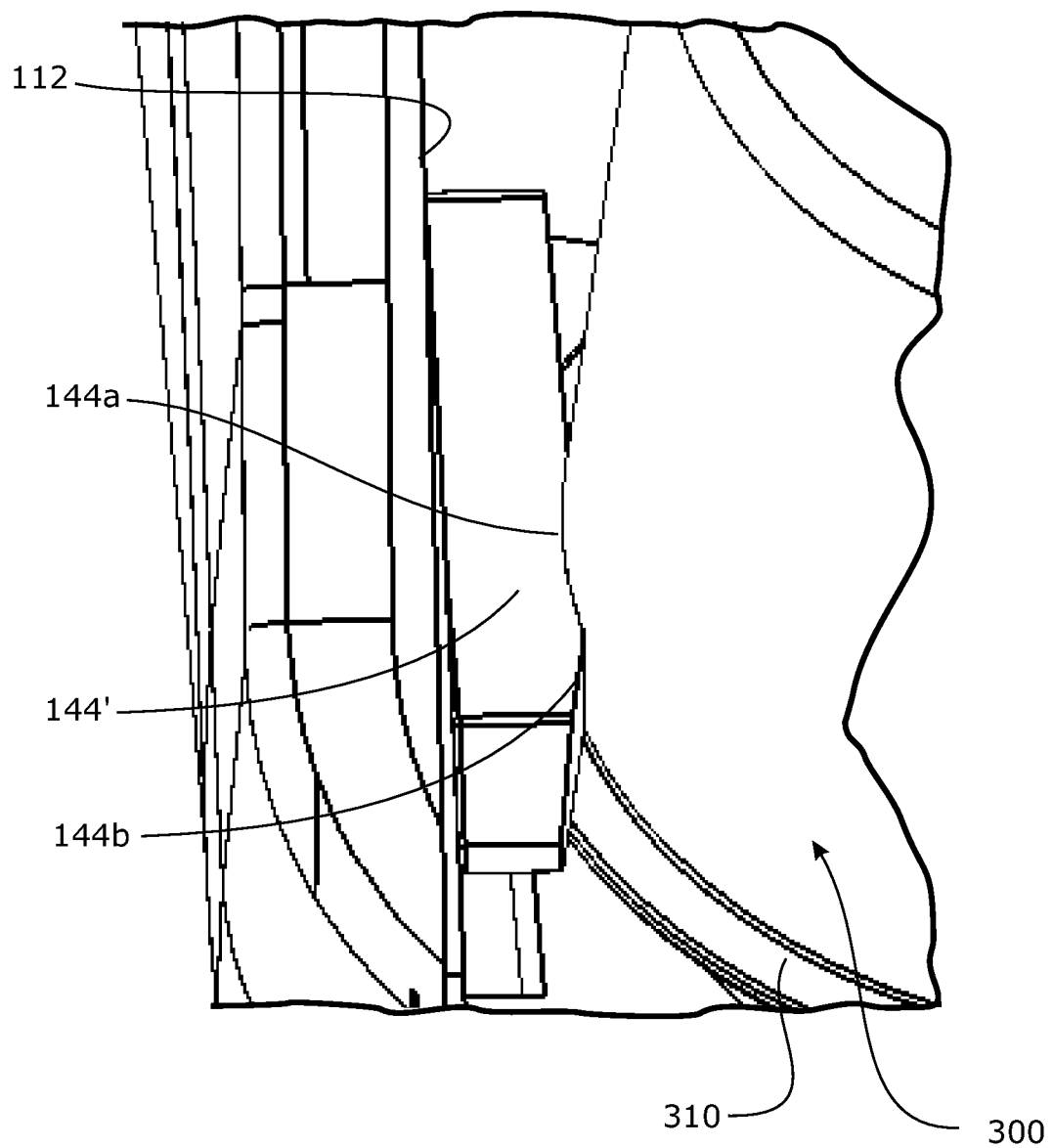
FIG. 43 is a front overhead perspective view of the left side of the apparatus of FIGS. 39 to 42 showing the humidifier chamber engaged with the detent.
Figure 44:
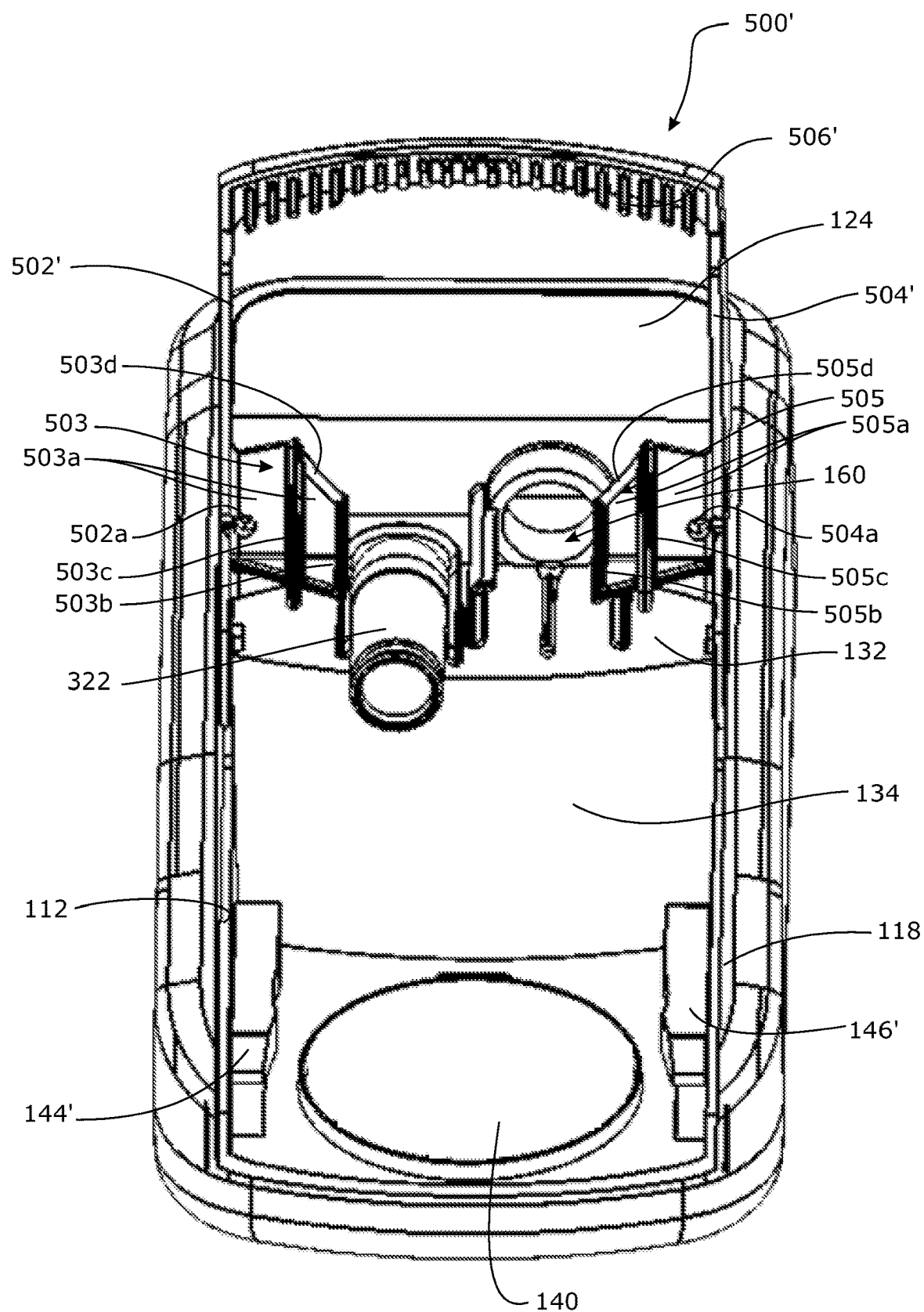
FIG. 44 is a front overhead perspective view of the apparatus of FIGS. 39 to 43, showing an alternative configuration handle/lever in a raised position.

The handle/lever 500 is pivotally attached to the main housing 100, and is movable from a first, raised or open position shown in FIG. 33 for example to a second, lowered or closed position shown in FIG. 38 for example. The handle/lever has a left side arm 502 that is pivotally attached to the left inner side wall 112 of the upper chassis 102, a right side arm 504 that is pivotally attached to the right inner side wall 118 of the upper chassis 102, and a cross-member handle portion 506 that interconnects the free ends of the left and right side arms 502, 504 and forms an engagement region for grasping by a user's fingers. When the handle 500 is in the raised position, the cross-member 506 can act as a carrying handle for the apparatus 10. The liquid chamber 300 can be inserted into or removed from the chamber bay 108 when the handle/lever 500 is raised. When the handle/ lever 500 is in the lowered position, it inhibits or prevents removal of the liquid chamber 300 from the chamber bay 108. Because the handle/lever encloses a portion of the chamber bay when the lever is in the closed or fully lowered position, when the handle/lever is in the fully raised position, a large space is created between the cross-member of the handle/lever and the housing of the apparatus including a large opening at the front of the chamber bay and around the liquid chamber, allowing easy insertion and removal of the liquid chamber to and from the chamber bay because a user's fingers can easily fit between housing walls and the liquid chamber.

An example pivot arrangement of the handle/lever 500 is described below with reference to FIGS. 44 to 51. The pivot arrangement enables pivotal movement of the handle/lever 500 but prevents translational movement of the handle/lever.

The left and right side arms 502, 504 of the handle/lever 500 comprise liquid chamber engaging features in the form of inwardly directed protrusions 510, 512. The spacing between the arms 502, 504 is sufficient to enable the widest part of the body 302 of the liquid chamber 300 above the flange 310 to be received therebetween. However, the spacing between the protrusions 510, 512 is not sufficient to enable the widest part of the body 302 of the liquid chamber 300 to be received therebetween.

In some configurations the edges of the protrusions 510, 512 might be bevelled, curved or angled such that they can more easily ride along and push the chamber 300.

In some configurations the protrusions 510, 512 may be formed from or include (for example, as an overmoulded layer) a soft (or at least softer than the handle 500) resilient material or component to prevent damage to the chamber 300 that might arise if the handle 500 is closed on the chamber 300 too forcefully.

Figure 34:
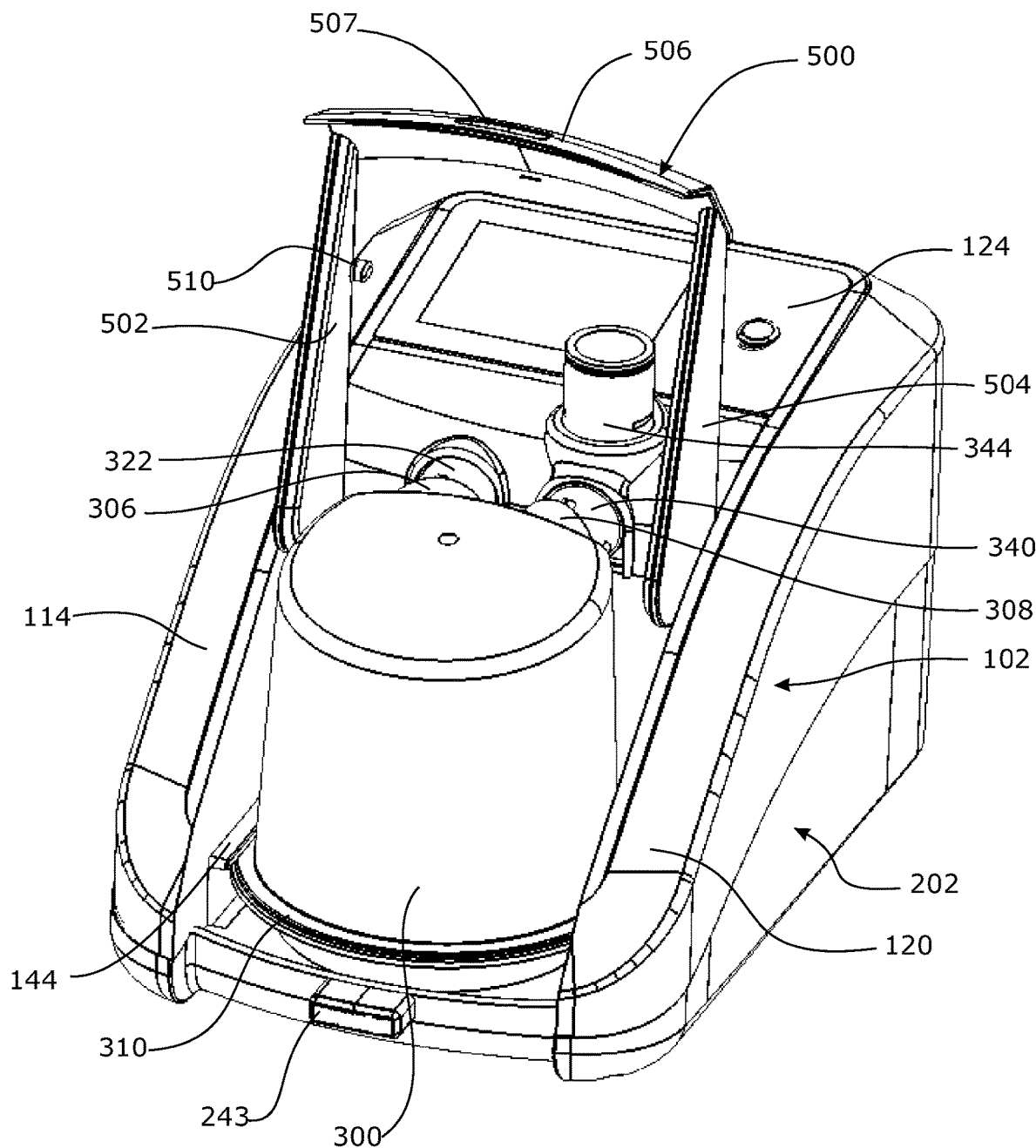
FIG. 34 is a view similar to FIG. 33 but with the humidifier chamber positioned partly in the humidifier bay and located by guide rails.

To insert the liquid chamber 300 in the chamber bay 108, initially the handle/lever 500 is in the raised position as shown in FIG. 33. The liquid chamber 300 is partially inserted into the bay 108 with its bottom surface resting on the heating plate 140 and its flange 310 positioned beneath the guide rails 144, 146, as shown in FIG. 34. The chamber 300 will be manually moved rearwardly in the housing a sufficient amount that the ports 322, 340, 306, 308 are at least partly engaged. For example, the O-ring seals between the ports 322, 340, 306, 308 may be engaged but the resilient fingers 372 may not be engaged.

Figure 35:
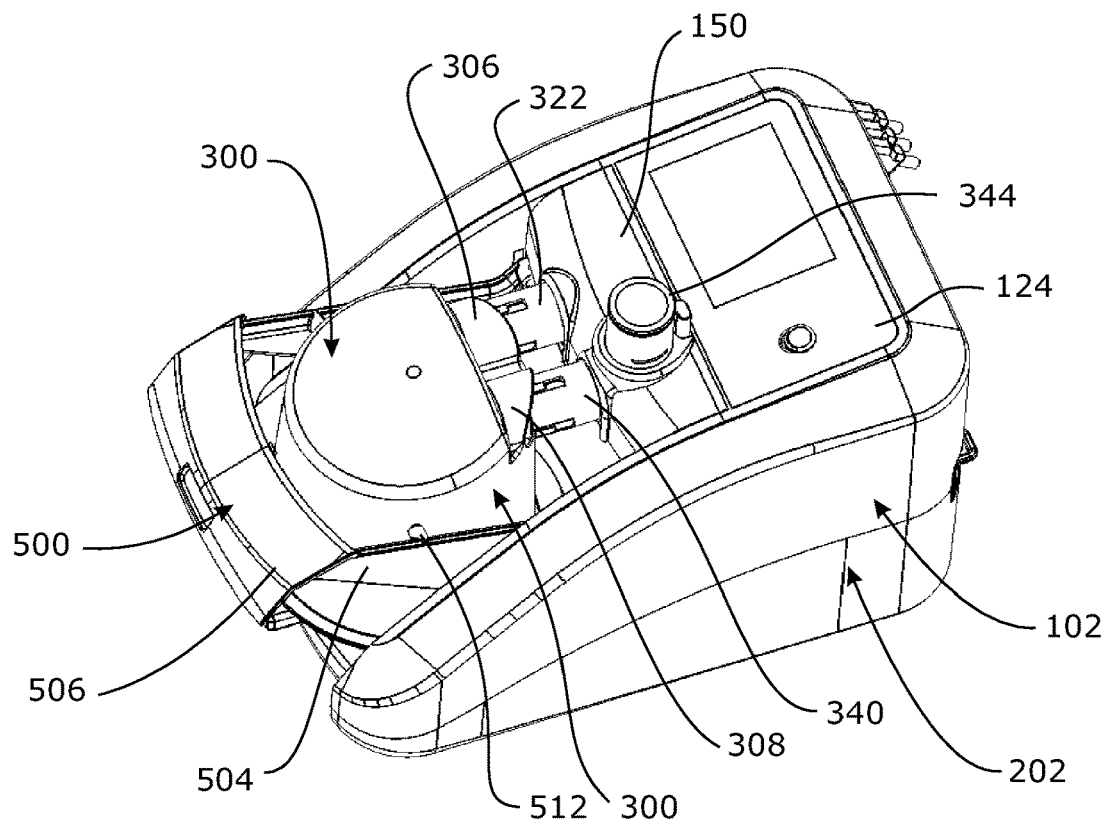
FIG. 35 is a view similar to FIG. 34 with the handle/lever partly lowered to move the humidifier chamber further into engagement in the humidifier bay.
Figure 36:
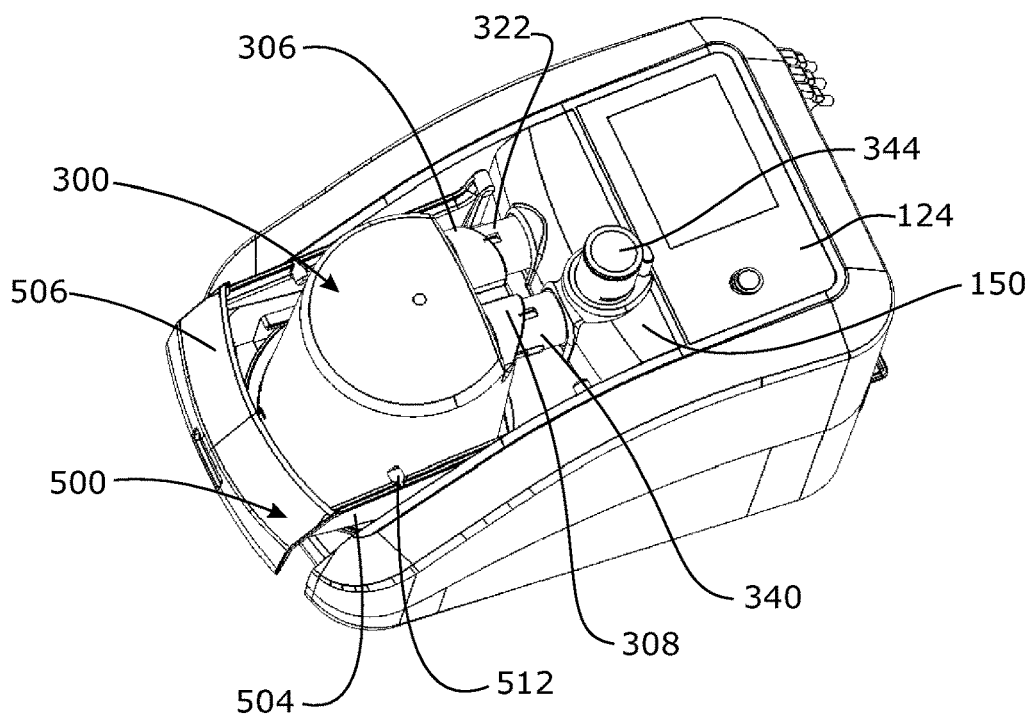
FIG. 36 is a view similar to FIG. 35 with the handle/lever further lowered.
Figure 37:
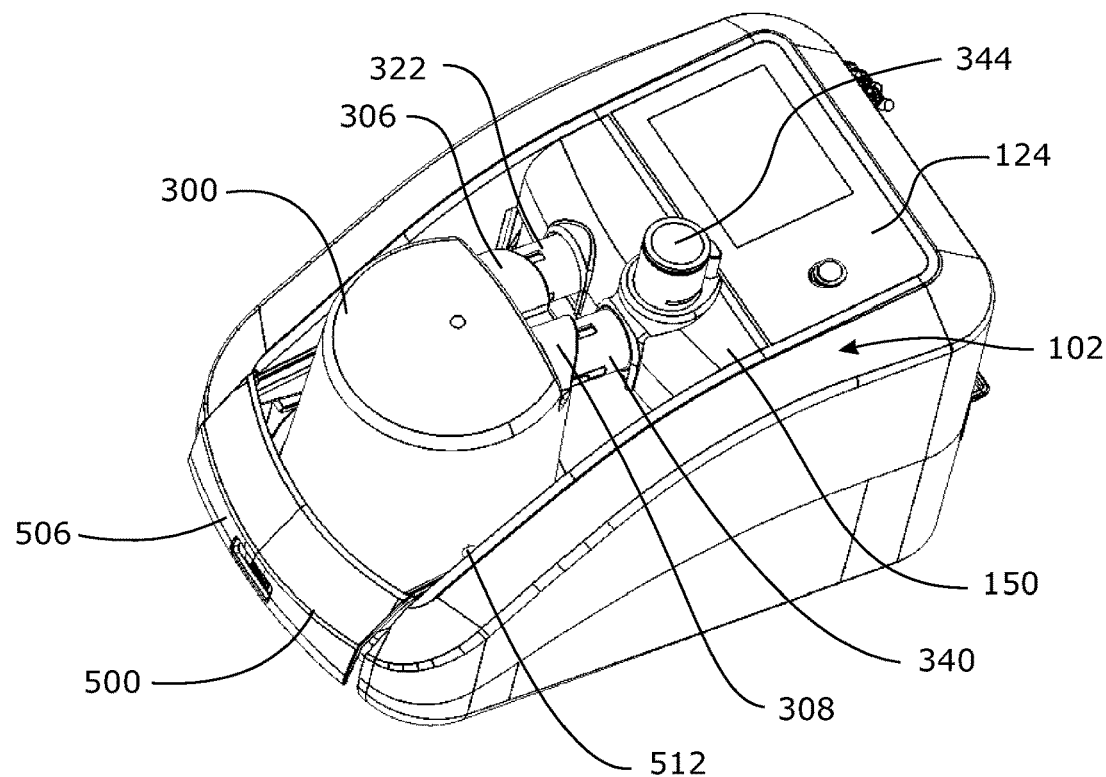
FIG. 37 is a view similar to FIG. 36 with the handle/lever nearly fully lowered.

The handle/lever 500 can then be pivoted downwardly toward its lowered position as shown in FIG. 35. In this intermediate position, the protrusions 510, 512 have engaged with the widest part of the housing 302 of the liquid chamber 300. Further downward movement of the handle/lever 500 through the positions shown in FIGS. 36, 37, and 38 progressively drives the liquid chamber 300 rearwardly into increased engagement with the ports 322, 340 of the apparatus 10, until the resilient fingers 372 (if present) are engaged with the lips in the ports 306, 308 in the liquid chamber 300.

In the closed or fully lowered position of the handle/lever 500 shown in FIG. 38, the cross-member 506 is located in the recess in front of the lips 142, 242 at the front of the upper and lower chassis parts, and encloses a portion of the chamber bay. The forwardly directed protrusion 243 of the lower chassis 202 is located in a complementary recess 507 in the cross-member, and acts as a positive engagement feature to positively engage the handle/lever 500 in the lowered position. With the handle/lever 500 in the lowered position, a portion of the cross-member 506 projects sufficiently above the floor of the chamber bay 108 and above the flange 310 of the liquid chamber that it prevents the liquid chamber 300 from being slid forward and removed from the liquid chamber bay 108. The guide rails 144, 146 prevent the liquid chamber 300 from being lifted and removed vertically from the liquid chamber bay 108.

The cross-member 506 of the handle/lever is resilient so that it can flex sufficiently to enable the protrusion 243 to be inserted into the recess or aperture 507 or removed therefrom.

To remove the liquid chamber 300 from the chamber bay 108, the steps shown in FIGS. 33 to 38 are reversed. When the handle/lever 500 is lifted a sufficient amount, the protrusions 510, 512 will clear the liquid chamber 300 so that the liquid chamber 300 can be slid forward until its flange 310 clears the guide rails 144, 146 and the ports 322, 340, 306, 308 disconnect. The liquid chamber 300 can then be removed from the housing 100.

In an alternative configuration of the handle/lever 500, rather than having protrusions 510, 512, only a single protrusion or other liquid chamber engaging feature may be provided. In another alternative configuration, part of the cross-member 506 may be configured to push against liquid chamber 300 and act as the liquid chamber engaging feature.

In an alternative configuration, the cross-member 506 may not be a sufficient size to act as a carrying handle for the apparatus when in a raised position.

The handle/lever 500 may be gas injection moulded so that it has smooth exterior surfaces to assist with cleaning of the handle/lever. The handle/lever may comprise an external seal to seal between the handle/lever and the housing. The sealing between the handle and the housing may be within the handle retainer about the aperture (in the region of item 4498 in FIG. 117) that the handle moves in and out of when raised/lowered. A seal could be used to seal between the handle and the upper chassis.

FIGS. 39 to 43 show an alternative guide rail configuration that assists with insertion and/or retention of the liquid chamber 300 in the chamber bay 108. In this configuration, the guide rails 144', 146' comprise detents 144a, 146a. The detents 144a, 146a comprise enlarged recesses that typically have a size and configuration corresponding substantially to the largest dimension of the body 302 of the liquid chamber 300. The detents 144a, 146a correspond in position to the fully inserted position of the liquid chamber 300 in the chamber bay 108, and the fully engaged position of the ports 322, 340, 306, 308.

A portion 144b, 146b of each guide rail 144', 146' located between the detent 144a, 146a and the front of the chamber bay 108 forms an inwardly directed ridge, with the ridges having a spacing therebetween that is smaller than the largest dimension of the body 302 of the liquid chamber 300. At least the ridges 144b, 146b of the guide rails 144', 146' have sufficient resilience, that as the liquid chamber 300 is inserted between the guide rails 144', 146' with its flange 310 beneath the guide rails 144', 146', the ridges 144b, 146b deform or flex outwardly (relative to the main housing 100) until the chamber 300 is fully engaged in the detents 144a, 146a between the guide rails 144', 146', following which the ridges 144b, 146b have flexed back inwardly. Alternatively or additionally, the liquid chamber 300 may be somewhat resilient and can deform to pass the ridges 144b, 146b, and can 'pop' back to its original shape once the liquid chamber is fully engaged in the detents 144a, 146a. Similarly, the ridges 144b, 146b deform or flex outwardly, and/or the liquid chamber 300 deforms inwardly, as the chamber 300 is removed from the detents 144a, 146a. The guide rails and, in particular the detents 144a, 146a and ridges 144b, 146b, provide tactile feedback to a user to enable the user to easily determine when the liquid chamber 300 is fully engaged in the chamber bay 108. The detents 144*a*, 146*a* and ridges 144*b*, 146*b* may be provided in addition to the resilient fingers on the port(s), or could be provided as an alternative to the resilient fingers.

The heater plate 140 is resiliently mounted; for example, on biasing device(s) such as spring(s). The resilient mounting enables the heater plate to move downwardly to accommodate the liquid chamber in the chamber bay, while maintaining good contact between the heater plate 140 and the base of the liquid chamber once the chamber is inserted in the chamber bay.

The handle/lever arrangement in combination with the guide rails positions and retains the liquid chamber in the correct position. The guide rails also enable the liquid chamber to be turned or rotated to align its ports with the ports in the main housing.

Rear portions of the guide rails 144', 146' may have ridges as shown to provide precise location of the liquid chamber 300 in the chamber bay 108. However, rather than the guide rails defining the rearmost position of the liquid chamber 300 in the chamber bay 108, the rearmost position of the liquid chamber 300 in the chamber bay 108 may instead be defined by engagement of the ports 322, 340, 306, 308 or by engagement of part of the liquid chamber 300 with part of the housing 100; for example, a rearward portion of the flange 310 with the wall 134 of the housing 100.

Rather than having recesses on the guide rails, the detents may be configured differently. For example, the guide rails may comprise protrusions, with the liquid chamber having recesses to receive the protrusions when the liquid chamber is fully engaged in the chamber bay.

In an alternative configuration, the detents may be provided adjacent to the guide rails rather than integrated into the guide rails. For example, the protrusions or recesses may be provided in a portion of the chamber bay 108 of the main housing adjacent the guide rails (for example, above or below the guide rails), with the liquid chamber configured to engage with the detents when inserted into the chamber bay 108. The detents will be aligned with the direction of insertion and removal of the liquid chamber into and from the chamber bay to enable that engagement. For example, if the liquid chamber is arranged to be inserted vertically into the chamber bay, the detents will be configured accordingly.

In an alternative configuration, only a single detent may be provided. For example, only one guide rail may have a recess and ridge. Alternatively, only one guide rail may have a projection for receipt in a recess on the liquid chamber. Alternatively, a single detent may be provided adjacent only one of the guide rails.

This configuration also differs from that described above in that rather than a protrusion 243 being provided on the front of the lower chassis 202, a recess 243' is provided in the main housing. The cross member 506' of the handle/lever 500' may be provided with a hook or projection (not shown) to engage in the recess 243'.

This configuration also differs in that the left and right side arms 502', 504' of the handle/lever 500' comprise apertures 502*a*, 504*a* for guiding liquid tubes from above into the liquid chamber 300, to enable the liquid chamber 300 to be refilled and/or emptied as desired. The apertures 502*a*, 504*a* are provided in bosses in pushers 503, 505 that are described below, but could be provided elsewhere on the handle/lever 500'.

Figure 45:
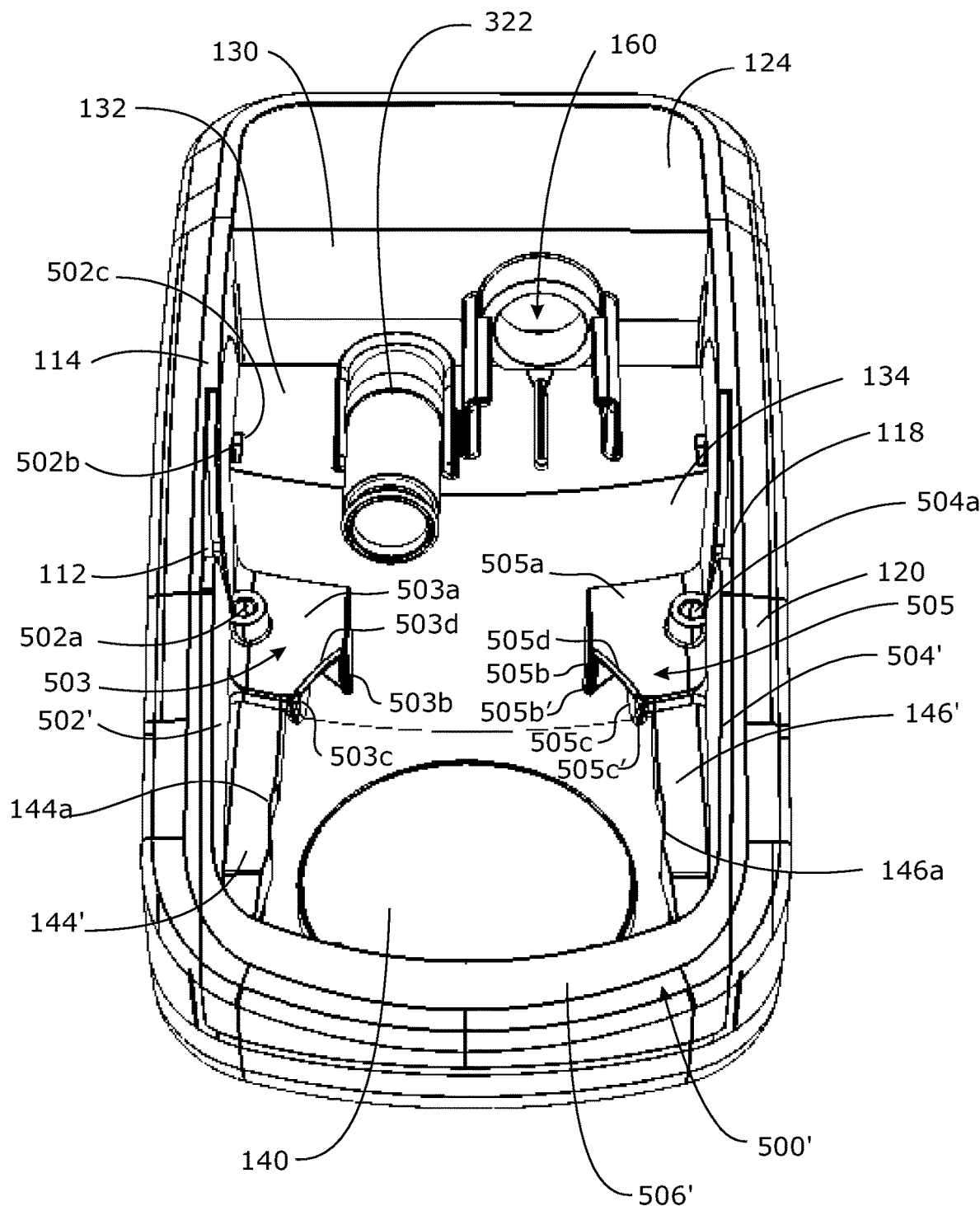
FIG. 45 is a front overhead perspective view of the apparatus of FIG. 44, showing the handle/lever in a lowered or closed position.
Figure 46:
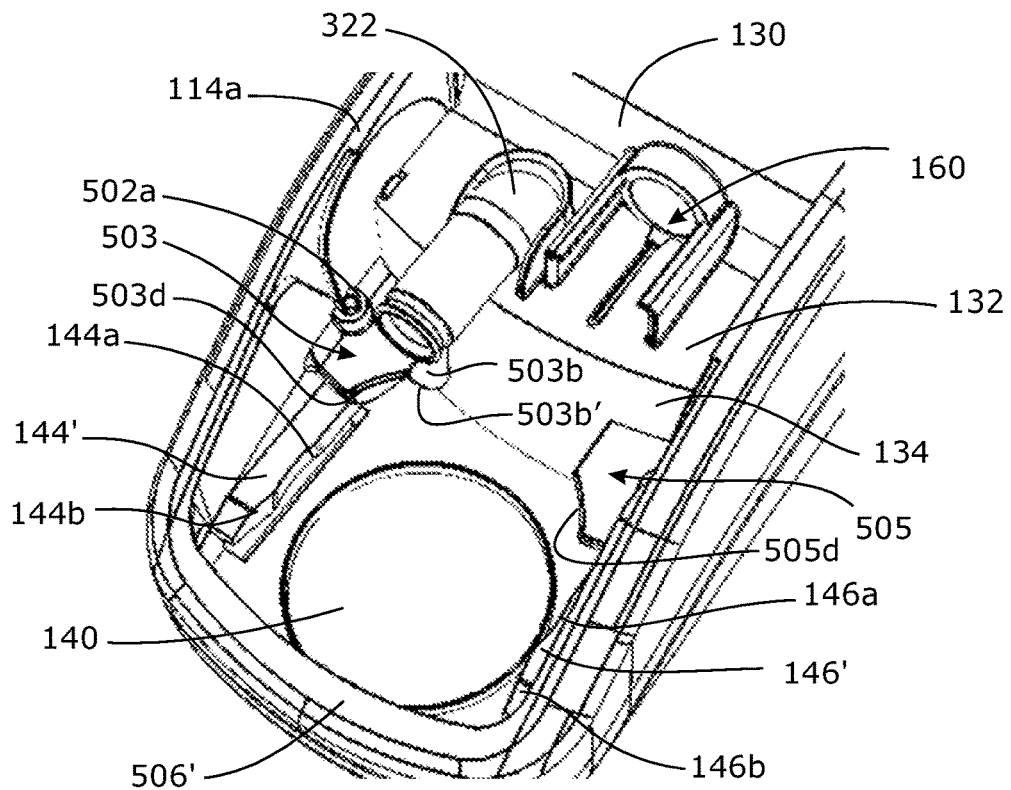
FIG. 46 is a front overhead perspective view of the left side of the apparatus of FIG. 44, showing detail of the handle/lever.
Figure 47:
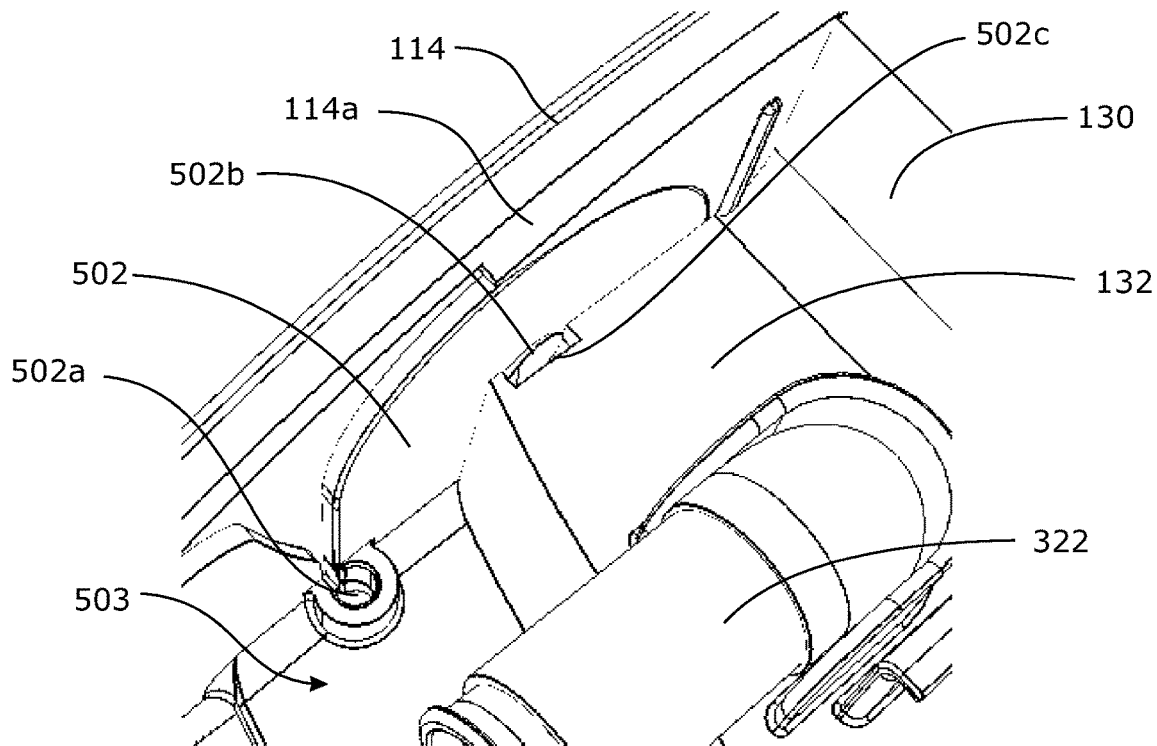
FIG. 47 is a front overhead perspective view of the left side of the apparatus of FIG. 44, showing exemplary pivot detail of the handle/lever.
Figure 48:
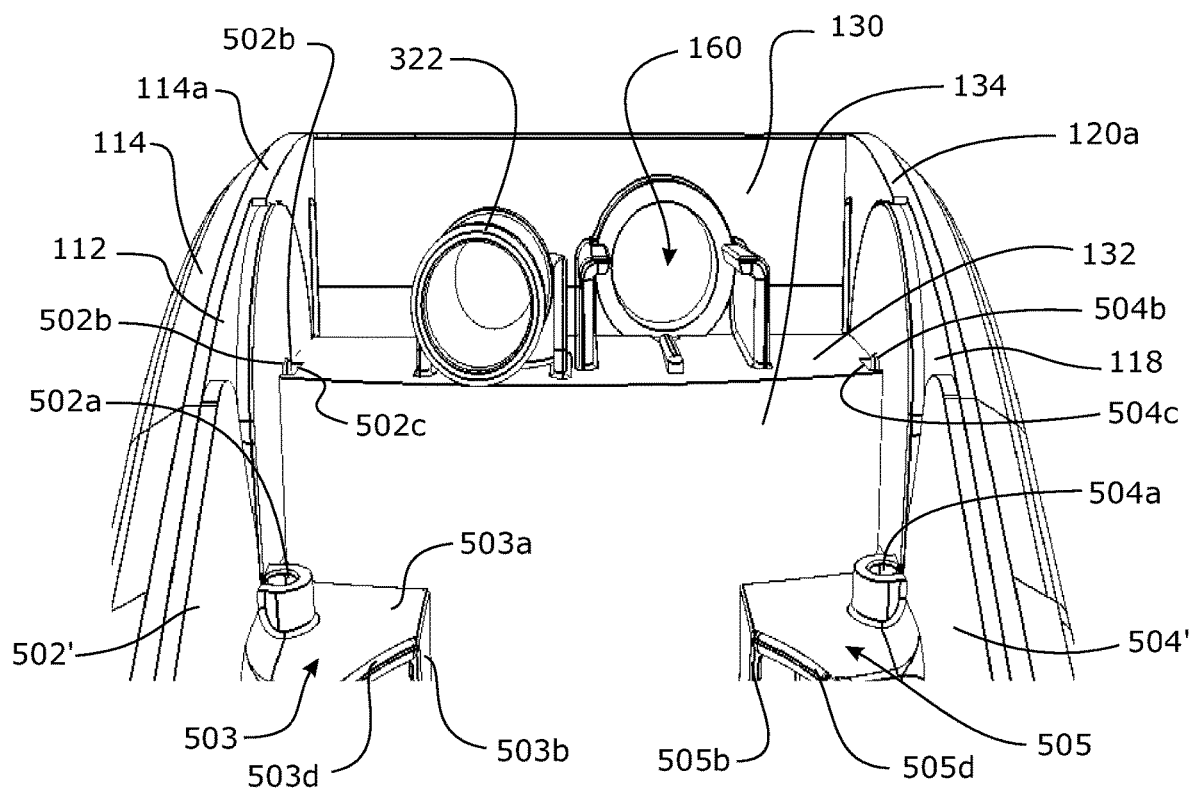
FIG. 48 is a front overhead perspective view showing detail of the handle/lever pivots.

The handle/lever 500' also assists with disengaging the liquid chamber 300 from the chamber bay 108. The handle/lever 500' comprises left and right side pushers 503, 505 to assist with that disengagement. The left side pusher 503 is connected to and extends inwardly from the left side arm 502', and the right side pusher 505 is connected to and extends inwardly from the right side arm 504', such that the pushers 503, 505 extend towards each other. As shown in FIG. 45, the pushers 503, 505 are positioned on the side arms 502', 504' so that when the handle/lever 500' is in its lowered or closed position, the pushers 503, 505 are located at the rear of the chamber bay 108 adjacent the vertical wall portion 134.

The pushers 503, 505 each comprise a platform portion 503*a*, 505*a*, which is substantially horizontal when the handle/lever 500' is in the lowered or closed position. Each pusher 503, 505 also comprises at least one engagement member 503*b*, 503*c*, 505*b*, 505*c* which is arranged to engage against the liquid chamber 300 and push the liquid chamber 300 out of engagement from the detents 144*a*, 146*a* of the guide rails 144', 146' when the handle/lever 500' is lifted from the lowered or closed position. As shown in FIG. 45, the engagement members 503*b*, 503*c*, 505*b*, 505*c* extend vertically downwardly from the platform portions 503*a*, 505*a* when the handle/lever 500' is in the lowered or closed position.

In some configurations the edges of the engagement members 503*b*, 503*c*, 505*b*, 505*c* might be bevelled, curved or angled such that they can more easily ride along and push the liquid chamber.

In some configurations the engagement members 503*b*, 503*c*, 505*b*, 505*c* may be formed from or include (for example, as an overmoulded layer) a soft (or at least softer than the handle 500') resilient material or component to prevent damage to the liquid chamber 300 that might arise if the handle is moved too forcefully.

Figure 49:
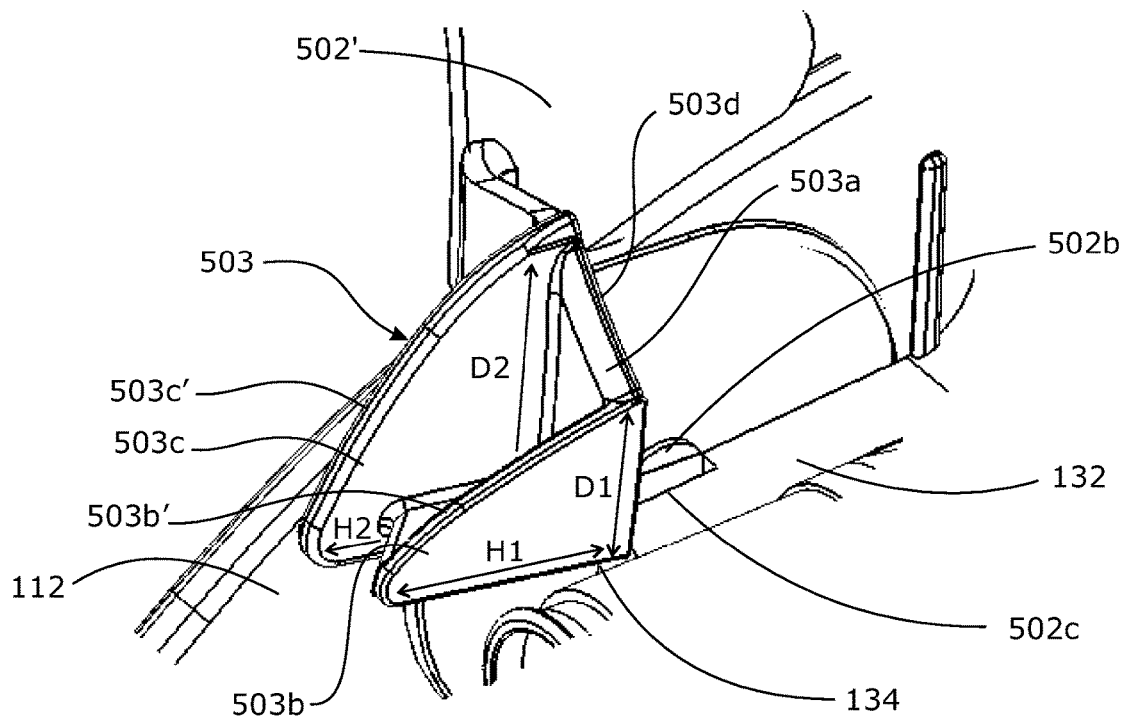
FIG. 49 is a front overhead perspective view of the left side of the apparatus of FIG. 44, with the handle/lever in a raised position.
Figure 50:
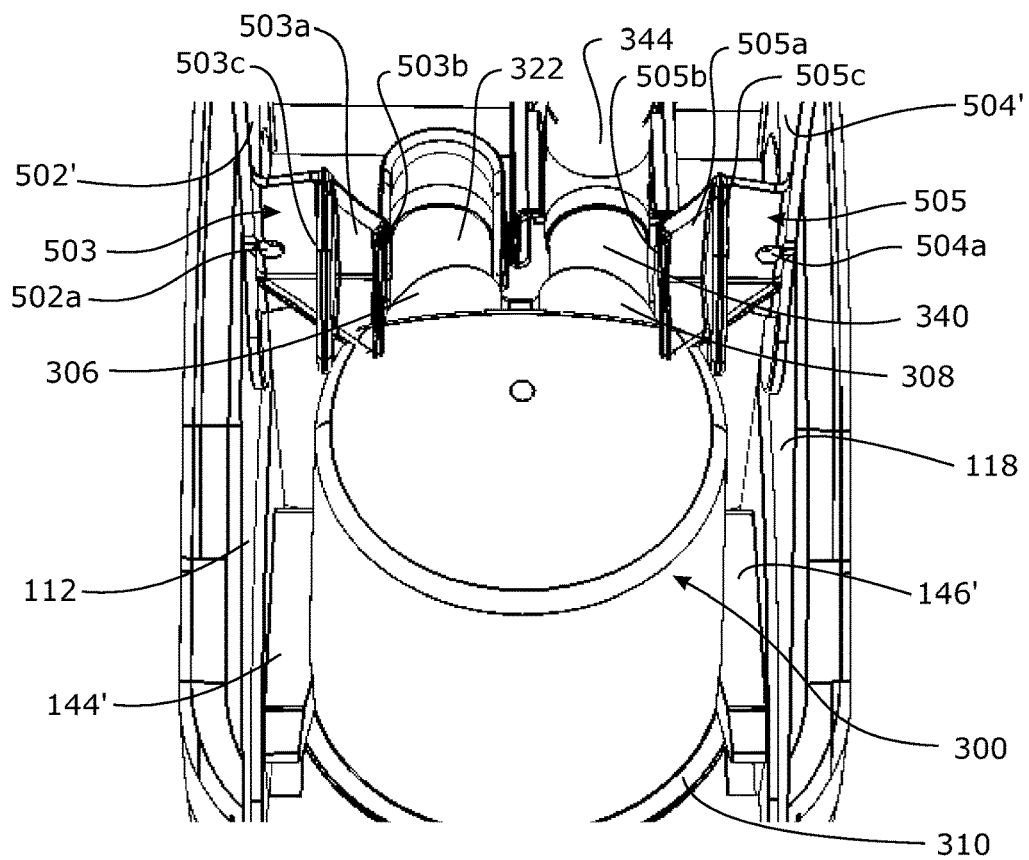
FIG. 50 is a front overhead perspective view of the apparatus of FIG. 44, showing a chamber positioned in the humidifier bay and with the handle/lever in a raised position.
Figure 51:
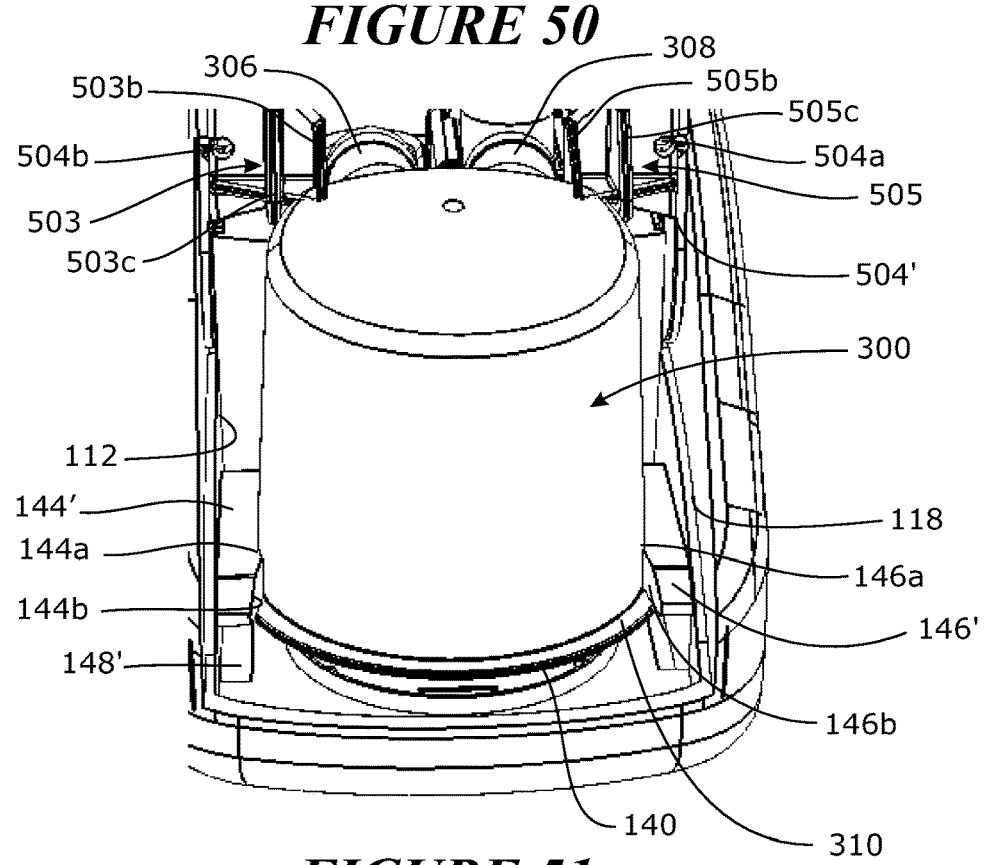
FIG. 51 shows the chamber positioned beneath the guide rails in the apparatus of FIG. 44.

Each inner engagement member 503*b*, 505*b* positioned toward the centre of the liquid chamber 300 has a shorter front/rear depth D1 than the depth D2 of the outer engagement members 503*c*, 505*c* positioned toward the side walls 112, 118 of the housing 100 (FIG. 49). Each inner engagement member 503*b*, 505*b* positioned toward the centre of the liquid chamber 300 has a smaller height H1 than the height H2 of the outer engagement members 503*c*, 503*d* positioned toward the side walls 112, 118 of the housing 100 (FIG. 49). Each engagement member 503*b*, 503*c*, 505*b*, 505*c* has an arcuate engagement surface 503*b'*, 503*c'*, 505*b'*, 505*c'* for engaging against the liquid chamber 300 as the handle/lever 500' is lifted. The inner engagement surfaces 503*b'*, 505*b'* have a steeper, more vertical angle, and a larger radius of curvature than the respective outer engagement surfaces 503*c'*, 505*c'*.

The outer engagement members 503*c*, 505*c* are arranged to engage against the flange 310 of the liquid chamber 300, and the inner engagement members 503*b*, 505*b* are arranged to engage against the housing 302 of the liquid chamber 300 as the handle/lever 500' is lifted from the lowered/closed position. That will push the liquid chamber 300 out of engagement of the guide rail recesses 144*a*, 146*a*, and overcome the force of the guide rail ridges 144*b*, 146*b*, to enable a user to easily remove the liquid chamber 300 from the chamber bay 108. The shape, and in particular the curvature, of the engagement members 503*b*, 503*c*, 505*b*, 505*c* is such that they will not interfere with insertion of the liquid chamber 300 into the chamber bay 108 as the handle/lever 500' is lowered from its raised/open position to insert the liquid chamber 300 into the chamber bay 108.

An inner forward edge 503*d*, 505*d* of each pusher platform is provided as an arcuate surface having a curvature corresponding at least generally to the curvature of the housing 302 of the liquid chamber 300. The edges 503d, 505d act as rearward stops for the liquid chamber 300 when the handle/lever 500' is in the lowered/closed position.

In the form shown, each pusher 503, 505 has two engagement members 503b, 503c, 505b, 505c; however, only a single engagement member may be provided on each pusher. The handle/lever 500' may only have a single pusher, but two spaced apart pushers will disengage the liquid chamber 300 from the guide rails 144', 146' more evenly.

In this configuration, there are no inwardly directed protrusions to force the liquid chamber 300 into full engagement in the chamber bay 108, but one or both of those protrusions or other liquid chamber engaging feature(s) may be provided. Alternatively, as discussed above for the previous configuration, rather than having inwardly directed protrusions, this handle/lever 500' may have a feature on its cross-member 506' that drives the liquid chamber 300 into engagement in the chamber bay 108.

Similarly, this handle 500' may be provided with feature(s) to assist with disengagement of the liquid chamber 300 from the detents 144a, 146a.

It will be appreciated that the detent(s) 144a, 146a could alternatively be used in a configuration with the handle/lever 500 of the earlier configuration.

FIGS. 45-48 show details of the pivot arrangement of the handle 500' which may also be used for the handle 500. A rearward portion of each side arm 502', 504' comprises an inwardly directed pivot protrusion 502b, 504b that is received in a respective pivot cavity 502c, 504c in ledge 132. The arms 502', 504' are captured, laterally, between the ledge 132 and the respective inner side walls 112, 118 so that the pivots cannot be moved laterally but the arms 502', 504' can pivot about horizontal pivot axes. A ledge 114a, 120a extends inwardly from the interconnecting walls 114, 120 to prevent the pivots from being lifted vertically.

Figure 53:
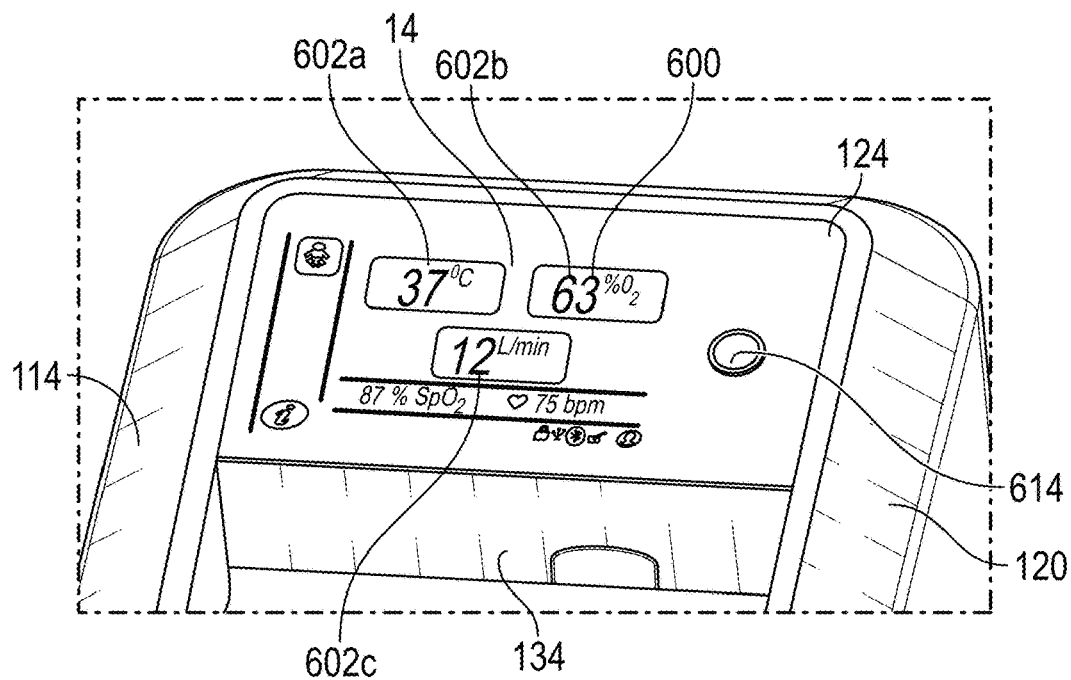
FIG. 53 is a view of a user interface display of the flow therapy apparatus of any one of the preceding figures.

FIGS. 53 and 54 show the display and user interface module 14 of the apparatus 10. The module 14 comprises a touch screen display 600 that provides information to a user of the apparatus 10 about the status of the apparatus 10, status of the therapy being provided, status of a patient, and/or status of an accessory or peripheral associated with the apparatus 10. The display 600 may comprise one or more indicia 602a, 602b, 602c that each provide information about a respective aspect of the therapy; for example gas temperature, oxygen concentration, gasflow rate, blood oxygen concentration ($SpO_2$), and heart rate. Other indicia may also be provided. The indicia may also act as touch screen 'buttons' where pushing on one of the indicia enables a user to change a setting of an aspect of the therapy, of the apparatus 10, and/or of an accessory or peripheral associated with the apparatus 10, which then causes the controller 13 to adjust the apparatus 10 or accessory or peripheral to that new setting.

The touch screen 600 may be in electrical communication with an interface printed circuit board 604 which, in turn, is in electrical communication with one or both of the electronics boards 272.

The interface 14 may also have one or more physical buttons to enable a user to power up or down the apparatus 10, or to change a setting. The upper wall 124 is advantageously angled toward a front of the apparatus 10, at an angle of 10 degrees relative to horizontal for example. This enables ease of use of the interface from a front of the apparatus 10.

A portion of the upper wall 124 defines an integrally formed cavity 606 comprising an outer cylindrical portion 608, an inner cylindrical portion 610, and an annular wall 612 that extends between and interconnects the bottom edges of the two cylindrical wall portions 608, 610. The axial direction of the cylindrical portions 608, 610 corresponds to an open/close direction of an injection-moulding tool to enable the component to be injection moulded.

A flexible button 614 is positioned adjacent the top of the outer cylindrical wall portion 608, and is substantially aligned with the upper wall 124. An underside of the button 614 comprises an elongate pusher 616 that extends through the inner cylindrical wall portion 610 and interacts with a microswitch 618 on the PCB 604. The outer cylindrical wall portion 608, annular wall 612, and inner cylindrical wall portion 610 form a continuous, unbroken, liquid impermeable configuration that acts as a liquid reservoir to capture any liquid that may enter the button arrangement around the flexible button 614, and prevents the liquid from reaching the underlying PCB 604.

The interface 14 may comprise one, two, or more buttons having this configuration. Alternatively, the interface 14 may solely be touch screen controlled, and have no buttons.

FIGS. 55 to 64 show an alternative configuration flow therapy apparatus 10' showing an alternative configuration handle/lever 1500. The flow therapy apparatus 10' will have the features and functionality described in relation to the different configurations above, but those features are not repeated here for simplicity. For the features that are shown, like numerals indicate like parts with the addition of a prime (') for most components, and with the addition of 1500 for the handle/lever.

This configuration differs from those described above, in that the handle/lever 1500 is a single sided configuration. That is, only one side of the handle/lever 1500 is pivotally connected to the main housing of the flow therapy apparatus 10', whereas there is no pivot connection of the other side of the handle/lever 1500 to the main housing. In the form shown, the left side of the handle/lever 1500 is pivotally connected to the main housing. However, in an alternative configuration, only the right side may be pivotally connected to the main housing.

The handle/lever 1500 and main housing are modified from those described above to provide that mounting.

The handle/lever has a left side arm 1502 that is pivotally attached to the left inner side wall 112' of the upper chassis 102'. The left side arm 1502 is configured to be substantially flush with the interconnecting wall 114' when the handle 1500 is in the lowered or closed position of FIG. 55. Rather than a right side arm, the handle/lever further comprises a right side member 1504 that is shorter than the left side arm 1502, and that is not pivotally attached to the right inner side wall 118' of the upper chassis 102'. The right side member 1504 is configured to be substantially flush with the interconnecting wall 120' when the handle 1500 is in the lowered or closed position of FIG. 55. The main housing is provided with recesses to enable the left side arm 1502 and right side member 1504 to be substantially flush with the interconnecting walls. The right side interconnecting wall 120' extends further toward the front of the apparatus 10' than the left side interconnecting wall 114', due to the shorter right side member 1504.

Figure 57:
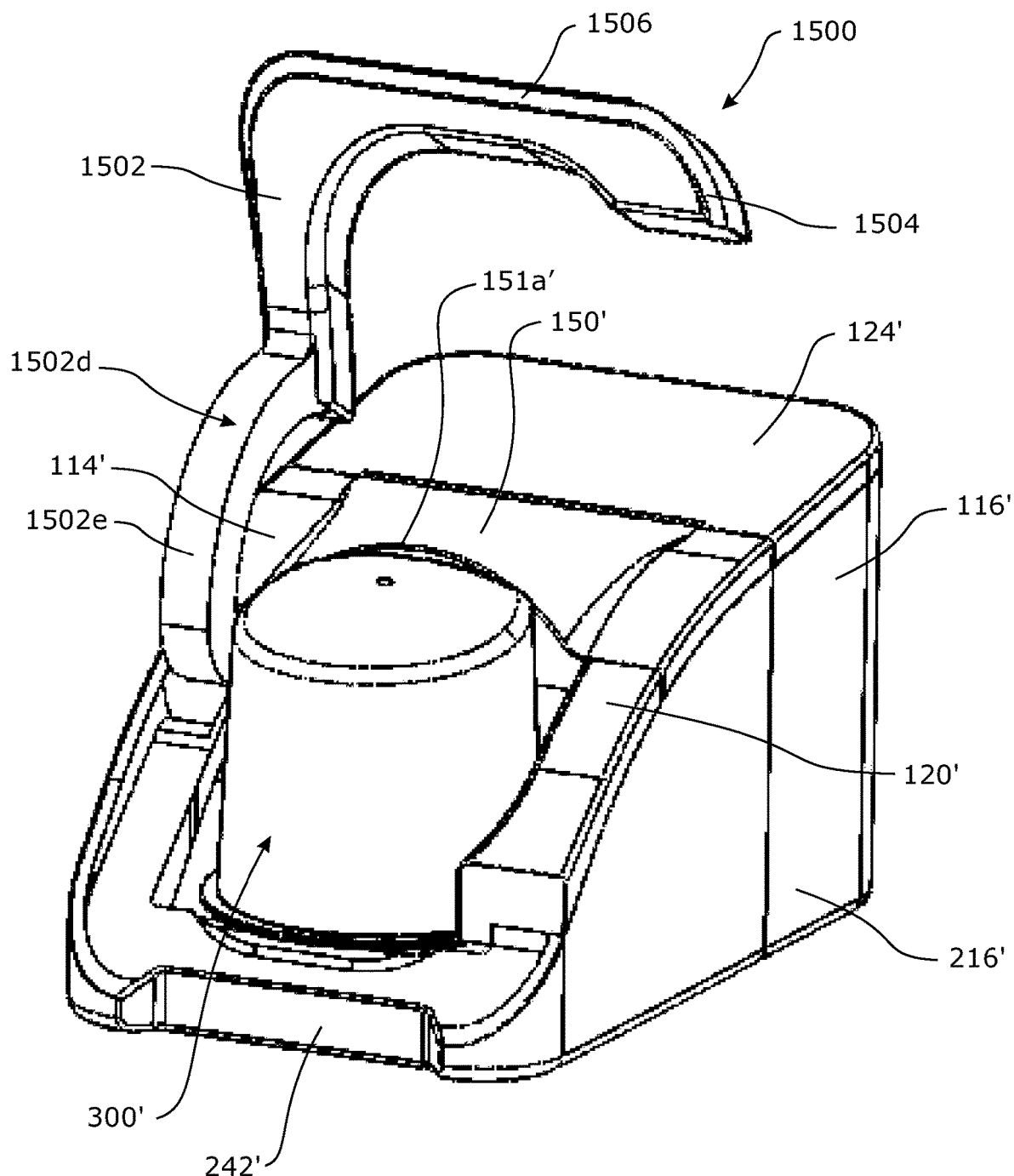
FIG. 57 is a view corresponding to FIG. 55, but with the handle in a fully raised or opened position, and with a liquid chamber positioned in the chamber bay.

A cross-member handle portion 1506 interconnects the forward ends of the left side arm 1502 and the right side member 1504 and forms an engagement region for grasping by a user's fingers. When the handle 1500 is in the raised position as shown in FIG. 57 for example, the cross-member 1506 can act as a carrying handle for the apparatus 10'. The liquid chamber 300' can be inserted into or removed from the chamber bay 108' when the handle/lever 1500 is raised. When the handle/lever 1500 is in the lowered position, it inhibits or prevents removal of the liquid chamber 300' from the chamber bay 108'.

Rather than having the right side member 1504, the handle/lever 1500 may terminate at the right side of the cross-member 1506. However, having the rearwardly directed member 1504 is preferred, as it reduces the likelihood of the apparatus 10' being dropped while it is being carried.

Figure 55:
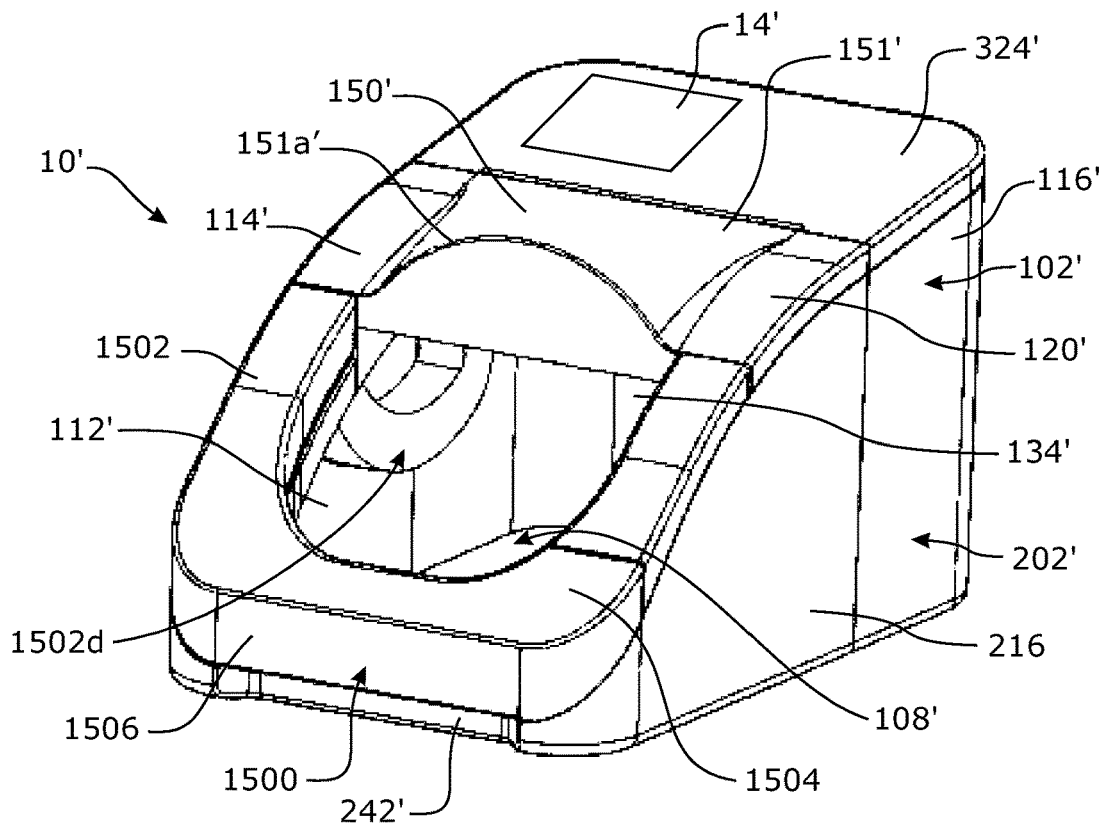
FIG. 55 is a front overhead perspective view of the flow therapy apparatus showing an alternative configuration handle/lever, with the handle/lever in a lowered or closed position.

In the closed or fully lowered position of the handle/lever 1500 shown in FIG. 55, the cross-member 1506 is located in the recess 242' at the front of the main housing and encloses a portion of the chamber bay. Although no join is shown in the figures, the main housing may be formed with upper and lower chassis parts 102', 202', and the recess 242' will be formed in the appropriate chassis part. The handle/lever 1500 and/or recess 242' may have a positive engagement feature, such as one of those described above, to positively engage the handle/lever 1500 in the lowered or closed position. With the handle/lever 1500 in the lowered or closed position, a portion of the cross-member 1506 projects sufficiently above the floor of the chamber bay 108' and above the flange 310' of the liquid chamber 300' that it prevents the liquid chamber 300' from being slid forward and removed from the liquid chamber bay 108'. Although not shown in this configuration, the liquid chamber 108' will comprise guide rails to prevent the liquid chamber 300' from being lifted and removed vertically from the liquid chamber bay 108' when the handle/lever 1500 is in the lowered or closed position. Because the handle/lever encloses a portion of the chamber bay when the lever is in the closed or fully lowered position, when the handle/lever is in the fully raised position, a large space is created between the cross-member of the handle/lever and the housing of the apparatus including a large opening at the front of the chamber bay and around the liquid chamber, allowing easy insertion and removal of the liquid chamber to and from the chamber bay because a user's fingers can easily fit between housing walls and the liquid chamber.

FIGS. 55, 56, and 60-64 show details of the pivot arrangement of the handle/lever 1500. A rearward portion of the left side arm 1502 is connected to a pivot arm 1502d. The pivot arm comprises a forward arcuate portion 1502e that extends downwardly and rearwardly from the left side arm 1502 when the handle is in the lowered or closed position. A rearward part of that forward arcuate portion 1502e is connected to a linear portion 1502f that extends upwardly and forwardly therefrom when the handle is in the lowered or closed position. An upper end of the linear portion 1502f is coupled to inwardly and/or outwardly directed pivot protrusion(s) 1502b that is/are received in a pivot cavity or cavities 1502c in a portion of the housing corresponding to the ledge 132' and/or in the left inner side wall 112'. The arm 1502 is captured, laterally, between the ledge 132' and the inner side wall 112' so that the pivot protrusions 1502b cannot be moved laterally but the arm 1502 can pivot about a horizontal pivot axis.

Figure 56:
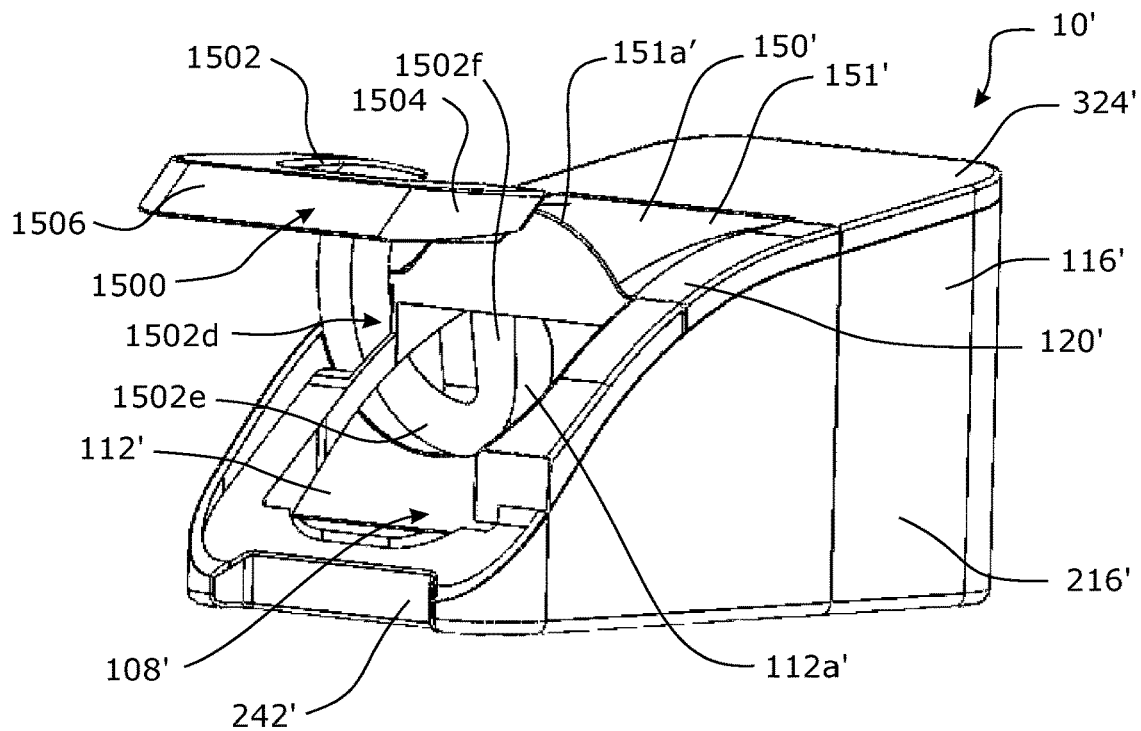
FIG. 56 is a view corresponding to FIG. 55, but with the handle/lever in a partly raised position.
Figure 61:
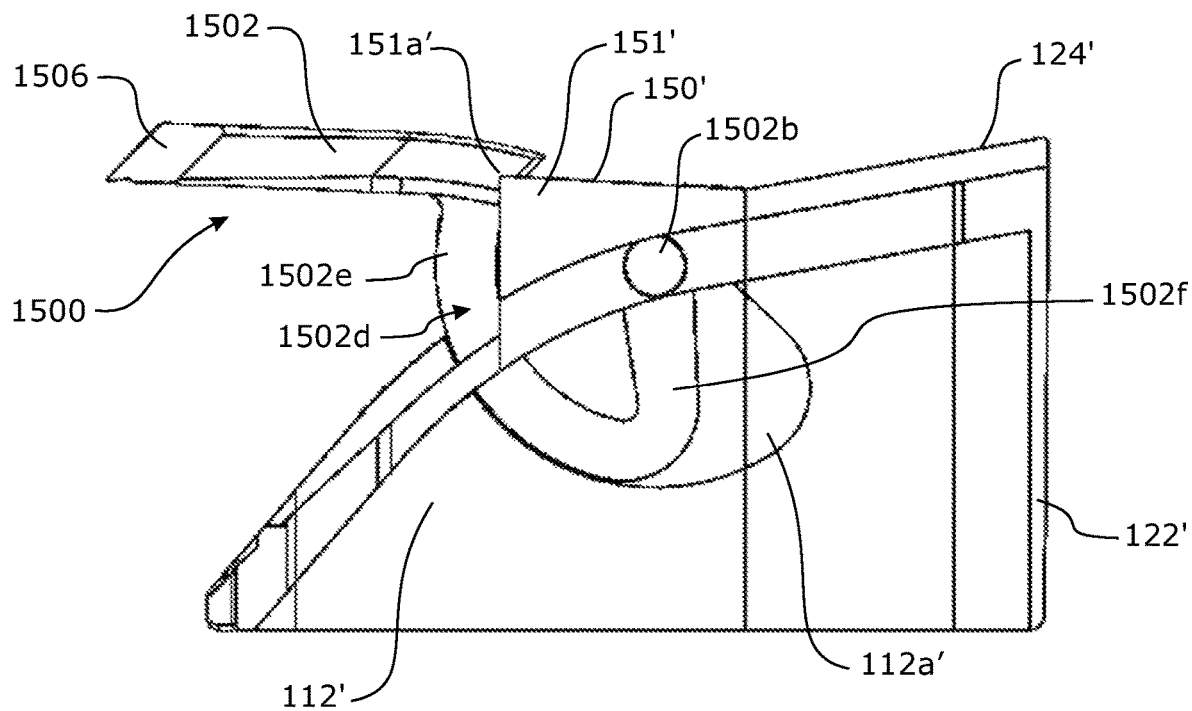
FIG. 61 is a view corresponding to FIG. 60, but with the handle/lever in a partly raised position.
Figure 62:
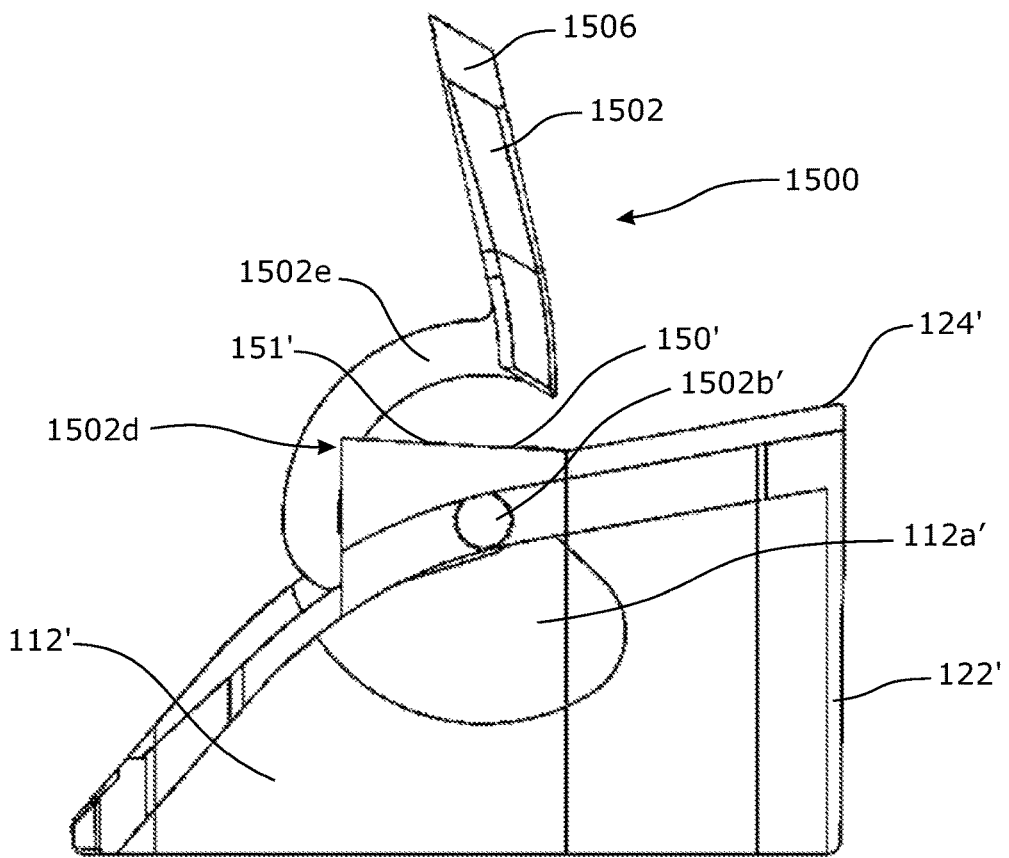
FIG. 62 is a view corresponding to FIG. 60, but with the handle/lever in the fully raised or opened position.
Figure 63:
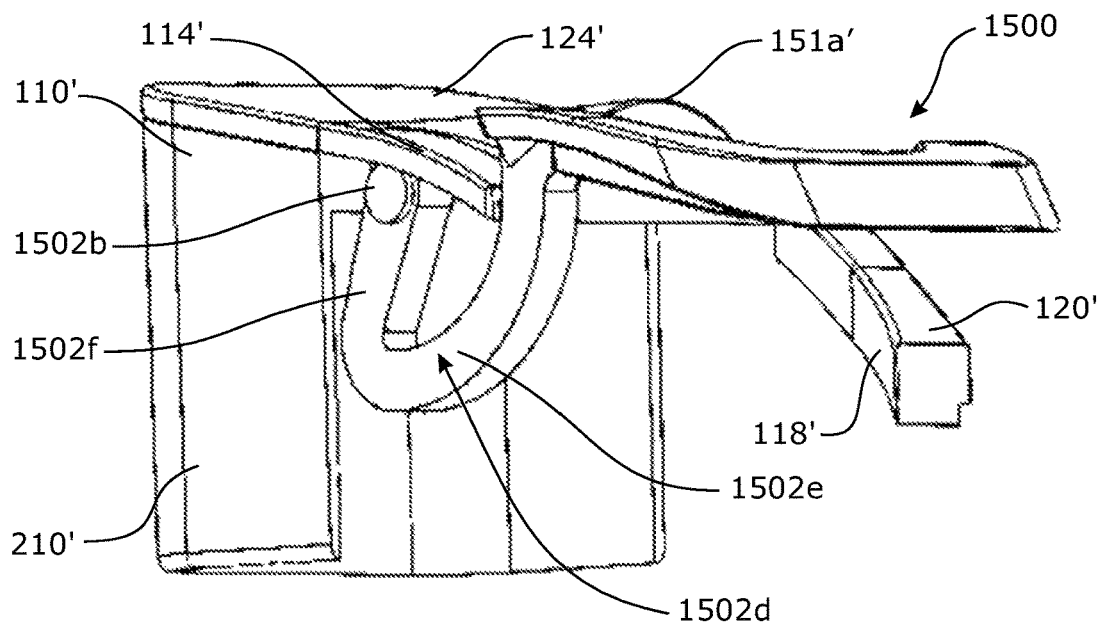
FIG. 63 is a cross-sectional perspective view with the handle/lever in the position of FIG. 61.
Figure 64:
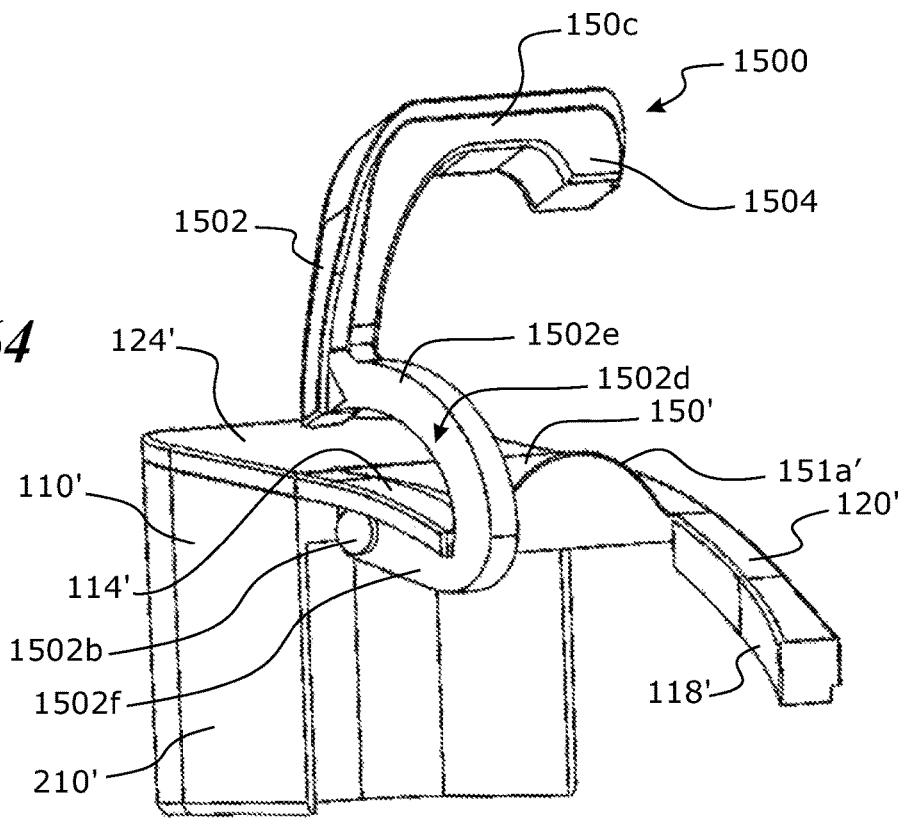
FIG. 64 is a view corresponding to FIG. 63 but with the handle/lever in the fully raised or opened position of FIG. 62.

As shown in FIGS. 56, 61, and 62, the left inner side wall 112' is provided with a shaped recess 112a' to receive the pivot arm 1502d. The recess 112a' enables the pivot arm 1502d to travel throughout its range of motion from the position shown in FIG. 60 to the position shown in FIG. 62, without encroaching significantly on the space in the liquid chamber bay 108'.

An upper forward portion of the main housing comprises a platform 150'. The platform 150' may also comprise apertures and may be removable to act as the removable retention cover for the removable elbow as described for the configuration above. An upper portion 151' of the platform forms a substantial continuation of the forwardly angled surface 124', and extends forwardly and downwardly from that surface 124'. A forward edge 151a' of the upper portion 151' extends at a more horizontal or upward orientation than the remainder of the upper portion 151'.

This configuration is suitable for use with a liquid chamber 300' that is filled from a flexible liquid bag. While hospitals and medical facilities will generally have bag stands for supporting liquid bags, people do not typically have suitable bag stands in a home environment. This configuration enables a liquid bag to be rested on top of the main housing, and particularly on the platform 150'. The forward edge 151a' will reduce the likelihood of the bag sliding forward off the housing. The one sided handle/lever 1500 will enable the handle/lever 1500 to be raised and lowered while enabling the liquid bag and/or liquid tube(s) that deliver liquid from the liquid bag to the liquid chamber 300' to be fed through the space between the right side member 1504 of the handle/lever 1500 and the main housing, when the handle/lever 1500 is in the raised position. Long tube(s) do not need to be provided.

Figure 52:
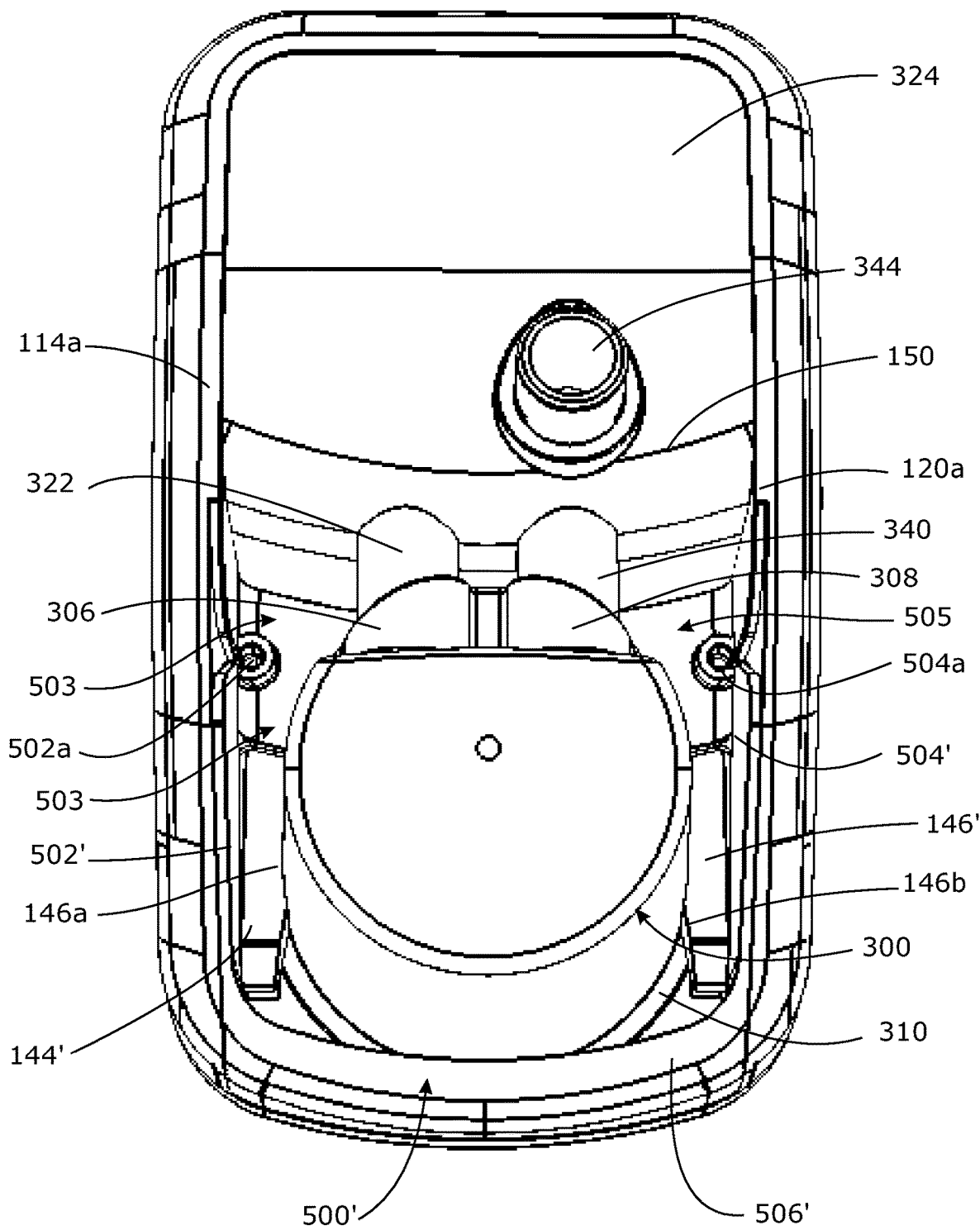
FIG. 52 is a front overhead perspective view of the apparatus of FIG. 44 with the chamber positioned beneath the guide rails and the handle/lever in the completely lowered or closed position.

The handle/lever 1500 may comprise one or more features, such as apertures 502a, 504a as shown in FIG. 52 for example, for guiding liquid tube(s) from above into the liquid chamber. The tube(s) will be coupled to the liquid chamber. The liquid chamber may comprise a float valve which controls flow of liquid from the tube(s) into the liquid chamber.

Figure 58:
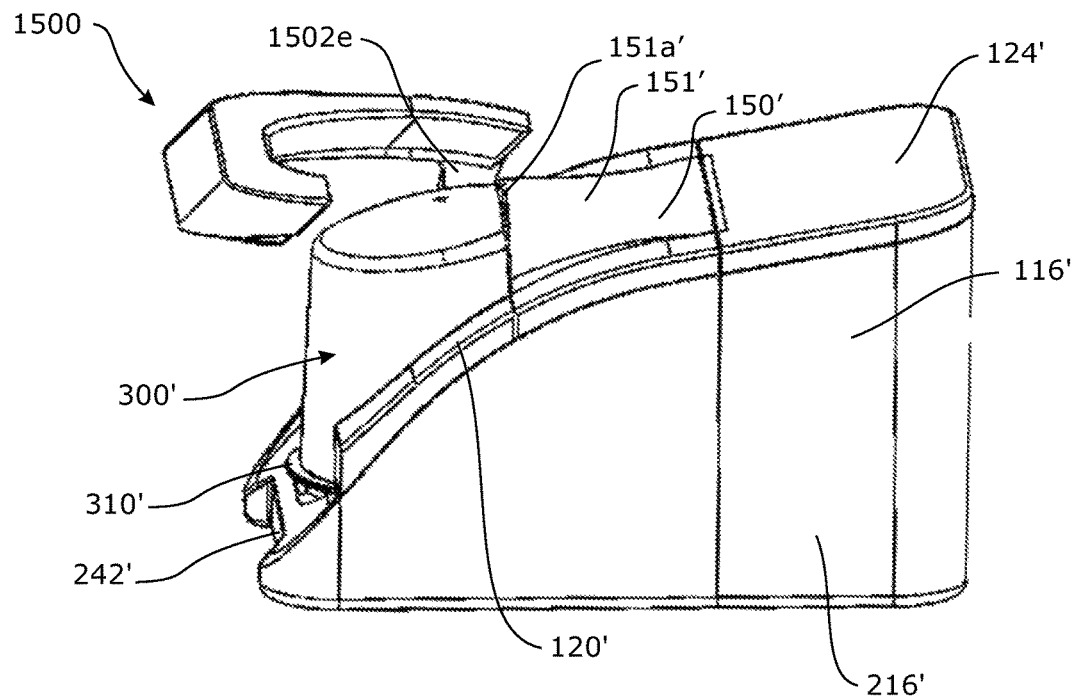
FIG. 58 is a right side view of the flow therapy apparatus, but with the handle/lever in a partly raised position, and with a liquid chamber positioned in the chamber bay.
Figure 59:
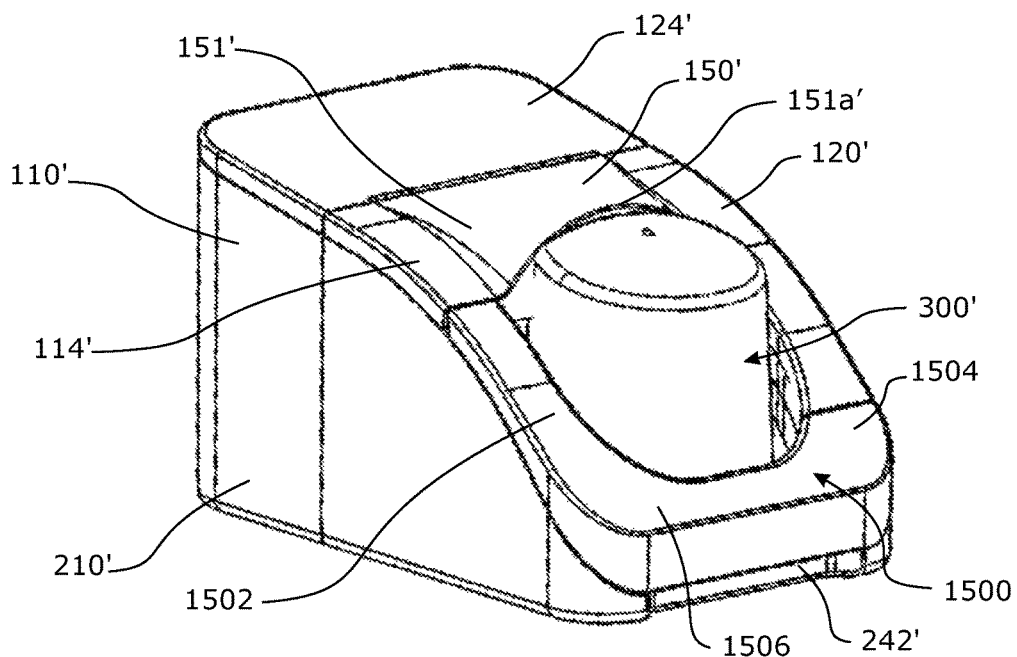
FIG. 59 is a view corresponding to FIG. 55, but with a liquid chamber positioned in the chamber bay.
Figure 60:
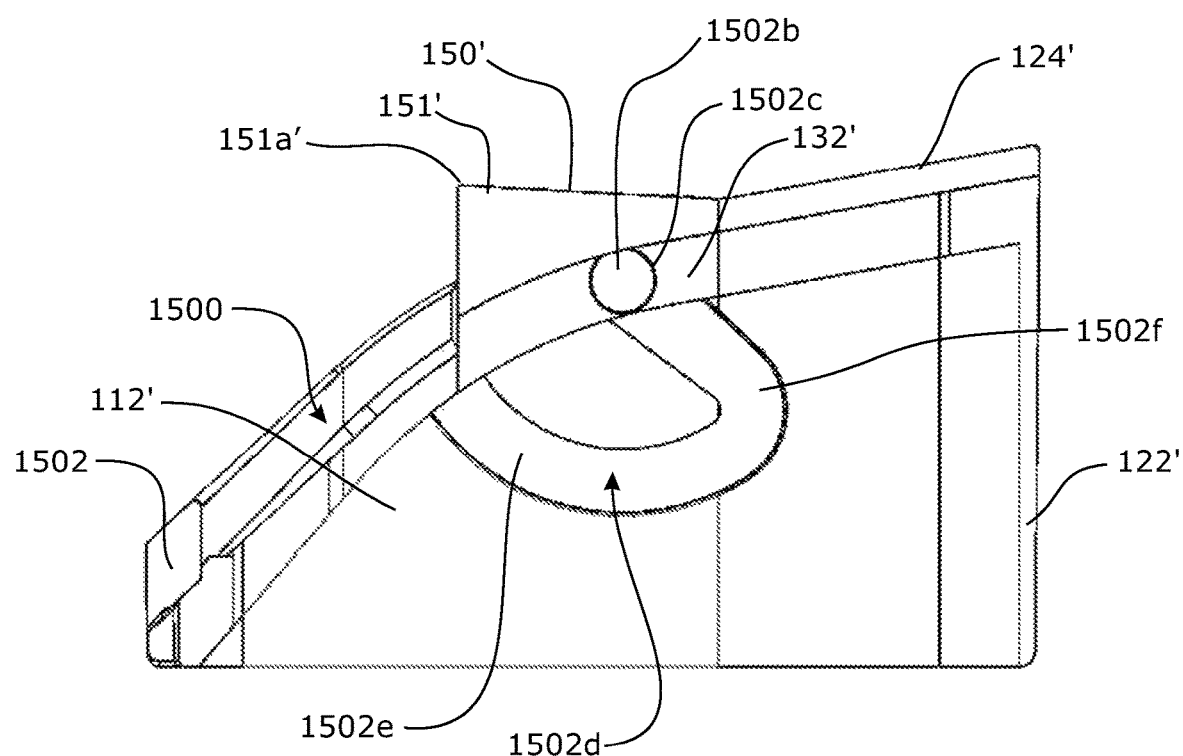
FIG. 60 is a longitudinal cross-sectional view of the flow therapy apparatus of FIGS. 55 to 59, showing the pivot mounting of the handle/lever to the main housing when the handle/lever is in the lowered or closed position.

As shown in FIGS. 57 to 59, the forward edge 151a' preferably also forms a recess for receiving the rear upper edge of the liquid chamber 300' when it is fully engaged in the liquid chamber bay 108'.

The handle/lever 1500 will be provided with one or more features to assist with insertion, retention, and/or removal of the liquid chamber 300' in or from the chamber bay 108'. Those features may be any one or more of the features described in relation to the configurations above.

By providing a handle/lever that assists with insertion and/or retention and/or removal of the liquid chamber in and/or from the chamber bay, a user can readily ensure that the liquid chamber is fully inserted in the chamber bay while still being able to easily remove the liquid chamber from the chamber bay when desired. This is particularly advantageous for users with limited mobility. Similarly, by providing detent(s) to assist with insertion and/or retention of the liquid chamber in the chamber bay, a user can readily ensure that the liquid chamber is fully inserted in the chamber bay. Full or correct insertion and/or retention may be required to ensure that a satisfactory seal is obtained and maintained between the liquid chamber and other component(s) that form part of the gasflow path.

6. Removable Gasflow Tube or Elbow and Receiver—Alternative Configurations

FIGS. 66 to 71 and 72 to 75 respectively show two alternative gas flow tubes or elbows 1342 and 2342 that can be used in the flow therapy apparatuses described herein. Unless described below, the gas flow tubes or elbows 1342 and 2342 have the features and functionality described in relation to the removable elbow 342 above, and like reference numerals indicate like parts with 1000 and 2000 respectively added to each reference numeral.

Figure 69:
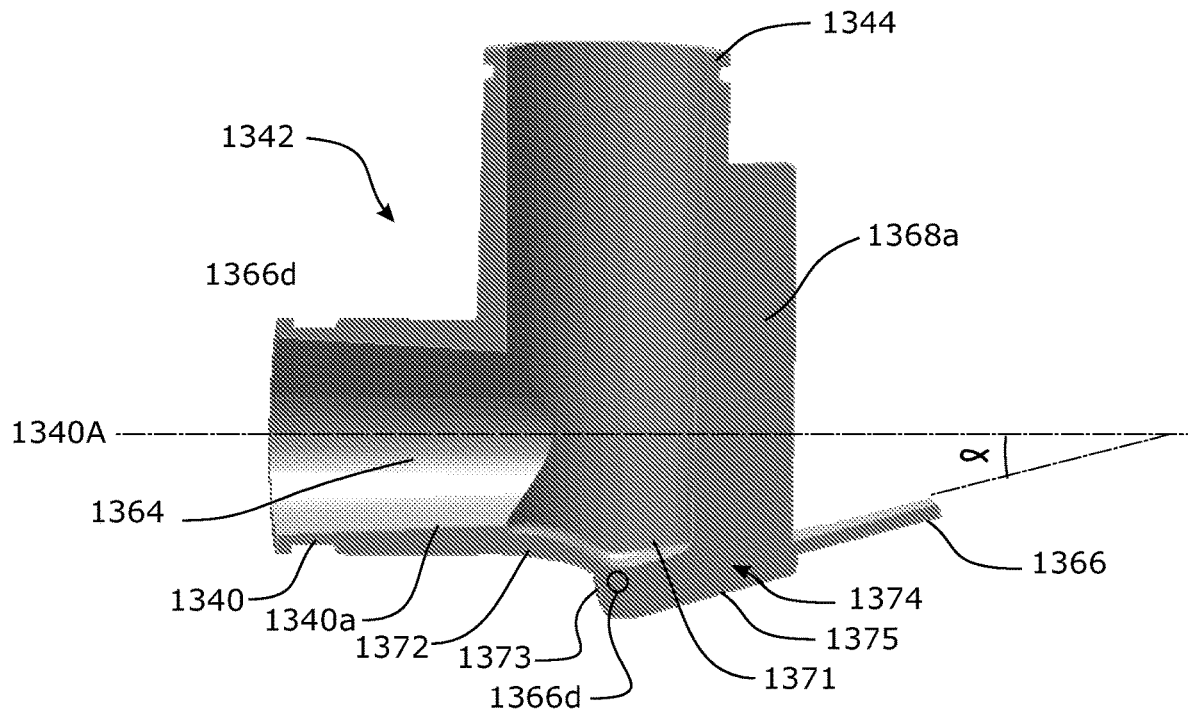
FIG. 69 is a partial cross-sectional view of the removable elbow of FIG. 66.

The removable elbow 1342 of FIGS. 66 to 71 is provided with an internal pool region 1371 in the gasflow passage at the interface of the two arms of the substantial L-shape; i.e., at the interface of the gasflow passage of the manifold gases inlet port 1340 (humidified gases return) and the gasflow passage of the patient outlet port 1344. As shown in FIG. 69, the pool region 1371 is provided by an enlarged region in the gasflow passage. The pool region is positioned vertically lower than an adjacent base wall portion 1340*a* of the manifold gases inlet port, so that liquid can pool in the pool region 1371 up to the depth of the adjacent base wall portion 1340*a*. The pool region 1371 allows pooling of liquid to help thermistors 1366*d* (described below) on the PCB connector 1366 determine a temperature that is representative of the gasflow passage 1364/gases characteristic. This can assist with the determination of a wet bulb temperature of the gases passing through the elbow 1342.

The body of the removable elbow is provided with an arcuate transition region 1372 that extends downwardly and in a direction away from the adjacent base wall portion 1340*a*, at a relatively shallow angle. The arcuate transition region 1372 forms a forward portion of the pool region 1371. The rearmost portion of the transition region 1372 terminates at an upper end of a wall portion 1373 that extends downwardly and rearwardly at a second relatively steep angle. The wall portion 1373 forms a front wall of a support portion 1374 of the body. An upper inner part of the support portion 1374 forms a rearward portion of the pool region 1371, which extends upwardly and rearwardly from its interface with the transition region 1372.

A lower angled outer edge 1375 of the support portion 1374 extends upwardly and rearwardly from the base of the front wall 1373. The support portion 1374 of the elbow serves two purposes. The first is to provide a mounting of the PCB electrical connector 1366 to the removable elbow 1342, as will be described below. The second is to provide a support surface to assist with aligning the PCB connector 1366 during insertion of the removable elbow into position in the main housing of the apparatus.

As can be seen most clearly from FIG. 69, the lower angled outer edge 1375 is oriented at a non-parallel and non-coaxial angle α relative to a longitudinal axis 1340A of the manifold gases inlet port 1340. The angle may be between about −15 degrees (downward) and about +30 degrees (upward) relative to the longitudinal axis 1340A. In one form, the angle is between about 0 degrees and about 30 degrees upward relative to the longitudinal axis 1340A. Advantageously, the upper limit is 30 degrees, as having too much tilt on the PCB electrical connector 1366 may result in the elbow providing an undesirable shallow flow path through the elbow and prevent the provision of a useful pooling region. In one form, the angle is between about 0 degrees and about 15 degrees upward relative to the longitudinal axis 1340A. In one form, the angle is about 15 degrees upward relative to the longitudinal axis 1340A. Within these ranges, the angle may be non-parallel and non-coaxial relative to the longitudinal axis, and may be oriented at least+/−5 degrees relative to the longitudinal axis 1340A. In an alternative form, the angle may be parallel to or coaxial with the longitudinal axis 1340A. The PCB electrical connector 1366 is mounted in the support portion 1374 to be collinear with, or parallel to, the lower angled outer edge 1375. Therefore, the PCB connector advantageously also extends upwardly and rearwardly at an angle of between about −15 degrees and about +30 degrees, in one form between about 0 degrees and about +30 degrees, in one form between about 0 degrees and about +15 degrees, and in one form at about +15 degrees, relative to the longitudinal axis 1340A. Again, within these ranges, the angle may be non-zero, and for example may be at least+/−5 degrees relative to the longitudinal axis. A base portion 1368*b* of the electrical connector portion may be aligned with the lower wall portion 1375. It can be seen that in this version, the interface of the PCB electrical connector with the elbow body is lower than in the version shown in FIG. 29.

Figure 76:
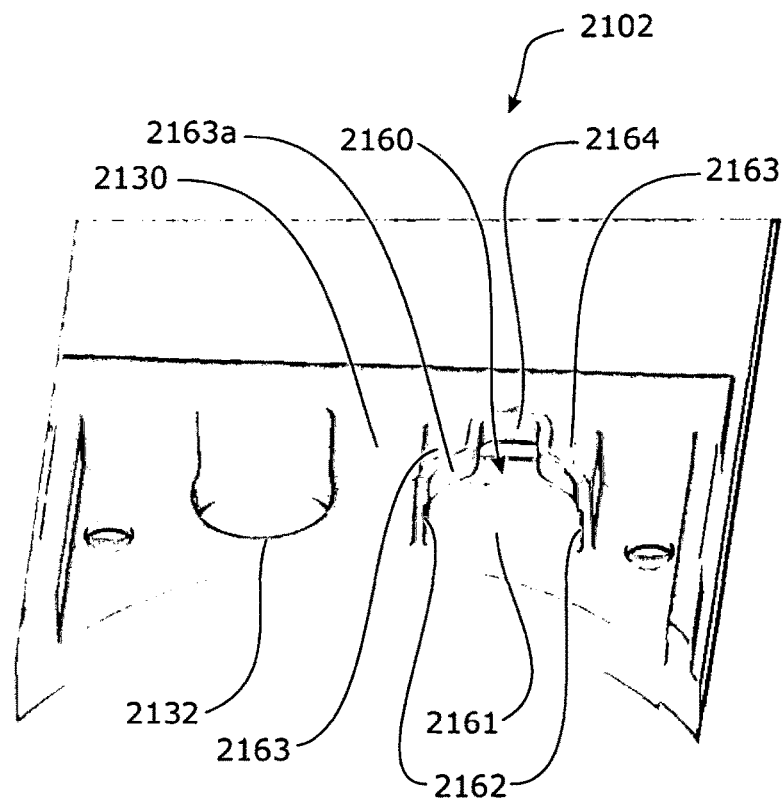
FIG. 76 is a partial front overhead perspective view of a carrier for the display and user interface module, the carrier being part of the main housing of one of the flow therapy apparatuses, with an elbow receiver configured for receipt of the removable elbow of FIG. 66 or 72.
Figure 77:
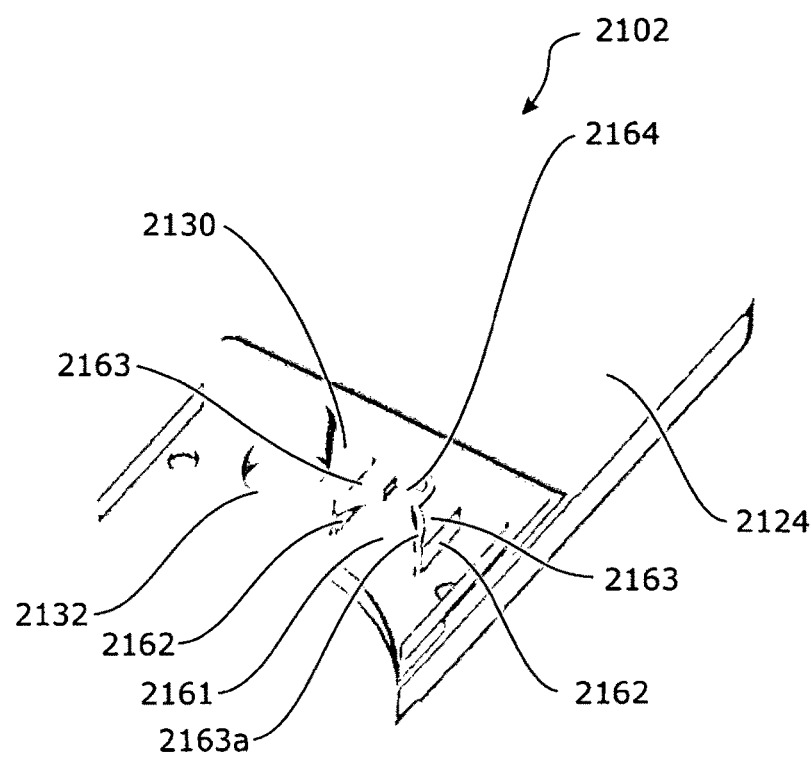
FIG. 77 is a front overhead perspective view of the carrier and elbow receiver of FIG. 76.
Figure 78:
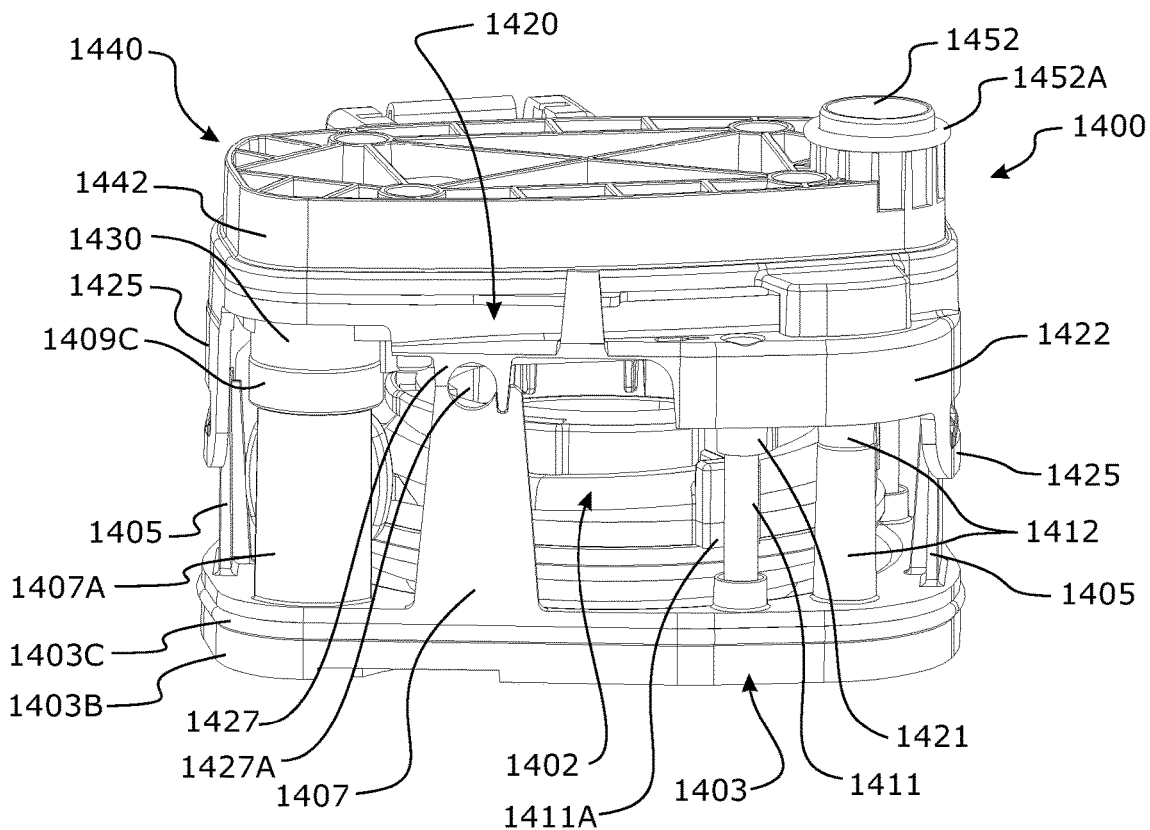
FIG. 78 is a perspective view of the motor and/or sensor sub-assembly for use in the flow therapy apparatuses.

FIGS. 76 and 77 show an alternative configuration upper main chassis/display and user interface carrier 2102 of the main housing that may be used in the flow therapy apparatuses described above, in combination with the removable elbow 1342 or 2342. Unless described below, the features and functionality will be the same as described for the flow therapy apparatuses above, and like reference numerals indicate like parts with 2000 added to each reference numeral.

The upper chassis/carrier 2102 comprises an elbow retainer 2160 extending forwardly from wall 2130. The retainer 2160 comprises a base wall 2161 and two spaced apart upright side walls 2162. Inwardly directed flanges 2163 extend towards each other from the upper ends of the side walls 2162, with a spacing between the flanges 2163 being large enough to enable the patient outlet port 1344 to extend upwardly therebetween. An upright ridge 2163*a* is formed by a substantially vertical wall portion at the inner edge of each flange 2163. The flanges 2163 and ridge 2163*a* are arcuate to form a mouth to receive the patient outlet port 1344. The upright ridge is arranged to be in close contact with the periphery of the patient outlet port 1344 when the removable elbow is received in the retainer 2160. A rear portion 2164 of the retainer has a dimension smaller than that of the patient outlet port 1344, and is provided to enable the power connector portion 1368*a* of the body to project upwardly therethrough.

The walls 2162, flanges 2163, and ridge 2163*a* form a hood region that substantially matches the shape of the removable elbow 1342, 2342 when it is inserted into the elbow retainer. The hood region assists with holding the elbow in place, and helps to reduce liquid ingress to the elbow or PCB connector, and encapsulates the PCB connector. The ridge 2163*a* further assists with directing liquid away from the connection between the PCB connector and the connector 278.

To insert the elbow into the retainer 2160, the elbow is oriented so that the lower wall portion 1375 of the support portion is resting on the base wall 2161 of the retainer. The elbow is moved rearwardly so that the patient outlet port 1344 is located between the flanges and the connector 1366 is inserted to extend through the slot in the retainer so that it can be inserted into the female connector 278 which is positioned in the upper chassis at the rear of the retainer 2160. The retainer is oriented at an angle corresponding to angle α of the PCB connector so that the PCB connector is parallel with the base wall 2161. The orientation of the manifold gases inlet port 1340 relative to the PCB connector provides for a horizontal connection with the liquid chamber. Thus, the PCB connector can be inserted directly into the retainer 2160 without needing to tilt or adjust the elbow to achieve that insertion. In alternative configurations, the PCB connector and elbow retainer 2160 may be oriented at different angles, such as those described above in relation to the elbow.

By having the PCB connector at a non-horizontal angle in use, any liquid that may ingress into the main housing should drain away from the connector. A removable retention cover 150 will again be used to assist with maintaining the removable elbow in position in the housing, and the operation of the cover and interaction of the elbow and liquid chamber will be as described above. The hood provides a lower profile retainer 2160 than the version shown in FIG. 30, with the hood sized to receive just the lower portion of the elbow 1342 that houses the PCB connector, rather than the entire height of the manifold gases inlet port.

In this configuration, the port 1344 is positioned closer to the liquid chamber than in the apparatus of FIG. 24, which means that the breathing conduit 16 will block the user display and user interface module less than in the apparatus of FIG. 24. As a result, the elbow is shorter in length than the elbow of FIG. 28.

Figure 70:
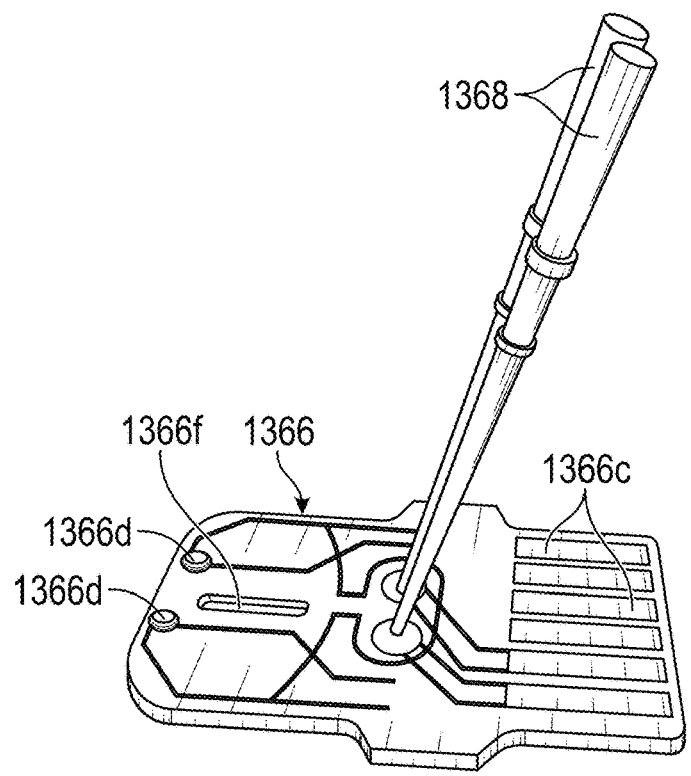
FIG. 70 is an overhead perspective view of a PCB electrical connector of the removable elbow of FIG. 66.
Figure 71:
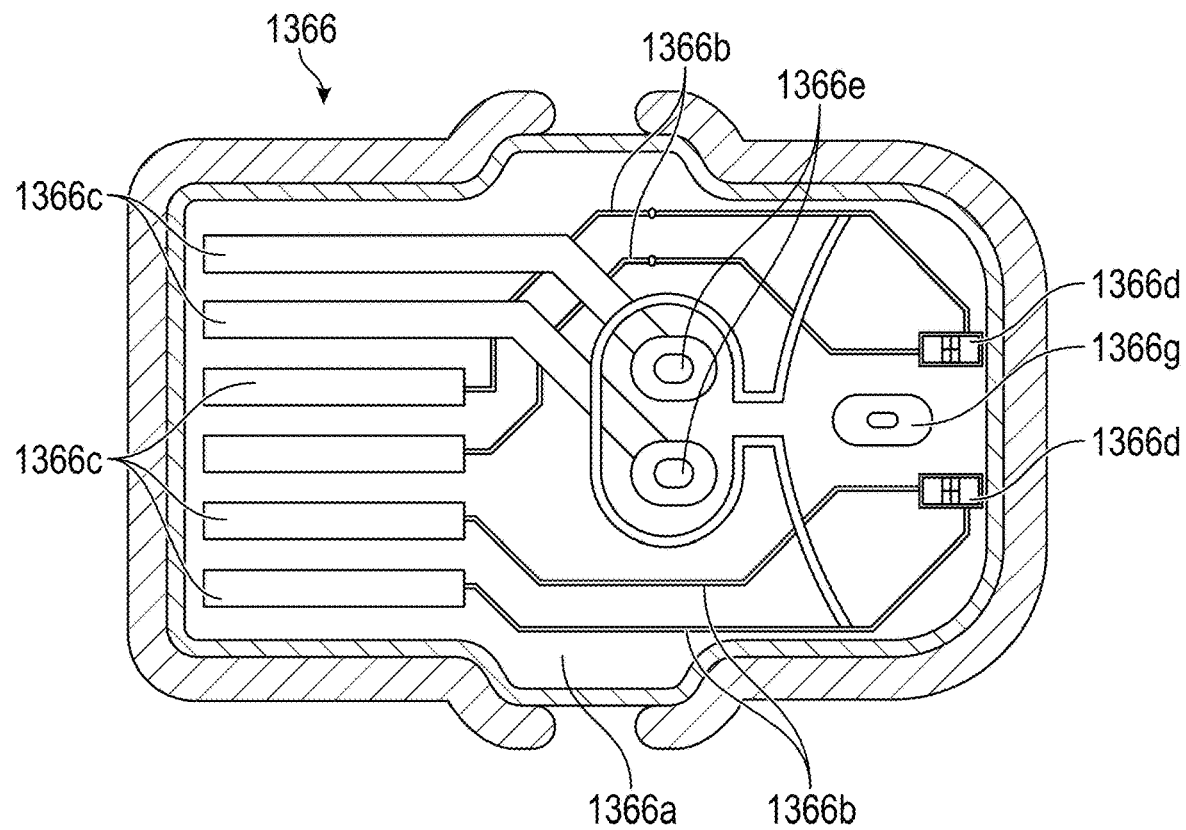
FIG. 71 is an overhead plan view of the PCB electrical connector of FIG. 70.

FIGS. 70 and 71 show details of the PCB electrical connector 1366 of the removable elbow 1342. The connector 1366 comprises a plastic board 1366a with a plurality of electrically conductive tracks 1366b embedded therein. A plurality of electrically conductive connector portions or pins 1366c are provided at one end of the PCB, which is the end that projects from the elbow. Those tracks are configured to engage with complementary conductors in the female connector 278 to provide an electrical and/or communication coupling of the PCB connector to other components of the apparatus. The connector portions 1366c and tracks 1366b may all be provided on one side of the PCB connector, or some may be provided on opposite sides of the PCB connector to reduce the risk of electrical shorting.

In the form shown in FIG. 71, four of the conductive connector portions 1366c are in electrical communication with thermistors 1366d that are positioned at or adjacent an opposite end of the PCB connector, and that are embedded in the elbow body. The remaining two connector portions 1366c are in electrical communication with couplings 1366e that receive bases of two substantially rigid upwardly projecting pin connectors 1368 for coupling to and powering the heater wire(s) 3c in the patient breathing conduit. As shown in FIG. 70, the pin connectors 1368 may be rigid members that extend at a non-perpendicular angle from the top of the PCB, the non-perpendicular angle corresponding to angle α of the PCB connector relative to the longitudinal axis 1340A (FIG. 69). The pin connectors may be any suitable angle relative to the PCB connector, including perpendicular. The pin connectors advantageously extend substantially parallel to a longitudinal axis of the patient outlet port 1344.

The two thermistors 1366d are surface mounted at the front of the PCB connector, and are embedded in the body of the removable elbow. They are located approximately in position 1366d shown in FIG. 69, in close proximity to the pooling region 1371. By positioning them close to the pooling region, they can provide a more representative gases measurement. Digital temperature sensor(s) could be used instead of thermistor(s).

The PCB connector can be mounted to the elbow body in any suitable manner. In one example, when surface mounted thermistors 1366d are used on the PCB connector, single shot overmoulding could be used to manufacture the elbow on the PCB connector, to simplify manufacturing. The single shot overmoulding can also encompass the elongate pin connectors 1368 in a chimney portion 1368a. Hole(s) 1366g in the PCB can allow overmoulded material to flow through the PCB, to reduce or prevent deflection of the PCB connector that could otherwise occur due to moulding pressures. The lower portion 1368b of the elbow body beneath the electrical connector portion under the PCB connector acts to cover the solder points at the base of the pin connectors.

The shape of the pooling region and surrounding elbow body is configured to remove as much mass as possible from around the thermistors to improve their performance. The pooling region may also assist with gasflow through the removable elbow by stopping the gases from 'clinging' tightly to the inner wall.

The removable elbow 1342 will be provided with suitable seals. For example, T-seals may be provided on the manifold gases inlet port 1340 to seal between that port and the liquid chamber gases outlet port 308 and an O-ring seal may be provided on the patient outlet port 1344.

Similar to the elbow 1342 described above, the removable elbow 2342 is provided with a support portion 2374 extending generally rearwardly from the elbow body at the base of the interface of the two arms of the substantial L-shape; i.e., substantially at the interface of the manifold gases inlet port 1340 and the patient outlet port 1344. The support portion comprises a body portion with a front wall 2373 and a lower angled outer edge 2375 that extends rearwardly therefrom. The body portion is shaped and configured to receive a PCB electrical connector 2366.

The lower angled outer edge 2375 extends upwardly and rearwardly from the base of the front wall 2373. The support portion 2374 of the elbow serves two purposes. The first is to provide a mounting and support for the PCB electrical connector 2366 to the removable elbow 2342, as will be described below. The second is to provide a support surface to assist with aligning the PCB connector during insertion of the removable elbow into position in the main housing of the apparatus.

The support portion 2374 provides additional plastic around the PCB connector to encapsulate the PCB connector. When the elbow 2342 is connected to the retainer 2160, the support portion 2374 interacts with the underside of the hood to reduce or prevent vertical movement of the elbow and rotation about the axis 1340A.

As can be seen most clearly from FIG. 72, the lower angled outer edge 2375 is oriented at a non-parallel and non-coaxial angle α relative to a longitudinal axis 2340A of the manifold gases inlet port 2340. The angle may be between about −15 degrees (downward) and about +30 degrees (upward) relative to the longitudinal axis 1340A. In one form, the angle is between about 0 degrees and about 30 degrees upward relative to the longitudinal axis 2340A. Advantageously, the upper limit is 30 degrees, as having too much tilt on the PCB electrical connector 2366 may result in the elbow providing an undesirable shallow flow path through the elbow and prevent the provision of a useful pooling region. In one form, the angle is between about 0 degrees and about 15 degrees upward relative to the longitudinal axis 2340A. In one form, the angle is about 15 degrees upward relative to the longitudinal axis 1340. Within these ranges, the angle may be non-parallel and non-coaxial relative to the longitudinal axis, and may be oriented at at least+/−5 degrees relative to the longitudinal axis 2340A. In an alternative form, the angle may be parallel to or coaxial with the longitudinal axis 2340A. The PCB electrical connector 2366 is mounted in the support portion 2374 to be parallel to, the lower angled outer edge 2375. Therefore, the PCB connector advantageously also extends upwardly and rearwardly at an angle of between about −15 degrees and about +30 degrees, in one form between about 0 degrees and about +30 degrees, in one form between about 0 degrees and about +15 degrees, and in one form at about +15 degrees, relative to the longitudinal axis 2340A. Again, within these ranges, the angle may be non-zero, and for example may be at least+/−5 degrees relative to the longitudinal axis.

This enables the removable elbow 2342 to be inserted into the elbow retainer 2160 of the upper main chassis of FIGS. 76 and 77 in the same way described for elbow 1342 above.

The removable elbow 2342 of FIGS. 72 to 75 is shown without an internal pool region, however a pool region may be provided as outlined for the elbow of FIGS. 66 to 71. In one configuration, the pool region may be provided internally in the elbow 2342 without changing the shape of the exterior of the elbow. By not including the pool region, the internal surface in the elbow may be smoother (and configured as shown in FIG. 29 for example). This also enables a more even wall thickness, which may strengthen the elbow.

FIG. 75 shows details of the PCB electrical connector 2366 of the removable elbow 2342. The connector 2366 comprises a plastic board 2366a with a plurality of embedded electrically conductive tracks 2366b. A plurality of electrically conductive connector portions or pins 2366c are provided at one end of the PCB, which is the end that projects from the elbow in use. Those connector portions are configured to engage with complementary conductors in the female connector 278 to provide an electrical and/or communication coupling of the PCB to other components of the device. In the form shown, some of the connector portions 2366c are in electrical communication with thermistors 2366d that are positioned at or adjacent an opposite end of the PCB connector and that are embedded in the elbow body. Each thermistor has two tracks extending from the connector portions 2366c to the thermistor, with the two tracks extending to the thermistor being positioned on opposite sides of the PCB to reduce the risk of electrical shorting between the tracks. Two connector portions 2366c are in electrical communication with couplings 2366e that receive bases of two upwardly projecting substantially rigid pin connectors 2368 for coupling to and powering the heater wire(s) 3c in the patient breathing conduit. Again, these tracks may be provided on opposite sides of the PCB to reduce the risk of electrical shorting. The pin connectors will be configured and angled as shown in FIG. 70. Additional connector portions 2366c may be used to power or provide communication coupling of other components.

Two of the tracks are coupled to a device 2366f that is configured to provide functionality which may include one or more of identification, calibration functionality, and information capture such as duration of use, power levels, and disinfection, for example. For example, the device 2366f may be configured to store and/or communicate usage/lifetime information of the removable gasflow tube/elbow. Example information may include one or more of: tracking data, how long the removable gasflow tube/elbow has been used, when the removable gasflow tube/elbow was first used, determining removable gasflow tube/elbow age (e.g. based on manufacturing date), how many times the removable gasflow tube/elbow has been used, determining and logging connection/disconnection of removable gasflow tube/elbow, determining whether disinfection has occurred, how many times the removable gasflow tube/elbow has been disinfected, time of use since last disinfection, when the removable gasflow tube/elbow should be disinfected, power levels, unique ID, calibration, when the removable gasflow tube/elbow should be replaced. The elbow may have a specified usage life stored in the device 2366f such as up to 5 years from manufacture, or a shorter period such as a 1 year life for example. In some configurations, the removable gasflow tube/elbow may have a specified maximum number of disinfection cycles before the removable gasflow tube/elbow should be replaced stored in the device 2366f. For example, the maximum number of disinfection cycles may be a specified number of disinfection cycles per week, for a specified number of weeks. For example, for a removable gasflow tube/elbow having a maximum usage life of one year, the maximum number of disinfection cycles may be 52 cycles; one cycle per week for one year. As another example, for a removable gasflow tube/elbow having a maximum usage life of 5 years, the maximum number of disinfection cycles may be 260 cycles; one cycle per week for five years.

The device 2366f may comprise one or more of a microprocessor, memory, or microprocessor with integrated memory for example. In one form, the device 2366f is an EEPROM. In some configurations, the device 2366f could be a flash memory or some other type of memory. The device 2366f may be configured to store the functionality data or may be configured to communicate the functionality data to the controller 13 of the apparatus via the connector portions 2366c or via a suitable wireless transmission protocol such as WI-FI, Bluetooth, or GSM for example.

The electronics of the removable elbow may be sealed against liquid or gas ingress by potting.

The PCB electrical connector may be provided with one or more apertures 2366g to assist with mounting the PCB connector to the elbow body, and/or to reduce liquid ingress to the PCB. In the form shown, the PCB is provided with two sets of apertures; one relatively large aperture near the narrow end of the PCB adjacent the thermistors 2366d, and five smaller apertures positioned closer to the wider end of the PCB with the connectors 2366c. There are also two of the smaller apertures positioned between the larger aperture and the smaller apertures. However, this configuration could be varied.

The two thermistors 2366d are surface mounted at the front of the PCB connector, and are embedded in the body of the removable elbow. They are located approximately in position 2366d shown in FIG. 72, in close proximity to the gas flow passage 2364. The plastic covering the thermistors may be thinned to enhance temperature measurement, which may slightly alter the internal curvature of the elbow from that shown.

The PCB connector 2366 can be mounted to the elbow body in any suitable manner. In one example, when surface mounted thermistors 2366d are used on the PCB connector, single shot overmoulding could be used to manufacture the elbow on the PCB connector, to simplify manufacturing. The single shot overmoulding can also encompass the elongate pin connectors 2368 in a chimney portion 2368a. The hole(s) in the PCB can allow overmoulded material to flow through the PCB, to reduce or prevent deflection of the PCB that could otherwise occur due to moulding pressures.

Digital temperature sensor(s) may be used instead of thermistor(s).

The support portion 2374 provides protection for the PCB. It can serve to reduce liquid ingress to the PCB by plugging the connection between the PCB connector and the main control board, along with an optional seal if desired or required. The support portion 2374 helps to fill the slot that receives the PCB when coupled to the elbow retainer. Thus, if liquid was to drip/splash into the coupling region, the support portion abuts the plastic of the retainer surrounding the slot and reduces the likelihood that the liquid would reach the PCB connector within. If the support portion did not exist, there would be a higher chance that the liquid could enter when the PCB and retainer are coupled through gaps between the PCB and the retainer slot.

This is also helpful with regards to keeping water out of the electrical connector and/or control board within the elbow retainer.

A seal can be located on the additional plastic of the support portion 2374, about the portion of the PCB connector/support portion that presses against the elbow retainer slot when inserted, or around the electrical connector that is within the slot to aid in sealing between the PCB connector and the connector of the retainer.

A combination of seals could be used.

These features, combined with the non-horizontal angle of the PCB connector in use, helps to drain liquid away from the PCB connector. Plastic surrounds the sides and upper portion of the PCB so that there is no join between the PCB and elbow where liquid could ingress. The support portion 2374 also provides protection for the thin wall section at the base of portion 2368*a*, and the plastic of the support portion encapsulates the PCB connector. It also provides a flat base to assist with alignment during insertion of the PCB connector into the elbow retainer.

The PCB connector may be plasma treated or coated with a conformal coating to aid with bonding between the PCB and overmoulded elbow.

The removable elbow 2342 will be provided with suitable seals. For example, a T-seal may be provided on the manifold gases inlet port 2340 to seal between that port and the liquid chamber gases outlet port 308, and an O-ring seal or other seal may be provided on the patient outlet port 2344. A T-seal can provide a symmetrical seal which is easier for manufacturing. The T-seal can deflect in both the insertion and removal directions, over a wide range of heights (where the seal is contacted by the inserting/removing part), which makes the T-seal more versatile than an O-ring seal.

FIG. 137 shows an exemplary T-seal 2342T in place on the manifold gases inlet port 2340 of the removable elbow 2342. The T-seal 2342T is received in an annular recess 2340R adjacent the outer end of the manifold gases inlet port 2340. As shown in FIG. 138, the T-seal has a relatively wide annular base or body 2342T1 that is sized and configured to be received in the annular recess of the elbow 2342. The body 2342T1 defines a recess 2342T2 that fits on an annular body portion in the annular recess of the elbow 2342. The radial thickness of the body 2342T1 may be sized to be slightly thinner than the radial thickness of the recess.

An annular sealing projection 2342T3 projects radially outwardly from the body 2342T1, and beyond the periphery of the manifold gases inlet port 2340, to seal against an inner surface of the liquid chamber gases outlet port 308. The annular sealing projection 2342 T3 comprises a relatively narrow resilient annular rib 2342T4 that extends radially outwardly from the body, and a wider bobble tip or annular head 2342T5 having a bulbous cross-sectional shape to provide a seal against the inner surface of the liquid chamber gases outlet port 308.

The bobble tip 2342T5 provides a smooth/continuous sealing surface, and advantageously reduces jamming or folding of the seal as it changes the direction it is deflected. The bobble tip also provides resistance to blow-over occurring from gas pressure in the circuit. If any flash remains on the bobble tip post-manufacture, the impact on effective sealing by this flash should be reduced because the flash location will not be on the contact surface of the liquid chamber gases outlet port 308 when the T-seal is deflected. The T-seal may be moulded in the axial direction so that flash will not affect sealing. The bobble tip 2342T5 may have a non-sticky surface finish to prevent it from sticking to the surface it seals against.

The following summarises the chosen exemplary dimensions and parameters of the T-seal for use on the manifold gases inlet port 2340 of the removable elbow 2342T, which have been found to improve locating and sealing between the liquid chamber and the removable elbow, with reference to FIG. 139.

The exemplary dimensions and parameters are selected for the specific embodiment described, but different values or combinations of dimensions and parameters can be used for different embodiments, applications, and/or materials.

Base Width 2342T1': 2.3 mm-6 mm, for Example 6 mm—

It is generally preferable to maximise the base width for a particular application, to minimise seal base lift. The width of the base can be optimised for stability of the seal. The base width will be chosen to be thick enough to prevent rolling or lifting of the base in use, which can compromise the seal.

Base Thickness 2342T1": 0.5 mm-0.9 mm, for Example 0.9 mm—

Chosen as a balance between minimising base lift and allowing space for the T-seal to deflect into when assembled. An excessively large base thickness may result in a compression fit between the base 2342T1 and bobble tip 2342T5 when assembled. If the base is too thick, the deflection of the T may be limited and cause a compression seal with the base rather than a deflection seal. This could cause the shape to remain deformed over time, which could lead to increased force to make a seal and could lead to failure over time. A thick base will allow more T deflection as it is less likely to roll or lift when the T is deflected.

Stretch: For Example 10%—

This configuration is chosen to allow stretching of the T-seal 2342T onto the recess 2342R of the manifold gases inlet port 2340. If the seal is overstreched it will have increased stress which can lead to tearing, and the height of the seal may be reduced which may lead to issues with sealing. If the seal is understretched, it may not hold onto the part very well. The stretch is dependent on the base thickness, and any suitable range may be chosen to optimise the seal.

T-Section/Annular Rib Thickness 2342T4': 0.35 mm-0.7 mm, for Example 0.7 mm—

Having a relatively thin thickness reduces the stiffness of the seal and helps prevent seal base lift. The thicker the T is, the thicker the base needs to be to prevent the base from lifting or rolling in use. Other materials could be used and different results would be obtained.

Bobble Tip Diameter 2342T5': 0.6 mm-0.9 mm, e.g. 0.9 mm—

This dimension was chosen as a combination of maximum resistance to "blow-over" while still providing an acceptable user insertion force and avoiding a compression fit against the seal base 2342T1 when assembled. Blow over would occur if gas could force the bobble tip beyond a sealing position and out of contact with a sealing surface. This "bobble" geometry provides a smooth sealing surface and reduces jamming or folding of the seal when it changes the direction it is deflected.

Shore-A Hardness: For Example 60 Shore A—

In testing of O-rings this was found to provide the best trade-off between softer materials that are "sticky" and cause the seal to extrude out of its recess on insertion, and harder materials that are too plastic and tear easily when assembled. The 60 Shore A for the given material (silicone) provided a smooth insertion feel. This material also has a higher elongation to break and tear resistance when compare to the equivalent 70 Shore A grade. The non-sticky surface finish will inhibit sticking of the seal to the liquid chamber port over time. Shore hardness is specific to material choice, so it will be appreciated that different Shore hardnesses will be suitable for different materials such as nitrile, PTFE, EPDM rubber, flurorcarbon, for example. Different Shore hardnesses may also be suitable depending on the desired properties.

Stretch, non-stickiness, and toughness are desirable material properties for the T-seal.

By inserting the base 2342T1 of the T-seal into the recess 2340R in the manifold gases outlet port 2340 of the removable elbow 2342, gas flow is prevented from getting under the seal and lifting the base 2342T1 of the seal away from the elbow during use. The ridges that are provided by the end walls at either end of the recess minimise the likelihood of base lift of the seal or damage when the liquid chamber is assembled with the removable elbow, helping to locate the seal correctly and prevent movement of the seal. The T-shape of the seal provides good resistance to leakage.

The T-seal 2342T may be removable from the elbow 2342, to enable the seal to be replaced when required.

In alternative configurations, the seal may be overmoulded onto the removable elbow 2342 or other suitable component. By overmoulding the seal onto the component, greater scope is provided to alter the dimensions discussed above. For example, the base width 2342T1' can be greatly decreased. The T-seal may no longer rest within a recess 2340R in the removable elbow 2342, which means that sealing can occur closer to the outer end of the manifold gases outlet port 2340 without requiring the manifold gases inlet port 2340 of the elbow to be pushed as far into the liquid chamber gases outlet port 308, and/or the base 2342I1 of the seal will not be lifted up during insertion/removal or due to flow beneath the seal.

FIGS. 140 and 141 show an alternative configuration T-seal 2342T' in position on the gases inlet port 2340 of a modified removable elbow 2342'. Unless described below, the features and functionality are as described above, and like reference numerals indicate like parts.

This configuration differs in that the T-seal 2342T' has an asymmetric shape, with one side of the base 2342I1 being narrower than the other side of the base 2342T1. In the configuration shown, the width of the base 2342I1 on the side of the seal adjacent the outer end of the inlet port 2340 is shorter than the width of the base 2342T1 on the side of the seal located further from the outer end of the inlet port. The dimensions and parameters may otherwise be the same as described above. While a recess 2340R is provided in the inlet port, that is a one-sided recess. The recess is open to the outer end of the inlet port 2340, and an inner edge of the recess 2340R forms a shoulder against the edge of the T-seal 2342T'. The overmoulding of the T-seal onto the inlet port 2340 means that the base 2342T1 of the T-seal 2342T' will not lift away from the inlet port 2340 during removal or insertion of the outlet port 2340 into the liquid chamber gases outlet port 308. Alternatively, a recess 2340R may not be provided in the inlet port, and the T-seal may be overmoulded directly onto the exterior of the port.

FIGS. 142 and 143 show an alternative configuration seal 2342T" in position on the gases inlet port 2340 of a modified removable elbow 2342". Unless described below, the features and functionality are as described above, and like reference numerals indicate like parts.

This seal 2342T" is adapted T-seal that resembles an L-seal, and has a generally L-shaped configuration, with the annular base 2342T1 of the seal extending from only one side of the radially extending annular rib 2342T3. In the configuration shown, the base 2342T1 only extends from the rib 2342T3 in a direction away from the edge of the inlet port 2340. With this configuration, sealing can occur right at the outer edge of the inlet port 2340. The dimensions and parameters may otherwise be the same as described above. While a recess 2340R is provided in the inlet port, that is a one-sided recess. The recess is open to the edge of the inlet port 2340, and an inner edge of the recess 2340 forms a shoulder against the edge of the T-seal 2342T". The overmoulding of the seal 2342T" onto the inlet port 2340 means that the base 2342T1 of the seal 2342T" will not lift away from the inlet port 2340 during removal or insertion of the outlet port 2340 into the liquid chamber gases outlet port 308. Alternatively, a recess 2340R may not be provided in the inlet port, and the T-seal may be overmoulded directly onto the exterior of the port.

The liquid chamber gases outlet port 308 and/or gases inlet port 2340 may be provided with one or more alignment features to limit eccentricity between the two ports and thereby reduce loading on the seal. FIG. 144 shows one example in which the alignment feature comprises a mechanical standoff located in the gases inlet port 2340. In the form shown, the mechanical standoff is provided by an inner shoulder 2340RS of the seal recess 2340R, which acts to locate and align the ports during insertion so that the seal only has to seal rather than align the ports or accommodate significant loading from the ports. The mechanical standoff(s) can be located either in front of or behind the sealing surface of the seal, and could have any suitable form.

Utilising a flexible T-seal or L-seal provides a good seal without requiring a high force to couple the liquid chamber with the removable elbow. The effective seal can be maintained over time, whereas other types of seals such as O-ring seals may creep or reduce sealing over time and require a compression fit.

Rather than being in the form of an elbow, the gasflow tube 1342, 2342, 2342', 2342" could have any other suitable configuration depending on the configuration of the apparatus. For example, the gasflow tube could be substantially linear or a non-liner configuration, with the manifold gases inlet port and the patient outlet port at ends of the tube. The inlet and outlet ports will typically be offset from each other. The direction of insertion and removal of the gasflow tube into and from the retainer (e.g. forward and rearward) may be at an angle to the longitudinal axis 1340A, 2340A, so that the elbow can form a connection with a desired orientation for coupling to the liquid chamber. The retainer may be modified as required, depending on the configuration of the gasflow tube.

7. Motor and/or Sensor Module—Alternative Configurations

FIGS. 78 to 100 show an alternative configuration removable motor and/or sensor module or sub-assembly 1400 that can be used as a flow generator in the flow therapy apparatuses described herein. Unless described below, the sub-assembly has the features and functionality described in relation to the sub-assembly of FIGS. 16 to 22f, and like reference numerals indicate like parts, with 1000 added to each reference numeral.

As discussed above, the motor and/or sensor module or sub-assembly 1400 has been designed as an individual and sealed component. Any seals that are breached will cause gases such as oxygen to leak to the atmosphere rather than into the electronics of the apparatus. The module 1400 is positioned in the apparatus slightly off-centre so that it fits a filter and oxygen manifold and is located close to the air/oxygen inlet arrangement 350 of the apparatus. The module 1400 is configured to be replaceable, so if a sensor fails the entire module can be replaced. The module may only contain electronics relevant to sensing.

The motor and/or sensor module 1400 comprises a stacked arrangement of three main components; a base 1403 of the sub-assembly 1400 (on which is positioned the motor 1402 with an impeller that forms a blower), an outlet gasflow path and sensing layer 1420 positioned above the base 1403, and a cover layer 1440. The cover layer 1440 and outlet gasflow path and sensing layer 1420 will typically be assembled together in use to form the sensing layer. The gases move through the module 1400 substantially as described above with reference to FIGS. 16 to 22f. An opening formed between the blower 1402 and the outlet gasflow path and sensing layer 1420 provides a gases inlet into the module and enables the temperature of incoming gases to be measured.

The base 1403 comprises a region 1403A for receipt of the gas blower motor 1402. The region 1403A may be concave. The diameter of the concave region is selected to correspond with the shape of the underside of the body 1408 of the motor 1402. The region 1403A guides gasflow to the blower. Ribs on the underside of the base 1403 give stiffness to the area and reduce noise in combination with the shape of the concave region. In an alternative configuration, the region 1403A may be a different shape, for example a non-concave shape.

Figure 79:
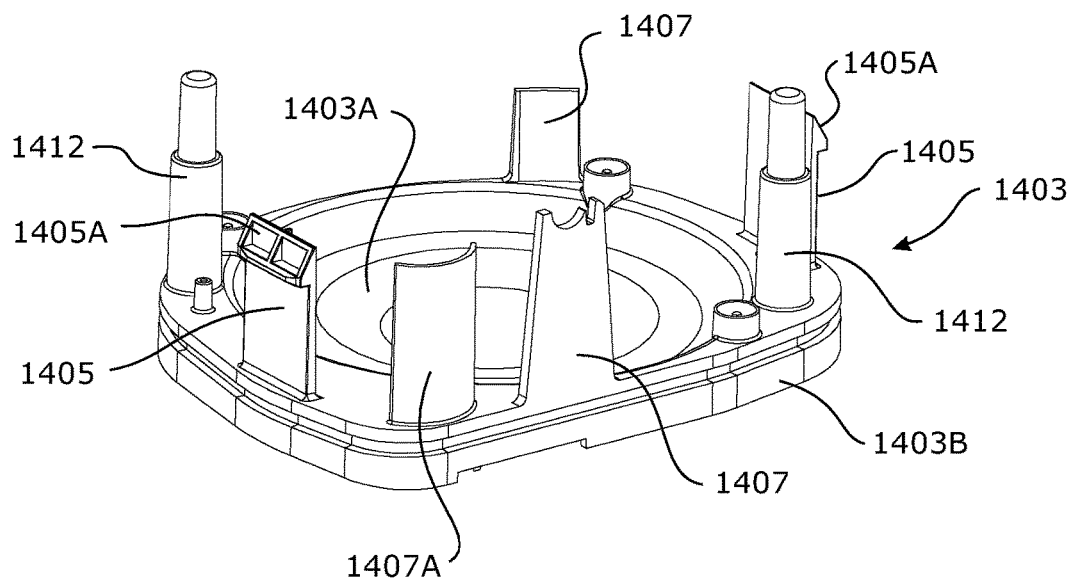
FIG. 79 is a perspective view of the base of the motor and/or sensor sub-assembly of FIG. 78.
Figure 80:
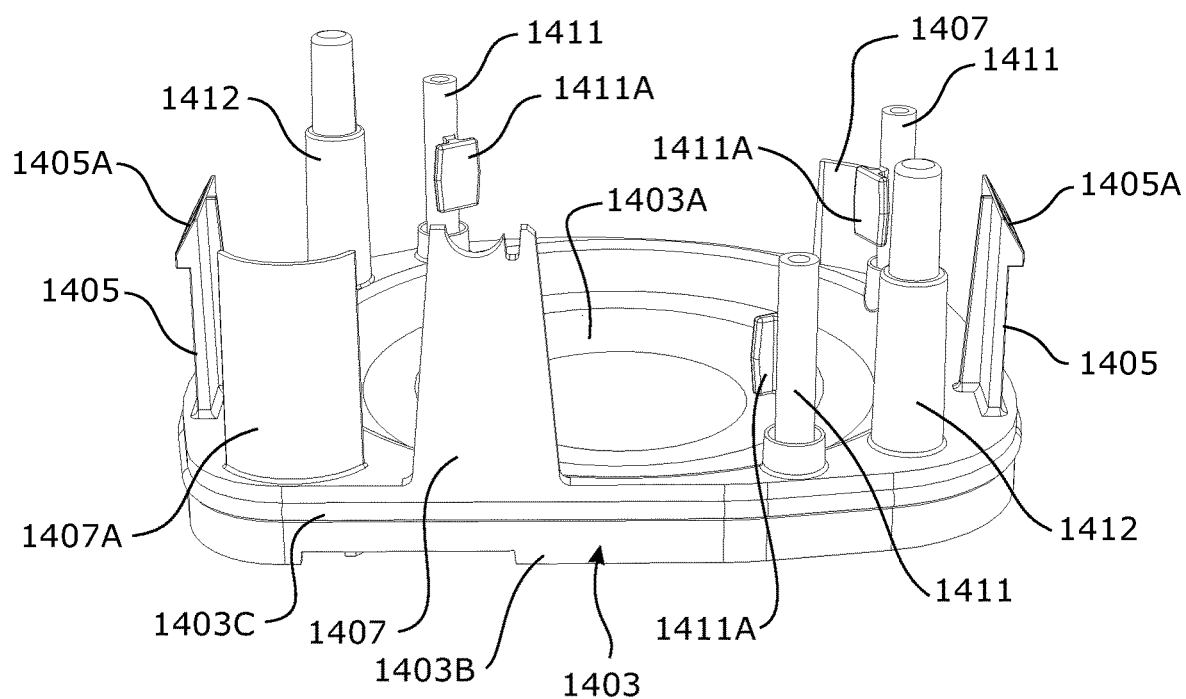
FIG. 80 is another perspective view of the base of the motor and/or sensor sub-assembly of FIG. 79.
Figure 81:
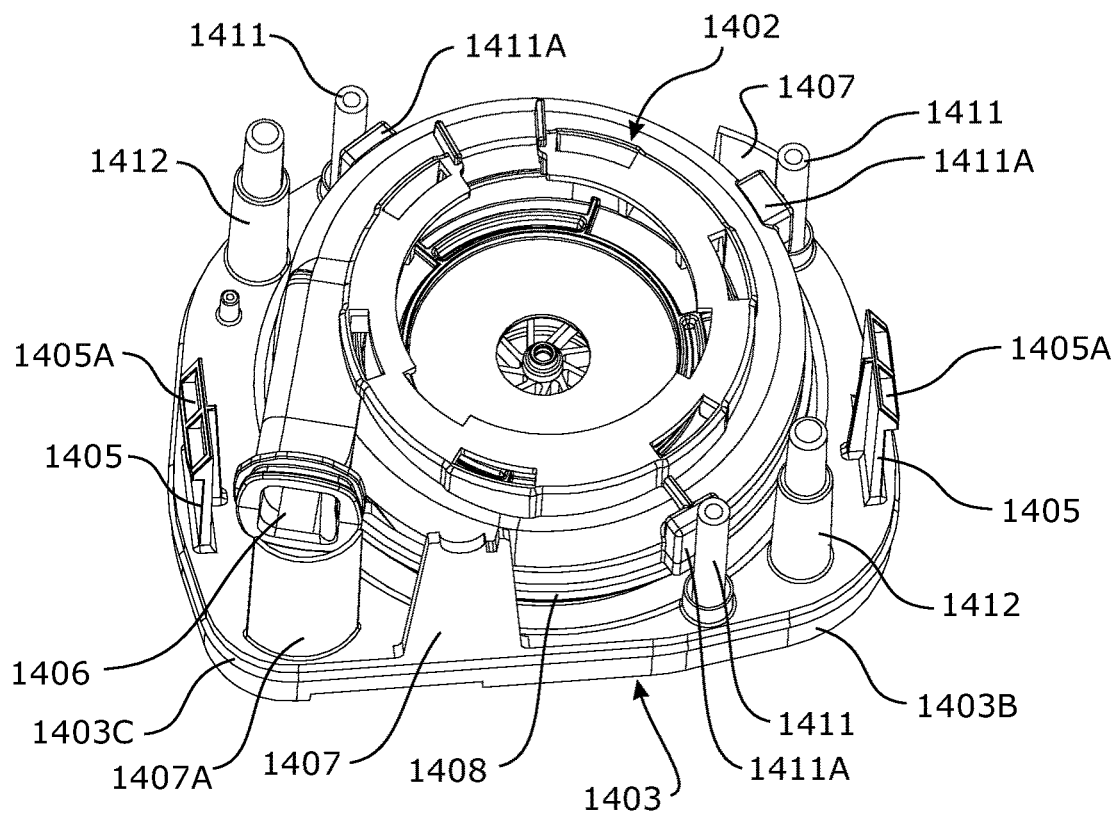
FIG. 81 is an overhead perspective view of the base of FIGS. 79 and 80 assembled with the motor/blower unit.

As shown in FIG. 79, the base 1403 comprises a plurality of flexible mounts 1411. The flexible mounts act as vibration isolating structures. Engagement plates 1411A are retained by the upper casing of the motor/blower body 1408, and provide a slot into which the mounts can slide. Any suitable number of flexible mounts 1411 may be provided. Upper ends of the mounts are received in complementary receiving portions such as cups in a body 1422 of the outlet gasflow path and sensing layer 1420.

As shown in FIGS. 78-82, 84, 85, and 88, the base 1403 and the body 1422 of the outlet gasflow path and sensing layer 1420 are provided with complementary securing features 1405, 1425 to secure the body 1422 to the base 1403. The base 1403 comprises a plurality of upstanding clips 1405 positioned at spaced apart locations around the periphery of the base. The upper ends of the clips comprise heads 1405A that are tapered toward their upper ends. The heads are provided with recesses or cut-outs to provide a substantially constant cross-sectional area in the plastic to enable the plastic to cool quickly.

The body 1422 comprises a corresponding plurality of receiver members 1425 at spaced apart locations around the periphery of the body. The receiver members comprise apertures 1425A towards their lower ends, the apertures 1425A sized and configured to receive the tapered heads 1405A of the clips. The body 1422 can be secured to the base 1403 by moving the body and the base towards each other so the clip heads 1405A are received in the apertures 1425A. The body can be separated from the base by moving the heads 1405A transversely so that they clear the apertures 1425A, then moving the body away from the base.

The clips 1405 and receiver members 1425 may be positioned at or close to the outer edge of the base 1403 and body 1422. There will suitably be at least two clips and receiver members, but may be three or more clips and receiver members. In the form shown, the clips 1405 are located on opposite sides of the base 1403 and the receiver members 1425 are located on opposite sides of the body 1422. The clips could alternatively be part of the body 1422 and the receiver members part of the base 1403, or there could be a combination of clips and receiver members mounted on both the base 1403 and the body 1422.

The clips 1405 and receiver members 1425 are configured to be strong enough to enable the removable motor and/or sensor module or sub-assembly 1400 to be removed from the housing as a single part, but are not required to carry load once assembled. The clips and receiver members could be used as the sole method of securing the base and body, or they could be used in combination with other fasteners such as screws or the like. Alternatively, a different securing method could be used.

The base 1403 and body 1422 comprise a plurality of vertically extending wall members 1407, 1427. The wall members are complementary with each other and the upper ends of the lower wall members 1407 engage with the lower ends of the upper wall members 1427 when the base 1403 is secured to the body 1422, to prevent rocking of the body 1422 relative to the base 1403. There will be at least two wall members at spaced apart locations around the body and base, but may be three or more wall members. The wall members may be provided on either side of the clips to help the clips to engage more securely, thereby providing a more stable assembly which is less likely to rock. The length and/or shape of the wall members may vary. An aperture 1427A is positioned in one of the wall members or between two of the wall members, to receive a temperature sensor for determining the temperature of incoming gases. Alternatively, the temperature sensor may be positioned elsewhere.

The base 1403 and/or body 1422 also comprise a plurality of locating pins 1412 to guide the base and body together during coupling. There will suitably be at least two locating pins 1412 to provide rotational and vertical locating, but there may be three or more pins 1412.

A periphery 1403B of the base 1403 is provided with a recess that receives a soft seal such as an O-ring seal 1403C. The seal 1403C seals the module 1400 against the housing of the apparatus and prevents atmospheric air entrainment which would bypass the filter. In particular, the seal 1403C seals between the base 1403 and the peripheral wall of the recess 250 of the apparatus housing. The seal 1403C also provides a force between the module 1400 and the housing of the apparatus that must be overcome to remove the module 1400 from the housing.

Figure 83:
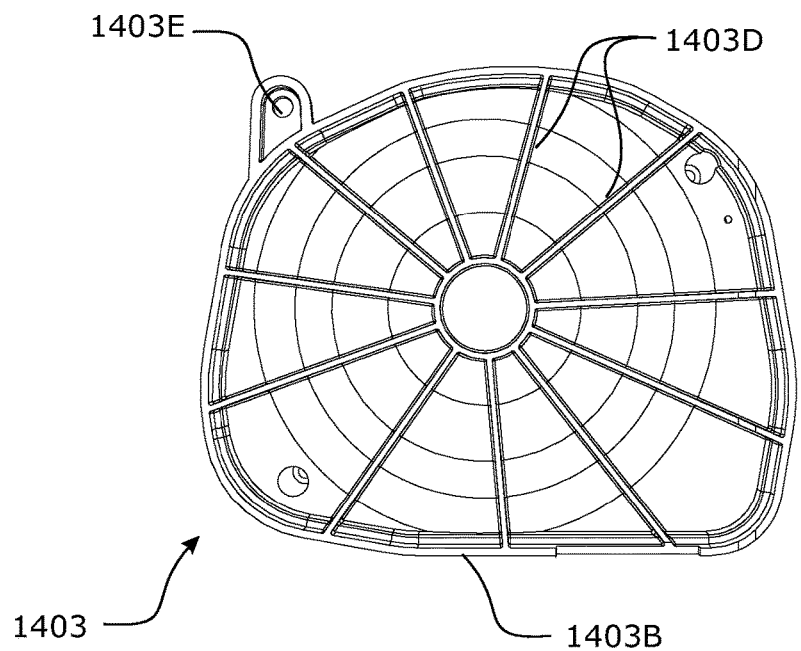
FIG. 83 is a bottom view of the base of the motor and/or sensor sub-assembly of FIG. 78.

As shown in FIG. 83, the underside of the base 1403 is scalloped and is provided with a plurality of strengthening ribs 1403D to provide structural strength and stability. The ribs are shown in a radial arrangement, but may be in any suitable configuration. One edge (the lower edge shown in FIG. 83) of the periphery 1403B is substantially linear to accommodate the shape of an oxygen inlet manifold in the apparatus. The sides of the peripheral edge may be tapered to assist with tooling. An aperture 1403E is provided in a projecting portion of the base 1403, to enable the module 1400 to be fastened to the housing of the apparatus using a fastener such as a screw for example.

Once gases enter the module 1400 via the inlet region, they move to the blower inlet, which is located underneath the blower 1402 in the concave portion 1403A of the base 1403. Gases entering the module may act to cool the motor. Gases then move through the blower 1402 and exit via the blower gases outlet port 1406. Gases exiting the blower gases outlet port 1406 enter a coupling tube or cuff 1409 which couples the blower gases outlet port 1406 to a gases inlet port 1430 of the outlet gasflow path and sensing layer 1420. The cuff has a gases inlet port 1409A that is coupled to the blower outlet port 1406, an arcuate body portion 1409B that directs the gases upwardly away from the gases inlet port 1409A, and a gases outlet port 1409C that delivers gases to the gases inlet port 1430 of the outlet gasflow path and sensing layer 1420. The arcuate body portion of the cuff directs the gases through an angular change of about 90 degrees from the blower outlet port 1406 to the gases inlet port 1430, but over a short horizontal distance, while minimising pressure drop. In one configuration, the maximum pressure drop between the blower outlet port 1406 and a centre of the gasflow path 1426, 1446 is a maximum of 2.5 cm $H_2O$.

It will be appreciated that the cuff can be configured to direct gases through different angles depending on the required configuration. The inlet 1409A and outlet ports 1409C of the cuff 1409 will be sealed to the blower outlet port 1406 and gases inlet port 1430 using a suitable sealing arrangement; for example, soft seals such as O-ring seals.

The cuff 1409 is configured to minimise the pressure drop of the gases passing though the cuff and to isolate blower vibration from the case of the unit in tight space constraints. The cuff is made from a soft flexible material and has localised region(s) that act as a diaphragm and serve as vibration isolators. Some regions of the cuffs may be thinned out to provide isolation to prevent or minimise any vibration from being transmitted to structural parts. This could be achieved by moulding thinner section(s) into the cuff. Additionally, or alternatively, a concertina may be provided in the cuff to assist with isolating vibrations from the case of the unit while allowing more movement of the module 1400 in the housing.

Figure 82:
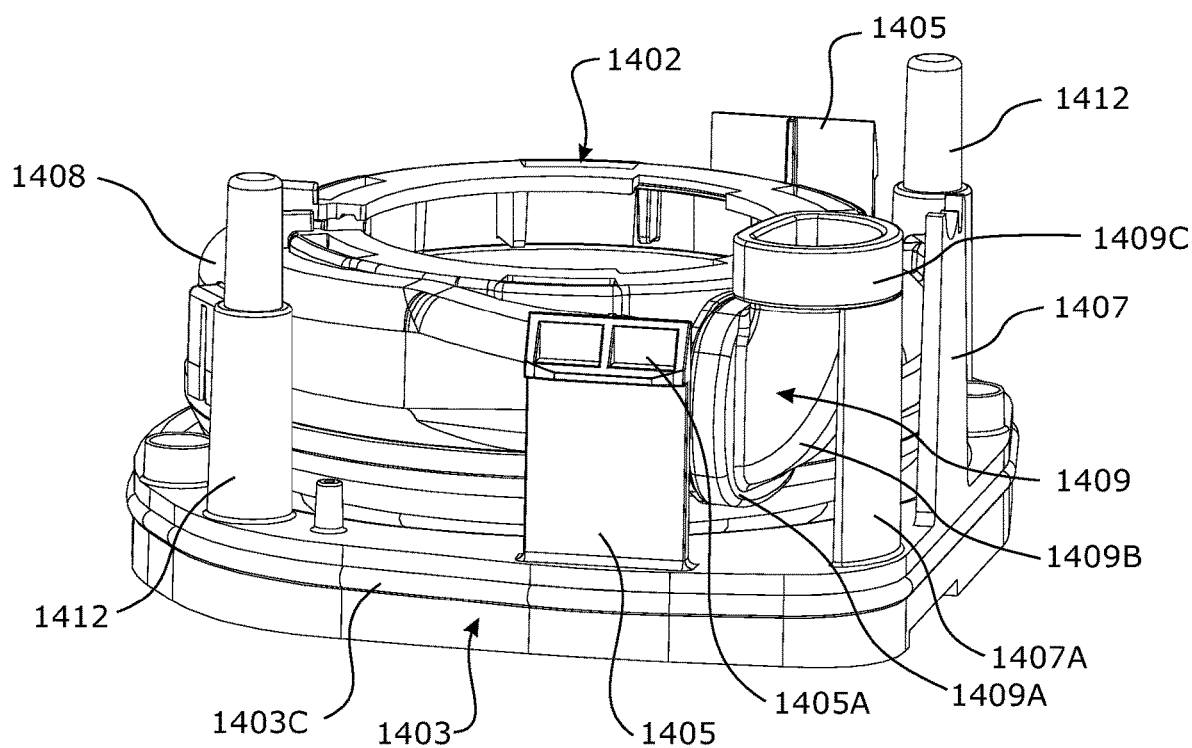
FIG. 82 is another overhead perspective view of the base and motor/blower unit of FIG. 81.

The base 1403 comprises an upstanding cuff support member 1407A projecting upwardly at or adjacent the periphery of the base. The cuff support member 1407A has an inwardly concave shape when viewed in overhead plan view, and is configured to receive and support the periphery of the cuff 1409. As shown in FIG. 82 for example, the gases outlet port 1409C end of the cuff comprises an enlarged diameter that rests on the upper end of the cuff support member 1407A.

The cuff support member 1407A holds the flexible cuff 1409 in a desired position and helps prevent the cuff from being blown off the inlet 1430 under pressurised flow. The centre of the cuff may be more flexible than either end of the cuff. The cuff may be manufactured from a low compression set material that reduces creep and allows the neck of the cuff to be stretched over and onto the port and held firmly in place. The cuff may be provided with one or more grab tabs to aid with the assembly process. The grab tab(s) may be provided on any suitable region of the cuff. However, the grab tabs will generally be positioned so as to not obstruct/interfere gasflow in the region where air and/or oxygen or other gases enter the motor and/or sensor module 1400. In one example, a grab tab may be positioned near an upper edge of the cuff. In another example, the grab tab may be positioned elsewhere on the cuff.

As an alternative to grab tab(s), edge(s) of the cuff may be chamfered to assist with putting the cuff in place.

The gasflow path and sensing layer 1420 comprises a gasflow path with one or more sensors, the gasflow path is arranged to deliver gas to the outlet port of the housing.

Figure 84:
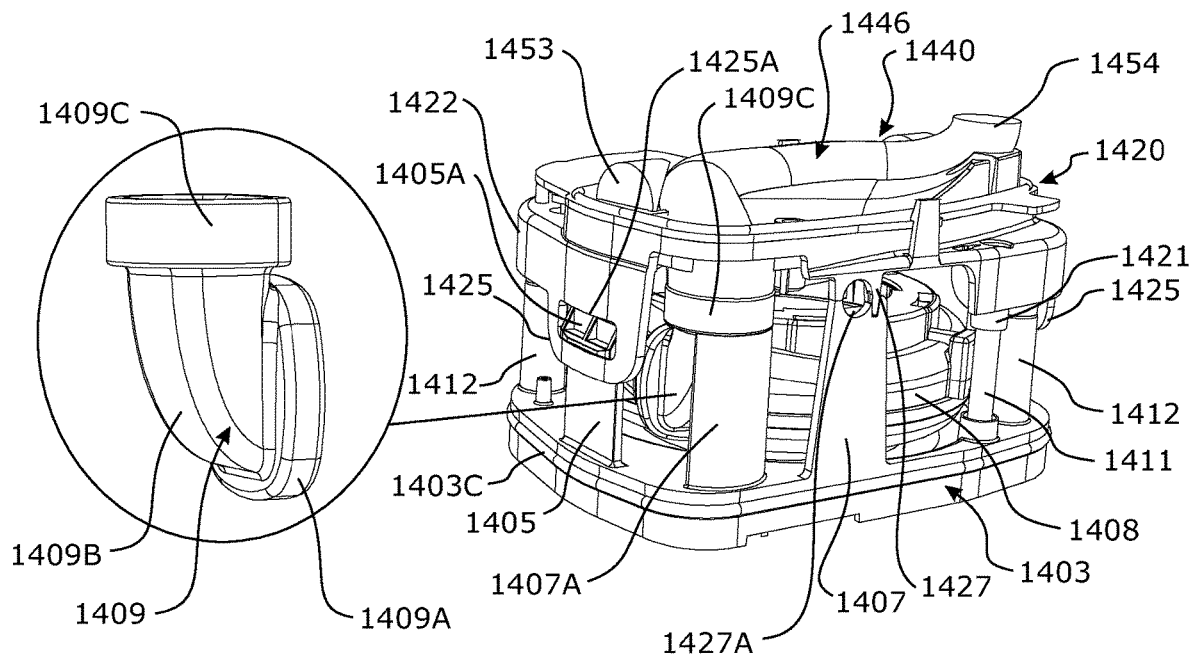
FIG. 84 is a perspective view of the motor and/or sensor sub-assembly of FIG. 78, with part of the cover layer not shown, and showing a coupling tube or cuff.
Figure 85:
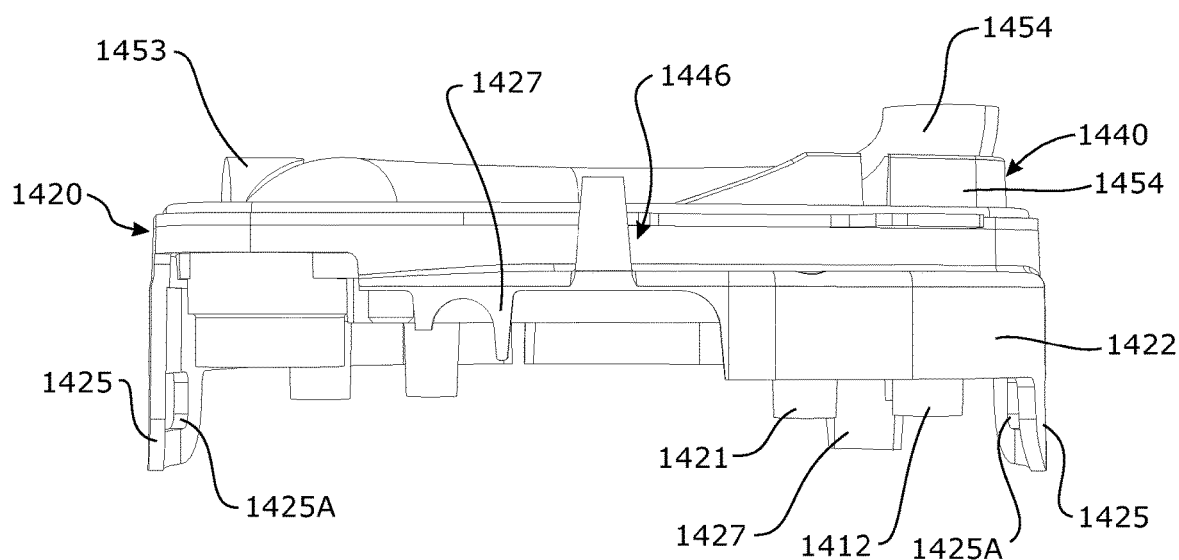
FIG. 85 is a perspective view of a mid-section of the motor and/or sensor sub-assembly of FIG. 78, and schematically showing an upper part of the gasflow path from the cover layer.
Figure 86:
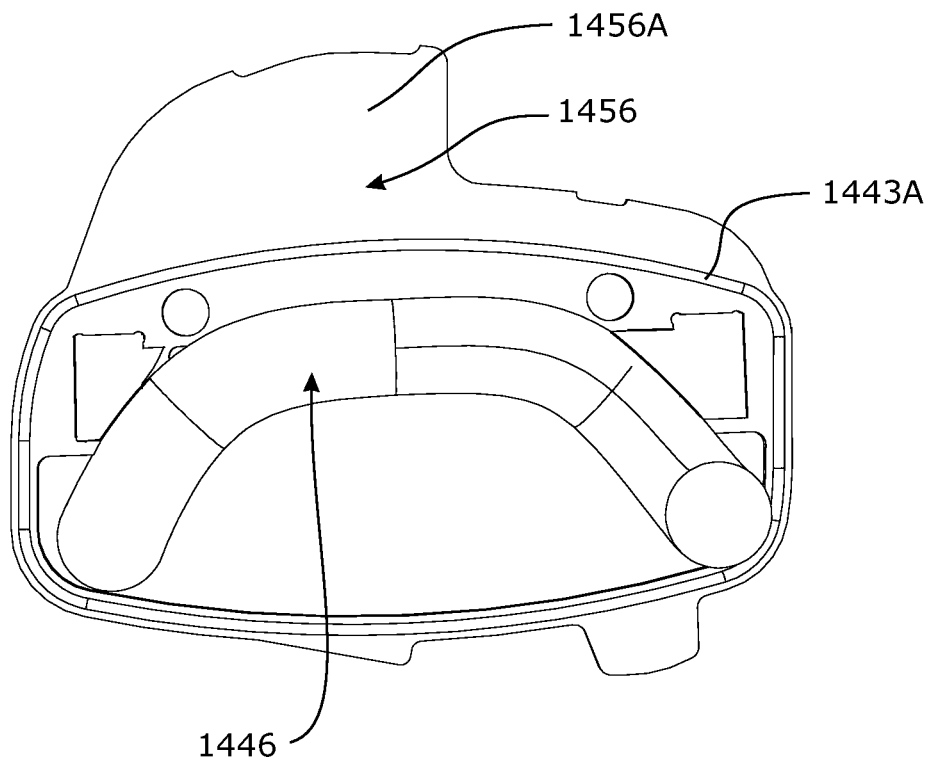
FIG. 86 is a top view of parts of the mid-section of FIG. 85.
Figure 87:
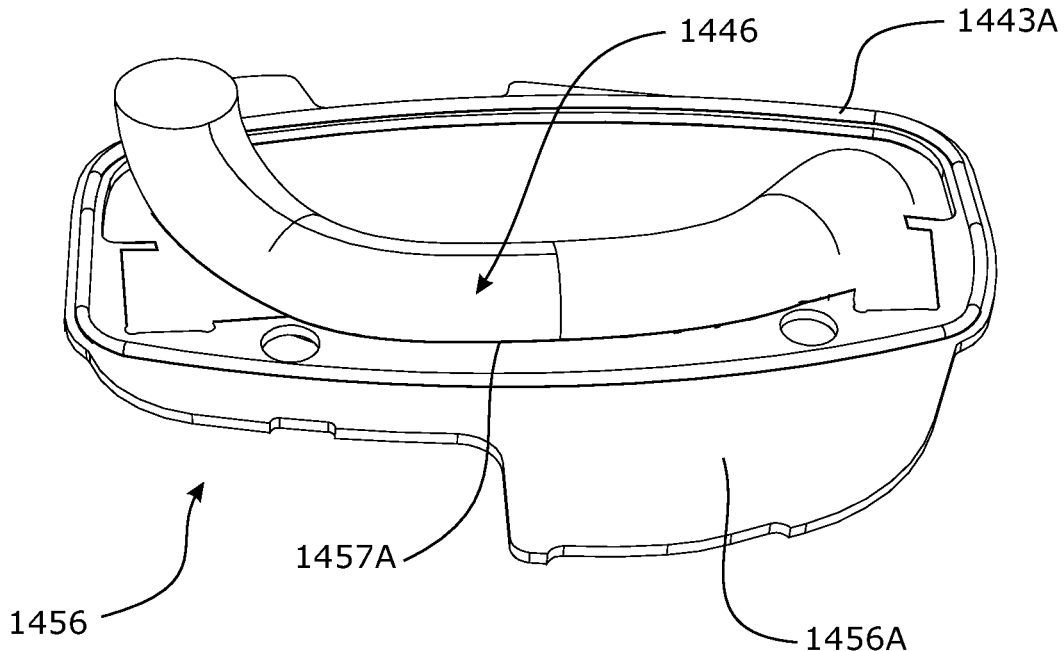
FIG. 87 is an overhead perspective view of the parts of FIG. 86.

A body 1422 of the gasflow path and sensing layer 1420 defines a lower portion 1426 of a sensing and gasflow path. The cover layer 1440 has a body 1442 that defines the upper portion 1446 of the sensing and gasflow path, with the shape of the upper and lower portions 1426, 1446 corresponding substantially to each other. Therefore, while FIGS. 84 and 85 schematically show the upper portion 1446 of the sensing and gasflow path, that will only be present when the cover layer 1440 is coupled to the body 1442, as will be clear from the cover layer shown in FIGS. 93 to 95.

Figure 88:
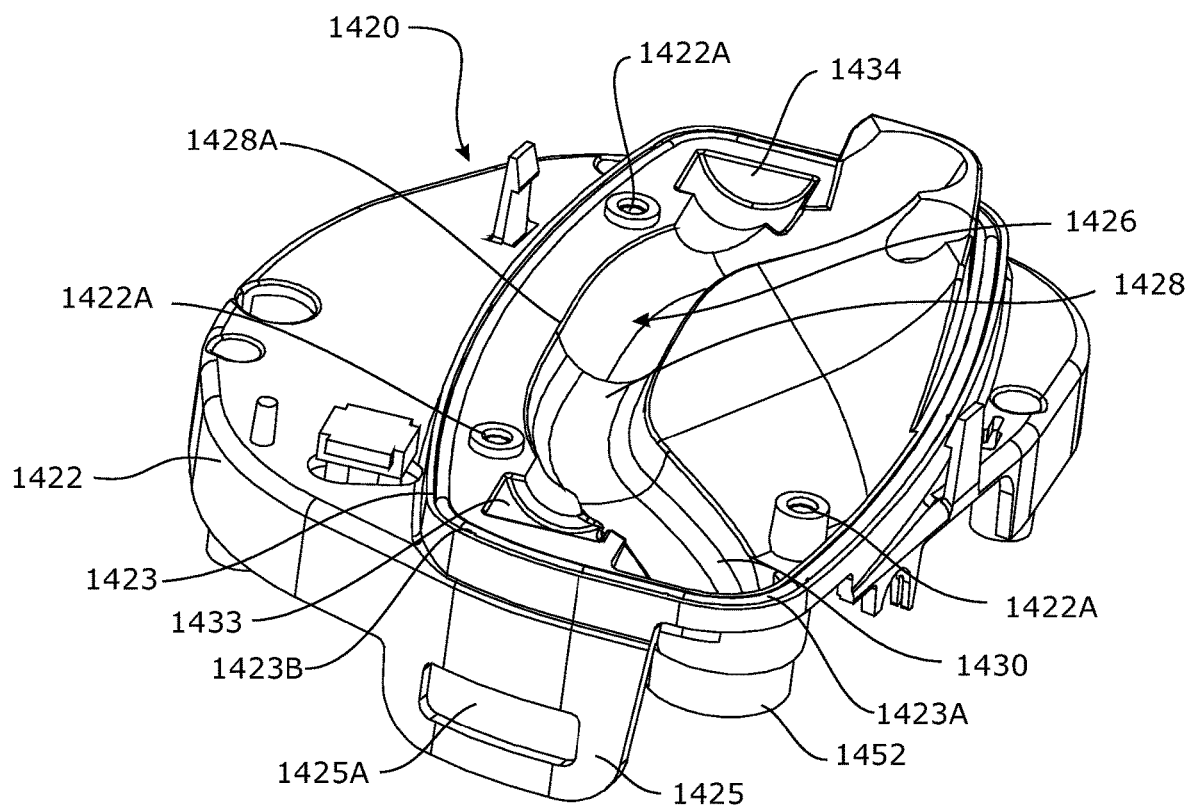
FIG. 88 is an overhead perspective view of an outlet gasflow path and sensing layer of the motor and/or sensor sub-assembly of FIG. 78, which forms a lower part of a gasflow path.
Figure 89:
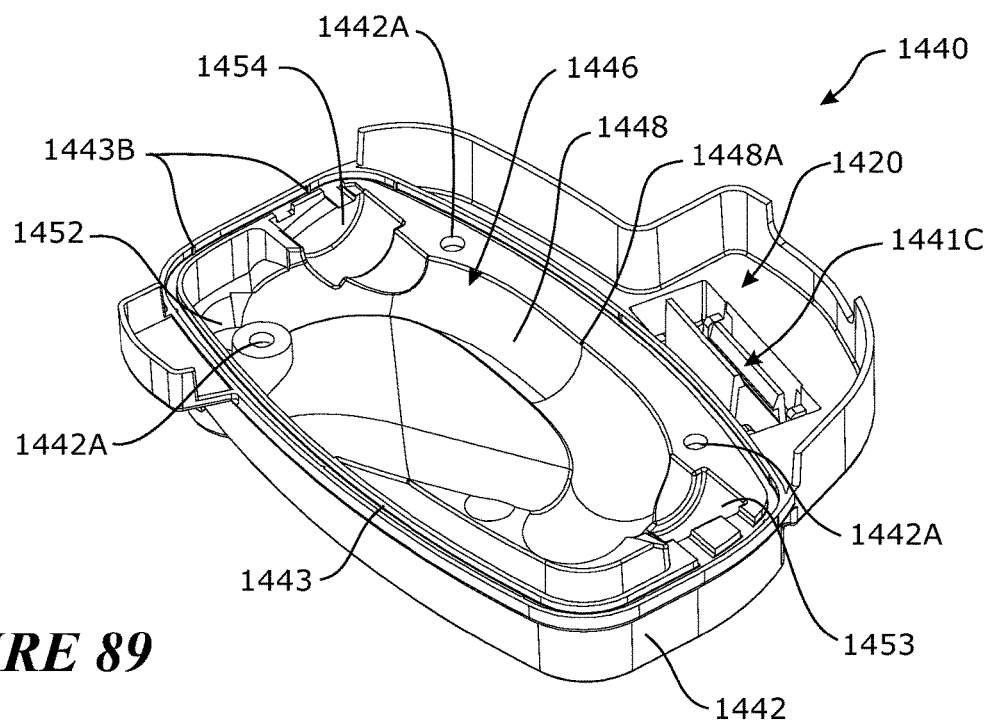
FIG. 89 is an underside perspective view of the cover layer of the motor and/or sensor sub-assembly of FIG. 78, which forms an upper part of a gasflow path.
Figure 90:
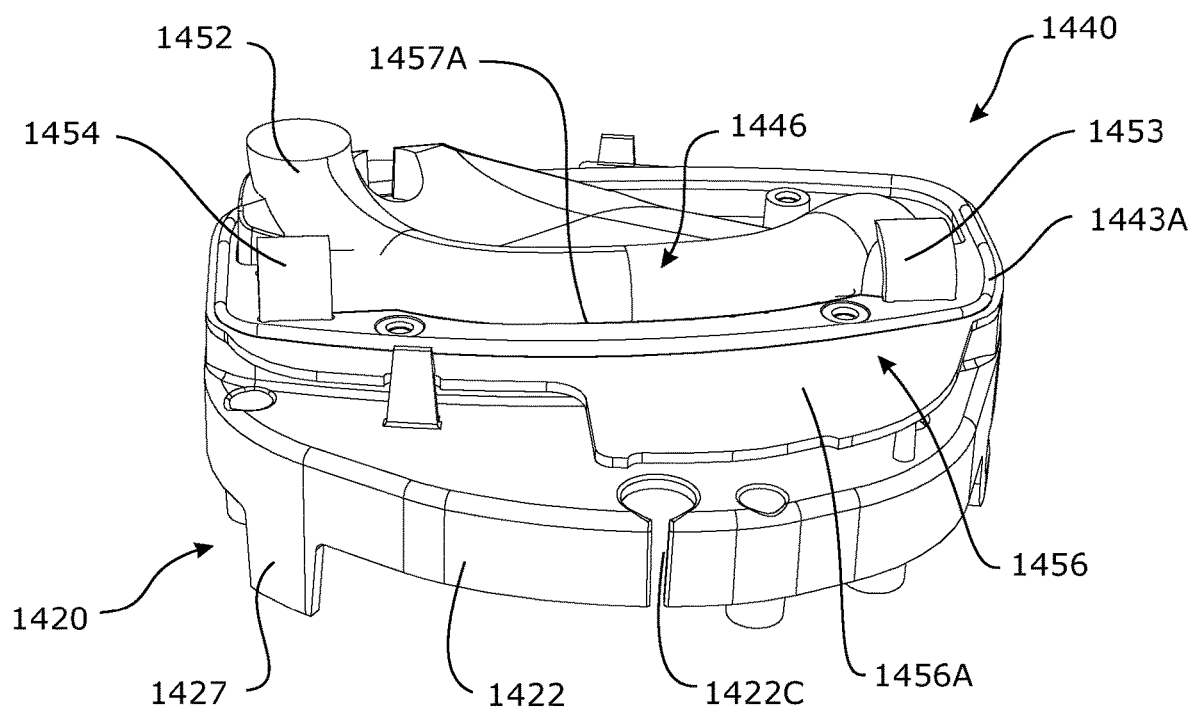
FIG. 90 is a rear overhead perspective view of the mid-section of the motor and/or sensor sub-assembly of FIG. 78 with a PCB in place, and schematically showing an upper part of the gasflow path from the cover layer.
Figure 91:
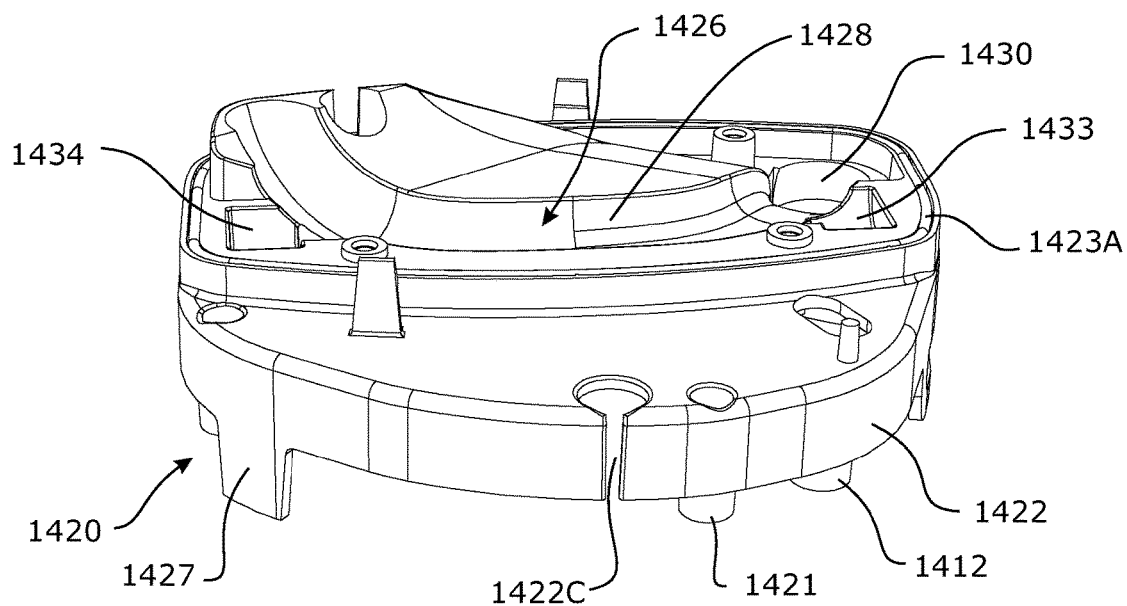
FIG. 91 is a rear overhead perspective view of the mid-section of the motor and/or sensor sub-assembly of FIG. 78 without the PCB in place.

As shown in FIGS. 88 and 89, the sensing and gasflow path comprises an arcuate elongate gasflow portion 1428, 1448. Recesses 1433, 1453, 1434, 1454 may be provided adjacent opposite ends of the arcuate elongate portion of the sensing and gasflow path.

In the form shown, the arcuate elongate gasflow portion 1428, 1448 is curved. In the form shown, the arcuate elongate gasflow portion has a length of about 85 mm. In the form shown, the ends of the gasflow path are more arcuate (i.e. have a tighter radius) than the centre, which is still arcuate but more linear. The gasflow path is curved to minimise the pressure drop of the gases as they travel along it, and yet to direct the gases through the module, which requires the gases to turn sharply several times. The curve helps to smooth the sharp turns as the gases move through the module. The gases enter the arcuate gasflow path shortly after/as they leave the cuff 1409.

An intermediate portion 1428A, 1448A of the gasflow path has a smaller diameter than portions on either end of the intermediate portion. Therefore, the gasflow path tapers inwardly slightly before widening again, to speed up flow going through the flow path.

A gasflow outlet port 1452 extends vertically through the body 1442 of the cover layer 1440, and is located at or adjacent an end of the arcuate elongate gasflow portion 1428, 1448 opposite to the inlet port 1430.

The sensing and gasflow path has a curved shape. The gas flow enters at inlet port 1430, flows along a curved sensing and gasflow path, and exits on the opposite side of the sensing and gasflow path at outlet port 1452. In some configurations, the entrance and exit may be positioned in vertically opposed directions, and the gas flow may enter the path in a vertical upwards direction, then curve around to a horizontal direction, and then curve around to a vertical upwards direction again. In some configurations, the sensing and gasflow path does not have sharp turns. In some configurations the sensing and gasflow path has curved ends with a straighter middle section. In some configurations, the sensing and gasflow path maintains a constant cross-section shape throughout the length of the flow path. In some configurations, the sensing and gasflow path tapers inward slightly from the first end of the sensing and gasflow path, and widens again to the second end of the sensing and gasflow path, which can speed up the flow. In some configurations, the surface of the sensing and gasflow path is lined with a surface modifier/lubricant to reduce friction within the sensing and gasflow path. A curved flow path shape can reduce a gas flow's pressure drop. A number of different flow path configurations could be used.

The sensing and gasflow path 1426, 1446 has a total distance between opposite ends of the arcuate elongate gasflow portion 1428, 1448 (between the closest portions of recesses 1433, 1453, 1434, 1454) of between about 10 mm and about 1000 mm, between about 40 mm and about 200 mm, between about 50 mm and about 150 mm, between about 70 mm and about 120 mm, between about 80 mm and 100 mm, or between any of the foregoing values, or about 95 mm.

The sensing and gasflow path 1426, 1446 can have a diameter greater than about 2 mm and less than about 100 mm, between about 5 mm and about 50 mm, between about 10 and about 30 mm, between about 15 and about 25 mm, between any of the foregoing values, or about 16 mm. Decreasing the diameter of the flow path can increase the gas velocity at high flows beyond useful velocities and can lead to pressure drops. Increasing the diameter of the flow path can take up more space in the system. Thus, an optimal balance can be obtained according to the ranges described above. Equivalent ranges can be used with devices that have different flow configurations.

Figure 100:
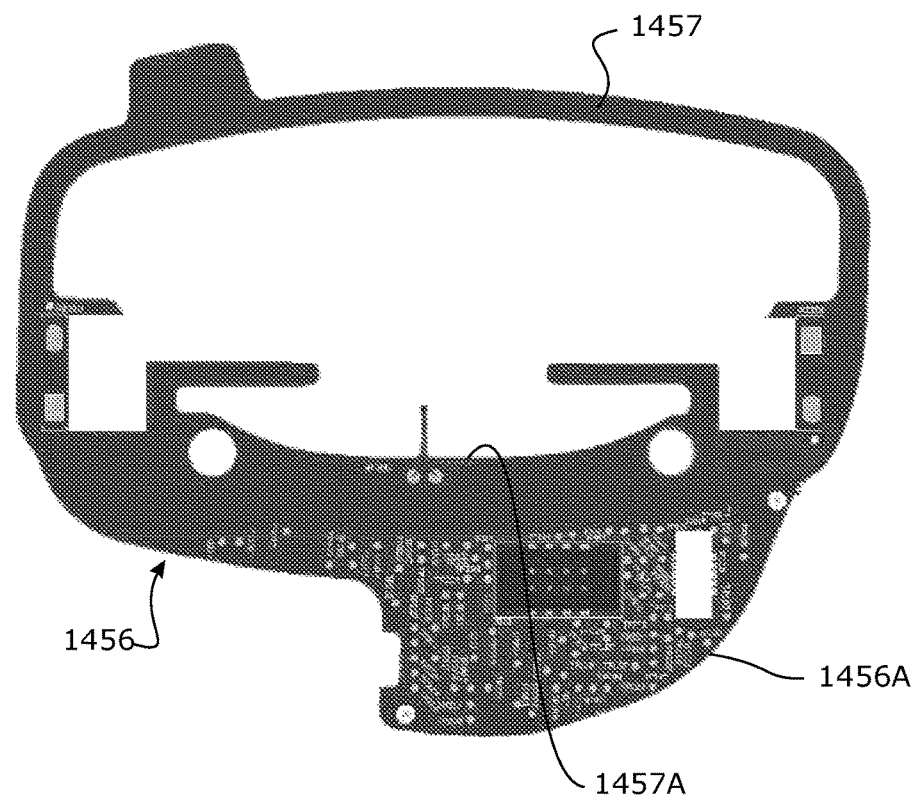
FIG. 100 is an overhead perspective view of the PCB of the motor and/or sensor sub-assembly of FIG. 78.

A slot 1422C is provided in the body 1422 to pass wires from the blower 1402 to a sensing printed circuit board (PCB) 1456. At least part of the PCB overlaps with the gas flow path through the gasflow path and sensing layer 1420. The PCB 1456 is sandwiched between the gasflow path sensing layer 1420 and cover layer 1440. Temperature sensors will be positioned on the portion of the PCB that is within/overlaps with the gasflow path. As shown in FIG. 100, the PCB 1456 comprises a recess 1457 with an arcuate portion 1457A that is a complementary shape to the curvature of the outer edge of the arcuate elongate gasflow portion 1428, 1448. A projecting portion 1456A of the PCB carries the electronics of the PCB, and is configured to be positioned externally of the flow path.

As shown in FIGS. 88 and 89, an upper side of the body 1422 of the layer 1420 is provided with a groove 1423 for receipt of a soft seal such as an O-ring 1423A to seal against an underside of the PCB 1456. A lower side of the body 1442 of the cover layer 1440 is provided with a groove 1443 for receipt of a soft seal such as an O-ring 1443A to seal against the upper side of the PCB 1456. The grooves 1423, 1443 are advantageously provided with inwardly-directed projections 1423B, 1443B (shown more clearly in FIG. 99) to assist with maintaining the O-ring seals in position in the grooves.

The soft seals 1423A, 1443A seal the high pressure region of the module, as gasses passing through the gasflow path have been pressurised by the blower. The seals 1423A, 1443A prevent gases from escaping and moving towards the electronics of the apparatus. The soft seals could alternatively be co-moulded to the bodies 1422 and 1442, with a soft layer co-moulded onto the more rigid bodies.

Figure 92:
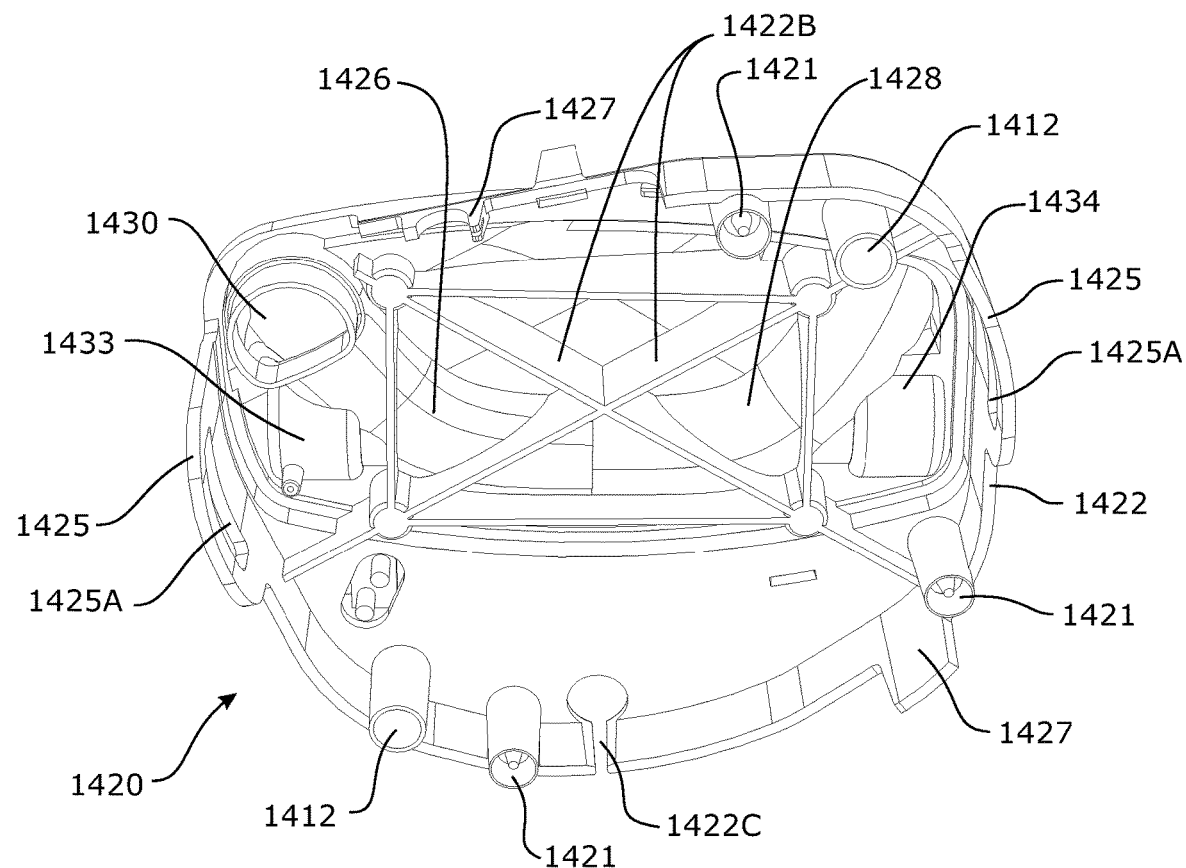
FIG. 92 is an underside perspective view of the outlet gasflow path and sensing layer of the motor and/or sensor sub-assembly of FIG. 78.

As shown in FIG. 92, the lower surface of the body 1422 is provided with a plurality of stiffening ribs 1422B in any suitable configuration, to decrease warping.

As discussed in relation to the configurations above, the electronics of the apparatus are positioned in the low pressure region of the housing to cause a tortuous path which decreases the likelihood of liquid or oxygen ingress to the electronics. The portion of the PCB 1456A comprising the electronics components is positioned 'outside' the O-rings. The portion of the PCB 1456 comprising the sensors is inside the flow path and is sealed from the outside by the O-rings 1423A, 1443A pressing tightly against the PCB 1456. Therefore, liquid or oxygen ingress may be at least substantially prevented.

The cover layer 1440 may be coupled to the gasflow path and sensing layer 1420 using fasteners such as screws. The fasteners sandwich the two sections together providing a compressive force to seal the soft seals 1423A, 1443A against the PCB board 1456. Any suitable number of apertures 1422A, 1442A (FIGS. 88 and 89) may be provided for receipt of the screws. Washers could be used on the underside of the screws. To minimise the chance of leakage around the screws to the low pressure region (which could impact performance), ridges could be added to the bosses on which the head of the screw will sit once inserted. Alternatively, once the screws have been inserted, adhesive or filler could be used to seal any possible openings. Alternatively, the cover layer 1440 could comprise clips or adhesive features to couple with the gasflow path and sensing layer 1420 to seal between the layers when force is applied.

Figure 93:
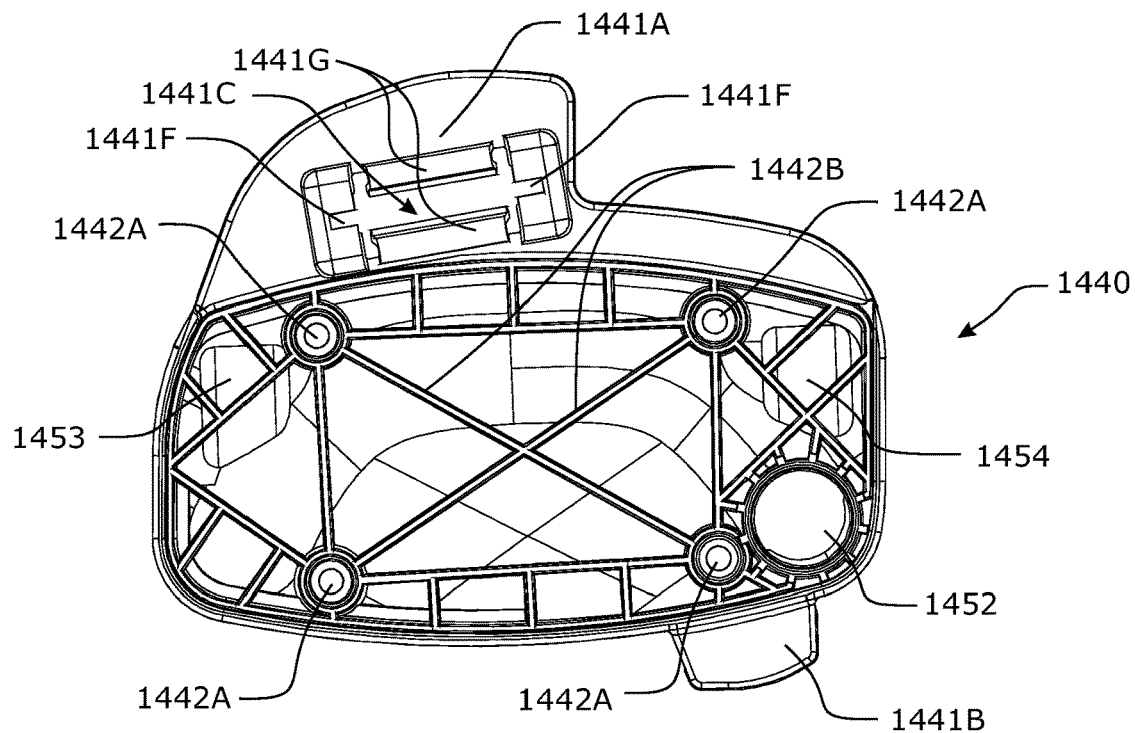
FIG. 93 is a top view of a cover layer of the motor and sensor sub-assembly of FIG. 78.
Figure 94:
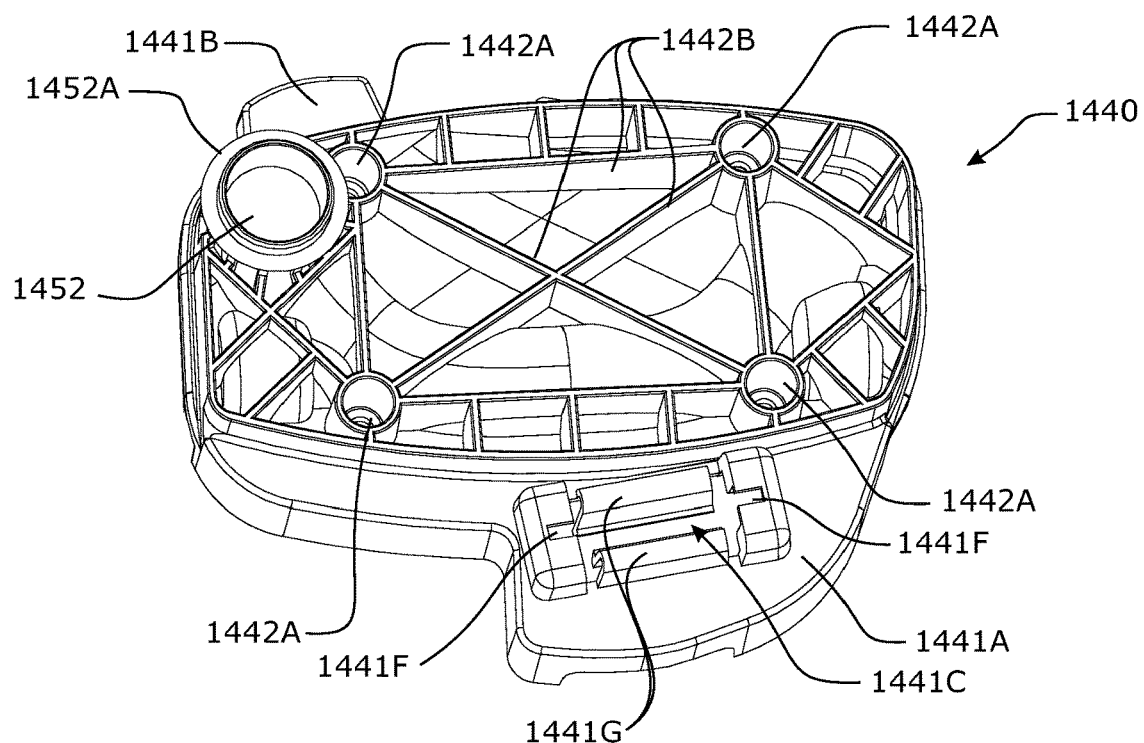
FIG. 94 is an overhead perspective view of the cover layer of FIG. 92.
Figure 95:
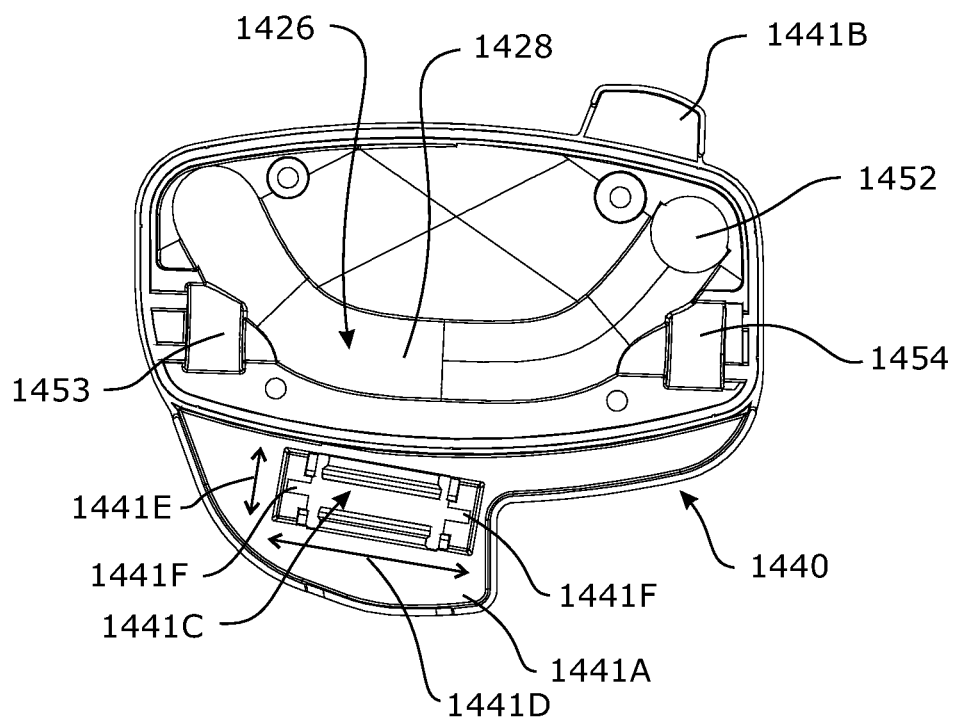
FIG. 95 is an underside view of the cover layer of FIG. 93.

As shown in FIGS. 93 and 94, the upper surface of the covering layer 1440 is provided with a plurality of stiffening ribs 1442B in any suitable configuration, to decrease warping. The covering layer 1440 is provided with a projecting portion 1441A that covers the projecting portion 1456A of the PCB, to protect the electronics of the PCB. The covering layer 1440 also has a projecting portion 1441B to cover and protect an electrical connection to the PCB.

The cover layer 1440 is provided with a shroud 1441C on the projecting portion 1441A, for receipt of an electrical component such as an edge card/connector of the PCB 1456. The edge card/connector may be directly connected to the PCB 1456 or may be connected by wires. The edge card/connector may be used to electrically couple the blower motor to the electronics of the main apparatus. The shroud is shown most clearly in FIGS. 93-95 and is configured to at least partly surround and protect the electrical component, the shroud may be configured to support the electrical component but to enable movement of the electrical component in the shroud in at least one dimension. In the form shown, an upper part of the shroud 1441C is open.

The shroud 1441C comprises an elongate body with a long dimension 1441D and a short dimension 1441E. Slots 1441F are provided adjacent each end of the body to receive the ends of the edge card/PCB. Sides of the body are provided by two resilient supports 1441G that support opposing faces of the edge card/connector.

In some configurations, the shroud 1441C is configured to enable movement of the edge card/connector in one dimension. For example, the shroud 1441C may be configured to enable movement of the edge card/connector transversely (in the short dimension 1441E of the shroud) due to the resilient supports 1441G, or may be configured to enable movement of the edge card/connector in the long dimension 1441D of the shroud, if the length of the edge card/connector is shorter than the distance between the ends of the slots 1441F. The PCB/edge card could alternatively be the same length as the long distance 1441D between the slots, and therefore less free to move.

In some configurations, the shroud 1441C is configured to enable movement of the electrical component in two dimensions. For example, the shroud may be configured to enable movement of the edge card/connector transversely (in the short dimension 1441E of the shroud) due to the resilient supports 1441G, and may be configured to enable movement of the edge card/connector in the long dimension 1441D of the shroud, if the length of the edge card/connector is shorter than the distance between the ends of the slots 1441F. The PCB/edge card could alternatively be the same length as the long distance 1441D between the slots, and therefore less free to move.

In this application, the shroud does not provide for vertical movement of the edge card/connector. In an alternative configuration, the shroud 1441C is configured to enable movement of the electrical component in three dimensions. For example, the shroud may be configured to enable movement of the edge card/connector transversely (in the short dimension 1441E of the shroud) due to the resilient supports 1441G, may be configured to enable movement of the edge card/connector in the long dimension 1441D of the shroud, if the length of the edge card/connector is shorter than the distance between the ends of the slots 1441F, and may be configured to enable vertical movement of the edge card/connector. The PCB/edge card could alternatively be the same length as the long distance 1441D between the slots, and therefore less free to move.

The shroud may be configured to allow limited movement of the edge card/connector in at least one dimension, the limited movement being sufficient to accommodate tolerance misalignment in components.

Figure 96:
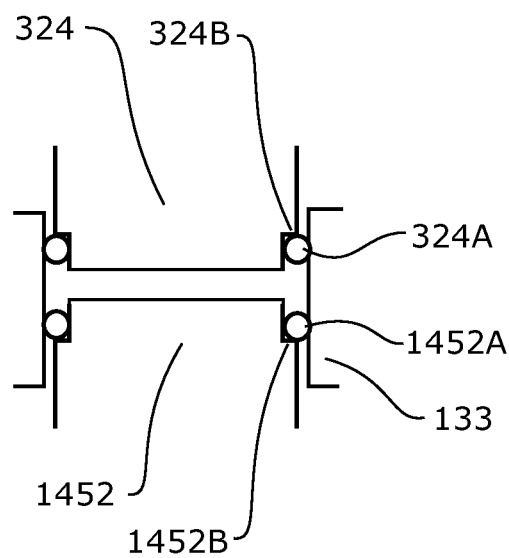
FIG. 96 is a schematic view of a sealing arrangement between a gas outlet port of the motor and/or sensor sub-assembly of FIG. 78 and a portion of the housing of the flow therapy apparatus of FIG. 1.

Once gases have passed through the gasflow path and sensing layer 1420, they exit the module 1400 via the gasflow outlet port 1452 which couples with the gasflow inlet elbow 324. A soft seal such as an O-ring seal 1452A may be provided to seal the gasflow outlet port 1452 of the module 1400. As shown in FIG. 96, the soft seal 1452A seals against an inner wall of a downward outer extension tube or conduit 133 of the housing, or another part of the housing. A soft seal such as an O-ring seal 324A may be provided to seal between the elbow 324 and the inner wall of the downward extension tube 133 of the housing, or another part of the housing. The soft seals function to keep the module 1400 sealed and reduce the likelihood of the pressurised gases flowing into the housing of the apparatus. The soft seals may be provided in annular grooves in the gasflow outlet port 1452 and the gasflow inlet elbow 324. Alternatively, one of both of those components may be provided with outwardly directed shoulders to provide a resting surface for the soft-seals. For example, the seal 1452A may rest on top of a shoulder 1452B on the gasflow outlet port 1452, and the soft seal 324A may rest under a shoulder 324B on the gasflow inlet elbow 324, as shown in FIG. 96.

In another configuration, a different type of seal may be provided to seal between the gasflow outlet port 1452, the gasflow inlet elbow 324, and/or the outer extension tube/housing 133. For example, rather than using O-rings, face seal(s), foam, or a bellows seal may be used, which will allow for some relative movement of the components in a direction that is lateral to a gasflow direction through the components, without breaking the seal. A seal that enables that movement will not over-constrain the module 1400 when it is in place in the lower chassis, but will enable sealing between the upper surface of the gasflow outlet port 1452 and the bottom surface of the inlet elbow 324, while enabling some lateral movement between the gasflow outlet port 1452 of the module 1400 and the inlet elbow 324. If a bellows seal is used to seal between the gasflow outlet port 1452 and the inlet elbow 324, that will enable both some lateral and some axial movement between the gasflow outlet port 1452 of the module 1400 and the inlet elbow 324.

The connection between the gasflow outlet port 1452 and gasflow inlet elbow 324 is formed outside the motor and/or sensor module 1400 such that any leakage that occurs from this connection will be directed outside the housing of the apparatus. Because the lower chassis extends up around the outside of the inlet elbow 324, and is formed as a single integral part including the walls and ceiling that define the recess 250 and gasflow tube 264 in the case of a leak the gas will follow the path of least resistance, which is to gather outside the leak region and exit to atmosphere via the outside of the inlet elbow 324. It is very unlikely that gases will flow into the housing and via a tortuous path to the electronics of the apparatus.

The PCB and other components of the module 1400 may be provided with reliefs or recesses as shown in various figures, to assist with mounting the components or to provide relief for other adjacent components.

Figure 97:
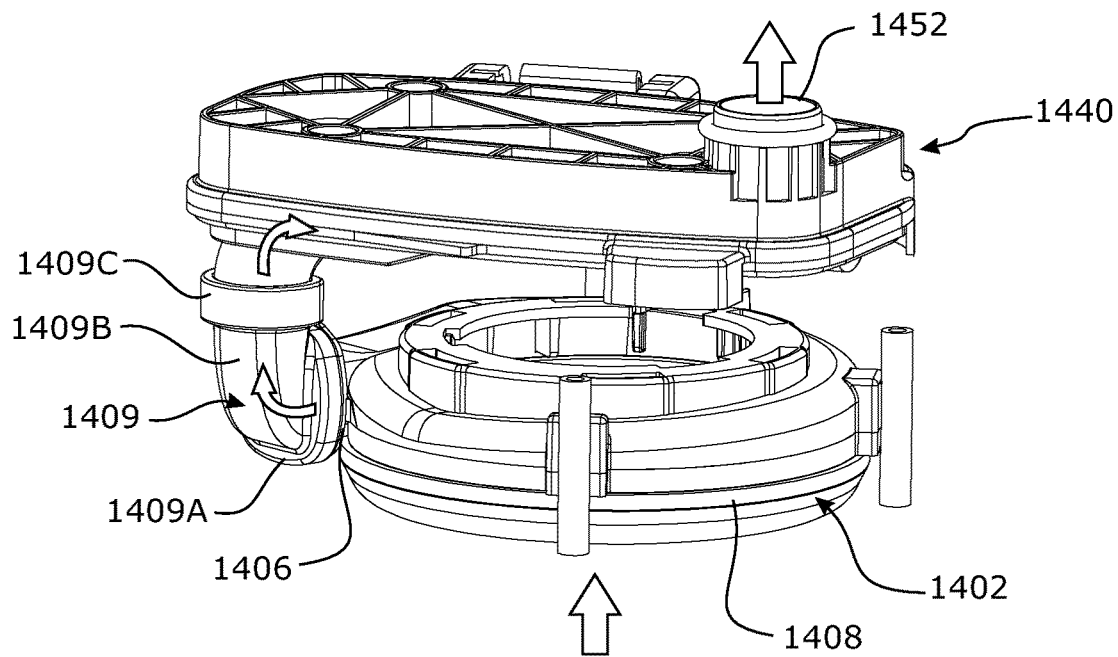
FIG. 97 shows the gasflow path through the motor and/or sensor sub-assembly of FIG. 78.
Figure 98:
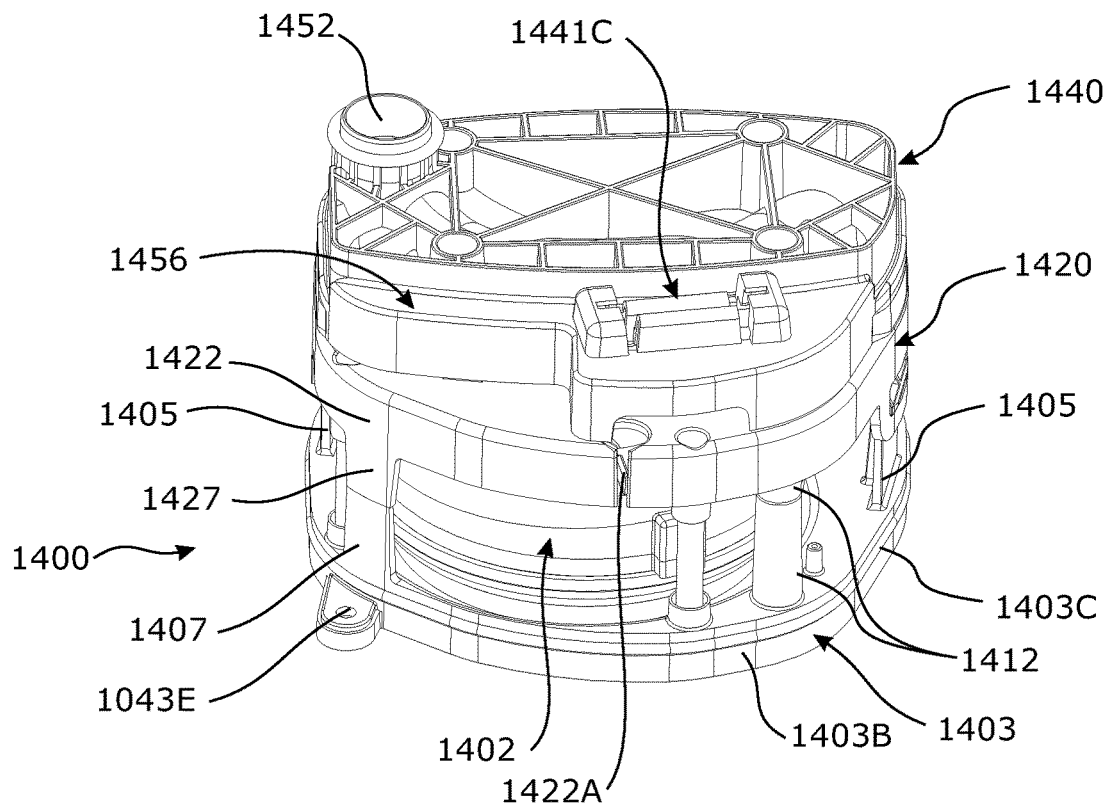
FIG. 98 is another overhead perspective view of the motor and/or sensor sub-assembly of FIG. 78.
Figure 99:
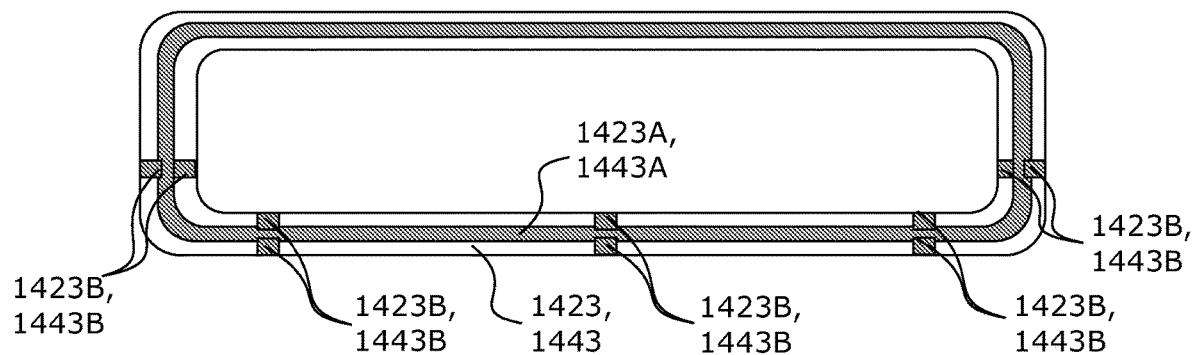
FIG. 99 is a schematic view of a sealing arrangement for the PCB of the motor and/or sensor sub-assembly of FIG. 78.

The overall flow of gases through the module 1400, once the gases have entered the module, is represented by the arrows in FIG. 97. If the pressure drop is assumed be of the form $P=kQ^2$ where Q is the flow in L min$^{-1}$, P is the pressure in Pa, and k is a pressure drop coefficient, then the pressure drop coefficient from the blower outlet port 1406 to the gasflow outlet port 1452 of the module will be between about 5 mPa (L min$^{-1}$)$^{-2}$ and about 50 mPa (L min$^{-1}$)$^{-2}$, in one configuration between about 10 mPa (L min$^{-1}$)$^{-2}$ and about 20 mPa (L min$^{-1}$)$^{-2}$, and in one configuration about 15 mPa (L min$^{-1}$)$^{-2}$. Equivalently, the pressure drop, at 100 L min$^{-1}$, will be between about 50 Pa and about 500 Pa, in one configuration between about 100 Pa and about 200 Pa, and in another configuration about 150 Pa. The inlet to the module/blower may add a small pressure drop, but that small drop may be negligible.

It will be appreciated that the module 1400 may have any of the alternative configurations described above for module 400.

8. Alternative Configurations

FIGS. 101 to 179 show features of an alternative configuration flow therapy apparatus 3010'. The flow therapy apparatus 3010' may have any of the features and/or functionality described herein in relation to other configurations, but those features are not repeated here for simplicity. Generally, like numerals are used to indicate like parts to the configurations of FIG. 2 to 54 or 55 to 64, with 3000 added to each reference numeral. Similarly, the features and/or functionality of this alternative configuration apparatus 3010' may be used in the other apparatuses described herein.

FIGS. 101 to 117 show details of the handle arrangement of the flow therapy apparatus 3010', with the handle arrangement having an alternative configuration handle/lever 4500. For the features that are shown in these figures, like numerals indicate like parts to FIGS. 55 to 64, with 3000 added to each reference numeral.

Similar to the configuration of FIGS. 55 to 64, the handle/lever 4500 is a single sided configuration. That is, only one side of the handle/lever 4500 is movably connected relative to the main housing of the flow therapy apparatus 3010', whereas there is no pivot connection of the other side of the handle/lever 4500 to the main housing. In the form shown, the left side of the handle/lever 4500 is pivotally connected relative to the main housing. However, in an alternative configuration, only the right side may be pivotally connected to the main housing. This configuration differs from that of FIGS. 55 to 64, in that the handle is pivotally and translationally connected to the main housing, so that the handle moves on a path having a varying radius relative to the main housing. The handle/lever 4500 and main housing are modified from those described above to provide that pivotal and translational connection.

The handle/lever 4500 has a left side arm 4502 that is pivotally and translationally attached relative to the left inner side wall 3112' of the upper chassis 3102'. The left side arm 4502 is configured to be substantially flush with the interconnecting wall 3114' when the handle 4500 is in the lowered or closed position of FIG. 101. Rather than a right side arm, the handle/lever further comprises a right side member 4504 that is shorter than the left side arm 4502, and that is not pivotally attached to the right inner side wall 3118' of the upper chassis 3102'. The right side member 4504 is configured to be substantially flush with the interconnecting wall 3120' when the handle 4500 is in the lowered or closed position of FIG. 101. The main housing is provided with recesses to enable the left side arm 4502 and right side member 4504 to be substantially flush with the interconnecting walls. In the form shown, the left side member 4502 is longer than the right side member 4504, so a spacer member 3120" is mounted to the upper chassis 3102' and sits substantially flush with the interconnecting wall 3120' and the right side member 4504 when the handle 4500 is in the lowered or closed position. The spacer member 3120" may carry a label or other indicia with information representing the device and/or its user.

Figure 111:
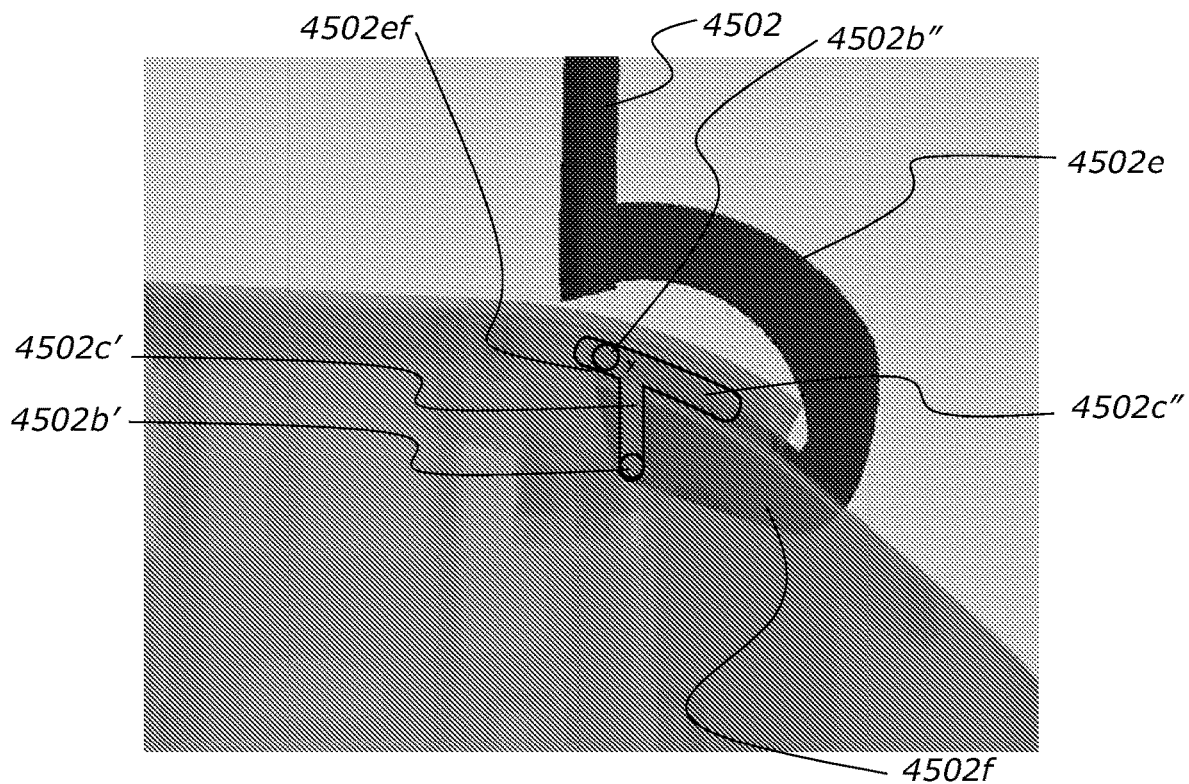
FIG. 111 is a view corresponding to FIG. 108, with the handle/lever in a fully raised position.

A terminal part of the handle has a cross-member handle portion 4506 that interconnects the forward ends of the left side arm 4502 and the right side member 4504 and forms an engagement region for grasping by a user's fingers. When the handle 4500 is in the raised position as shown in FIG. 111 for example, the cross-member 4506 can act as a carrying handle for the apparatus 3010'. With the configuration shown, when the handle is in the fully raised position, the cross-member 4506 is positioned generally above and generally in line with the centre of gravity of the apparatus (including the liquid chamber). In one configuration, the cross-member 4506 may be positioned substantially directly above and substantially directly in line with the centre of the gravity of the apparatus. The liquid chamber 300'—shown in FIG. 55 for example—can be inserted into or removed from the chamber bay 3108' when the handle/lever 4500 is raised. When the handle/lever 4500 is in the lowered position, it inhibits or prevents removal of the liquid chamber 300' from the chamber bay 3108'.

Rather than having the right side member 4504, the handle/lever 4500 may terminate at the right side of the cross-member 4506. However, having the rearwardly directed member 4504 is preferred, as it reduces the likelihood of the apparatus 3010' being dropped while it is being carried.

In the closed or fully lowered position of the handle/lever 4500 shown in FIG. 101, the cross-member 4506 is located in the recess 3242' at the front of the main housing and encloses a portion of the chamber bay. The main housing may be formed with upper and lower chassis parts 3102', 3202', and the recess 3242' will be formed in the appropriate chassis part. In the form shown, both chassis parts have a corresponding recess. The handle/lever 4500 and/or recess 3242' may have a positive engagement feature, such as one of those described above, to positively engage the handle/lever 4500 in the lowered or closed position. With the handle/lever 4500 in the lowered or closed position, a portion of the cross-member 4506 projects sufficiently above the floor of the chamber bay 3108' and above the flange 310' of the liquid chamber 300' that it prevents the liquid chamber 300' from being slid forward and removed from the liquid chamber bay 3108'. The liquid chamber bay 3108' comprises guide rails 3144, 3146 to prevent the liquid chamber 300' from being lifted and removed vertically from the liquid chamber bay 3108' when the handle/lever 4500 is in the lowered or closed position.

The guide rails 3144, 3146 may have a curved shape and/or upwardly angled leading portions 3144a (FIG. 102) to assist with easing the liquid chamber 300' into the liquid chamber bay 3108'. Alternatively, or additionally, the guide rails 3144, 3146 may be oriented to be non-parallel with a base of the chamber bay 3108', and thereby with the heater plate. In particular, the guide rails may be oriented so that a major part of the length of the guide rails is oriented so that the front of that major part is positioned further from the base of the liquid chamber 3108', than the rear of the major part. That is, the front of that major part is higher than the rear of that major part, to guide the base of the liquid chamber 300' into tighter engagement with the heater plate, as the liquid chamber is inserted into the chamber bay 3108'. This may be instead of, or in addition to, the upwardly angled leading portions 3144a of the guide rails. The guide rails help with usability of the apparatus as they guide the user while inserting the liquid chamber 300' into the liquid chamber bay 3108'.

FIGS. 102 to 114 show details of the pivot arrangement of the handle/lever 4500. A rearward portion of the left side arm 4502 is connected to a pivot arm 4502d. The pivot arm 4502d comprises a forward arcuate portion 4502e that extends downwardly and rearwardly from the left side arm 4502 when the handle is in the lowered or closed position. A rearward part of that forward arcuate portion 4502e is connected to a body portion 4502f that extends upwardly and forwardly therefrom when the handle is in the lowered or closed position. The body portion 4502f has a tapered configuration with a base of the body portion being relatively small and an upper terminal portion of the body portion being relatively large. The body portion 4502f is relatively large so as to provide additional mass to help stabilise the handle in the raised position and reduce side-to-side movement of the handle in that position.

A spacing is provided between the majority of the pivot arm 4502d and the body portion 4502f. An upper end of the body portion 4502f comprises two pivot protrusions, a rear, outwardly directed, first pivot protrusion 4502b' and a forward, inwardly directed, pivot protrusion 4502b".

The rear pivot protrusion 4502b' is received in a first pivot cavity 4502c'. The first pivot cavity 4502c' comprises a slot or a channel, and is a substantially vertically extending pivot cavity. The first pivot cavity is generally straight so that the rear pivot protrusion 4502b' follows a substantially linear path LP as the handle is moved between the lowered position and the raised position. The rear pivot protrusion 4502b' is configured to be retained in the first pivot cavity 4502c', but to substantially freely move along the length of that pivot cavity.

The front pivot protrusion 4502b" is received in a second pivot cavity 4502c". The second pivot cavity comprises a slot or a channel, and is a relatively horizontal pivot cavity extending substantially in a forward-rearward direction of the apparatus. The second pivot cavity 4502c" is generally arcuate so that the front pivot protrusion 4502b" follows a substantially arcuate path AP as the handle is moved between the lowered position and the raised position. In the form shown, the second pivot cavity 4502c" substantially follows the curvature of the left side interconnecting wall 3114', and has a convex curvature relative to a position above the pivot cavity. The front pivot protrusion 4502b" is configured to be retained in the second pivot cavity 4502c", but to substantially freely move along the length of that pivot cavity.

Figure 106:
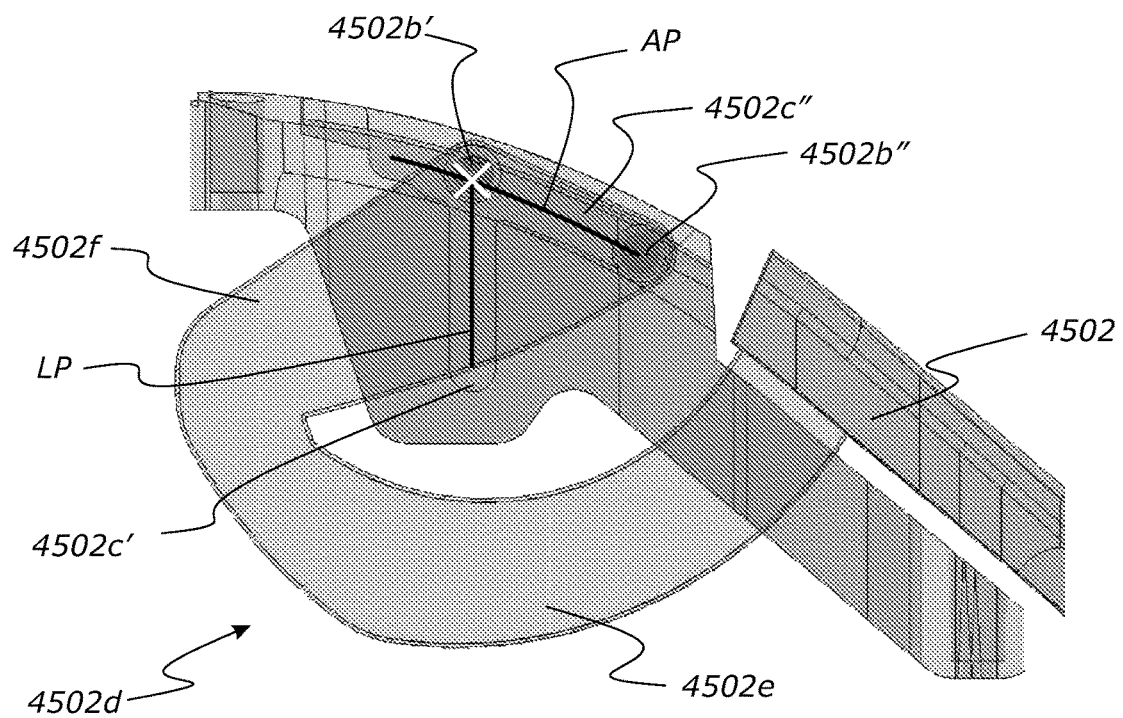
FIG. 106 is a left side view similar to FIG. 105, but showing movement paths of the pivots of the handle/lever.
Figure 107:
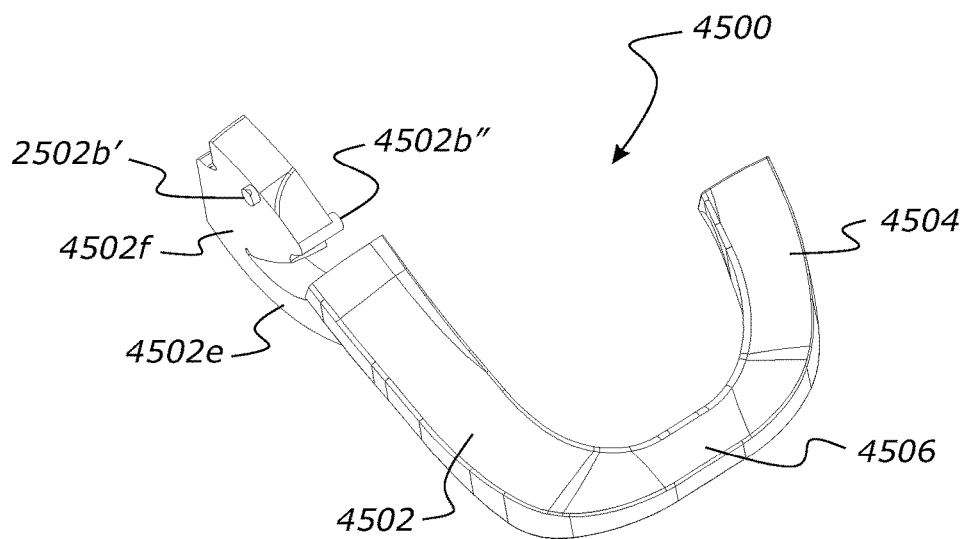
FIG. 107 is an overhead perspective view showing the handle/lever of the apparatus of FIG. 101.

In the form shown in FIG. 106, the upper end of the first pivot cavity 4502c' is located at a height higher than a corresponding portion of the second pivot cavity 4502c", where the two pivot cavities overlap in side view (represented by an X in FIG. 106). The position represented by an X is referred to herein as the origin.

The rear and front pivot protrusions 4502b', 4502b" may comprise pins that are received in corresponding apertures in the body portion 4502f of the handle. Alternatively, the pivot protrusions may be integrally formed with the body portion 4502f.

Figure 102:
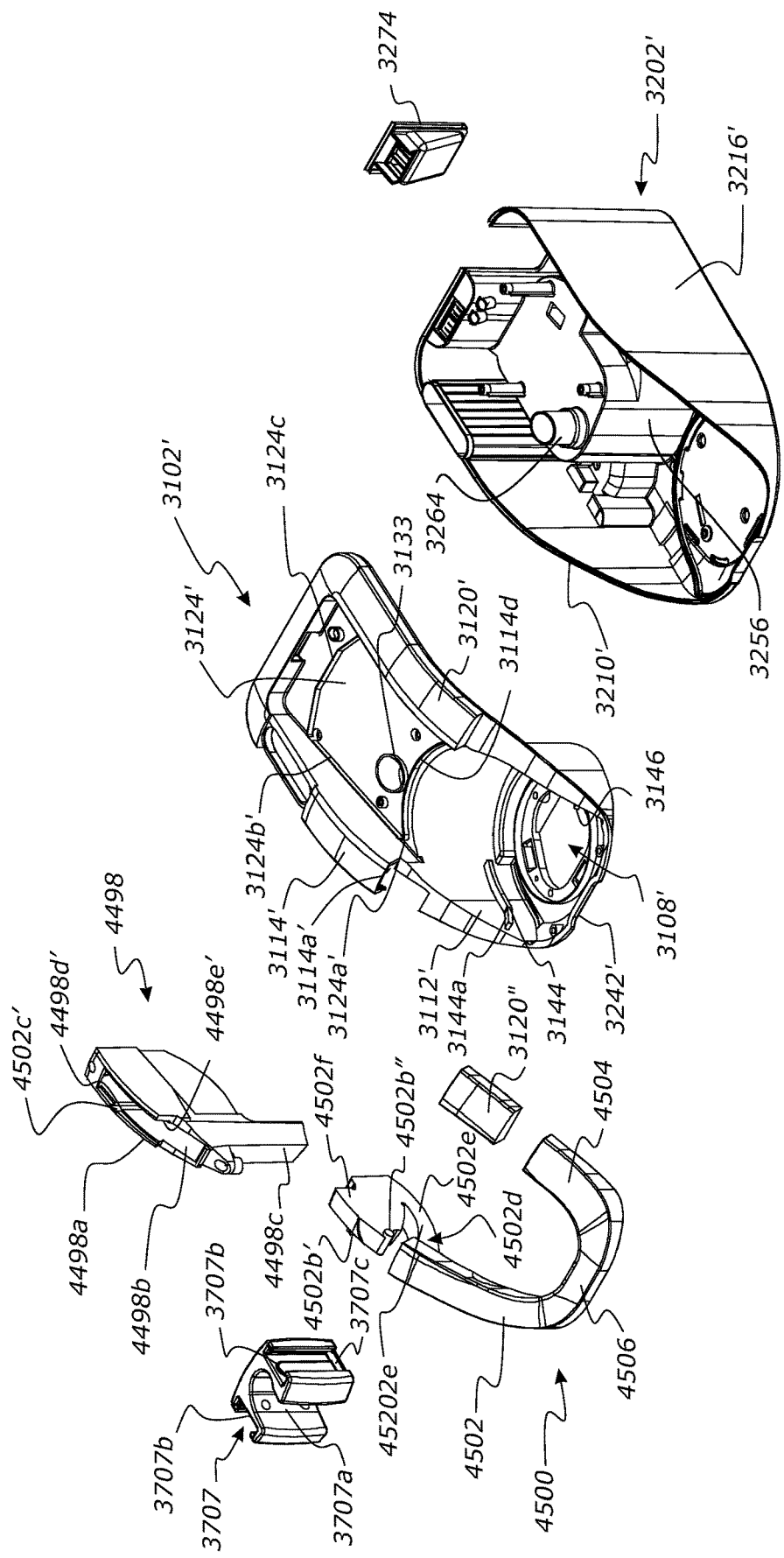
FIG. 102 is an exploded front overhead perspective view of some of the components of the apparatus of FIG. 101.
Figure 103:
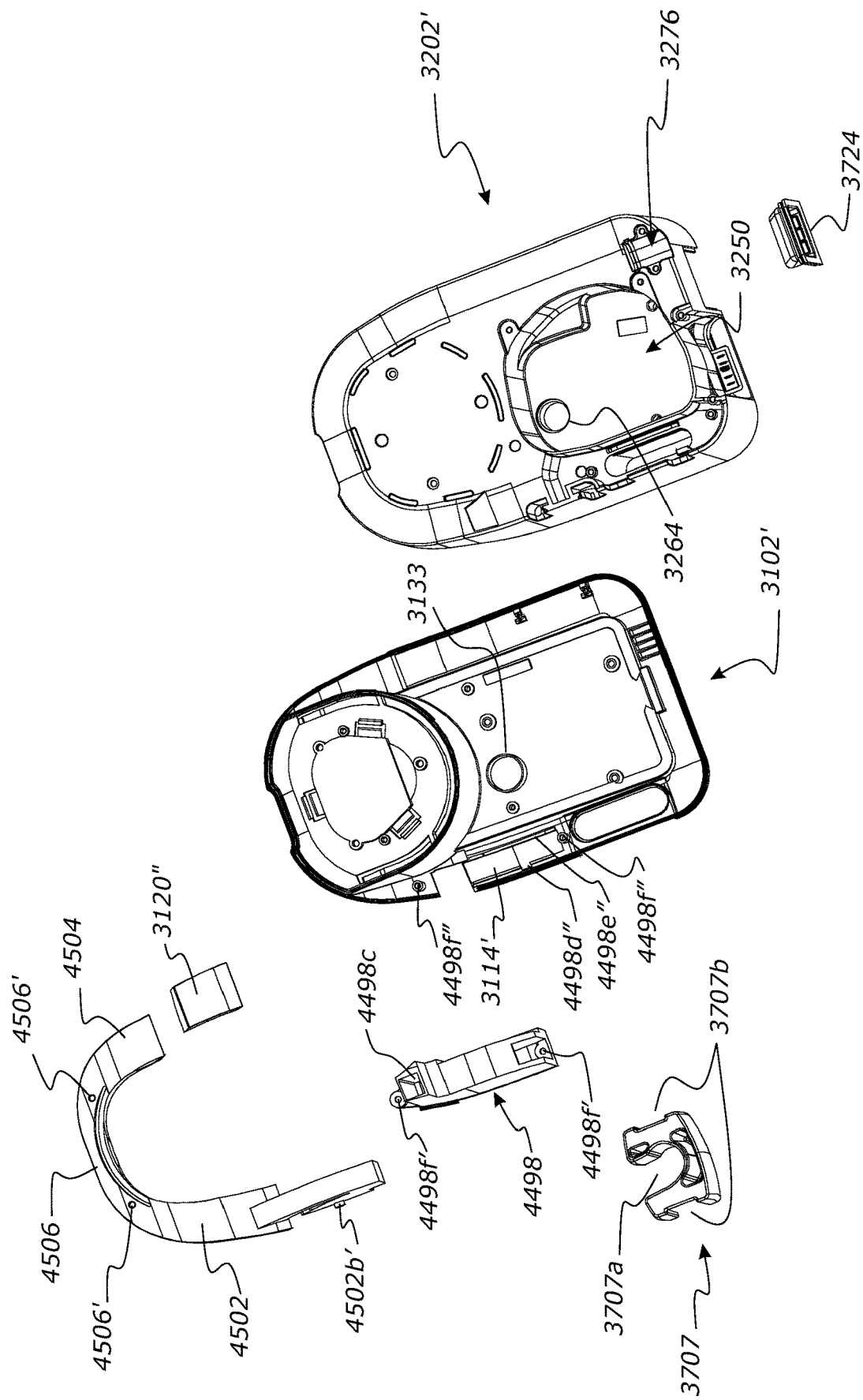
FIG. 103 is an exploded underside perspective view of some of the components of the apparatus of FIG. 101.
Figure 104:
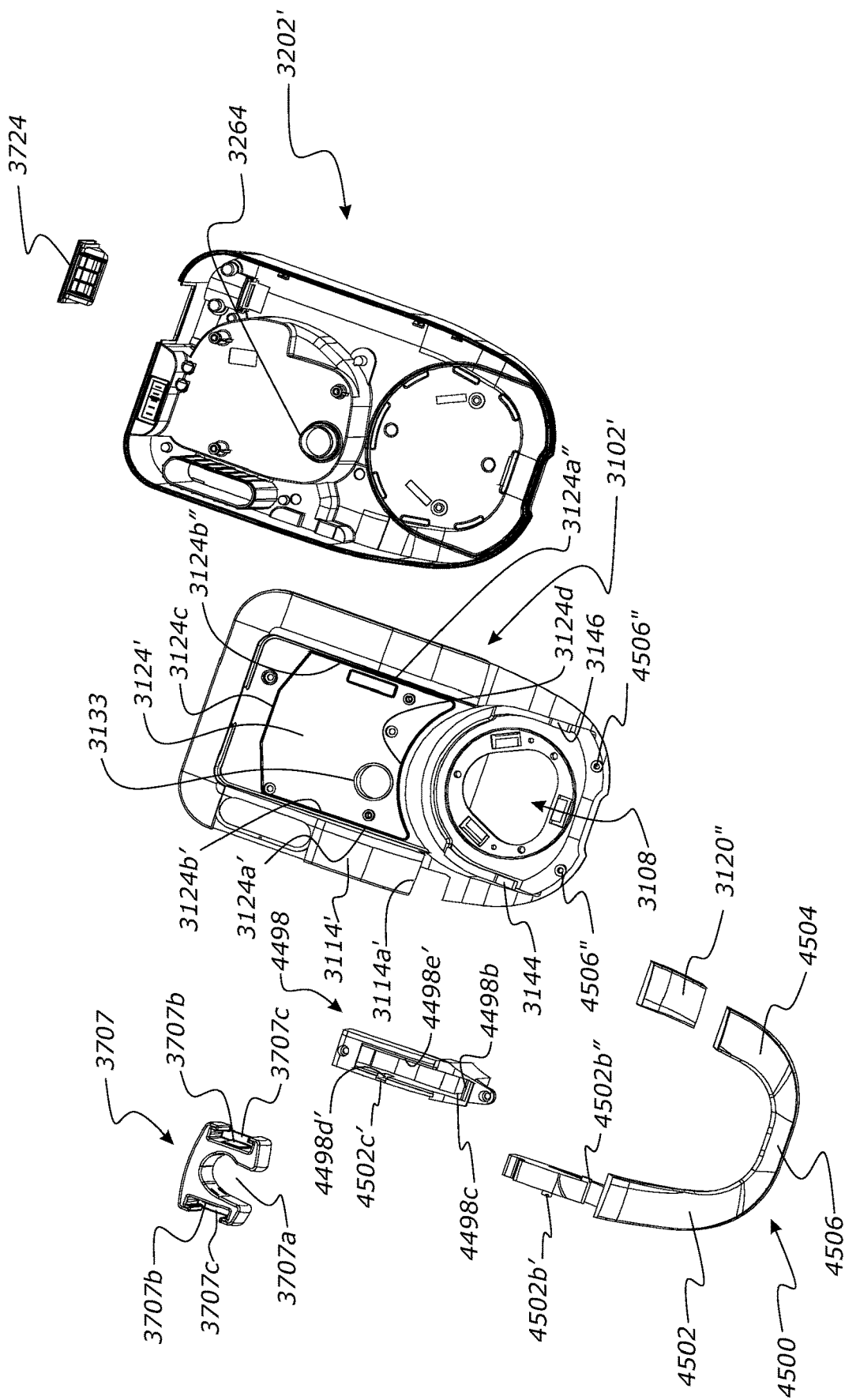
FIG. 104 is an exploded overhead perspective view of some of the components of the apparatus of FIG. 101.
Figure 105:
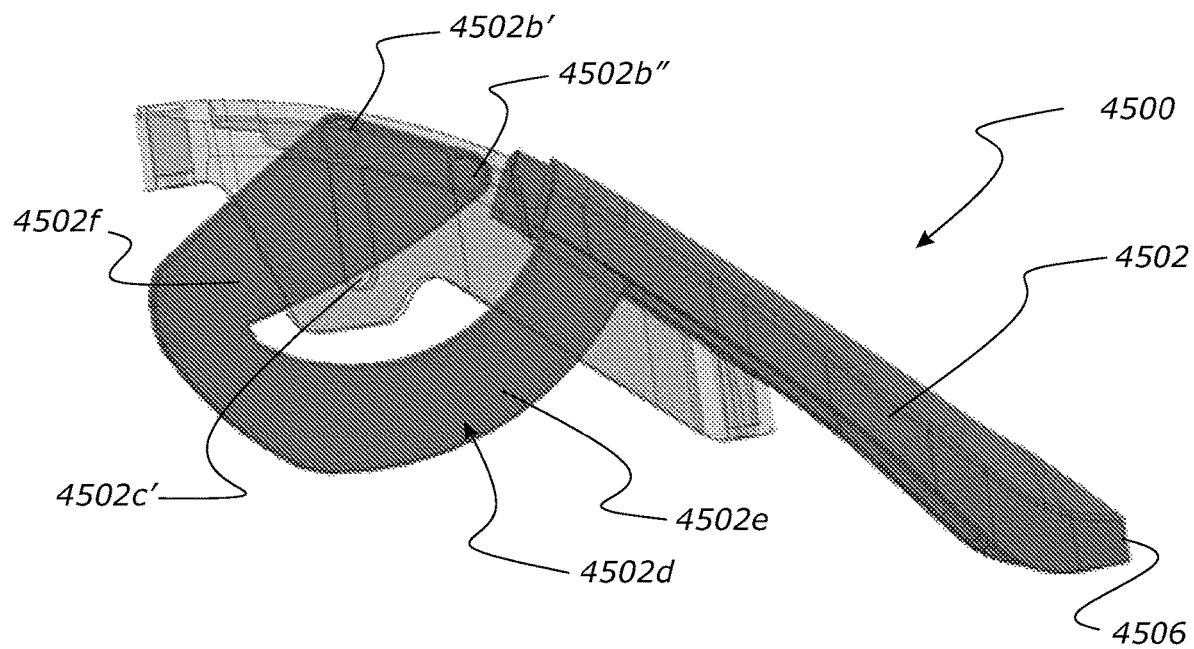
FIG. 105 is a left side view of some of the components of the handle/lever arrangement of the apparatus of FIG. 101.
Figure 115:
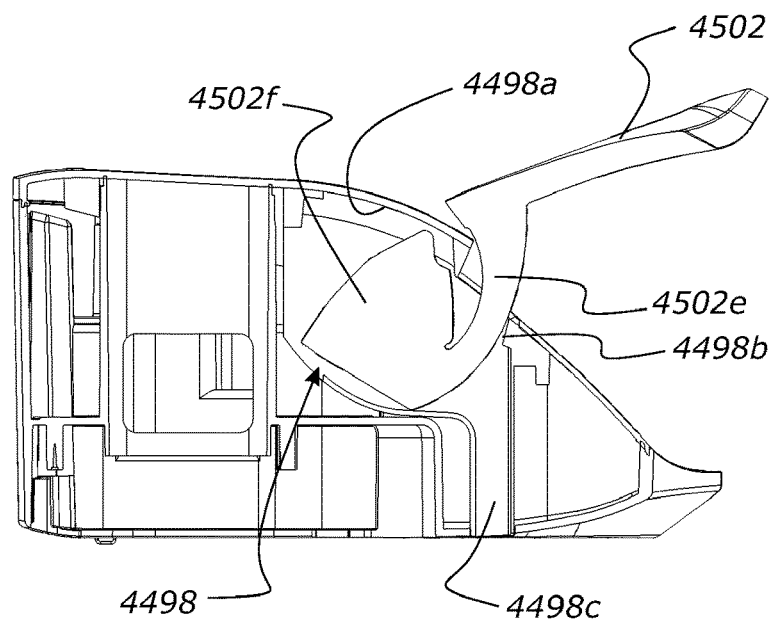
Figure 116:
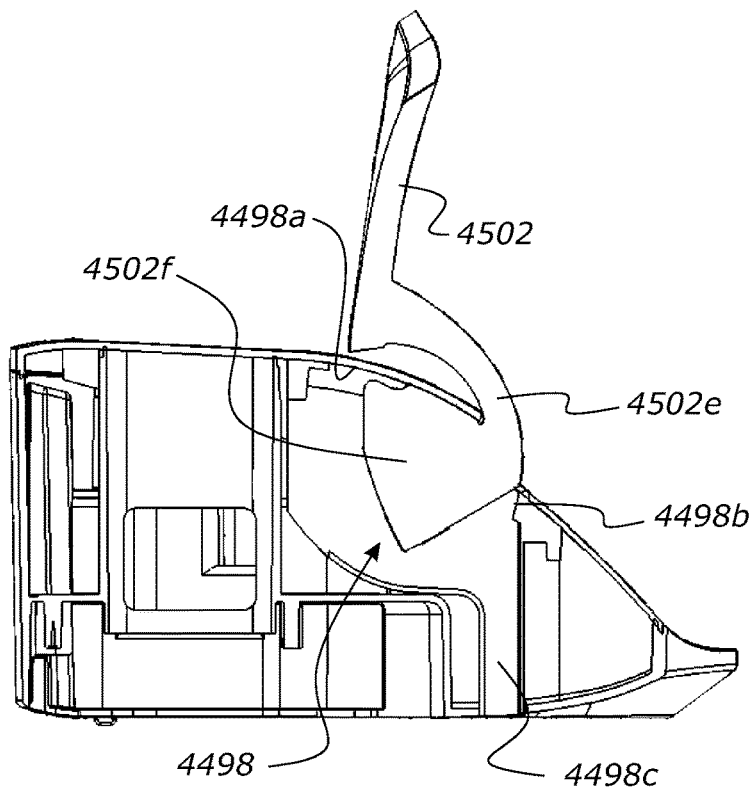
Figure 117:
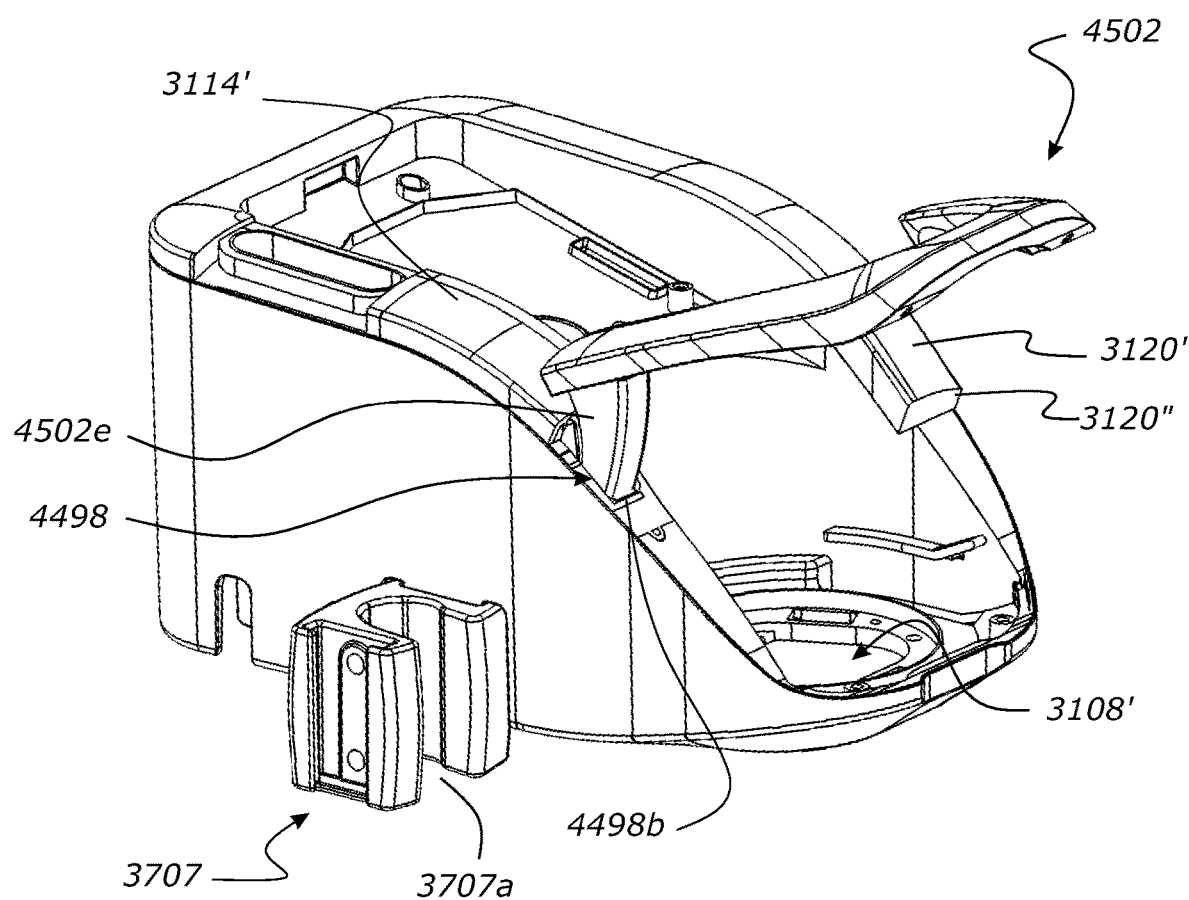

The apparatus comprises a handle retainer 4498, which is shown most clearly in FIGS. 102, 103, and 104. The handle retainer comprises a substantially hollow body that has an upper edge 4498a corresponding substantially in shape to the underside of the interconnecting wall 3114'. However, the handle retainer 4498 projects further forward than a front edge of the interconnecting wall 3114', so that an aperture 4498b in the handle retainer 4498 is positioned in front of the interconnecting wall 3114'. The shape of the aperture 4498 corresponds substantially to that of the forward arcuate portion 4502e of the pivot arm. The aperture 4498b is sized so as to be only slightly larger than that of the forward arcuate portion 4502e of the pivot arm, so that there is no space for foreign objects to be entered into the aperture when the handle is raised. The positioning of the handle 4500 relative to that aperture 4498*b* is shown in FIGS. 115, 116, and 117.

The handle retainer 4498 comprises a base wall that opens into a liquid drain channel 4498*c* that extends down the side of the housing. The liquid drain channel 4498*c* may be in communication with a cavity in the base of the main housing (as shown in FIGS. 115 and 116), so that any liquid that enters the handle mechanism can drain through the liquid drain channel 4498*c* and exit through the base of the main housing. The handle retainer provides a diffusion based mechanism to remove liquid/gas. Additionally, the holes in the chassis parts for receipt of the handle retainer/handle are small and self-contained and are spaced apart from sources of gas to reduce the likelihood of gas leakage into the case of the apparatus. Apertures do not need to be punched into the walls of the chassis parts for receipt of the handle pivots.

The handle retainer 4498 seals between the upper chassis 3102' and the lower chassis 3202' in the region of the handle retainer. In an alternative configuration, the handle retainer 4498 could seal against the upper chassis 3102' and/or the handle 4500 to prevent liquids/gases from entering the case or the handle retainer. Face seals, convoluted path seals, and/or tongue and groove arrangements could be provided for example.

As shown in FIG. 104, an inner portion of the left side wall of the handle retainer 4498 comprises a channel that forms a base 4498*d'* of the first pivot cavity 4502*c'*. As shown in FIG. 103, an underside 4498*d"* of an outer wall portion of the upper chassis part 3102' forms an upper edge of the first pivot cavity 4502*c'*.

As shown in FIG. 104, an inner portion of the right side wall of the handle retainer comprises a ledge 4498*e'* that forms a base of the second pivot cavity 4502*c"*. As shown in FIG. 103, an underside 4498*e"* of an inner wall portion of the upper chassis part 3102' forms an upper edge of the second pivot cavity 4502*c"*.

To mount the handle 4500 to the apparatus, the handle 4500 is positioned in the handle retainer 4498 so that the second pivot protrusion 4502*b"* is positioned on the ledge 4498*e'* and so that the first pivot protrusion 4502*b'* is positioned in the channel 4498*d'*. The handle and handle retainer can then be moved into engagement with the upper chassis part 3102' such that apertures 4498*f'* in the handle retainer are aligned with apertures 4498*f"* in the upper chassis part 3102', and fasteners such as screws or the like are used to fasten the components together. Therefore, the handle retainer 4498 becomes part of the main housing of the apparatus when the handle retainer is fixed to the upper chassis part.

Movement of the pivot protrusions 4502*b'*, 4502*b"* and the handle 4500 can be split into several phases. Those phases are shown in FIGS. 108 to 112, and are represented graphically in FIG. 113. Referring to FIG. 113, the path of movement of the terminal end 4506 of the handle relative to the apparatus housing is shown by curve TEP. That path has a varying radius of movement of the terminal end of the handle from a fully lowered to a fully raised position. In the form shown, the path is generally elliptical; that is, it follows the shape of a part of an ellipse. In the form shown, the path corresponds to slightly over one quarter of an ellipse. The radial lines represent a general transition point from one phase to another or indicate the beginning and ending of a phase relative to the position of the end of the handle.

Figure 108:
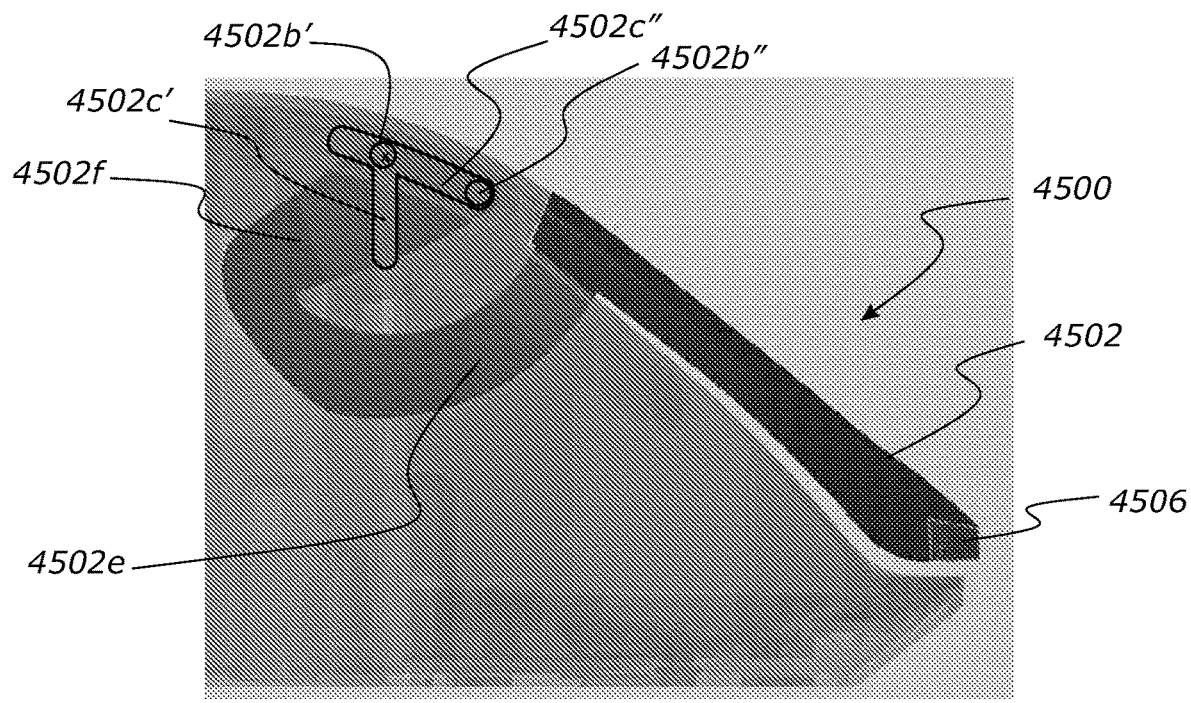
FIG. 108 is a left side view of part of the apparatus of FIG. 101, with the handle/lever in a substantially lowered or closed position.

FIG. 108 shows the handle as it has been moved away from a fully lowered position. During this first phase P1 of movement, the second pivot protrusion 4502*b"* remains at the terminal forward end of the second pivot cavity 4502*c"*. The first pivot protrusion 4502*b'* is caused to translate downward toward the origin X. This urges the end 4506 of the handle forward and upward away from the lowered/closed position. Because the first pivot protrusion 4502*b'* is initially positioned above the origin X, the initial movement of the terminal end of the handle 4500 is out and away from the housing so that the handle does not collide with the housing at either end.

Figure 109:
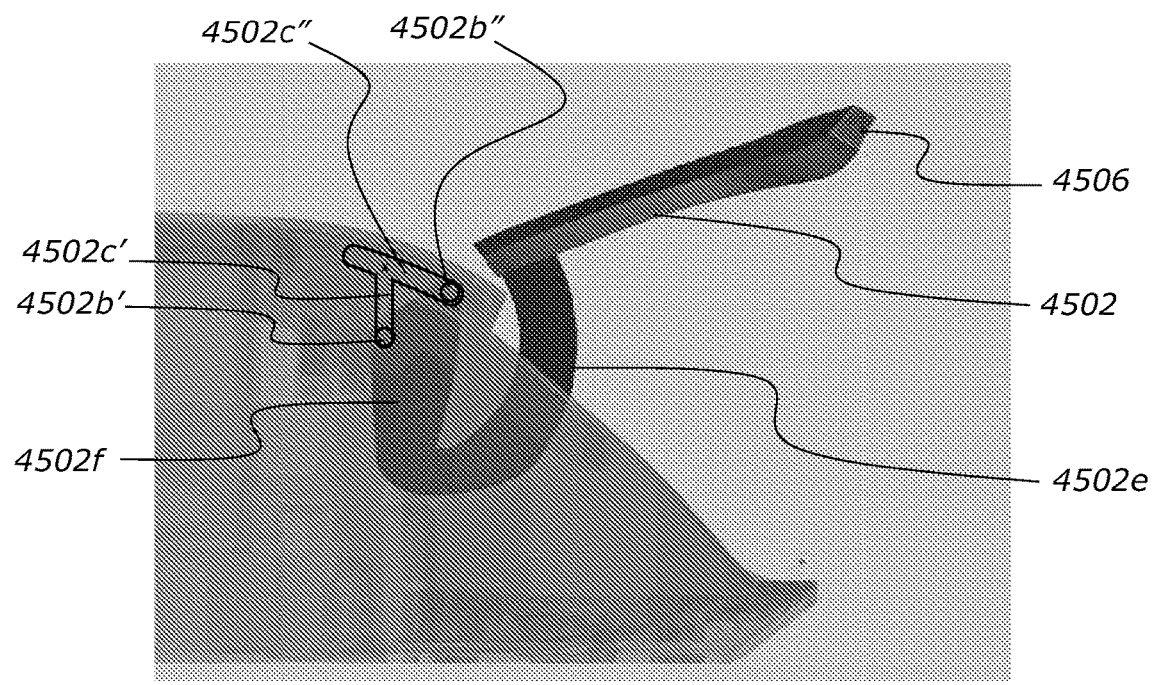
FIG. 109 is a view corresponding to FIG. 108, with the handle/lever in a partly raised position.

FIG. 109 shows the handle as it has been moved further away from the closed position. During this second phase P2 of movement, the first pivot protrusion 4502*b'* has translated further downward in the first pivot cavity 4502*c'* relative to the housing, toward the lower terminal end of the first pivot cavity 4502*c'*. The second pivot protrusion 4502*b"* has started to translate rearwardly along the second pivot cavity 4502*c"*. This results in a relatively steep upward and rearward movement of the terminal end 4506 of the handle relative to the housing.

Figure 110:
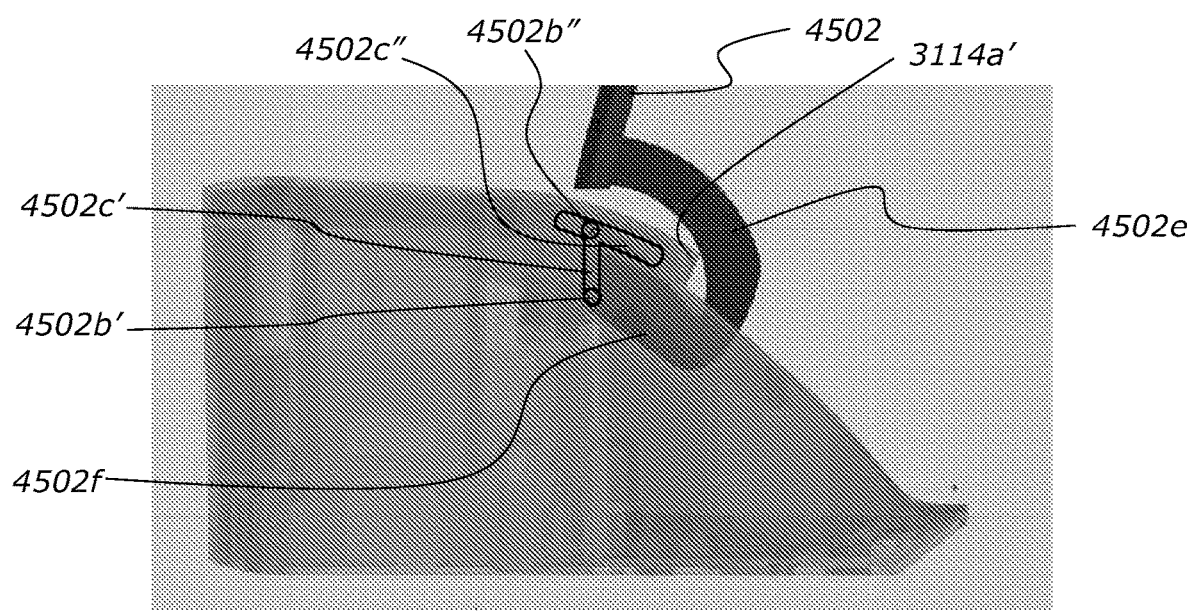
FIG. 110 is a view corresponding to FIG. 108, with the handle/lever in a further raised position.

FIG. 110 shows the handle as it has been moved further away from the closed position. During this third phase P3 of movement, the first pivot protrusion 4502*b'* has reached the lower terminal end of the first pivot cavity 4502*c'*. The second pivot protrusion 4502*b"* has translated further rearwardly in the second pivot cavity 4502*c"* to pass through the origin X. This has resulted in a relatively flat upward and rearward movement of the terminal end 4506 of the handle relative to the housing.

As shown in FIG. 111, during the third phase P3 of movement, after passing the origin X the second pivot protrusion 4502*b"* has reached an engagement feature 4502*ef* at or adjacent a rear end of the second pivot cavity 4502*c"*. The purpose of the engagement feature 4502*ef* is to retain the second pivot protrusion 4502*b"* in position at or adjacent the rear end of the second pivot cavity 4502*c"*.

Figure 112:
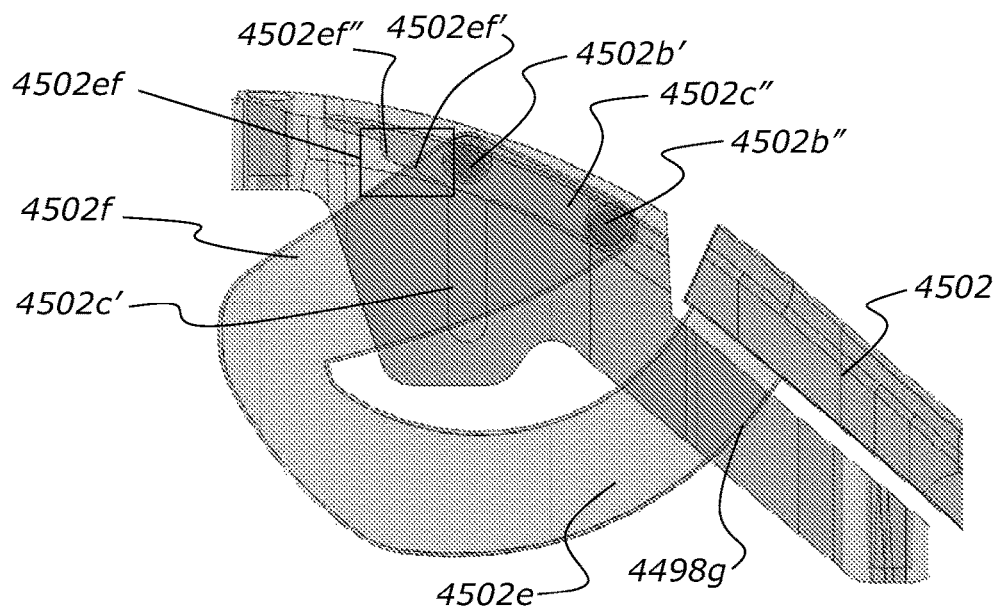
Figure 113:
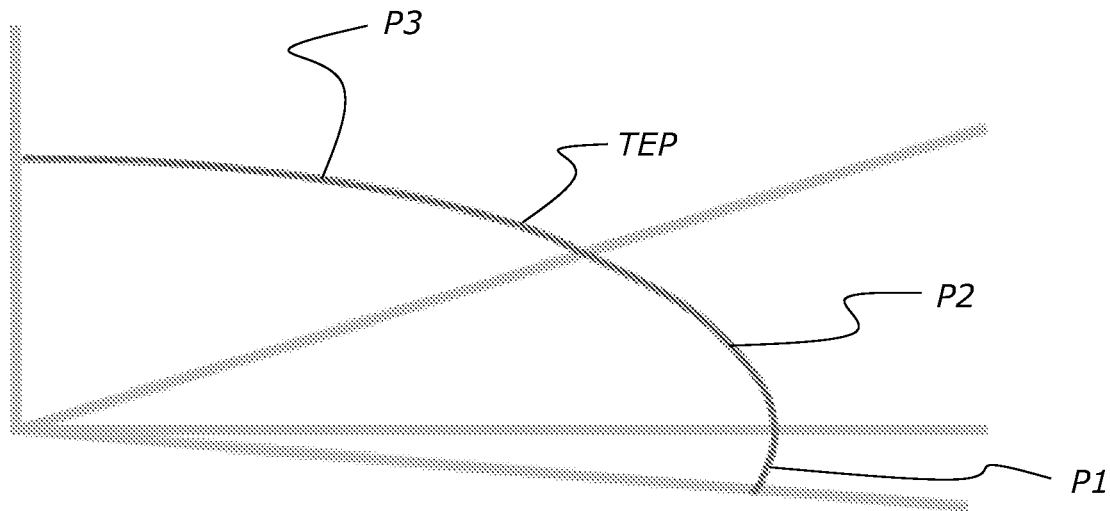

The engagement feature 4502*ef* is shown in more detail in FIG. 112. In the form shown, the engagement feature comprises a step 4502*ef'* in the base of the second pivot cavity 4502*c"* followed by a region 4502*ef"* of decreased depth. As the handle 4500 reaches its fully raised position, the second pivot protrusion 4502*b"* moves over the step 4502*ef'* and into engagement with the region 4502*ef"* of decreased depth. While the second pivot protrusion can move substantially freely over most of the length of the second pivot cavity 4502*c"*, the second pivot protrusion 4502*b"* is a tight fit in the region 4502*ef"* of decreased depth. This arrangement biases the handle into the fully raised position in which the user can carry the apparatus, without fear of the handle moving from the fully raised position. When the user has finished transporting the apparatus, a force can be applied to the handle in the forward direction of the apparatus, to remove the second pivot protrusion 4502*b"* from the region 4502*ef"* of decreased depth.

The above describes one exemplary engagement feature 4502*ef*, and other feature(s) could be used. For example, a spring-loaded retainer could be provided to engage the handle in the fully raised position. Additionally or alternatively, the handle may be provided with an actuator such as a user-actuable button, to enable the user to urge the first pivot protrusion away from the engagement feature and/or to release the spring-loaded retainer. As another example, an engagement feature such as any of those described could be used to retain the handle in the fully lowered position, either in addition to or instead of retaining the handle in the fully raised position.

The handle 4500 is designed so that when the handle is in the fully raised position and is being used to carry the apparatus 3010', the handle is located generally above the centre of gravity of the apparatus including a liquid chamber containing liquid. This reduces swinging of the apparatus as the apparatus is being carried, making the apparatus easier to carry and reducing the likelihood that liquid will enter the apparatus from the liquid chamber. The apparatus may be configured so that the raised handle is over or generally over the centre of mass with a full liquid chamber inserted. The apparatus is heaviest with a full liquid chamber, and that is when liquid is most likely to spill back into the apparatus. Alternatively, the apparatus may be configured so that the raised handle is over or generally over the centre of the mass of the apparatus with a partially full liquid chamber inserted, such as a half-full liquid chamber for example.

Depending on whether the fully raised handle is positioned directly over the centre of mass of the apparatus, or close to that position, the base of the apparatus may sit substantially flat while the apparatus is being carried, or alternatively may be slightly angled while the apparatus is being carried. The force provided by the user in holding the apparatus is not offset significantly from the centre of mass. This also means that the liquid in the liquid chamber 300' remains substantially horizontal, reducing the risk of liquid flow into the gasflow path. The generally elliptical movement path of the handle 4500 enables the handle to move from the fully lowered position to a fully raised position located generally above and generally in-line with the centre of mass. Additionally, the movement path is such that there is a substantially constant spacing between the handle and an upper portion of the housing, at least between a half-raised position (FIG. 117) and fully raised position (FIG. 116) of the handle, to minimise possible pinch points between the handle and the housing.

The handle is designed so that the pivot protrusions 4502b', 4502b" do not carry the apparatus load when the handle is in the fully lowered position or in the fully raised position. When the handle is in the fully lowered position, the load is carried by a front wall 4498g of the handle retainer, which engages against a lower edge of the forward arcuate portion 4502e of the handle. When the handle is in the fully raised position, the load is carried by an upper edge 3114a' of the interconnecting wall 3114', which engages against an opposite edge of the forward arcuate portion 4502e of the handle. Additionally or alternatively, when the handle is in the fully raised position, the load may be carried by an underside of the interconnecting wall 3114' which is in contact with the upper surface of the body portion 4502f of the handle that is shown as contacting the underside of the interconnecting wall 3114' in FIG. 116. The handle arrangement is configured to carry the full apparatus load including a liquid chamber 300' containing liquid. The handle may comprise honeycomb or rib feature(s) or fibre reinforcement to strengthen and stiffen the handle. The handle may be made from a suitable stiff and strong material. For example, the material may be a plastic material such as polycarbonate.

When the handle is in the fully raised position, the second pivot protrusion 4502b" is located at the upper rear end of the second pivot cavity 4502c". The handle is held in that position due to the angle of the second pivot cavity 4502c". When the handle is in the fully raised position the second pivot protrusion 4502b" will try to move upward and the top wall of the second pivot cavity 4502c" will interact with the chassis of the apparatus. To move the handle to the lowered position, the handle is moved horizontally and downwardly to release the handle from its fully raised position.

Figure 114:
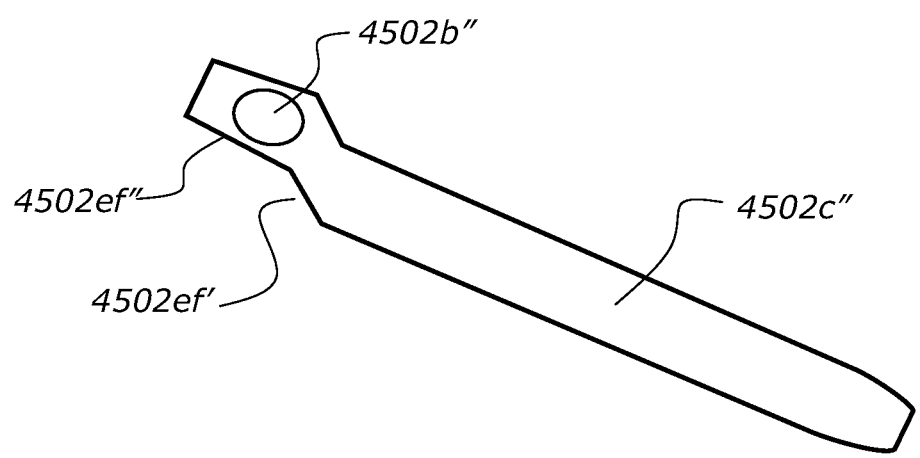

That required movement is accentuated by the shape and position of the region of decreased depth 4502ef". Alternatively, the region of decreased depth may not be provided. As another alternative, the required movement could be accentuated by having portion 4502ef" raised further relative to an adjacent portion of the second pivot cavity 4502c", such that the upper wall and lower wall of portion 4502ef" are positioned higher than the respective upper wall and lower wall of the adjacent portion of the second pivot cavity. Such a configuration is shown in FIG. 114. Rather than a step being provided, portion 4502ef" forms a ramp between the rearward portion 4502ef" and the adjacent portion of the second pivot cavity 4502c". Although the first pivot cavity 4502c' is not shown in FIG. 114, it will be understood that the first pivot cavity will be provided.

In the form shown, the first pivot protrusion 4502b' and first pivot cavity 4502c' are located toward an outer portion of the apparatus, and the second pivot protrusion 4502b" and the second pivot cavity 4502c" are located toward a centre of the apparatus. In an alternative configuration, the sides could be reversed. By having the pivot protrusions and pivot cavities on opposite sides of the handle, the handle mechanism is less likely to bind during movement of the handle 4500, particularly at the intersection between the first pivot cavity 4502c' and the second pivot cavity 4502c", adjacent the step 4502ef. Alternatively, the pivot protrusions 4502b', 4502b" and the pivot cavities 4502c', 4502c" could be provided on one side of the device (either towards the centre or the outer side), with a more rounded edge provided at the intersection between the first and second pivot cavities to reduce the likelihood of binding.

A surface of the handle 4500 bears against a surface of the handle retainer 4498 throughout movement of the handle from the fully lowered position to the fully raised position, to support the handle and prevent it from wobbling. For example, a left side face of the body portion 4502f of the handle may bear against the left side wall of the handle retainer throughout that movement. Alternatively, a right side face of portions 4502e, 4502f of the handle may bear against the right side wall of the handle retainer throughout that movement. The surfaces that bear against each other are load-bearing and remain load-bearing throughout the movement of the handle.

The body portion 4502e and arcuate portion 4502f are wide to deal with bending moments through the single sided handle. The length of the base of the handle (between and extending beyond the pivot protrusions 4502b', 4502b") may be made as long as possible to reduce wobbling of the handle.

As shown in FIG. 101, when the handle 4500 is in the fully lowered position, the handle is flush with the upper portion of the housing. That is, a substantially continuous surface is formed around the upper sides, front, and rear of the upper chassis 3102' of the housing, including the handle 4500.

When forward/downward force is applied to the handle 4500 to lower it from the fully raised position, the force is applied via the handle to the handle retainer 4498 rather than directly to the upper or lower chassis. The force is not carried by the pivot protrusions in the pivot cavities.

In some configurations, the main housing and/or handle 4500 may be provided with one or more magnets to retain the handle in the fully lowered and/or fully raised positions For example, the handle may comprises magnet(s) and the housing may comprise magnet(s) or conductive component(s) that are attracted by the magnets, or vice versa. FIG. 103 shows recesses 4506' in the underside of the handle 4500 on or adjacent the cross-member 4506, and FIG. 104 shows corresponding recesses 4506" in the upper chassis part 3102' of the housing. Each recess may comprise a suitable magnet or conductive component. The apparatus may comprise one or more sensors, such as Hall Effect sensor(s) to determine whether the handle is in a lowered or raised position.

The magnets can provide a tactile and/or audible indication of engagement of the handle in the fully raised and/or lowered position. When using magnets, there is less likelihood of a liquid supply tube to the chamber being compressed and stopping liquid flow, as there may be with a mechanical latch (with which a liquid supply tube could potentially be captured between the handle and main housing and water flow cut off and/or the tube damaged). Magnets also have the benefit of reduced wear compared to a mechanical engagement feature.

The single-sided handle/lever 4500 enables tube(s) that connect a liquid bag to the liquid chamber 300' to be fed through the space between the right side member 4504 of the handle/lever 4500 and the main housing, when the handle/lever 4500 is in the raised position.

Instead of the pivot cavities 4502c' 4502c" being provided between the upper chassis part of the housing and the handle retainer 4498, the pivot cavities could instead be provided in the upper chassis part 3102' or between the upper and lower chassis parts 3102', 3202' of the housing, and the handle retainer 4498 not used.

An upper portion of the main housing comprises a forwardly angled surface 3124'. The surface 3124' is configured for receipt of a display and user interface module 14. As shown in FIGS. 101, 102, and 104, the surface 3124' has elongate drainage channels 3124a', 3124a" extending in a forward/rearward direction of the apparatus. The channels are provided externally of respective upstanding walls 3124b', 3124b". The walls 3124b', 3124b" are connected at their rear ends by a rear transverse upstanding wall arrangement 3124c and at their front ends by a front transverse upstanding wall arrangement 3124d. The front transverse upstanding wall arrangement 3124d has an arcuate shape corresponding to the curvature of wall 3134'. The upstanding walls 3124b', 3124b", 3124c, 3124d form a continuous wall and are configured to cause any liquid that falls onto the top of the apparatus to drain toward the base of the chamber bay 3108' and out of the base of the apparatus through aperture(s), rather than into the regions of the apparatus with gasflow paths or electrical or electronic components. Adhesive may be provided between the display 14 and the surface 3124' to minimise liquid ingress.

This configuration is also suitable for use with a liquid chamber 300' that is filled from a flexible liquid bag, as discussed in relation to the configuration of FIGS. 55 to 64.

The handle/lever 4500 may comprise one or more features, such as apertures 502a, 504a as shown in FIG. 52 for example, for guiding liquid tube(s) from above into the liquid chamber. The tube(s) will be coupled to the liquid chamber. The liquid chamber may comprise a float valve which controls flow of liquid from the tube(s) into the liquid chamber.

The handle/lever 4500 will be provided with one or more features to assist with insertion, retention, and/or removal of the liquid chamber 300' in or from the chamber bay 3108'. Those features may be any one or more of the features described in relation to the configurations above.

By providing a handle/lever 4500 that assists with insertion and/or retention and/or removal of the liquid chamber in and/or from the chamber bay, a user can readily ensure that the liquid chamber 300' is fully inserted in the chamber bay 3108' while still being able to easily remove the liquid chamber from the chamber bay when desired. This is particularly advantageous for users with limited mobility. The handle/lever also avoids the use of a separate finger-guard. The chamber bay may have detent(s) to assist with insertion and/or retention of the liquid chamber in the chamber bay, such as those described above in relation to other configurations. Those details will enable a user to readily ensure that the liquid chamber is fully inserted in the chamber bay. Full or correct insertion and/or retention may be required to ensure that a satisfactory seal is obtained and maintained between the liquid chamber and other component(s) that form part of the gasflow path. Because the handle/lever encloses a portion of the chamber bay when the lever is in the closed or fully lowered position, when the handle/lever is in the fully raised position, a large space is created between the cross-member of the handle/lever and the housing of the apparatus including a large opening at the front of the chamber bay and around the liquid chamber, allowing easy insertion and removal of the liquid chamber to and from the chamber bay because a user's fingers can easily fit between housing walls and the liquid chamber.

The handle/lever 4500 may be configured so that the liquid chamber 300' can be inserted into the chamber bay 3108' when the handle/lever is in the raised position. When the handle/lever 4500 is in the lowered position, the handle/lever will act as a chamber guard to both prevent the removal of the liquid chamber 300' from the chamber bay 3108', and to prevent a user from touching the heater plate in the base of the liquid chamber.

Removal of the liquid chamber 300' from the chamber bay 3108' is a two-step procedure. First, the user lifts the handle 4500 to the fully raised position. Second, the user removes the liquid chamber 300' from the chamber bay 3108'. Each of these steps can be done with a single hand, and the force required to perform each of the steps is low. This makes the apparatus particularly suitable for home use by a user who is unwell.

Figure 118:
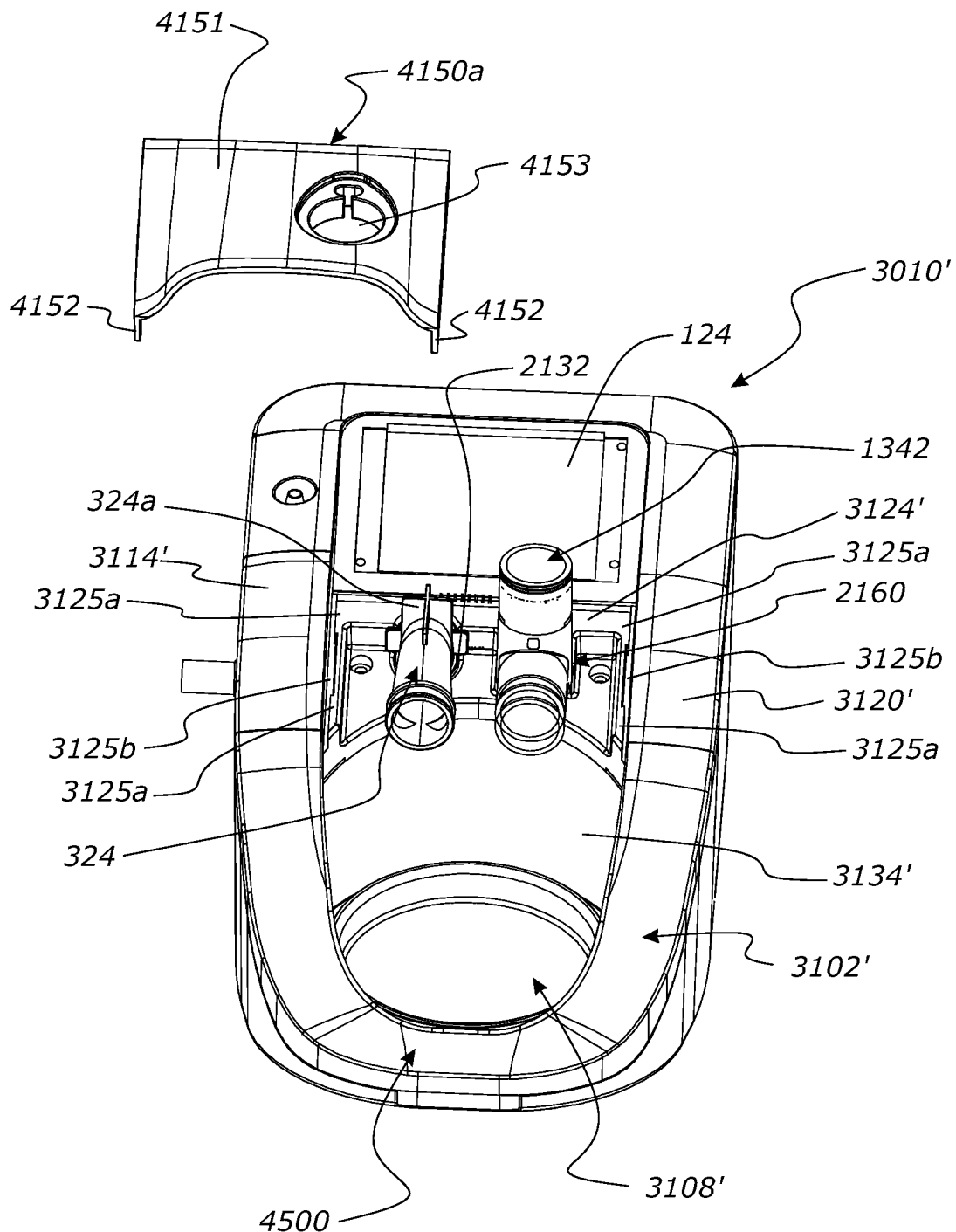
Figure 119:
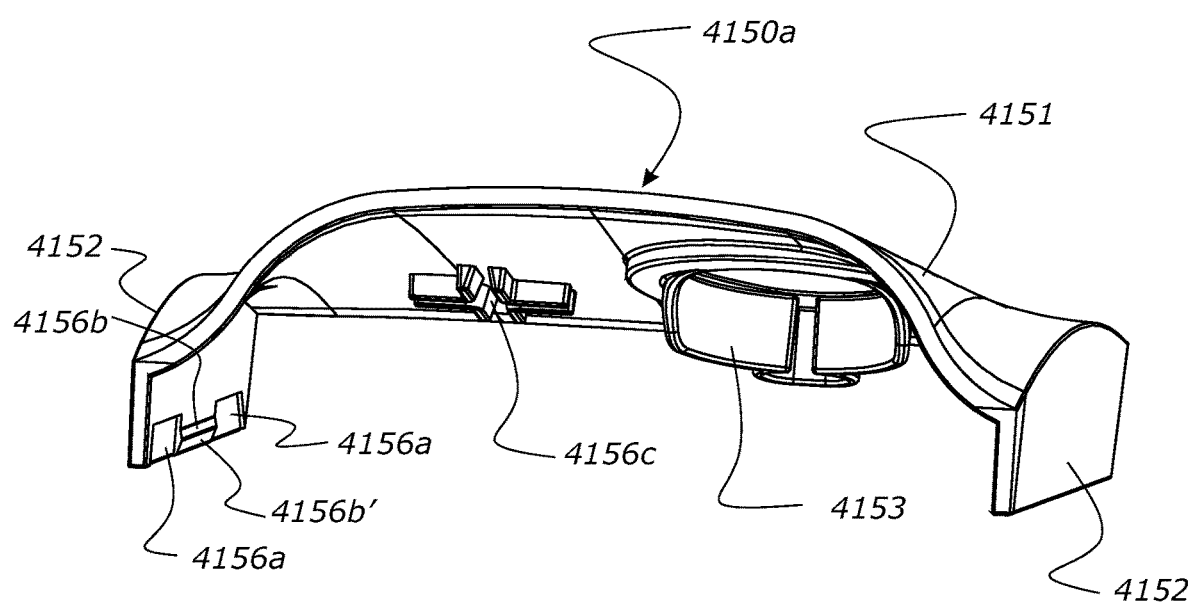

FIGS. 118 and 119 show an alternative configuration removable retention cover 4150a to retain a removable gasflow tube or elbow 1342 in place in the apparatus. The apparatus has the removable gasflow tube or elbow configuration of FIGS. 66 to 77, but could have any other suitable configuration such as that of FIGS. 25 to 33 for example.

Similar to the configuration of FIGS. 25 to 26b, with the removable retention cover 4150a removed from the upper chassis 3102', the elbow 1342 can be removed from the elbow retainer 2160. With the removable retention cover 4150a connected to the upper chassis 3102', the elbow 1342 cannot be removed from the elbow retainer 2160.

The retention cover 4150a has an upper ceiling portion 4151 with a curved configuration and two substantially vertical side wall portions 4152. The ceiling portion 4151 comprises a recess 4153 for receipt of the patient outlet port of the removable elbow 1342.

The retention cover 4150a is configured such that it can only be removed from the upper chassis 3102' of the housing by moving it in a direction that is transverse to the removal and insertion direction of the elbow 1342. To that end, each side wall portion comprises at least one guide recess 4156a at a base thereof. In the form shown, the two spaced apart guide recesses 4156a are provided at the base of each side wall portion 4152. The guide recesses are shown as being square or rectangular, but could be any suitable shape. The forwardly angled surface 3124' of the upper chassis 3102' comprises complementary guide projections 3125a that are sized and configured to engage with the guide recesses 4156a.

Each side wall portion of the removable retention cover 4150*a* also has a guide projection 4156*b* positioned between the guide recesses 4156*a*. The forwardly angled surface 3124' of the upper chassis 3102' comprises complementary guide recesses 3125*b* that are sized and configured to engage with the guide projections 4156*b*. The guide projections 4156*b* of the removable retention cover have enlarged portions or barbs 4156*b*' that engage under lips of the guide recesses 3125*b* when the removable retention cover is engaged with the housing of the device, to provide a positive engagement of those components.

The configuration of guide recesses and guide projections is such that the removable retention cover 4150*a* can only be engaged and disengaged from the upper chassis 3102' by substantially vertical movement of the removable retention cover relative to the main chassis, which is transverse to the insertion and removal direction of the removable elbow 1342 to and from the elbow retainer 2160. Alternatively, the retention cover could be configured to be engaged and disengaged from the upper chassis by movement in a sideways direction, which is transverse to the insertion and removal direction of the removable elbow to and from the elbow retainer.

An upper portion of the gasflow inlet elbow 324 is provided with an engagement feature 324*a* which engages with a complementary engagement feature 4156*c* on the underside of the removable retention cover 4150*a*, to assist with locating the removable retention cover in position on the upper chassis. In the form shown, the engagement feature 324*a* comprises a cross-shaped projection and the engagement feature 4156*c* comprises a complementary cross-shaped recess. However, any suitable shapes could be used.

If the retention cover 4150*a* is in position on the upper chassis 3102' and the elbow 1342 is in position in the elbow retainer 2160, attempting to pull elbow 1342 forward will be unsuccessful, because of engagement between the cover 4150 and the upper chassis 3102'. The electrical connection between the removable elbow 1342 and the elbow retainer 2160 and related electrical receiver, will also provide some structural coupling between the removable elbow and the housing.

A flexible tether (not shown) such as a silicon cord may couple the retention cover 4150*a* to the housing to minimise the likelihood of that being lost.

Figure 120:
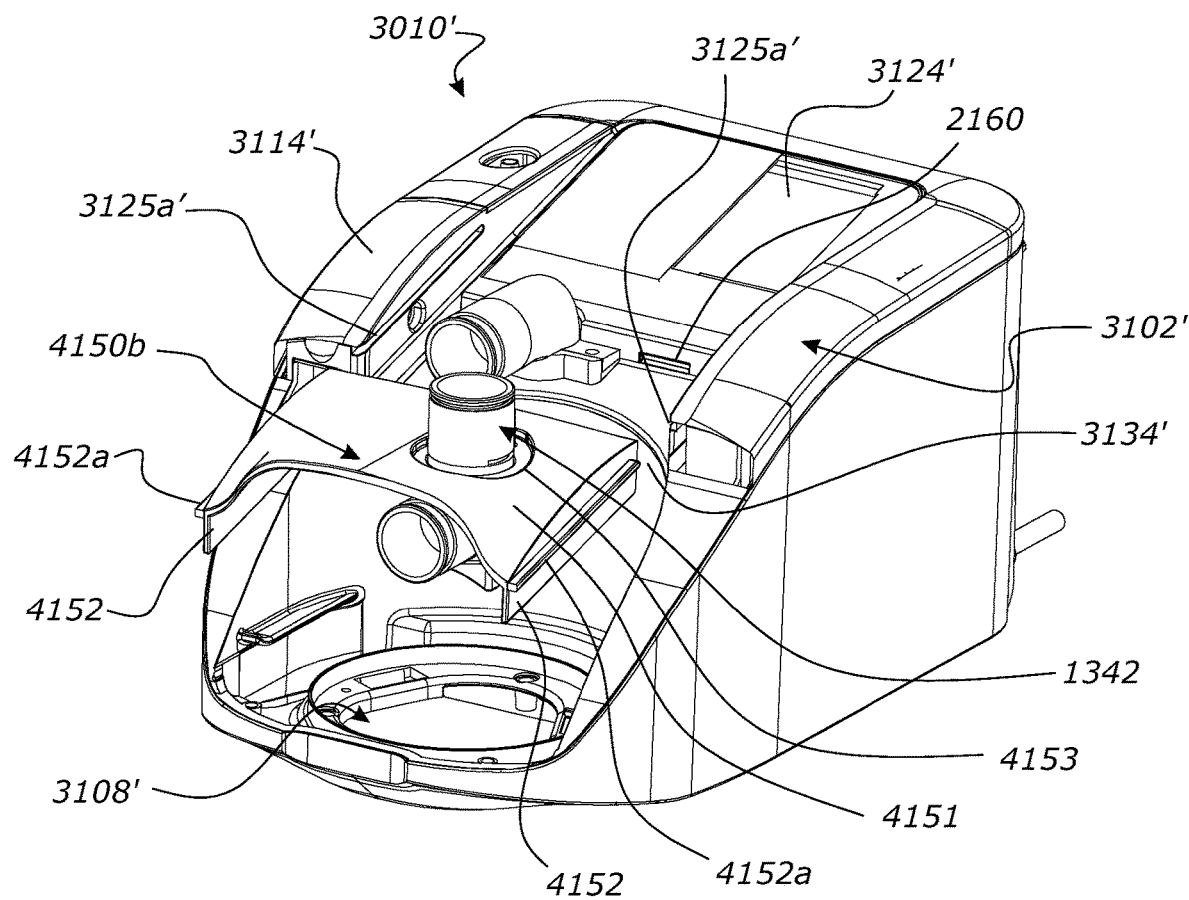
Figure 121:
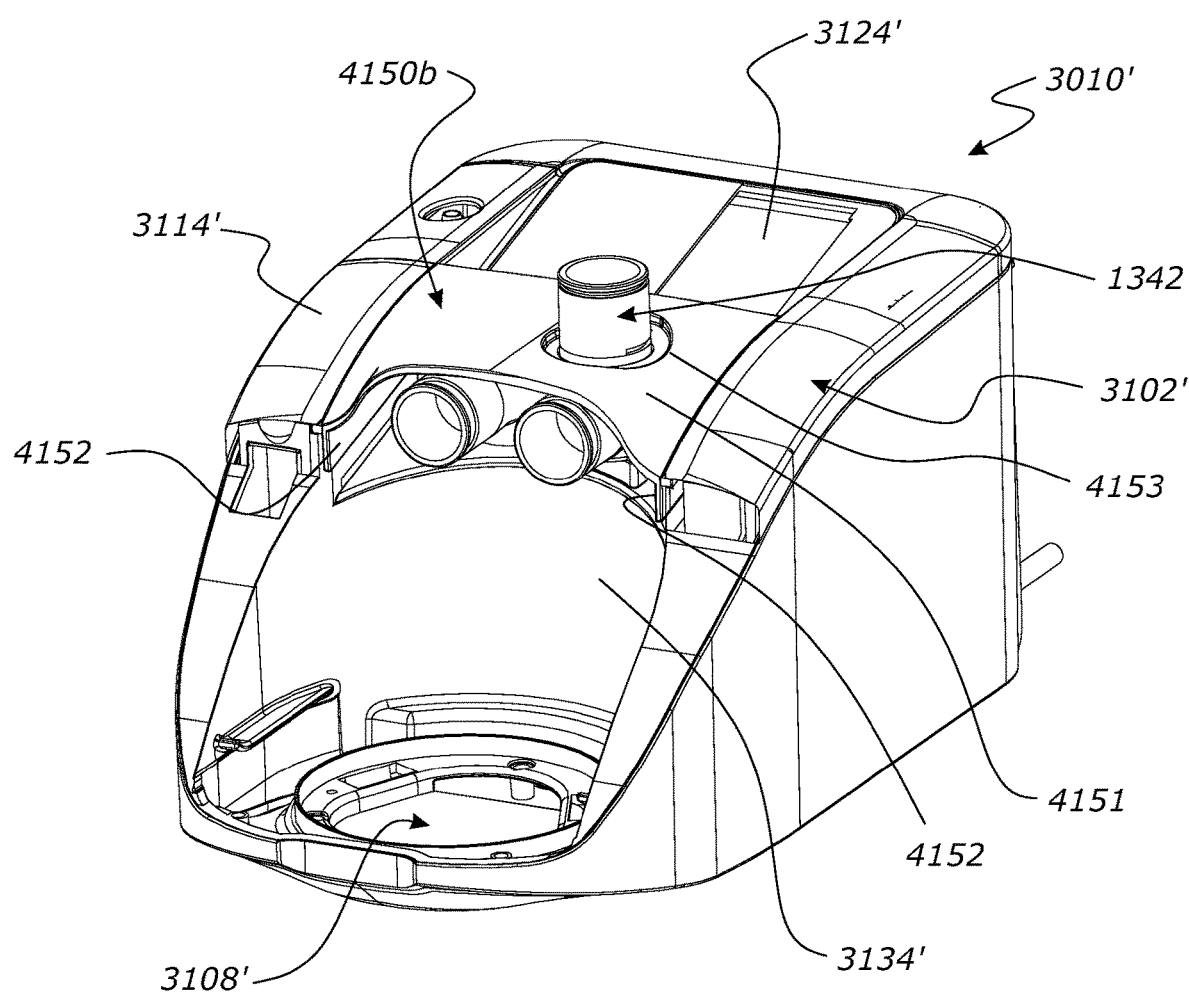

In an alternative configuration, the removable retention cover may be arranged to slide on and off the upper chassis part in substantially the same plane as the removable gasflow tube or elbow 1342 inserts into and removes from the elbow retainer 2160. FIGS. 120 and 121 show one alternative removable retention cover 4150*b* with that configuration. The apparatus may have the removable elbow 1342 configuration of FIGS. 66 to 77, but could have any other suitable configuration such as that of FIGS. 25 to 33 for example.

The retention cover 4150*b* has an upper ceiling portion 4151 with a curved configuration and two substantially vertical side wall portions 4152. The ceiling portion 4151 comprises a recess 4153 for receipt of the patient outlet port of the removable elbow 1342.

In this configuration, the upper chassis 3102' comprises elongate guide recesses 3125*a*' in the form of channels that extend substantially in a forward and rearward direction of the apparatus. The side wall portions 4152 of the retention cover 4150*b* have complementary projections 4152*a* in the form of elongate rails that project outwardly from the side wall portions 4152, and that are sized and configured to slidably engage with the guide recesses 3125*a*'. In another configuration, the recesses may be provided in the side wall portions 4152 and the rails may be provided in the upper chassis 3102'. Alternatively, the rails and recesses could be provided elsewhere. For example, rails could be provided on the base of the forwardly angled surface 3124', and recesses provided on the side wall portions 4152, or vice versa. The handle/lever 4500 (not shown in FIGS. 120 and 121) tapers slightly so that the retention cover 4150*b* can be inserted/removed when the handle/lever 4500 is in a raised position.

To insert the removable elbow 1342 and retention cover 4150*b* into the housing, the elbow can be inserted through the aperture 4153 in the retention cover 4150*b*. The elbow 1342 and cover 4150*b* can then be slid as one unit into the main housing, so that the elbow 1342 is received in the elbow retainer 2160 and the retention cover 4150*b* is engaged with the guide rails 3125*a*'. This provides an easier assembly of the elbow and retention cover into the housing with movement in a single degree of freedom.

As discussed above, the PCB connector 1366 of the elbow 1342 may be oriented at a suitable non-parallel and non-coaxial angle relative to the longitudinal axis 1340A of the manifold gases inlet port 1340 of the removable elbow. The guide rails 3125*a*' and the PCB connector 1366 will be on substantially the same plane so that the retention cover 4150*b* and elbow 1342 can be inserted together in one movement. The guide rails 3125*a*' and the PCB connector may act to guide the retention cover and elbow into successful engagement.

The difference between the insertion angle of the elbow 1342 and retention cover 4150*b* into the housing, and the insertion angle of the chamber 300' into the chamber bay 3108', means that removal of the chamber 300' from the chamber bay 3108' will not cause the elbow 1342 or retention cover 4150*b* to be removed from the upper chassis.

The retention cover 4150*b* and/or removable elbow 1342 may have one or more features to assist with retaining the removable elbow 1342 in engagement with the retention cover. The feature(s) may assist with aligning the retention cover 4150*b* and elbow 1342 with each other, so they are correctly aligned for insertion into the apparatus. The feature(s) may, for example, comprises protrusion(s) and/or recess(es), or an interference fit between the retention cover 4150*b* and the elbow 1342.

The handle/lever 4500 may comprise feature(s) to prevent removal of the removable retention cover 4150*a*, 4150*b* from the apparatus housing, when the handle is in the fully lowered position, but to enable the removal of the retention cover 4150*a*, 4150*b* from the apparatus housing when the handle is in the fully raised position. Alternatively, in some configurations the retention cover 4150*a*, 4150*b* can be inserted into or removed from the apparatus housing when the handle 4500 is in any position.

The removable retention covers 4150*a*, 4150*b* are shown as being substantially open at their front ends. A rear end of either retention covers 4150*a*, 4150*b* may be arranged to provide a rearwardly-directed outcropping region that is spaced above a front of the apparatus display. The open front end and/or outcropping region may be used as additional handles to assist with carrying the apparatus 3010'.

FIGS. 122 to 125 show an electrical connector 3276 that is provided in a bottom rear corner of the lower chassis 3202' of the main housing of the apparatus 3010'. The electrical connector 3276 is arranged to provide mains or battery power to the components of the apparatus 3010', such as the electronics boards 272 and other electrical components.

The electrical connector 3276 comprises a receiving socket 3276a that is arranged to receive the plug of a power cord 3277. The receiving socket 3276a and other components of the electrical connector are oriented in the main housing such that the power cord can be inserted into the electrical connector 3276 in a plane that is coplanar or parallel with the base of the apparatus; i.e. with a horizontal movement.

The electrical connector 3276 comprises a retainer 3276b to maintain the power cord 3277 in engagement with the socket 3276a. As shown in FIG. 125, the retainer 3276b comprises a generally U-shaped body to receive an underside of the plug of the power cord 3277. An entrance end 3276c of the retainer comprises at least one upstand 3276c' that forms a protrusion to engage with a recess in the plug of the power cord. In the form shown, the retainer comprises a pair of upstands that are configured and sized to receive a necked portion 3277a of the plug of the power cord. Once the plug of the power cord 3277 is inserted into the socket 3276a and the retainer 3276 is engaged with the plug, the protrusions 3276c' will prevent the removal of the plug of the power cord from the socket, by engaging against a widened surface adjacent the necked region 3277a of the power cord if the power cord is pulled.

A fastener aperture 3276d is provided in the base of the retainer 3276a, to enable the retainer to be attached to the lower chassis part 3202' with a suitable fastener such as a screw.

A mounting foot 3276e extends from the bottom of the retainer to minimise the likelihood of slippage on a supporting surface.

The retainer 3276b comprises at least one projecting wing 3276f, and in the form shown has two projecting wings. The projecting wings extend transversely to the insertion direction of the plug of the power cord 3277 into the electrical connector 3276. The wings 3276f interact with complementary recesses in the lower chassis to prevent horizontal movement of the retainer 3276b.

To insert the power cord into the apparatus, the plug of the power cord 3277 is inserted into the electrical connector 3276 in horizontal insertion direction (direction 1 of FIG. 125). Once the plug of the power cord is inserted into the socket 3276a, the retainer 3276b is inserted vertically into the base of the lower chassis part 3202' in insertion direction 2. The wings 3276f of the retainer engage in the recesses in the lower chassis, and the projections of the retainer engage with the necked portion 3277a of the power cord, so that the power cord cannot be removed from the electrical connector. A fastener is then used to fasten the retainer to the lower chassis. The process needs to be reversed to remove the power cord from the electrical connector.

The horizontal entry electrical connector makes it easier to retain the power cord in the apparatus and to hide most of the power plug when inserted. The horizontal entry also positions the wires nearer to the mains inlet, and enables the electrical connector to only take up a small space in the apparatus.

Rather than being on a horizontal orientation, the described electrical connector 3276 features could be used on an angled orientation that is non-horizontal and non-vertical relative to the main housing of the apparatus. An angled orientation may reduce the likelihood of liquid ingress, and may result in the power cord projecting less from the apparatus which has benefits if the apparatus is to be pole-mounted. The power cord may have an elbow plug that is retained in position with retention features similar to those described above.

In addition to the power cord retainer 3276b described above, the apparatus 3010' may have the power harness guide 4276 shown in FIGS. 126 to 130. The power harness guide 4276 will suitably be made from a plastic material, and is used to position the wires or power harness that connect to the inside portion of the receiving socket 3276a.

The power harness guide 4276 comprises an inverted generally C-shaped base portion 4276a that defines a recess 4276a' that receives the body of the receiving socket 3276a. The base portion 4276a has a pair of inwardly directed flanges 4276a" that are positioned beneath the receiving socket 3276a, when the receiving socket 3276a is positioned in the base portion 4276a. A support arm 4276b extends from the base portion 4276a and has a generally L-shaped cross-section. The support arm 4276b has a generally linear portion 4276p' adjacent to the base portion, and a generally arcuate portion 4276p" distal the base portion. A plurality of holders 4276b' are provided along the support arm 4276b to receive and hold wires or cables. Although two holders are shown, any suitable number of holders could be provided.

A passage 4276b" is located in a portion of the support arm 4276b that is distal from the base portion 4276a, and enables wires or cables to be routed out of the support arm 4276b and connected to a portion of the apparatus to be powered, such as PCB 272. A portion 4276tp of the arm adjacent the passage is tapered, to provide a smooth surface for routing the wires or cables out of the support arm.

A locator/coupler 4276d is located at an end of the support arm 4276b opposite to the base portion, to locate and couple the power harness guide 4276 to the PCB 272. The generally linear portion 4276p' is oriented to be substantially parallel to a plane of the PCB 272 in use.

The power harness guide 4276 couples wires or cables from the receiving socket 3276a to the PCB 272, to control the position of the wires or cables and allow ease of assembly of the apparatus, as the PCB 272 assembly can be inserted into the main housing in one movement.

FIGS. 129 and 130 show details of the lower chassis 3202' in the region where the electrical connector 3276 is located. The lower chassis 3202' defines an aperture 3800 through which the power cord plug 3277 can be inserted into the receiving socket 3276a. An exterior base part is provided with a curved cavity 3802 to receive the power cord plug 3277. Transverse recesses 3804 are provided on either side of the cavity 3802 to receive the projecting wings 3276f of the retainer 3276b. The recesses have threaded apertures to receive fasteners.

As shown in FIG. 130, the lower chassis is provided with an upstand 3806 that has channels 3808 at either end thereof. The upstand has a height slightly greater the height of the receiving socket 3276a. The channels are complementary to a front flange 3276a' on the receiving socket 3276a, so the receiving socket 3276a can be inserted into the upstand 3806 from above. A base rib 3810 is provided to engage behind the front flange of the receiving socket 3276a, to prevent liquid getting underneath the receiving socket 3276a. Recesses 3812 are provided on either side of the rib 3810, so that liquid will drip off the bottom of the front flange 3276a' rather than wicking under the flange into the main housing of the apparatus. A channel 3814 is provided in the lower chassis between the curved cavity 3802 and the aperture 3800, to prevent liquid bridging across from the cavity 3802 to the receiving socket 3276a.

FIGS. 146 and 147 show an alternative retainer 3276b' for use in the electrical connector 3276. Unless described below, the features and functionality are as described above, and like reference numerals indicate like parts. The shape of the retainer 3276b' has been modified to correspond with the external shape of the housing of the lower chassis. The retainer 3286b' has two fastener apertures 3276d; one on either side of the retainer. That provides more symmetrical loading through the retainer; however, a single aperture could alternatively be provided.

FIG. 145 shows an alternative configuration of the lower chassis 3202" in the region where the electrical connector 3276 is located. Unless described below, the features and functionality are as described above with reference to FIGS. 129 and 130, and like reference numerals indicate like parts. The cavity 3802 is shaped to receive the power cord plug and to receive the retainer 3276b'. A drainage aperture 3809 is provided through the base of the lower chassis 3202", inward of the retainer 3276b'. The drainage aperture is positioned beneath the power cord plug when the power cord plug is inserted into the electrical connector. The drainage aperture 3809 is configured to enable liquid to drain from the lower chassis to an exterior of the housing, if any liquid enters the lower chassis. The aperture causes a break in the wall to help prevent water tracking from inside to outside the case, or vice versa.

FIGS. 131 and 132 show details of a communication connector arrangement 3274 in an upper portion of the rear wall of the lower chassis 3202'. The connector arrangement 3274 is in electrical communication with the electronics boards 272

In the form shown, the connector arrangement 3274 comprises three USB ports. While three ports are shown, any suitable number of ports could be used. The port(s) could be different types of communication port(s).

The port(s) could be positioned at any suitable angle relative to a vertical axis of the apparatus. The insertion angle of a plug into the connector may be between 0 degrees and 90 degrees relative to the vertical axis. The angle may be non-horizontal to reduce the likelihood of the inserted plugs being bumped, and may be non-horizontal and non-vertical to reduce the likelihood of liquid ingress; i.e. the port(s) may face at least partly downwardly so that the insertion angle of plug(s) into the connector(s) is at least partly upward. Another benefit of an angled USB connection is that the PCB can be larger. In the configuration shown, the plug inserts into the connector at an angle that is perpendicular to the PCB and thus the PCB can better use the space within the housing if the configuration is angled. In one form, the port(s) may be at an angle of between about 5 degrees and about 30 degrees relative to the vertical axis. In one form, the port(s) may be at an angle of between about 10 degrees and about 20 degrees relative to the vertical axis. In one form, the angle is about 15 degrees relative to the vertical axis of the apparatus, to allow the USB plug upon insertion into the ports, to be at an angle of 90 degrees relative to the PCB 272. As shown in FIG. 132, the lower chassis part may have a recess with a wall 3274d that is angled relative to vertical at the insertion angle of the plug into the connector, to provide support for the plug once inserted. A lip may be provided on each port to reduce the likelihood of water ingress into the port(s).

As shown in FIG. 131, each connector of the connector arrangement 3274 preferably has chamfered lead-in ribs 3274b positioned above and below an entrance to the USB port 3274a, to assist with the insertion of the USB plug 3274c into the port 3274a. The lead-in ribs 3274b may be positioned above and below, and/or on either side of the USB port.

An upper outer horizontal edge 3274e of the recess of the communication connector arrangement 3274 may comprise a sharp edge or a liquid deflector, to minimise the likelihood of liquid seeping into the connectors of the connector arrangement, by encouraging liquid to drop off the sharp edge or liquid deflector rather than running into the recess. For example, the sharp edge may be provided by an inwardly directed wall portion that extends towards, or below, the connectors and that intersects with the rear wall portion 3222 of the lower chassis on a sharp angle, such as an orthogonal angle for example. Alternatively, a liquid deflector may be provided by extending the rear wall portion 3222 downwardly beyond the connectors, or by providing a louvre or ramp that overhangs the connectors to deflect liquid away from the connectors.

As shown in FIG. 132, the apparatus 3010' may have a battery 3222a to provide power to the apparatus when there is a power outage. The battery may be replaceable.

In the form shown, the battery is coupled to an exterior of the back wall of the apparatus. This provides a large surface area to cool the battery and reduces the amount of heat entering the apparatus from the battery. Additionally, this configuration reduces the influence of heat generated by components of the apparatus on the battery, particularly when the battery is being charged. In an alternative configuration, the battery may be internally mounted in the main housing.

The back wall may comprise a recess and/or electrical connector(s) to connect with the battery terminals, the electrical connector(s) being in electrical communication with the PCBs 272. A wall may be provided around the electrical connection to reduce liquid ingress in that region.

As shown in FIGS. 133 and 134, the apparatus 3010' may have a mount 3700 for mounting the apparatus to a stand or pole 3701. This enables the apparatus to be used in an elevated position, without taking up horizontal storage space on bedside tables.

The mount 3700 may be integrally formed with part of the main housing of the apparatus. In the form shown, the mount 3700 is integrally formed with the left side wall 3210' of the lower chassis 3202' of the housing. The mount could instead be integrally formed with any of other walls of the housing, such as a rear wall, right side wall, or other wall.

The side of the apparatus comprises a recess 3702. A downwardly projecting tongue 3704 has an upper end that is integrally formed with the wall, and is positioned in the recess. A free, lower end of the tongue 3704 is provided with a projecting bump 3706. The bump projects outwardly a greater distance than the remainder of the tongue.

When the apparatus is mounted to the stand using the mount 3700, the bump 3706 causes the apparatus to lean towards the stand as shown schematically in FIG. 134. Without the bump, a user may perceive the apparatus leaning away from the stand (due to the base of the apparatus swinging in towards the stand) and be concerned that the apparatus is not securely held. The bump 3706 therefore positions the apparatus such that it leans inwardly towards the stand so that a user is unlikely to be concerned regarding the coupling between the stand and the apparatus.

The mounting 3700 will be sufficient that the apparatus 3010' is securely held with a reasonable buffer strength to hold the apparatus through likely usage cases (e.g. a user leaning on the apparatus, accidental bumping of the apparatus), whether or not the bump is present. The bump addresses the visual look and user's perception of the case.

The bump 3706 may be configured to cause the unit apparatus to lean in towards the stand 3701 by any suitable angle. For example, angle $\theta 1$ may be approximately 1-15°, or approximately 1-10°, or approximately 1-7°, or approximately 1-5°, or approximately 1-2°. Therefore $\theta_2$ is $\geq 0°$.

The main housing of the apparatus may be formed from any suitable material that will allow the mounting 3700 to be integrally formed. For example, the case may be formed from polycarbonate.

The integral mount 3700 has greater impact strength compared to an additional, screwed in part. Strengthening of the mount 3700 may also be done by, for example, varying the wall thickness, ribbing, or varying internal geometries.

The apparatus could be mounted to the pole or the stand by a c-clamp 3707 such as that shown in FIGS. 102 to 104 and 117. The c-clamp 3707 has an arcuate recess 3707a that is configured to snap-fit onto a suitable pole or stand 3701. A side of the c-clamp comprises an engagement region 3707b having two inwardly-directed flanges that are configured to receive the tongue 3704. The bump 3706 on the bottom of the tongue may engage with a bump 3707c at the base of the engagement region 3707b. These features are shown in FIGS. 102 and 104.

To mount the apparatus to the pole or stand 3701, the c-clamp 3707 will be fixed to the pole or stand at a suitable height, by inserting the pole or stand into the arcuate recess 3707a. The apparatus 3010' is then mounted to the c-clamp 3707 and thereby the pole or stand 3701, by inserting the tongue 3704 into the engagement region 3707b of the c-clamp until the bumps 3706, 3707c engage. The c-clamp 3707 may have two engagement regions 3707b, to enable two apparatuses 3010' to be supported by one c-clamp. The apparatuses 3010' can be lifted vertically relative to the c-clamps 3707 to disengage them from the c-clamps and the stand or pole.

Alternatively, the integral mount 3707 could couple with any complementary structure so that the apparatus 3010' can be mounted to any suitable support, such as a wall, shelf, or pole for example.

FIGS. 135 and 136 show electrical connection arrangements 3722 that can be used in the apparatus 3010'. Electrical connections will occur between PCBs and components of the apparatus.

To form each electrical connection, a PCB 3722a is provided. A generally annular collar 3722b made of a suitable plastic material is then over-moulded onto the PCB 3722a. As shown in FIG. 135, the PCB will be provided with suitable apertures(s) 3722c to enable collar material to flow through the PCB during the over-moulding process, to provide a strong connection between the collar 3722b and the PCB 3722a.

The collar 3722b and PCB 3722a assembly is then over-moulded onto part of the main housing, for example onto a wall or floor of the main housing, to form a structural connection and seal between the PCB 3722a and the main housing of the apparatus.

The collar can be formed from any suitable plastics material. In one example, the collar is formed from polycarbonate. The formed collar is substantially rigid, meaning that the PCB 3722a would need to be snapped out of the collar 3722b to be removed from the housing, as opposed to a soft grommet that could possibly be pushed through by a user. The collar will provide a better seal than a soft grommet that could be torn or damaged.

The PCB 3722 could be plasma treated to help with bonding between the over-moulded collar 3722b and the PCB 3722a. That may also assist with sealing against oxygen leakage into the regions of the housing that house electrical and/or electronics components.

The exposed portion of the PCB 3722a will be coupled to suitable electrical connector(s).

FIG. 136 shows two exemplary locations for the PCB and collar assemblies 3722, 3722' in the lower chassis 3202' of the apparatus. Alternative positions are possible.

FIGS. 148 to 150 show an alternative configuration gasflow inlet elbow 1324 for delivering gases from the outlet port 1452 of the motor and/or sensor module 1400 to the liquid chamber gases inlet port 306 of the liquid chamber in the flow therapy apparatuses. Unless described below, the gasflow inlet elbow 1324 has the features and functionality described above for elbow 324, and like numerals indicate like parts, with 1000 added to each numeral.

The inlet elbow 1324 comprises a first body component 1324' and a second body component 1324". The first and second body components are injection moulded plastic components. The first body component comprises a tube that forms the manifold gases outlet port 1322 and a first interface portion 1324A.

The first interface portion 1324A is provided at a base of the manifold gases outlet port 1322 and comprises a stepped arrangement comprising upper and lower angled sections 1324A1, 1324A2 that are oriented on any suitable angle relative to a longitudinal axis 1322A of the gasflow outlet port, such as between 30 and 60 degrees, or 45 degrees, for example. The first interface portion also includes a section 1324A3 that extends forward from the base of the upper angled section, a section 1324A4 that extends upward from the top of the lower angled section, and an angled transition section 1324A5 between the sections 1324A3, 1324A4.

The second body component 1324" comprises a second interface portion 1324A' at an upper end of a gasflow inlet port 1325. The second interface portion comprises a stepped arrangement, comprising upper and lower angled sections 1324A1', 1324A2' that are oriented on any suitable angle relative to a longitudinal axis 1322A of the gasflow outlet port, such as between 30 and 60 degrees, or 45 degrees for example. The second interface portion also includes a section 1324A3' that extends forward from the base of the upper angled section, a section 1324A4' that extends upward from the top of the lower angled section, and an angled transition section 1324A5' between the sections 1324A3', 1324A4'. The first and second interface portions are complementary so that they can mate together. A suitable soft seal, such as an O-ring seal, will be provided between the first and second interface parts. The first and second interface parts can be fastened together by clips or suitable fasteners 1324F such as screws for example.

The first and second interface portions 1324A, 1324A' comprise recesses 1324R to receive fasteners or locating protrusions on the main housing of the apparatus, to prevent rotation of the inlet elbow 1324 relative to the housing and/or to prevent the elbow from being pulled out of the housing. The inlet elbow 1324 may be configured to mount to the upper and/or lower chassis of the housing.

Alternatively, the inlet elbow 1324 may be configured to mount to the forwardly angled surface 124, 124', 3124' and/or the display carrier of the apparatus.

A one-way valve 1326 is mounted in the interior of the elbow 1324, at or adjacent the interface between the manifold gases outlet port 1322 tube and the gasflow inlet port 1325 tube. In the form shown, the non-return valve 1326 comprises a plate that is movably mounted in the elbow to enable gas to flow in a direction from the inlet port 1325 to the outlet port 1322, but not in the reverse direction. The non-return valve may be biased in to a closed position in the absence of gasflow, or may be configured to close under pressure if gas attempts to flow in a direction from the outlet port 1322 to the inlet port 1325. The valve is configured to prevent liquid from flowing backwards through the elbow and into the housing.

The outlet port 1322 is provided with a recess 1322R to receive a T-seal or L-seal as described herein, and the inlet port 1325 is provided with a recess 1325R to receive a suitable soft seal such as an O-ring.

The smoother exterior shape of the inlet elbow 1324 will likely make it easier to clean than inlet elbow 324.

The apparatus of FIG. 101 advantageously has tongue and groove arrangements between components of the apparatus to reduce water and oxygen ingress into the unit. As shown in FIGS. 151 to 160, the apparatus advantageously has tongue and groove arrangements between the top of the rear outer wall 3222' of the lower chassis 3202' and the bottom of the rear outer wall 3122' of the upper chassis 3102', between the top of the left side outer wall 3210' of the lower chassis and the bottom of the left side outer wall 3110' of the upper chassis, between the top of the right side outer wall 3216' of the lower chassis and the bottom of the right side outer wall 3116 of the upper chassis, and between the top of the front lip 3242' of the lower chassis and the bottom of the front lip 3142 of the upper chassis.

The tongue and groove arrangements provide a substantially continuous liquid/gasflow-resistant coupling around the periphery of the upper and lower chassis parts 3102', 3202'. In the form shown, the lower chassis 3202' is provided with grooves 3210G, 3222G, 3216G, 3242G, and the upper chassis 3102' is provided with complementary tongues 31101, 3122T, 3116T, 3142T that are configured to be at least partly received in the respective grooves when the upper and lower chassis parts are assembled together. The continuous coupling advantageously extends along the front, sides, and at least most of the rear of the chassis parts, as shown, including around any corners between those surfaces. Advantageously, tongue and groove arrangements are also provided around the communication coupling portion 3274, as will be described below with reference to FIG. 160.

FIG. 156 shows details of the tongue and groove arrangement between the top of the rear outer wall 3222' of the lower chassis 3202' and the bottom of the rear outer wall 3122' of the upper chassis 3102'. The top of the rear outer wall 3222' is provided with a groove 3222G, and the bottom of the rear outer wall 3122' is provided with a tongue 3122T that is sized and configured to be received in the groove. The bottom of the rear outer wall 3122' of the upper chassis 3102' may also be provided with a groove 3222G' to receive a tongue 3222aT of the battery to mount the battery to the housing.

The tops of the side walls 3210', 3216' of the lower chassis 3202' are also provided with grooves 3210G, 3216G, and the bottoms of the side walls 3110, 3116 of the upper chassis 3102' are provided with tongues 3110T, 3116T that are sized and configured to be received in the grooves.

As shown in FIG. 159, the top of the front lip 3242' of the lower chassis is provided with a groove 3242G, and the bottom of the front lip 3142' of the upper chassis is provided with a tongue 3142T that is sized and configured to be received in the groove 3242G.

A portion of the upper chassis 3102' in front of the floor portion 3136 of the chamber bay (that defines a recess 3138 to receive a heater arrangement), comprises a downwardly oriented transversely extending groove 3136G, and a bottom wall 3230 of the lower chassis 3202' comprises an upwardly extending tongue 3230T that is sized and configured to be received in the groove 3136G.

The sides and rear of the heater arrangement receiving region also comprise a tongue and groove arrangement. As shown in FIGS. 151 to 154, the upper chassis 3102' comprises a downwardly extending tongue 3136T that extends around the sides and rear of the heater arrangement receiving region. The ends of the tongue 3136T meet with the ends of the groove 3136G. The lower chassis 3202' comprise an upwardly oriented groove 3230G that extends around the sides and rear of the heater arrangement receiving region. The ends of the groove 3230G meet the ends of the tongue 3230T. Therefore, there is a continuous tongue and groove arrangement around substantially the entire perimeter of the chamber bay.

FIG. 158 shows an alternative configuration of the tongue and groove arrangement between the upper and lower chassis parts at the rear of the heater arrangement receiving region. In this configuration, the lower chassis part comprises an upwardly extending tongue 3230T', and the upper chassis part comprises a downwardly oriented groove 3134G in the base of wall 3134, with the tongue 3230T' sized and configured to be received in the groove 3134G.

In one configuration, the upper and lower chassis parts may have a downwardly projecting tongue and upwardly projecting groove in a rear portion of the housing, and the configuration may be reversed at a front portion of the housing; e.g. from approximately the region where the handle mechanism joins with the upper chassis in FIG. 117.

FIGS. 151, 152, and 160 show details of the tongue and groove arrangements between the communication coupling portion 3274 and the upper and lower chassis parts. The bottom of the rear outer wall part 3122 of the upper chassis is provided with a downwardly extending tongue 3122T, and the top of an outer wall of the communication coupling portion 3274 comprises an upwardly oriented groove 3274G that is sized and configured to receive the tongue 3122T. The top of the rear outer wall part 3222 of the lower chassis is provided with an upwardly extending tongue 3222T, and the bottom of an outer wall of the communication coupling portion 3274 comprises a downwardly oriented groove 3274G' that is sized and configured to receive the tongue 3222T. Two surfaces (e.g. T2B and G2B) are configured to meet so as to seal the upper and lower chassis together. Alternatively, or in addition to this, other surfaces may be configured to meet. An inner wall of the groove 3274G' is advantageously shorter than an outer wall of the groove, to enable the communication coupling portion to be snap fit into place on the lower chassis. The tongue and groove arrangement preferably extends around the entire periphery of the communications coupling portion 3274. For example, the lower chassis part may comprise a tongue 3222T that is sized and configured to be received in a groove 3274G' that extends along the base and up the sides of the communications coupling portion 3274.

As shown in FIG. 157, a tongue and groove arrangement is also provided between the outer extension tube or conduit 3133 of the upper chassis 3102' and the gasflow passage tube 3264 of the lower chassis 3202'. An outer wall portion of the gasflow passage tube 3264 comprises an upwardly oriented annular groove 3264G that is spaced from the upper end of the gasflow passage tube 3264, and is positioned close to the ceiling 3262 of the motor and/or sensor sub-assembly recess 3250. A bottom edge of the extension tube 3133 of the upper chassis comprises a downwardly extending annular tongue 3133T that is sized and configured to be received in the groove 3264G. It can be seen from FIG. 157 that the gasflow passage tube 3264 extends up through the extension tube 3133 at least to the upper edge of the extension tube, and in the form shown beyond the upper edge of the extension tube and beyond the angled surface 3124'.

Because the gasflow passage tube 3264 extends up through the extension tube 3133 and around the outside of the inlet elbow 324, 1324, and is formed as a single continuous unbroken integral part including the walls 3256 and ceiling 3262 that define the recess 3250, in the case of a leak the gas will follow the path of least resistance, which is to gather outside the leak region and exit to atmosphere via the outside of the inlet elbow 324, 1324. It is very unlikely that gases will flow into the housing and via a tortuous path to the electronics of the apparatus A tongue and groove arrangement is also provided between the upper edge of a filter housing 3354 in the lower chassis 3202' and a corresponding aperture 3354A in the upper chassis 3102'. The tongue and groove arrangement may extend around the entire periphery of the filter housing 3354 and aperture 3354A, to prevent gas from leaking from the interior of the filter housing to the exterior of the filter housing and into the main housing of the apparatus. One of the filter housing 3354 and wall around aperture 3354A will have a groove, with the other of the filter housing and wall around the aperture having a tongue that is sized and configured to be received in the groove.

Any one or more of the tongue and groove arrangements may have the configuration shown in FIG. 161, where the groove G1 has a base G1B and substantially parallel side walls G1SW, and the tongue T1 has a tip or edge T1E and substantially parallel side walls T1SW. Alternatively, or additionally, any one or more of the tongue and groove arrangements may have the configuration shown in FIG. 162 where the groove G2 has a base G2B, a first side wall G2SW1 that extends orthogonally from the base, and a second side wall G2SW2 that initially extends orthogonally from the base and then terminates at a chamfer G2C or angled surface. The chamfer helps to trap any liquid particles between G2C/G2SW1 and T2SW. Alternatively, the angled surface or chamfer G2C may extend all the way to the base G2B. The angled surface or chamfer G2C is configured to, along with the respective side wall of the tongue T2, minimise or prevent wicking of liquid past the angled surface or chamfer. The groove G2 will typically be oriented such that the chamfered surface G2C is positioned on the side of the groove corresponding to the part of the apparatus which liquid should be kept away from. For example, the grooves 3210G, 3216G on at least the side walls 3210', 3216' of the lower chassis 3202' may have the chamfered surface G2C on their inner edges, to prevent liquid from wicking into the interior of the side walls. The non-chamfered outer side wall G2SW1 of the grooves will allow any moisture that enters the tongue and groove to wick in an outwards direction toward the exterior of the apparatus.

Alternatively, or additionally, an enlarged space may be provided between at least one surface of the tongue T1, T2 and respective surface(s) of the groove G1, G2 to reduce or prevent wicking.

The tongues T1, T2 and grooves G1, G2 may have the orientations shown in FIGS. 161 and 162.

The described and shown configurations and orientations are examples only, and any suitable combination of the tongue and groove arrangements and/or orientations of the tongue and groove arrangements may be used in the apparatus.

The main housing of the apparatus comprises a small number of parts. The upper chassis 3102' including forwardly angled surface 3124' and the curved wall portion 3134 that surrounds the majority of the chamber bay is integrally formed as a single part (by injection moulding for example), which seals the chamber bay from the interior of the upper chassis part behind the wall portion 3134, and reduces the likelihood of liquid/gases ingress into the region behind wall portion 3134 from the chamber bay. Similarly, the lower chassis 3202' including the walls and ceiling that define the recess 3250 for receipt of the motor and/or sensor module and the gasflow passage tube 3264 is integrally formed as a continuous unbroken single part (by injection moulding for example), which seals the interior of the recess 3250 from the upper region of the lower chassis, and reduces the likelihood of gases ingress into the upper region of the lower chassis from the recess 3250 and into the part of the main housing formed between the upper and lower chassis.

In the form shown, the upper and lower chassis 3102', 3202' can be fastened together using a small number of fasteners. The fasteners could be screws, or any other suitable fasteners. The fasteners simply act to couple the upper and lower chassis parts together. The nature of the tongue and groove seals between the upper and lower chassis parts is such that the fasteners do not need to provide continuous compression between the upper and lower chassis parts to provide adequate sealing, which would be required if soft seals were used. In an alternative configuration, the upper and lower chassis parts could be coupled together using clips or some other suitable arrangement.

FIGS. 163 and 164 show a modified battery 3222a that is coupled to an exterior of the back wall of the apparatus, as discussed above with reference to FIG. 156. The battery provides functionality to the apparatus by powering the apparatus. The battery shown in FIGS. 163 and 164 is larger than that shown in FIG. 132, and has a higher capacity. Additionally, this battery 3222a differs in that the battery has a retention feature at the base of the battery that is configured to overlap with part of the motor and/or sensor module 400, 1400 to maintain the motor and/or sensor module 400, 1400 in position in the recess 3250 in the housing.

In the form shown, the retention feature of the battery comprises a base flange 3222a' that extends under, and contacts, part of the bottom wall 3230 of the lower chassis 3202'. The base flange 3222a' is sized and configured to also extend under, and contact, part of the base 1403 of the motor and/or sensor module 1400. When the motor and/or sensor module 1400 is positioned in the recess 3250 and the battery 3222a is secured to the housing of the apparatus, the motor and/or sensor module cannot be removed from the recess due to the overlap between the base flange 3222a' and the motor and/or sensor module.

To assemble the battery 3222a to the housing, the motor and/or sensor module 1400 is inserted in the recess 3250. A fastener can be inserted through aperture 1403E in the tab on the base 1403 of the motor and/or sensor module, to fasten the module to the lower chassis 3202'. The upper end of the battery 3222a is coupled to the lower chassis part by inserting the tongue 3222aT into the groove 3222G' as described above with reference to FIG. 156. The lower part of the battery can then be tilted forward so that the base flange 3222a' contacts and overlaps with the base 1403 of the motor and/or sensor module. Fasteners are then inserted through the apertures 3222a" in the base flange to fasten the base flange 3222a' to the lower chassis 3202'. The process can be reversed to remove the battery 3222a and motor and/or sensor module 1400 from the housing.

Rather than being a base flange 3222a' that extends the entire width of the battery 3222a, the retention feature could have any other suitable form. For example, the battery may have a single shorter flange, a plurality of shorter flanges, or one or more other projections that can overlap with the base 1403 of the motor and/or sensor module 1400 to retain the motor and/or sensor module in position in the recess 3250 in the housing. Such retention feature(s) could be incorporated in a smaller battery such as that shown in FIG. 132 for example. As another alternative, the base flange 3222a' or other retention feature(s) could be provided in a different removable component that provides functionality to the apparatus, with the retention feature(s) of that removable functional component overlapping and contacting part of the motor and/or sensor module 1400 to retain that in position in the recess 3250 of the housing when the removable component is secured to the housing. It will be appreciated that the battery or other functional component does not solely act to fasten the module 1400 to the housing, but additionally provides other functionality to the apparatus.

The communications connector arrangement 3274 shown in these figures differs from that of FIGS. 131 and 132 in that it comprises only two USB ports due to the increased size of the battery. However, while two ports are shown, any suitable number of ports could be used. The port(s) could be different types of communication port(s).

FIGS. 165 and 166 show an alternative removable elbow 3342 for use in the flow therapy apparatuses, the elbow having the PCB connector 3366 shown in FIGS. 167 and 168. Unless described below, the elbow will have the same features and functionality as the removable elbow of FIG. 74, and the PCB connector will have the same features and functionality as FIG. 75. Like reference numerals indicate like parts, with 1000 added to each numeral.

Compared to the PCB connector 2366 of FIG. 75, the PCB connector 3366 of FIGS. 167 and 168 has shortened electrically conductive connector portions or pins 3366c. A pair of opposed recesses 3366h are provided in the sides of the PCB connector 3366, adjacent the inner ends of the connector portions 3366c. In the form shown, the recesses 3366h are triangular cut-outs, but they could have any suitable shape.

The plastic support portion 3374 of the elbow has angled edges 3374a to allow for the recesses 3366h on the PCB connector 3366.

The base at the inner end of the horizontal limb (corresponding to the manifold gases inlet port 3340) of the removable elbow has an upwardly curved region 3340c prior to the bend in the elbow to assist with tooling.

The PCB electrical connector may be modified so that the thermistors 3366d or other temperature sensors are less affected by the patient breathing conduit heater wire, the electrically conductive tracks 3366b and the plastic board 3366a, and ambient temperature. This reduces temperature sensor wall effects or stem effects, to enable the temperature sensors to more accurately measure gas temperature.

For example, as shown in FIG. 170, the cross-section and length of at least one of the electrically conductive tracks 3366b' that connect the thermistors 3366d' or other temperature sensors to the connector portions 3366c', may have a reduced cross-section and/or increased length compared to that shown in FIG. 169. For example, one or more of the tracks 3366b' may have a tortuous path along at least part of its length from the respective connector portion 3366c' to the respective thermistor 3366d'. The track(s) may have a sinuous configuration, a stepped or castellated configuration as shown in FIG. 169, or any other suitable configuration to provide additional length of the track.

As another example, as shown in FIG. 171, the shape of part of the plastic board 3366a" may be made convoluted. The convoluted configuration may be provided by one or more apertures 3366g" in the board. In the form shown, the board has two apertures 3366g"; a large aperture close to the interface between the two limbs of the elbow, and a smaller aperture close to the connector portions 3366c" of the PCB. That configuration could be varied. This enables the thermal resistance at the join between the plastic overmould and the plastic board 3366a" to be exploited, to help prevent the patient conduit heater wire from affecting thermistor measurements and reduce stem effects.

As another example, as shown in FIG. 172, at least one of the electrically conductive tracks 3366b''' may be provide with one or more enlarged conductive portions 3366b''' having a relatively large area and located near to the thermistors 3366d''' or other temperature sensors. The enlarged conductive portion 3366be''' may be provided by a widened portion of the track, a separate piece of conductive material that is coupled to the track, or any suitable configuration. In the form shown, the PCB electrical connector 3366 has one enlarged conductive portion that is substantially rectangular or square, but any suitable number and/or shape of conductive portions may be provided. The enlarged conductive portion(s) 3366be''' increase heat transfer from the overmoulded plastic to the board 3366a''' in the region of the thermistors to reduce stem effects.

The features described and shown with reference to FIGS. 170-172 may be used alone or in any suitable combination.

FIG. 173 shows a carrier 3102 for the display and user interface module in the flow therapy apparatuses. Unless described below, the features and functionality are the same as for the carrier 2102 of FIGS. 76 and 77, and like reference numerals indicate like parts with 1000 added to each numeral. The carrier 3102 is configured for use with the removable retention cover 5150a of FIG. 175. Unless described below, the features and functionality of the removable retention cover are the same as for the cover 4150a of FIGS. 118 and 119, and like reference numerals indicate like parts with 1000 added to each numeral.

Each side wall 5152 of the removable retention cover 5150a has a guide recess 5156a that is defined by upward/downward oriented guide projections 5156b at either end of the recess. Each side of the carrier 3102 has a projecting ridge 3102p that is sized and configured to fit in the recess 5156a of the cover. Either end of the projecting ridge 3102p terminates at a guide recess 3102r that is sized and configured to receive a respective one of the cover guide projections 5156b.

Each side wall 5152 of the removable retention cover 5150a has at least one downwardly oriented tongue with an enlarged portion or barb 5156b' that engages under the respective projecting ridge 3102p of the carrier 3102 when the removable retention cover is engaged with the carrier 3102, to provide a positive engagement of those components. Slots are provided on either side of each tongue to enable the tongues to flex for the barbs 5156b' to pass the projecting ridges 3102p of the carrier when the removable retention cover is being engaged with, or removed from, the carrier 3102. While two tongues are shown on either side wall of the cover 5150a, the cover could alternatively have one or more than two tongues.

In an alternative configuration, the carrier 3102 could have the tongue(s) and barb(s), and the cover 5150a could have the ridges. In another alternative configuration, the removable elbow and/or retention cover 5150a may have positive engagement feature(s) to provide additional restraint to the cover.

The carrier 3102 comprises a plurality of first apertures 3102A1 to enable mounting of the display and user interface module 14 to the carrier 3102 through the use of fasteners such as screws or the like. The carrier 3102 has a plurality of second apertures 3102A2 to enable mounting of the carrier 3102 to the upper chassis 3102' through the use of fasteners such as screws or the like.

The removable retention cover 5150a is coupled to the carrier 3102, and thereby to the main housing, by a flexible tether 6000 shown in FIG. 176. The tether comprises an elongate body 6002, an aperture 6004 at or toward a first end of the tether, and enlarged head 6006 at or toward an opposite second end of the tether. The tether 6000 is coupled to the removable retention cover 5150a by inserting the enlarged head 6006 through a slot (not shown) in the removable retention cover. The enlarged head inhibits removal of the tether from the removable retention cover. The tether 6000 is coupled to the carrier 3102 by inserting the first end of the tether between the carrier 3102 and the upper chassis 3102' so its aperture 6004 is aligned with the respective aperture 3102A2, and is maintained in position by the fastener that is used to fasten the carrier 3102 to the upper chassis 3102'. The tether may be manufactured from a suitable resilient and robust material, such as TPU for example.

FIGS. 177 to 183 show an alternative configuration removable motor and/or sensor module or sub-assembly 2400 that can be used as a flow generator in the flow therapy apparatuses. Unless described below, the sub-assembly has the features and functionality described in relation to the sub-assembly of FIGS. 78 to 95, and like reference numerals indicate like parts, with 1000 added to each reference numeral. The sub-assembly contains only minor modifications from the sub-assembly of FIGS. 78 to 95.

Referring to FIG. 177, the base 2403 of the motor and/or sensor module comprises a first recess or cut-out 2403R1 at an end of the base 2403 for receipt of the base flange 3222a' of the battery 3222a shown in FIG. 164. The flange 3222a' extends into the recess 2403R1 to hold the motor and/or sensor module in position in the lower chassis 3202' of the apparatus. A second recess or cut-out 2403R2 is provided in a side of the base 2403 to enable a flange of another removable component to be used to hold the motor and/or sensor module in position in the lower chassis 3202' of the apparatus, when the other removable component is secured to the lower chassis. The protrusion that is shown between the recesses 2403R1, 2403R2 may not be present.

Rather than having the component 1407 with an aperture 1427A, the base 2403 has upstanding post 2407.

Referring to FIG. 178, the base 2403 is provided with a plurality of mechanical stops 2403S in the region 2403A for receipt of the motor/blower unit 2402. The mechanical stops 2403S are angularly spaced around the region and are arranged to prevent the motor/blower unit 2402 from coming off its mounts. In the form shown, the mechanical stops comprise upstands. However, they could be any suitable form. The upstands are sized so that they sit clear of the motor/blower case to allow a small amount of movement of the case. For example, the upstands may be sized to sit about 3 mm clear of the blower case.

The base may have three or more mechanical stops, and in the form shown six mechanical stops are provided. The mechanical stops may be provided anywhere in the radial region represented by arrow 2403R; however, the further outward they are positioned and the more stops there are, the less rocking the motor/blower unit is able to do. The underside of the layer 2420 may also comprise mechanical stops 2420S as shown in FIG. 180, to act against the top of the motor/blower unit.

The protrusions 2411P are longer than those shown in the configuration of FIGS. 78 to 95 to hold the motor/blower mounts more securely in case the apparatus is dropped or knocked.

Referring to FIG. 179, an electrical connector 2456EC is connected to the sensing printed circuit board 2456, to electrically couple the sensing PCB to other electrical component(s). Referring to FIG. 182, the cover layer 2440 is provided with apertures 2440A1, 2440A2. Apertures 2440A1, 2440A2 facilitate clearance between electronic or sensing components and the flow module.

The apparatuses described herein will advantageously have removable and replaceable components, including, an oxygen valve assembly, the motor and/or sensor module, a filter, the screen carrier module that includes the display and interface PCBs, the removable gasflow tube or elbow, the retainer cover, power cord and retainer part, and PCBs. T-seals on the removable gasflow tube or elbow and/or the inlet gasflow tube and/or elbow may be removable. Alternatively, the seals may be fixed to the tubes and/or elbows, with those components being removable/replaceable as one item. The upper and lower chassis parts and other housing parts may also be replaceable.

T-seals or L-seals may be used on the removable gasflow tube or elbow and on the inlet gasflow tube or elbow, of the apparatuses described herein, to couple with the fluid chamber. T-seals or L-seals provide a decreased insertion force to insert the liquid chamber compared to O-rings or soft couplers. The reaction force of a T-seal or L-seal is determined by the width of its rib. A softer material reduces the force. The liquid chamber will seal against the bent limb of the T-seal or L-seal. Use of a T-seal or L-seal makes the chamber slightly harder to remove than insert, but this is easier to remove than if an O-ring or a soft coupler was used.

The T-seals 2342T, 2342T' of FIGS. 137 to 141 or the L-seals 2342T" of FIGS. 142 and 143 can be provided in an alternative apparatus to that described above. FIGS. 184 to 186 show a patient breathing conduit arrangement 7000 that incorporates such a T-seal 2342T. The patient breathing conduit arrangement 7000 comprises a patient breathing conduit 7002. A helical recess 7004 along the periphery of the patient breathing conduit 7002 has a heater wire to heat gasflow that is passing through the breathing conduit. One end of the patient breathing conduit 7002 is coupled to a connector 7006. The connector 7006 is arranged to be coupled to a patient interface such as a nasal cannula with a manifold and nasal prongs, and/or a face mask, and/or a nasal pillows mask, and/or a nasal mask, and/or a tracheostomy interface, for example.

The opposite end of the patient breathing conduit 7002 is coupled to a connector 7010 for coupling to another apparatus, such as a gasflow output port of a flow therapy apparatus, or the outlet of a humidification apparatus, for example. The connector 7010 comprises an outer housing part 7012 and an inner part 7014 that is at least partly received in the outer housing part.

The inner part is shown in detail in FIG. 185 and comprises a tapered tube 7016 that is received in the end of the patient breathing conduit 7002 to deliver gas to the patient breathing conduit. An outer surface towards the outer end of the tapered tube 7016 comprises a recess 7018 for receipt of the T-seal 2342T or L-seal. Alternatively, the T-seal or L-seal may be overmoulded onto the tapered tube 7016. The inner part also comprises an electrical connector 7020 to provide power to the heater wire and/or enable communication between the patient interface and apparatus to which the patient breathing conduit arrangement will be connected.

The connector 7010 of the patient breathing conduit arrangement 7000 can be connected to another apparatus such as a flow therapy apparatus, or the outlet of a humidification apparatus, by inserting the outer part of the tube 7016 into a gasflow outlet port of the flow therapy apparatus, or the outlet of a humidification apparatus.

The inner tube 7016 forms a pneumatic connection with the outlet of a flow therapy apparatus or humidification apparatus. The inner tube 7016 may be inserted into the outlet or may engage around the outlet of a flow therapy apparatus or humidification apparatus to form a pneumatic pathway. The electrical connector 7020 connects with a corresponding electrical connector positioned on or adjacent or around the outlet of the flow therapy apparatus or humidification apparatus. In one example the connector 7010 connects to the outlet of a humidification chamber that is part of the flow therapy apparatus or humidification apparatus.

The T-seal 2342T or L-seal will seal against the interior of the gasflow outlet port, and the electrical connector 7020 will connect to a complementary electrical connector on the apparatus. The T-seal 2342T or L-seal may have the parameters, dimensions, and/or modifications described above with reference to FIGS. 137 to 144. The T-seal or L-seal provide an improved seal over an O-ring type element. Further the T-seal or L-seal also provide a reduced force to engage the connector on to the outlet of the humidification apparatus since the T-seal or L-seal flexes/bends more easily along an axis. The T-seal or L-seal deflects in response to a force applied to it from a user connecting the connector onto the outlet of a flow therapy apparatus or humidification apparatus, as compared to compressing along all faces, making fitting the connector to the outlet easier for a user.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. For example, while the motor and/or sensor sub-assembly recess is described as being in the underside of the main housing, it could alternatively be in a rear, side, front, or top of the housing. With such a variant, the air and/or oxygen inlets may also be positioned differently as required.

As another example, rather than the liquid chamber and chamber bay being configured so that the liquid chamber is inserted into and removed from the chamber bay from a front of the housing, the configuration could be such that the liquid chamber is inserted into and removed from the chamber bay from a side, rear, or top of the housing.

The features are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy).

Alternatively, one, some, or all of the features may be provided in an apparatus for a different purpose. The apparatus may be a high flow therapy apparatus, or may be a low flow therapy apparatus. For example, the features may be provided in an apparatus for providing continuous positive airway pressure (CPAP), which may deliver gases (humidified or otherwise) at lower flow rates.

One or some of the features may alternatively be provided in an apparatus that does not require a humidifier and therefore does not require the liquid chamber 300 or chamber bay 108 features. For example, it will be appreciated that the configuration that isolates the motor and gas flow path from the electrical and electronic components has broad applications in other types of gas delivery apparatuses.

The 'flow therapy apparatus' language is intended to cover all such variants.

Reference to any prior art in this specification is not, and should not be taken as, an acknowledgement or any form of suggestion that that prior art forms part of the common general knowledge in the field of endeavour in any country in the world.

Where reference is used herein to directional terms such as "up", "down", "forward", "rearward", "horizontal", "vertical" etc, those terms refer to when the apparatus is in a typical in-use position, and are used to show and/or describe relative directions or orientations.

The invention claimed is:

1. A breathing assistance apparatus for delivering a flow of gas, comprising:
   an apparatus main housing with a recess configured for receipt of, or containing, a motor and/or sensor module, and
   a gasflow passage extending from an outlet of the recess and in fluid communication with an outlet port for the flow of gas toward a liquid chamber for humidifying the gas,
   wherein the recess is fully defined by a single wall of the apparatus main housing,
   wherein the recess comprises a recess opening in an exterior wall of the apparatus main housing, and wherein the recess extends into the apparatus main housing from the recess opening,
   wherein the single wall comprises a peripheral wall and a ceiling,
   wherein an interior of the apparatus main housing comprises electrical and/or electronic components, and wherein the single wall of the recess is configured to pneumatically isolate the electrical and/or electronic components from gasflow through or from the motor and/or sensor module, and
   wherein a gasflow passage tube is integrally formed with the ceiling, wherein the gasflow passage is provided by the gasflow passage tube.

2. A breathing assistance apparatus according to claim 1, wherein the recess opening is configured for receipt of a motor and/or sensor module and is in a bottom of the apparatus main housing.

3. A breathing assistance apparatus according to claim 1, comprising a motor and/or sensor module positioned in the recess.

4. A breathing assistance apparatus according to claim 3, wherein the motor and/or sensor module comprises a base, a sensing layer, and a cover layer assembled together to form a sub-assembly housing.

5. A breathing assistance apparatus according to claim 4, wherein the sub-assembly housing has a shape that is complementary to a shape of the recess.

6. A breathing assistance apparatus according to claim 4, wherein the motor and/or sensor module comprises a motor with an impeller, the motor arranged to deliver gas through the gasflow passage.

7. A breathing assistance apparatus according to claim 6, wherein the motor is positioned on the base of the sub-assembly housing.

8. A breathing assistance apparatus according to claim 4, wherein the base is configured to close the recess opening when the sub-assembly housing is positioned in the recess.

9. A breathing assistance apparatus according to claim 3, wherein the motor and/or sensor module is maintained in position in the recess by a fastener, a clip, or a quick release arrangement.

10. A breathing assistance apparatus according to claim 4, wherein the sensing layer comprises a gasflow path with one or more sensors.

11. A breathing assistance apparatus according to claim 10, wherein the gasflow path is arranged to deliver gas through the gasflow passage.

12. A breathing assistance apparatus according to claim 3, wherein the motor and/or sensor module comprises a gasflow path that comprises a sinuous arrangement.

13. A breathing assistance apparatus according to claim 1, wherein the apparatus main housing comprises an upper chassis and a lower chassis, and wherein the interior of the apparatus main housing is defined between the upper chassis and the lower chassis.

14. A breathing assistance apparatus according to claim 13, wherein the recess opening is in a bottom of the apparatus main housing, and wherein the exterior wall is an outer bottom wall of the lower chassis, and wherein said single wall that defines the recess is integrally formed with the outer bottom wall.

15. A breathing assistance apparatus according to claim 14, wherein the gasflow passage tube extends through an outer tube that is integrally formed with the upper chassis.

16. A breathing assistance apparatus according to claim 14, wherein the outlet port is provided in an elbow, and wherein the gasflow passage tube is in fluid communication with a gasflow inlet port of the elbow.

17. A breathing assistance apparatus according to claim 1, wherein the single wall of the recess is configured such that if there is any leaking of gas from the motor and/or sensor module or gasflow passage, the leaking gas will vent to atmosphere rather than ingressing into the interior of the apparatus main housing that comprises the electrical and/or electronic components.

18. A breathing assistance apparatus according to claim 3, wherein the motor and/or sensor module is removable from the recess.

19. A breathing assistance apparatus according to claim 1, wherein gas that is or comprises oxygen flows through the gasflow passage and/or the outlet port.

20. A breathing assistance apparatus according to claim 19, wherein the gas is isolated from electrical and/or electronics components in the apparatus main housing.

21. A breathing assistance apparatus according to claim 1, wherein the electrical and/or electronic components comprise one or more printed circuit boards.

* * * * *

UNITED STATES PATENT AND TRADEMARK OFFICE
CERTIFICATE OF CORRECTION

PATENT NO. : 11,278,700 B2
APPLICATION NO. : 15/739096
DATED : March 22, 2022
INVENTOR(S) : Andre Van Schalkwyk It is certified that error appears in the above-identified patent and that said Letters Patent is hereby corrected as shown below:

On the Title Page

Column 1, Line 13, item [72], under Inventors, delete "Chui" and insert --Chul--.

In the Specification

Column 50, Line 11, delete "23661" and insert --2366f--.

Column 53, Line 29, delete "234211" and insert --2342T1--.

Column 53, Line 38, delete "234211" and insert --2342T1--.

Column 53, Line 40, delete "234211" and insert --2342T1--.

Column 62, Line 17, delete "FIG." and insert --FIGS.--.

Column 76, Line 67, delete "θ1" and insert --$\theta_1$--.

Column 79, Line 31, delete "31101," and insert --3110T,--.

Column 84, Line 12, delete "3366b''''" and insert --3366be'''--.

Signed and Sealed this
Twenty-eighth Day of June, 2022

*Katherine Kelly Vidal*
*Director of the United States Patent and Trademark Office*